US007232909B2

(12) United States Patent
Murata et al.

(10) Patent No.: US 7,232,909 B2
(45) Date of Patent: Jun. 19, 2007

(54) PYRIDINE DERIVATIVES

(75) Inventors: Toshiki Murata, Nara-ken (JP); Masaomi Umeda, Nara-ken (JP); Sachiko Sakakibara, Nara-ken (JP); Takashi Yoshiro, Nara-ken (JP); Hiroki Sato, Nara-ken (JP); Tsutomu Masuda, Nara-ken (JP); Yuji Koriyama, Nara-ken (JP); Mitsuiyuki Shimada, Meerbusch (DE); Takuya Shintani, Kyoto-fu (JP); Hiroshi Kadono, Hyogo-ken (JP); Timothy B. Lowinger, Guilford, CT (US); Karl B. Ziegelbauer, Haan (DE); Kinji Fuchikami, Kyoto-fu (JP); Hiroshi Komura, Nara-ken (JP)

(73) Assignee: Bayer Aktiengesellschaft, Leverkusen (DE)

( * ) Notice: Subject to any disclaimer, the term of this patent is extended or adjusted under 35 U.S.C. 154(b) by 18 days.

(21) Appl. No.: 11/240,728

(22) Filed: Sep. 30, 2005

(65) Prior Publication Data

US 2006/0100246 A1 May 11, 2006

Related U.S. Application Data

(60) Continuation of application No. 10/402,500, filed on Mar. 28, 2003, now Pat. No. 6,984,649, which is a division of application No. 09/956,618, filed on Sep. 18, 2001, now Pat. No. 6,562,811.

(30) Foreign Application Priority Data

Sep. 22, 2000 (JP) ............................ 2000-289173

(51) Int. Cl.
*C07D 213/73* (2006.01)

(52) U.S. Cl. ...................................... 546/250; 546/167

(58) Field of Classification Search ................ 546/250, 546/167

See application file for complete search history.

(56) References Cited

U.S. PATENT DOCUMENTS 4,003,908 A 1/1977 Denzel et al.

FOREIGN PATENT DOCUMENTS

WO WO 01/27103 A1 4/2001

OTHER PUBLICATIONS

Nagai, W., et al., "Structures and Fluorescence of Secondary Products Produced from the Cope-Knoevenagel Reaction of 2-Phenylpropionaldehyde with Methyl Cyanoacetate", J. Heterocyclic Chem., 33: 123-128 (1996).

Sakurai, A., et al., "The Cyclization of Ethyl Cyanoacetate and Salicylaldehyde or 3-Methoxysalicylaldehyde with Ketones by Means of Ammonium Acetate", Bull. Chem. Soc. Japan, 43: 2925-2933 (1970).

Manna, F., et al., "Anti-inflammatory, Analgesic and Antipyretic 4,6-disubstituted 3-cyano-2-aminopyridines" , Eur. J. Med. Chem., 34: 245-254 (1999).

Chem. Abstr. 92: 163866, Takeuchi, I. et al., "Syntheses of Nitrogen-containing Heterocyclic Compounds. XXXVII. On the Antimicrobial Activity and Synthesis of 2-phenylquinoline 1-oxides and phenyl-1, 8-naphthyridines", Yakugaku Zasshi, 99: 451-457 (1979).

Manna, F., et al., "Anti-inflammatory, Analgesic and Antipyretic 4, 6-disubstituted 3-cyanopyridine-2-ones and 3-cyano-2-aminopyridines" , Eur. J. Med. Chem., 27: 627-632 (1992).

Chem. Abstr. 134: 222965, Singh, G., et al., "Synthesis of Some Novel 4-imino-3, 5, 7-trisubstituted Pyrido[2,3- d]pyrimidine-2(1H)-thiones and Their Nucleosides as Potential Therapeutic Agents" , Phosphorus, Sulfur, and Silicon, 165: 107-116 (2000).

Chem. Abstr. 126: 89234, Desai, J., et al., "Synthesis and Biological Studies of Some 2-amino-3-cyano-4-aryl-6-(2'-hydroxy-3'bromo/3'-nitro-5-'methylphenyl) Pryidines" , Oriental J. Chem., 12: 209-210 (1996).

Singh, B., et al., "Novel cAMP PDE III Inhibitors: Imidazo [4,5-b]pyridin-2(3H)-ones and Thiazolo[4,5-b]pyridin-2(3H)-ones and Their Analogs", J. Med. Chem., 37: 248-254 (1994).

*Primary Examiner*—Bernard Dentz

(57) ABSTRACT

This invention is to provide a process for producing 2-amino-4,6-disubstituted nicotinic acid ester analogs and salts thereof, comprising the reaction shown by the following scheme. The ester analogs can be prepared in one pot, and in good yield by using tertiary alkyl cyanoacetate. Furthermore, the method is useful for preparing derivatives of various analogs of the ester, e.g. alkyl substituted and aryl substituted analogs.

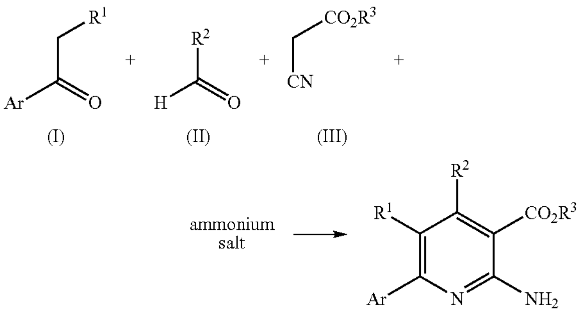

(I) (II) (III) (IV)

5 Claims, No Drawings

```
                         SEQUENCE LISTING


<160> NUMBER OF SEQ ID NOS: 1

<210> SEQ ID NO 1
<211> LENGTH: 30
<212> TYPE: PRT
<213> ORGANISM: Homo sapiens

<400> SEQUENCE: 1

Lys Ile Ser Asp Phe Gly Leu Ser Lys Ala Leu Arg Ala Asp Glu Asn
1               5                   10                  15

Tyr Tyr Lys Ala Gln Thr His Gly Lys Trp Pro Val Lys Trp
            20                  25                  30
```

PYRIDINE DERIVATIVES

This application is a continuation of Ser. No. 10/402,500 filed Mar. 28, 2003 now U.S. Pat. No. 6,984,649 which is a divisional of Ser. No. 09/956,618 filed Sep. 18, 2001 now U.S. Pat. No. 6,562,811.

TECHNICAL FIELD

The present invention relates to novel pyridine derivatives, processes for preparing them and pharmaceutical preparations containing them. The pyridine derivatives of the present invention inhibit IκB kinase β (IKK-β or IXK-beta) activity, thus inhibit nuclear factor kappa B (NF-κB) activity, and can be used for the prophylaxis and treatment of diseases associated with NF-κB activity, in particular for the treatment of inflammatory diseases.

BACKGROUND ART

Nuclear factor kappa B (NF-κB) belongs to a family of closely related homo-and hetero-dimeric transcription factor complexes composed of various combinations of the Rel/NF-κB family of polypeptides. NF-κB and related family members are involved in the regulation of more than 50 genes relating to immune and inflammatory responses ((Barnes P J, Karin M (1997) N Engl J Med 336, 1066–1071) and (Baeuerle P A, Baichwal V R (1997) Adv Immunol 65, 111–137)). In most cell types, NF-κB is present as a heterodimer comprising a 50 kDa and a 65 kDa subunit (p50/RelA). The heterodimer is sequestered in the cytoplasm in association with inhibitor of NF-□B (IκB)-family of proteins to be kept in an inactive state. IκB-family proteins mask the nuclear translocation signal of NF-κB. Upon stimulation of cells with various cytokines (e.g. TNF-α, IL-1), CD40 ligand, lipopolysaccharide (LPS), oxidants, mitogens (e.g. phorbol ester), viruses or many others. IκB proteins are phosphorylated at specific serine residues, polyubiquitinated, and then degraded through a proteasome-dependent pathway. Freed from IκB, the active NF-κB is able to translocate to the nucleus where it binds in a selective manner to preferred gene-specific enhancer sequences. Among the genes being regulated by NF-κB are many coding for pro-inflammatory mediators, cytokines, cell adhesion molecules, and acute phase proteins. Expression of several of these cytokines and mediators in turn can lead to further activation of NF-κB via autocrine and paracrine mechanisms.

Broad evidence is available that suggests a central role of NF-κB in many inflammatory disorders including airway inflammation and asthma ((Yang L et al., J Exp Med 188 (1998), 1739–1750), (Hart L A et al. Am J Respir Crit Care Med 158 (1998), 1585–1592), (Stacey M A et al., Biochem Biophys Res Commun 236 (1997), 522–526) (Barnes P and Adcock I M, Trends Pharmacol Sci 18 (1997), 46–50)).

Further, it has been shown that glucocorticoids, which are by far the most effective treatment for asthma, inhibit airway inflammation by directly interacting with and inhibiting the activity of the transcription factors NF-κB and activating peptide-1 (AP-1) ((Barnes P (1997) Pulmon Pharmacol Therapeut 10, 3–19) and (Dumont A et al. (1998) Trends Biochem Sci 23, 233–235)).

In general, inhibition of NF-κB activation results in strong anti-inflammatory effects similar or superior to those brought upon by steroids. Consequently, NF-□B inhibition should improve inflammatory symptoms typical for asthma; allergic rhinitis; atopic dermatitis; hives; conjunctivitis; vernal catarrh; rheumatoid arthritis; systemic lupus erythematosus; psoriasis; diabrotic colitis; systemic inflammatory response syndrome; sepsis; polymyositis; dermatomyositis; Polyaritis nodoa; mixed connective tissue disease; Sjoegren's syndrome; gout, and the like.

Further, several studies imply that NF-κB plays an essential role in neoplastic transformation. For example, NF-κB is associated with cell transformation in vitro and in vivo as a result of gene overexpression, amplification, rearrangement, or translocation (Mercurio, F., and Manning, A. M. (1999) Oncogene, 18:6163–6171). In certain human lymphoid tumor cells, the genes of NF-κB family members are rearranged or amplified. Its possible involvement in cancer pathology is also disclosed in Mayo, M. W., Baldwin A. S. (2000) Biochmica et Biophysica Acta 1470 M55–M62. Mayo M. W. et al., discloses the inhibition of NF-κB results in the blockage the initiation and/or progression of certain cancer, particularly colorectal cancer.

Finally, NF-κB may also be involved in the regulation of neuronal cell death. It has been shown that NF-κB becomes activated and promotes cell death in focal cerebral ischemia (Nature medicine Vol. 5 No. 5, May 1999).

Extensive research during the past years led to the identification of an IκB kinase (IKK) complex as being responsible for the signal-induced IκB phosphorylation ((Mercurio, F., and Manning, A. M. (1999) Current Opinion in Cell Biology, 11:226–232), (Mercurio, F., and Manning, A. M. (1999) Oncogene, 18:6163–6171), (Barnkett, M., and Gilmore T. D. (1999) Oncogene 18, 6910–6924), (Zandi, E., and Karin, M., (1999) 19:4547–4551), (Israel, A., (2000) trends in CELL BIOLOGY 10:129–133), and (Hatada, E. N, et al. (2000) Current Opinion in Immunology, 12:52–58)). This complex is most likely the site of integration of all of the different stimuli leading to NF-κB activation. The IKK-complex (molecular weight 700–900 kDa) is composed of various proteins including two homologous IκB kinases, called IKK-α and IKK-β, an upstream kinase, NIK which induces NF-κB, a scaffold protein called IKAP, which tethers together the three kinases, and a regulatory subunit IKK-γ, which preferentially interacts with IKK-β.

IKK-β is a 756 amino acid serine-threonine kinase showing 52% identity to and the same domain structure as IKK-α ((Mercurio F et al. (1997) Science 278, 860–866.), (Woronicz J D et al. (1997) Science 278, 866–869.), (Zandi E et al. (1997) Cell 91, 243–252.). IKK-β forms homo-dimers and hetero-dimers with IKK-α in vitro and in cells, respectively. IKK-β also interacts with IKK-γ, IKAP, NIK and IκBα. Recombinant IKK-β phosphorylates IκBα and IκBβ at specific serine residues with equal efficacy (Li J et al. (1998) J Biol Chem 273, 30736–30741.), (Zandi E, Chen Y, Karin M (1998) Science 281, 1360–1363.). IKK-β shows a higher constitutive kinase activity as compared to IKK-α. This is in agreement with data suggesting that over-expression of IKK-β activates the transcription of a NF-κB-dependent reporter gene with a higher efficacy as compared to IKK-α. IKK-β has been shown to be activated in various cell lines or fresh human cells in response to various stimuli including TNF-α, IL-1β, LPS, anti-CD3/anti-CD28 co-stimulation, protein kinase C and calcineurin, B-cell receptor/CD40 ligand stimulation, and vanadate. IKK-β is activated in fibroblast-like synoviocytes (FLS) isolated from the synovium of patients suffering from rheumatoid arthritis or osteoarthritis (Zandi E et al. (1997) Cell 91, 243–252.), (O'Connell M A et al. (1998) J Biol Chem 273, 30410–30414.), (Kempiak S J et al. (1999) J Immunol 162, 3176–3187.). Furthermore, IKK-β can be activated by the structurally related upstream kinases MEKK-1 and NIK, most likely through phosphorylation of specific serine residues within the T-loop (activation loop) and by certain protein kinase C isoforms ((Nakano H et al. (1998) Proc Natl Acad Sci USA 95, 3537–3542.), (Lee F S et al. (1998) Proc Natl Acad Sci USA 95, 9319–9324.), (Nemoto S et al. (1998) Mol Cell Biol 18, 7336–7343.), (Lallena M J et al. (1999) Mol Cell Biol 19, 2180–2188.)). A catalytically inactive mutant of IKK-β has been shown to inhibit activation of NF-κB by TNF-α, IL-1β, LPS, anti-CD3/anti-CD28 stimulation ((Mercurio F et al. (1997) Science 278, 860–866.), (Woronicz J D et al. (1997) Science 278, 866–869.)). The same effects are observed when MEKK1 or NIK are overexpressed. Additionally, IKK-β mutations in the activation loop inhibited IL-1 and TNF-α signaling (Delhase M et al. (1999) Science 284, 309–313.). Based on the experimental results described above, there is clear-cut evidence for a pivotal involvement of IKK-β in various pathways leading to NF-κB activation.

In summary, the specific inhibition of IKK-β should result in a strong anti-inflammatory and immuno-modulatory effect in vivo with the potential of improving the underlying causes of asthma and other diseases. In addition, anti-tumor and anti-ischemic effects of an IKK-β inhibitor may be expected.

Manna et al., disclose 4,6-disubstituted 3-cyano-2-aminopyridines represented by general formulas:

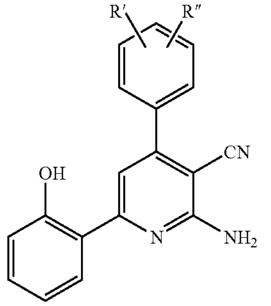

wherein (R', R") represent ($OCH_3$, $OCH_3$), (Cl, Cl), (H, Cl), (H, Br), (H, $CH_3$), (H, $OCH_3$), (H, $NO_2$), or (H, $N(CH_3)_2$), or

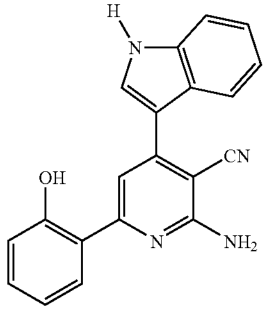

as a general anti-inflammatory, analgesic, and antipyretic agent (Eur J. Med. Chem. 34, 245–254(1999)).

Manna et al. neither disclose pyridine derivatives with aliphatic groups at position 4 of the pyridine ring, nor suggest IKK-β kinase or NF-κB inhibitory activity on the above known pyridine derivatives.

The development of a novel compound having effective anti-inflammatory actions based on a specific and selective inhibitory activity to NF-κB has been desired.

SUMMARY OF THE INVENTION

As the result of extensive studies on chemical modification of pyridine derivatives, the present inventors have found that the compound of novel chemical structure related to the present invention have unexpectedly excellent IKK-β kinase inhibitory activity. This invention is to provide the following general formula (I) and the salts thereof:

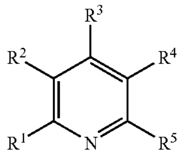

wherein —$R^1$ represents

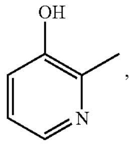, 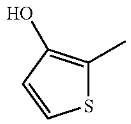 or 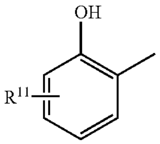

in which $R^{11}$ is hydrogen, $C_{1-6}$ alkyl, halogen, hydroxy, $C_{1-12}$ alkoxy, nitro, amino, $C_{1-6}$ alkylsulfonylamino, $C_{1-6}$ alkoxycarbonyl, $C_{1-6}$ alkylamino, di($C_{1-6}$ alkyl)amino, $C_{1-6}$ alkanoylamino, phenyl $C_{1-6}$ alkylamino, phenylsulfonylamino, or $—O—(CH_2)_n—R^{111}$, wherein n represents an integer selected from 0 to 6, and $R^{111}$ is $C_{2-6}$ alkenyl, benzoyl, diphenylmethyl, di($C_{1-6}$ alkyl) amino, $C_{1-6}$ alkanoyl, $C_{1-6}$ alkoxycarbonyl, or a 3 to 10 membered saturated or unsaturated ring having 0 to 3 heteroatoms selected from the group consisting of S, O and N as heteroatoms and is optionally substituted by $C_{1-6}$ alkyl, mono or di halogen, halogen substituted $C_{1-6}$ alkyl, nitro, ciano, $C_{1-6}$ alkoxycarbonyl, phenyl, hydroxy, amino, $C_{1-6}$ alkylamino, di($C_{1-6}$ alkyl)amino, $C_{1-6}$ alkanoylamino, $C_{1-6}$ alkoxy, or carbamoyl;

$R^2$ represents hydrogen or halogen;

$R^3$ represents hydrogen or 1,2,3,6-Tetrahydro-pyridine, $—CR^{31}R^{32}R^{33}$, wherein $R^{31}$ is hydrogen or $C_{1-6}$ alkyl, $R^{32}$ is hydrogen, α-aminobenzyl, $C_{1-6}$ alkyl optionally substituted by one or two substituents selected from the group consisting of hydroxy, amino, amino substituted phenyl, phenyl, halogen substituted phenyl, and $C_{1-6}$ alkoxy substituted phenyl, or a 5 to 8 membered saturated ring having 0 to 3 atoms selected from the group consisting of S, O and N as heteroatoms and optionally substituted by $C_{1-6}$ alkyl, and $R^{33}$ is hydrogen, amino, $C_{1-6}$ alkoxycarbonylamino, $C_{2-6}$ alkenyloxycarbonylamino, piperidino-$C_{1-6}$ alkylcarbonylamino, piperidinyl-$C_{1-6}$ alkylcarbonylamino, or $R^{32}$ and $R^{33}$ may form, together with the adjacent carbon atom, a 5 to 8 membered saturated ring having 0 to 3 heteroatoms selected from the group consisting of N, O and S as heteroatoms, which ring is optionally substituted by phenyl-$C_{1-6}$ alkyl, $C_{1-6}$ alkoxy substituted phenyl-$C_{1-6}$ alkyl, $C_{1-6}$ alkyl, amino, ciano, hydroxy, carbamoyl, carboxy, $C_{1-6}$ alkylamino, $C_{1-6}$ alkoxycarbonyl, di($C_{1-6}$ alkyl)amino, benzylamino, $C_{1-6}$ alkylsulfonyl, piperidino $C_{1-6}$ alkyl carbonyl, or optionally fused by benzene;

or $—NR^{34}R^{35}$, wherein $R^{34}$ is hydrogen or $C_{1-6}$ alkyl and $R^{35}$ is hydrogen, a 5 to 8 membered saturated ring having 0 to 3 heteroatoms selected from the group consisting of N, O and S as heteroatoms, or $—(CH_2)_m—NR^{351}R^{352}$ (m represents any of integers from 1 to 6)

wherein $R^{351}$ represents hydrogen, $C_{1-6}$ alkyl, $R^{352}$ represents hydrogen, $C_{1-6}$ alkyl, $C_{1-6}$ alkanoyl, $C_{1-6}$ alkyl substituted phenyl, benzoyl, $C_{1-6}$ alkanoyl, phenylaminocarbonyl, phenylsulfonyl, or $R^{34}$ and $R^{35}$ may form, together with the adjacent N atom, a 5 to 8 membered saturated heterocyclic ring, and said ring may optionally contain NH, S or O atom other than the adjacent N atom and optionally substituted by carbamoyl, amino, or $C_{1-6}$ alkyl;

$R^4$ represents hydroxycarbonyl, $C_{1-6}$ alkanoyl, carbamoyl, nitro, cyano, carboxyl, $C_{1-6}$ alkoxycarbonyl, $C_{1-6}$ alkylcarbamoyl, $C_{1-6}$ alkylamino, 5 to 10 membered heteroaryl (hydroxy)methyl, 5 to 10 membered heteroaryl-$C_{1-6}$ alkyl, or methyl substituted by hydroxy and a 5 to 7 membered saturated cyclic ring, $C_{1-6}$ alkyl optionally substituted by one selected from the group consisting of hydroxy, $C_{1-6}$ alkoxy, $C_{1-6}$ alkylsulfonylamino, $C_{1-6}$ alkylcarbonylamino, $C_{5-10}$ aryl, $C_{5-10}$ arylsulfonyl, $C_{5-10}$ arylsulfanyl, $C_{5-10}$ aryloxy, imidazolyl, or dioxo substituted pyrolidino-oxy, $—(CH_2)_pNHCOR^{41}$, $—(CH_2)_pNHC(=S)R^{41}$ wherein p represents any of integer from 1 to 6 and $R^{41}$ represents $C_{1-6}$ alkoxy, amino, phenylamino, $C_{1-6}$ alkyl, $C_{1-6}$ alkylamino, di($C_{1-6}$ alkyl)amino, $C_{3-10}$ cycloalkylamino, $R^3$ and $R^4$ may form, together with the carbon atoms in the pyridine ring, 4 to 10 membered monocycloalkyl or bicycloalkyl optionally interrupted by NH and optionally substituted by benzyl, =NH, or =O;

$R^5$ represents $NR^{51}R^{52}$, wherein $R^{51}$ is hydrogen, $C_{1-6}$ alkyl, $R^{52}$ is hydrogen, $C_{1-6}$ alkyl, phenyl, benzyl, $C_{1-6}$ alkanoyl, or NR51 R52 may form saturated 5–6 membered ring optionally contain NH or O as other heteroatom than the adjacent N atom, or $R^4$ and $R^5$ may form, $—R^{40}—CO—NH—$, $—R^{40}—SO_2—NH—$, $—R^{40}—C(=S)—NH—$ $—R^{40}—CH_2—NH—$, wherein said $—R^{40}—$ represents $—CHR^{401}—O—$, $—CH_2—N\ R^{401}—$, $—CO—NR^{401}—$, $—CH_2—CHR^{401}—$, $—CH=CR^{401}—$, (in which $R^{401}$ is $C_{1-6}$ alkanoyl, $C_{1-6}$ alkyl, phenyl, $C_{1-6}$ alkylsulfonyl, $C_{3-8}$ cycloalkylaminocarbonyl, hydrogen, halogen, nitro, amino, ciano, benzoylamino, phenylsulfonyl, carbamoyl, hydroxycarbonyl, $C_{1-6}$ alkoxycarbonyl, $C_{1-12}$ alkylaminocarbonyl, halogen substituted $C_{1-6}$ alkylaminocarbonyl, $C_{1-6}$ alkanoylamino, $C_{1-6}$ alkylamino, di($C_{1-6}$ alkyl)aminocarbonyl, di($C_{1-6}$ alkyl)amino$C_{1-6}$ alkylaminocarbonyl, hydroindenylaminocarbonyl, diphenylmethylaminocarbonyl, pyrrolidinocarbonyl, $C_{1-6}$ alkoxy $C_{1-6}$ alkyl amino carbonyl, morpholinocarbonyl, piperazinocarbonyl, phenyl$C_{1-6}$alkylaminocarbonyl, hydroxycarbonyl$_{C1-6}$alkyl-aminocarbonyl, $C_{3-8}$ cycloalkylaminocarbonyl, $C_{3-8}$ cycloalkyl$C_{1-6}$alkylamino-carbonyl, hydroxy-$C_{1-6}$alkylaminocarbonyl, carboxyethylaminocarbonyl, $C_{1-6}$alkyl-sulfonylaminocarbonyl)

$—CR^{41}=N—NH—$ ($R^{41}$ is hydrogen, amino, or $C_{1-6}$alkanoylamino), $—C^{42}=N—C=N—$ ($R^{42}$ is hydrogen or amino).

The compounds of the present invention surprisingly show excellent IKK-β kinase inhibitory activity and cytokine inhibitory activity. They are, therefore suitable especially as NF-κB inhibitors and in particular for the production of medicament or medical composition, which may be useful to treat NF-κB dependent diseases.

More specifically, since the pyridine derivatives of the present invention inhibit IKK-β kinase activity, they are useful for treatment and prophylaxis of diseases involving NF-κB activity as follows: inflammatory symptoms including asthma; allergic rhinitis; atopic dermatitis; hives; conjunctivitis; vernal catarrh; chronic arthrorheumatism; systemic lupus erythematosus; psoriasis; diabrotic colitis; systemic inflammatory response syndrome (SIRS); sepsis; polymyositis; dermatomyositis (DM); Polyaritis nodoa (PN); mixed connective tissue disease (MCTD); Sjoegren's syndrome; gout; and the like.

The compounds of the present invention are also useful for treatment and prophylaxis of diseases like ischemia and tumor, since the diseases also relate to IKK-β kinase and NF-κB activity.

Preferred compounds of formula (I) are those wherein:

$—R^1$ represents

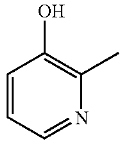, 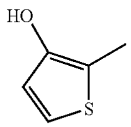 or 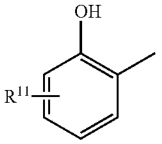

in which $R^{11}$ is hydrogen, $C_{1-6}$ alkyl, halogen, hydroxy, $C_{1-12}$ alkoxy, amino, $C_{1-6}$ alkanoylamino, phenyl $C_{1-6}$ alkylamino, phenylsulfonylamino, or $—O—(CH_2)_n—R^{111}$, wherein n represents an integer selected from 1 to 6, and $R^{111}$ is $C_{2-6}$ alkenyl, benzoyl, diphenylmethyl, di($C_{1-6}$ alkyl) amino, $C_{1-6}$ alkanoyl, $C_{1-6}$ alkoxycarbonyl, or a 3 to 10 membered saturated or unsaturated ring having 0 to 3 heteroatoms selected from the group consisting of S, O and N as heteroatoms and is optionally substituted by $C_{1-6}$ alkyl, mono or di halogen, halogen substituted $C_{1-6}$ alkyl, nitro, ciano, $C_{1-6}$ alkoxycarbonyl, phenyl;

$R^2$ represents hydrogen;

$R^3$ represents hydrogen, 1,2,3,6-tetrahydro-pyridine $—CR^{31}R^{32}R^{33}$, wherein $R^{31}$ is hydrogen or $C_{1-6}$ alkyl, $R^{32}$ is hydrogen, α-aminobenzyl, $C_{1-6}$ alkyl optionally substituted by one or two substituents selected from the group consisting of hydroxy, amino, amino substituted phenyl, phenyl, halogen substituted phenyl, and $C_{1-6}$ alkoxysubstituted phenyl, or a 5 to 8 membered saturated ring having 0 to 3 atoms selected from the group consisting of S, O and N as heteroatoms and optionally substituted by $C_{1-6}$ alkyl, and $R^{33}$ is hydrogen, amino, $C_{1-6}$ alkoxycarbonylamino, $C_{2-6}$ alkenyloxycarbonylamino, piperidino-$C_{1-6}$ alkylcarbonylamino, or $R^{32}$ and $R^{33}$ may form, together with the adjacent carbon atom, a 5 to 8 membered saturated ring having 0 to 3 heteroatoms selected from the group consisting of N, O and S as heteroatoms, which ring is optionally substituted by phenyl-$C_{1-6}$ alkyl, $C_{1-6}$ alkoxy substituted phenyl-$C_{1-6}$ alkyl, $C_{1-6}$ alkyl, amino, carboxy, $C_{1-6}$ alkylamino, $C_{1-6}$ alkoxycarbonyl, di($C_{1-6}$ alkyl)amino, benzylamino, $C_{1-6}$ alkylsulfonyl, piperidino $C_{1-6}$ alkyl carbonyl, or optionally fused by benzene;

or $—NR^{34}R^{35}$, wherein $R^{34}$ is hydrogen and $R^{35}$ is hydrogen, a 5 to 8 membered saturated ring having 0 to 3 heteroatoms selected from the group consisting of N, O and S as heteroatoms, or $—(CH_2)_m—NR^{351}R^{352}$(m represents any of integers from 1 to 6)

wherein $R^{351}$ represents hydrogen, $C_{1-6}$ alkyl, $R^{352}$ represents hydrogen, $C_{1-6}$ alkyl, $C_{1-6}$ alkanoyl, $C_{1-6}$ alkylsubstituted phenyl, benzoyl, $C_{1-6}$ alkanoyl, phenylaminocarbonyl, phenylsulfonyl, or $R^{34}$ and $R^{35}$ may form, together with the adjacent N atom, a 5 to 8 membered saturated heterocyclic ring, and said ring may optionally contain NH, S or O atom other than the adjacent N atom and optionally substituted by carbamoyl, amino, or $C_{1-6}$ alkyl;

$R^4$ represents hydroxycarbonyl, $C_{1-6}$ alkanoyl, carbamoyl, cyano, carboxyl, $C_{1-6}$ alkoxycarbonyl, $C_{1-6}$ alkylcarbamoyl, $C_{1-6}$ alkylamino, 5 to 10 membered heteroaryl(hydroxy) methyl, 5 to 10 membered heteroaryl-$C_{1-6}$ alkyl, or methyl substituted by hydroxy and a 5 to 7 membered saturated cyclic ring, $C_{1-6}$ alkyl optionally substituted by one selected from the group consisting of hydroxy, $C_{1-6}$ alkoxy, $C_{1-6}$ alkylsulfonylamino, $C_{1-6}$ alkylcarbonylamino, $C_{5-10}$ aryl, $C_{5-10}$ arylsulfanyl, $C_{5-10}$ arylsulfenyl, $C_{5-10}$ aryloxy, imidazolyl, or dioxo substituted pyrolidino-oxy, $—(CH_2)_pNHCOR^{41}$, $—(CH_2)_pNHC(=S)R^{41}$ wherein p represents any of integer from 1 to 6 and $R^{41}$ represents $C_{1-6}$ alkoxy, amino, phenylamino, $C_{1-6}$ alkyl, $C_{1-6}$ alkylamino, di($C_{1-6}$ alkyl)amino, $C_{3-10}$ cycloalkylamino, $R^3$ and $R^4$ may form, together with the carbon atoms in the pyridine ring, 4 to 10 membered monocycloalkyl or bicycloalkyl optionally interrupted by NH and optionally substituted by benzyl, =NH, or =O;

$R^5$ represents $NR^{51}R^{52}$, wherein $R^{51}$ is hydrogen, $C_{1-6}$ alkyl, $R^{52}$ is hydrogen, $C_{1-6}$ alkyl, phenyl, benzyl, $C_{1-6}$ alkanoyl, or $NR^{51}$ $R^{52}$ may form piperidino, or $R^4$ and $R^5$ may form, $—R^{40}—CO—NH—$, $—R^{40}—SO_2—NH—$, $—R^{40}—C(=S)—NH—$ or $—R^{40}—CH_2—NH—$, wherein said $—R^{40}—$ represents $—CHR^{401}—O—$, $—CH_2—N\ R^{401}—$, $—CO—NR^{401}—$, (in which $R^{401}$ is hydrogen, $C_{1-6}$ alkanoyl, $C_{1-6}$ alkoxycarbonyl, $C_{1-6}$ alkyl, phenyl, $C_{1-6}$ alkylsulfonyl, $C_{3-8}$ cycloalkylaminocarbonyl, $C_{1-6}$ alkylaminocarbonyl, carbamoyl, di($C_{1-6}$ alkyl)aminocarbonyl), $—CH_2—CHR^{402}—$, $—CH{=}CR^{402}—$, (in which $R^{402}$ is hydrogen, halogen, nitro, amino, ciano, benzoylamino, phenylsulfonyl, carbamoyl, hydroxycarbonyl, $C_{1-6}$ alkoxycarbonyl, $C_{1-12}$ alkylaminocarbonyl, halogen substituted $C_{1-6}$ alkylaminocarbonyl, $C_{1-6}$ alkanoylamino, $C_{1-6}$ alkylamino, di($C_{1-6}$ alkyl)aminocarbonyl, di($C_{1-6}$ alkyl) amino$C_{1-6}$ alkylaminocarbonyl, hydroindenylaminocarbonyl, diphenylmethylaminocarbonyl, pyrrolidinocarbonyl, $C_{1-6}$ alkoxy $C_{1-6}$ alkyl amino carbonyl, morpholinocarbonyl, piperazinocarbonyl, phenyl$C_{1-6}$alkylaminocarbonyl, $C_{3-8}$ cycloalkylaminocarbonyl, hydroxycarbonyl$C_{1-6}$alkylaminocarbonyl, $C_{3-8}$ cycloalkyl$C_{1-6}$alkylaminocarbonyl, hydroxy$C_{1-6}$alkyl-aminocarbonyl, carboxyethylaminocarbonyl, methylsulfonylaminocarbonyl,)

$—CR^{41}{=}N—NH—$ ($R^{41}$ is hydroxy, amino, $C_{1-6}$alkanoylamino) or $—CR^{42}{=}N—C{=}N—$ ($R^{42}$ is amino)

or a salt thereof.

More preferred compound of formula (I) are those wherein:

$—R^1$ represents

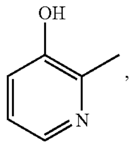
, or
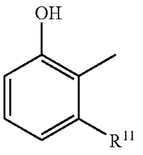

in which $R^{11}$ is hydrogen, $C_{1-12}$ alkoxy, or $—O—(CH_2)_n—R^{111}$, wherein n represents an integer selected from 1 to 6, and $R^{111}$ is phenyl, $C_{3-8}$ cycloalkyl;

$R^2$ represents hydrogen;

$R^3$ represents 1,2,3,6-tetrahydro-pyridine, $—CR^{31}R^{32}R^{33}$, wherein $R^{31}$ is hydrogen, and $R^{32}$ and $R^{33}$ form, together with the adjacent carbon atom, a 5 to 8 membered saturated ring interrupted by NH, which ring is optionally substituted by phenyl-$C_{1-6}$ alkyl, $C_{1-6}$ alkoxy substituted phenyl-$C_{1-6}$ alkyl, $C_{1-6}$ alkyl, amino, carboxy, $C_{1-6}$ alkylamino, $C_{1-6}$ alkoxycarbonyl, di($C_{1-6}$ alkyl)amino, benzylamino, $C_{1-6}$ alkylsulfonyl, piperidino $C_{1-6}$ alkyl carbonyl, or optionally fused by benzene;

or $—NR^{34}R^{35}$, wherein $R^{34}$ is hydrogen and $R^{35}$ is $—(CH_2)_m—NR^{351}R^{352}$(m represents any of integers from 1 to 6)

wherein $R^{351}$ represents hydrogen, $C_{1-6}$ alkyl, $R^{352}$ represents hydrogen, $C_{1-6}$ alkyl, $C_{1-6}$ alkanoyl, $C_{1-6}$ alkylsubstituted phenyl, benzoyl, $C_{1-6}$ alkanoyl, phenylaminocarbonyl, phenylsulfonyl; and $R^4$ represents cyano, $C_{1-6}$ alkyl optionally substituted by hydroxy or $C_{1-6}$ alkoxy, or $—(CH_2)_pNHCOR^{41}$, $—(CH_2)_pNHC(=S)R^{41}$ wherein p represents any of integer from 1 to 6 and $R^{41}$ represents $C_{1-6}$ alkoxy, amino, phenylamino, $C_{1-6}$ alkyl, $C_{1-6}$ alkylamino, di($C_{1-6}$ alkyl)amino, $C_{3-10}$ cycloalkylamino;

$R^5$ represents amino, or $R^4$ and $R^5$ may form, $—R^{40}—CO—NH—$, $—R^{40}—SO_2—NH—$, $—R^{40}—C(=S)—NH—$ or $—R^{40}—CH_2—NH—$, wherein said $—R^{40}—$ represents $—CHR^{401}—O—$, $—CH_2—N\ R^{401}—$, $—CO—NR^{401}—$, (in which $R^{401}$ is hydrogen, $C_{1-6}$ alkanoyl, $C_{1-6}$ alkoxycarbonyl, $C_{1-6}$ alkyl, phenyl, $C_{1-6}$ alkylsulfonyl, $C_{3-8}$ cycloalkylaminocarbonyl, $C_{1-6}$ alkylaminocarbonyl, carbamoyl, di($C_{1-6}$ alkyl)aminocarbonyl), $—CH_2—CHR^{402}—$, $—CH=CR^{402}—$, (in which $R^{402}$ is hydrogen, halogen, nitro, amino, ciano, benzoylamino, phenylsulfonyl, carbamoyl, hydroxy-carbonyl, $C_{1-6}$ alkoxycarbonyl, $C_{1-12}$ alkylaminocarbonyl, halogen substituted $C_{1-6}$ alkylaminocarbonyl, $C_{1-6}$ alkanoylamino, $C_{1-6}$ alkylamino, di($C_{1-6}$ alkyl)amino-carbonyl, di($C_{1-6}$ alkyl)amino$C_{1-6}$ alkylaminocarbonyl, hydroindenylaminocarbonyl, diphenylmethylaminocarbonyl, pyrrolidinocarbonyl, $C_{1-6}$ alkoxy $C_{1-6}$ alkyl amino carbonyl, morpholinocarbonyl, piperazinocarbonyl, phenyl$C_{1-6}$alkylaminocarbonyl, $C_{3-8}$ cycloalkylaminocarbonyl, hydroxycarbonyl$C_{1-6}$alkylaminocarbonyl, $C_{3-8}$ cycloalkyl$C_{1-6}$alkylaminocarbonyl, hydroxy$C_{1-6}$alkylaminocarbonyl, carboxyethylamino-carbonyl, methylsulfonylaminocarbonyl,)

$—CR^{41}=N—NH—$ ($R^{41}$ is hydroxy, amino, $C_{1-6}$alkanoylamino) or $—CR^{42}=N—C=N—$ ($R^{42}$ is amino)

or a salt thereof.

The preferable compounds of the present invention are as follows or the salt thereof:

7-(2-hydroxyphenyl)-5-(3-piperidinyl)-1,4-dihydro-2H-pyrido[2,3-d][1,3]oxazin-2-one;

2-amino-6-[2-(benzyloxy)-6-hydroxyphenyl]-4-(3-piperidinyl)nicotinonitrile;

2-amino-6-(2-hydroxy-6-propoxyphenyl)-4-(3-piperidinyl)nicotinonitrile;

2-[6-amino-5-(hydroxymethyl)-4-(3-piperidinyl)-2-pyridinyl]-3-(benzyloxy)phenol;

7-[2-(benzyloxy)-6-hydroxyphenyl]-5-(3-piperidinyl)-1,4-dihydro-2H-pyrido[2,3d][1,3]oxazin-2-one;

2-amino-6-[2-(cyclopropylmethoxy)-6-hydroxyphenyl]-4-(3-piperidinyl)nicotino-nitrile trifluoroacetate;

7-(2-hydroxyphenyl)-5-(3-piperidinyl)-3,4-dihydro-1,8-naphthyridin-2(1H)-one;

2-amino-6-[2-(cyclobutylmethoxy)-6-hydroxyphenyl]-4-(3-piperidinyl)nicotino-nitrile;

2-[6-amino-5-(hydroxymethyl)-4-(3-piperidinyl)-2-pyridinyl]-3-propoxyphenol;

7-(2-hydroxy-6-propoxyphenyl)-5-(3-piperidinyl)-1,4-dihydro-2H-pyrido[2,3d][1,3]-oxazin-2-one;

ethyl 7-(2-hydroxy-6-propoxyphenyl)-2-oxo-5-(3-piperidinyl)-1,2,3,4-tetrahydro-1,8-naphthyridine-3-carboxylate;

7-(2-hydroxy-6-propoxyphenyl)-5-(3-piperidinyl)-3,4-dihydro-1,8-naphthyridin-2(1H)-one;

2-[6-amino-5-(hydroxymethyl)-4-(3-piperidinyl)-2-pyridinyl]-3-(cyclopropyl-methoxy)phenol;

2-[6-amino-5-(hydroxymethyl)-4-(4-piperidinyl)-2-pyridinyl]-3-(cyclopropyl-methoxy)phenol;

7-[2-(cyclopropylmethoxy)-6-hydroxyphenyl]-5-(3-piperidinyl)-3,4-dihydro-1,8-naphthyridin-2(1H)-one;

ethyl 7-[2-(cyclopropylmethoxy)-6-hydroxyphenyl]-2-oxo-5-(3-piperidinyl)-1,2,3,4-tetrahydro-1,8-naphthyridine-3-carboxylate;

7-[2-(cyclopropylmethoxy)-6-hydroxyphenyl]-5-(4-piperidinyl)-1,4-dihydro-2H-pyrido[2,3-d][1,3]oxazin-2-one;

6'-amino-5'-(hydroxymethyl)-4'-(3-piperidinyl)-2,2'-bipyridin-3-ol;

7-[2-(cyclopropylmethoxy)-6-hydroxyphenyl]-5-(4-piperidinyl)-3,4-dihydro-1,8-naphthyridin-2(1H)-one;

7-[2-(cyclopropylmethoxy)-6-hydroxyphenyl]-3-fluoro-5-(3-piperidinyl)-1,8-naphthyridin-2(1H)-one;

7-(2-hydroxy-6-propoxyphenyl)-5-(4-piperidinyl)-1,4-dihydro-2H-pyrido[2,3-d][1,3]oxazin-2-one;

7-[2-(cyclopropylmethoxy)-6-hydroxyphenyl]-5-(3-piperidinyl)-1,4-dihydro-2H-pyrido[2,3-d][1,3]oxazin-2-one;

3-(cyclopropylmethoxy)-2-[5-(3-piperidinyl)-1,4-dihydro-2H-pyrido[2,3-d][1,3]oxazin-7-yl]phenol;

2-[6-amino-5-(hydroxymethyl)-4-(3-piperidinyl)-2-pyridinyl]-3-(neopentyl-oxy)phenol;

2-[6'-amino-5'-(hydroxymethyl)-1,2,5,6-tetrahydro-3,4'-bipyridin-2'-yl]phenol;

7-[2-(cyclopropylmethoxy)-6-hydroxyphenyl]-5-(3-piperidinyl)-1,8-naphthyridin-2(1H)-one;

N-{[2-amino-6-[2-(cyclopropylmethoxy)-6-hydroxyphenyl]-4-(3-piperidinyl)-3-pyridinyl]methyl}acetamide;

7-[2-(cyclopropylmethoxy)-6-hydroxyphenyl]-2-oxo-5-(3-piperidinyl)-1,2-dihydro-1,8-naphthyridine-3-carboxamide;

3-acetyl-7-[2-(cyclopropylmethoxy)-6-hydroxyphenyl]-5-(3-piperidinyl)-3,4-dihydro-pyrido[2,3-d]pyrimidin-2(1H)-one;

2-amino-6-[2-(cyclopropylmethoxy)-6-hydroxyphenyl]-4-(4-piperidinyl)nicotino-nitrile;

2-amino-4-[(2-aminoethyl)amino]-6-[2-(cyclopropylmethoxy)-6-hydroxy-phenyl]nicotinonitrile;

N-{[2-amino-6-[2-(cyclopropylmethoxy)-6-hydroxyphenyl]-4-(3-piperidinyl)-3-pyridinyl]methyl}-N'-propylurea;

7-[2-(cyclopropylmethoxy)-6-hydroxyphenyl]-5-(3-piperidinyl)-3,4-dihydro-pyrido[2,3-d]pyrimidin-2(1H)-one;

ethyl [2-amino-6-[2-(cyclopropylmethoxy)-6-hydroxyphenyl]-4-(3-piperidinyl)-3-pyridinyl]methylcarbamate;

2-amino-6-{2-hydroxy-6-[(4-methylpentyl)oxy]phenyl}-4-(4-piperidinyl)nicotino-nitrile;

7-[2-(cyclopropylmethoxy)-6-hydroxyphenyl]-2-oxo-5-(3-piperidinyl)-1,2,3,4-tetrahydro-1,8-naphthyridine-3-carboxamide;

7-[2-(cyclopropylmethoxy)-6-hydroxyphenyl]-N-isopropyl-2-oxo-5-(3-piperidinyl)-1,2-dihydro-1,8-naphthyridine-3-carboxamide;

ethyl 7-[2-(cyclopropylmethoxy)-6-hydroxyphenyl]-2-oxo-5-(3-piperidinyl)-1,4-dihydropyrido[2,3-d]pyrimidine-3(2H)-carboxylate;

N-{[2-amino-6-[2-(cyclopropylmethoxy)-6-hydroxyphenyl]-4-(3-piperidinyl)-3-pyridinyl]methyl}urea;

2-amino-6-(2-hydroxy-6-propoxyphenyl)-4-(4-piperidinyl)nicotinonitrile;

N-cyclohexyl-7-[2-(cyclopropylmethoxy)-6-hydroxyphenyl]-2-oxo-5-(3-piperidinyl)-1,4-dihydropyrido[2,3-d]pyrimidine-3(2H)-carboxamide;

2-amino-6-[2-(cyclobutylmethoxy)-6-hydroxyphenyl]-4-(4-piperidinyl)nicotinonitrile;

7-[2-(cyclopropylmethoxy)-6-hydroxyphenyl]-N,N-dimethyl-2-oxo-5-(3-piperidinyl)-1,4-dihydropyrido[2,3-d]pyrimidine-3(2H)-carboxamide;

2-amino-6-[2-(cyclopropylmethoxy)-6-hydroxyphenyl]-4-(1-methyl-3-piperidinyl)nicotinonitrile;

7-[2-(cyclopropylmethoxy)-6-hydroxyphenyl]-2-oxo-5-(3-piperidinyl)-1,4-dihydro-pyrido[2,3-d]pyrimidine-3(2H)-carboxamide;

isopropyl [2-amino-6-[2-(cyclopropylmethoxy)-6-hydroxyphenyl]-4-(3-piperidinyl)-3-pyridinyl]methylcarbamate;

isopropyl 7-[2-(cyclopropylmethoxy)-6-hydroxyphenyl]-2-oxo-5-(3-piperidinyl)-1,4-dihydropyrido[2,3-d]pyrimidine-3(2H)-carboxylate;

isobutyl 7-[2-(cyclopropylmethoxy)-6-hydroxyphenyl]-2-oxo-5-(3-piperidinyl)-1,4-dihydropyrido[2,3-d]pyrimidine-3(2H)-carboxylate;

neopentyl 7-[2-(cyclopropylmethoxy)-6-hydroxyphenyl]-2-oxo-5-(3-piperidinyl)-1,4-dihydropyrido[2,3-d]pyrimidine-3(2H)-carboxylate;

neopentyl [2-amino-6-[2-(cyclopropylmethoxy)-6-hydroxyphenyl]-4-(3-piperidinyl)-3-pyridinyl]methylcarbamate;

2-amino-6-[2-(hexyloxy)-6-hydroxyphenyl]-4-(4-piperidinyl)nicotinonitrile; and

7-[2-(cyclopropylmethoxy)-6-hydroxyphenyl]-N-ethyl-2-oxo-5-(3-piperidinyl)-1,4-dihydropyrido[2,3-d]pyrimidine-3(2H)-carboxamide The compound of the formula (I) of the present invention can be, but not limited to be, prepared by combining various known methods. In some embodiments, one or more of the substituents, such as amino group, carboxyl group, and hydroxyl group of the compounds used as starting materials or intermediates are advantageously protected by a protecting group known to those skilled in the art. Examples of the protecting groups are described in "Protective Groups in Organic Synthesis (2nd Edition)" by Greene and Wuts.

The compound (I-a)

(I-a)

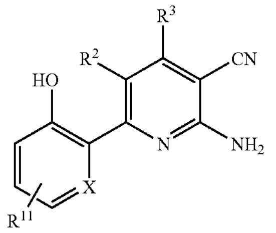

wherein X is CH or N, $R^{11}$, $R^2$, and $R^3$ are the same as defined, or a salt thereof, can be prepared, for example, by the following reaction A.

The compound of the formula (II)

(II)

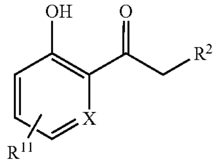

in which $R^{11}$ and $R^2$ are the same as defined above, are reacted with an aldehyde of the formula $R^3$—CHO(III), a nitrile of the formula $NCCH_2CN$ (IV), and an ammonium salt such as ammonium acetate. $R^3$ is the same as defined above. $R^{3'}$—CHO(III') can be advantageously used instead of $R^3$—CHO(III) in some instances. $R^{3'}$ can represent esterified $R^3$ by ethyl, tertiary butyl or the like: or other esters or other substituents which can be easily converted to $R^3$ by conventional methods. Hydroxyl group of the compound of the formula (II) is protected by an appropriate protecting group (e.g., benzyl, methoxybenzy, and silyl) during the reaction, and deprotected afterward. $R^{3'}$ can also be treated by acids to obtain $R^3$.

Reaction A

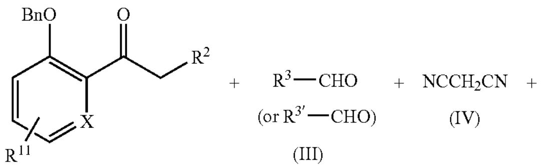

(II') (III) (IV)

-continued

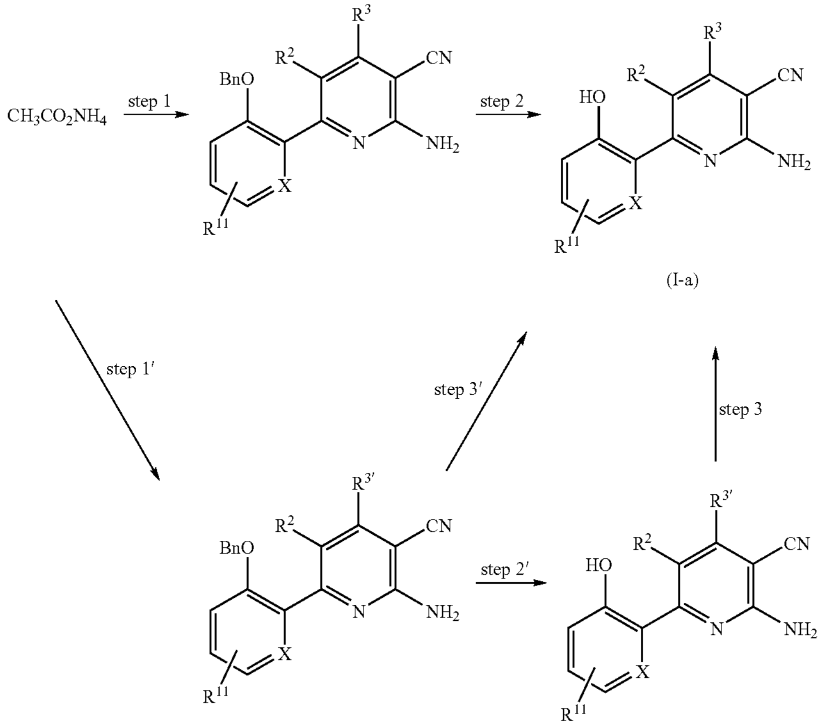

(I-a)

In the sketch above, CN at position C-3 can be replaced by carboxylates derived from tertiary alcohol, such as COOtBu with the use of $NCCH_2$—COOtBu (IV') instead of $NCCH_2CN$ (IV). In this case the following compound (I-a') can be obtained.

(I-a')

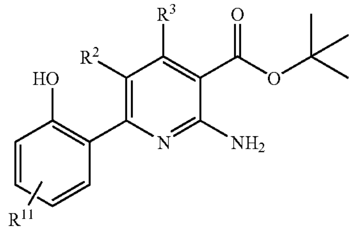

The step 1 and step 1' of the reaction A can be carried out without a solvent or in a solvent including, for instance, ethers, such as dioxane, and tetrahydrofuran; aromatic hydrocarbons such as benzene, toluene and xylene; nitrites such as acetonitrile; amides such as dimethylformamide (DMF) and dimethylacetamide; sulfoxides such as dimethyl sulfoxide, and others.

The reaction temperature can be optionally set depending on the compounds to be reacted. The reaction temperature is usually, but not limited to, about 50° C. to 200° C. The reaction may be conducted for, usually, 30 minutes to 48 hours and preferably 1 to 24 hours.

The compounds of the general formula (II), (III), (III') can be commercially available, or can be prepared by the use of known techniques.

Step 2 and step 2' of the reaction A can be carried out for example, under the hydrogen atmosphere with hydrogeneous catalysis, such as Pd—C in a solvent including, for instance, esters, such as ethyl acetate, ethers, such as dioxane, and tetrahydrofuran; aromatic hydrocarbons such as benzene, toluene and xylene; nitrites such as acetonitrile; amides such as dimethylformamide (DMF) and dimethylacetamide; sulfoxides such as dimethyl sulfoxide, and others.

The reaction temperature can be, but not limited to, about 50° C. to 200° C. The reaction may be conducted for, usually, 30 minutes to 48 hours and preferably 1 to 24 hours.

Step 3 and Step 3' of the reaction A can be any kind of conventional reaction starting from ester to obtain $R^3$, e.g., acid treatment, alkali treatment, amidation, and hydrogenation: or other reaction such as alkylation or the like to obtain $R^3$.

Alternatively, the compound (I-b)

(I-b)

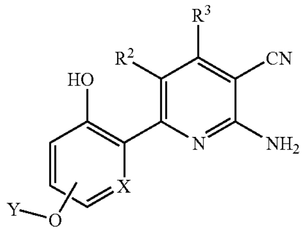

wherein X, $R^2$, and $R^3$ are the same as defined above and Y is $C_{1-12}$ alkyl or $R^{111}$—$(CH_2)_n$—, in which $R^{111}$ and n are the same as defined above, or a salt thereof can be obtained by the following reaction B.

The compound (I-b') can be also obtained in the reaction B.

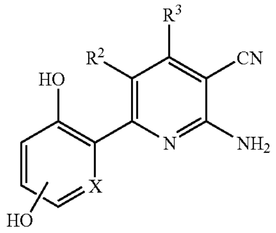
(I-b')
Reaction B
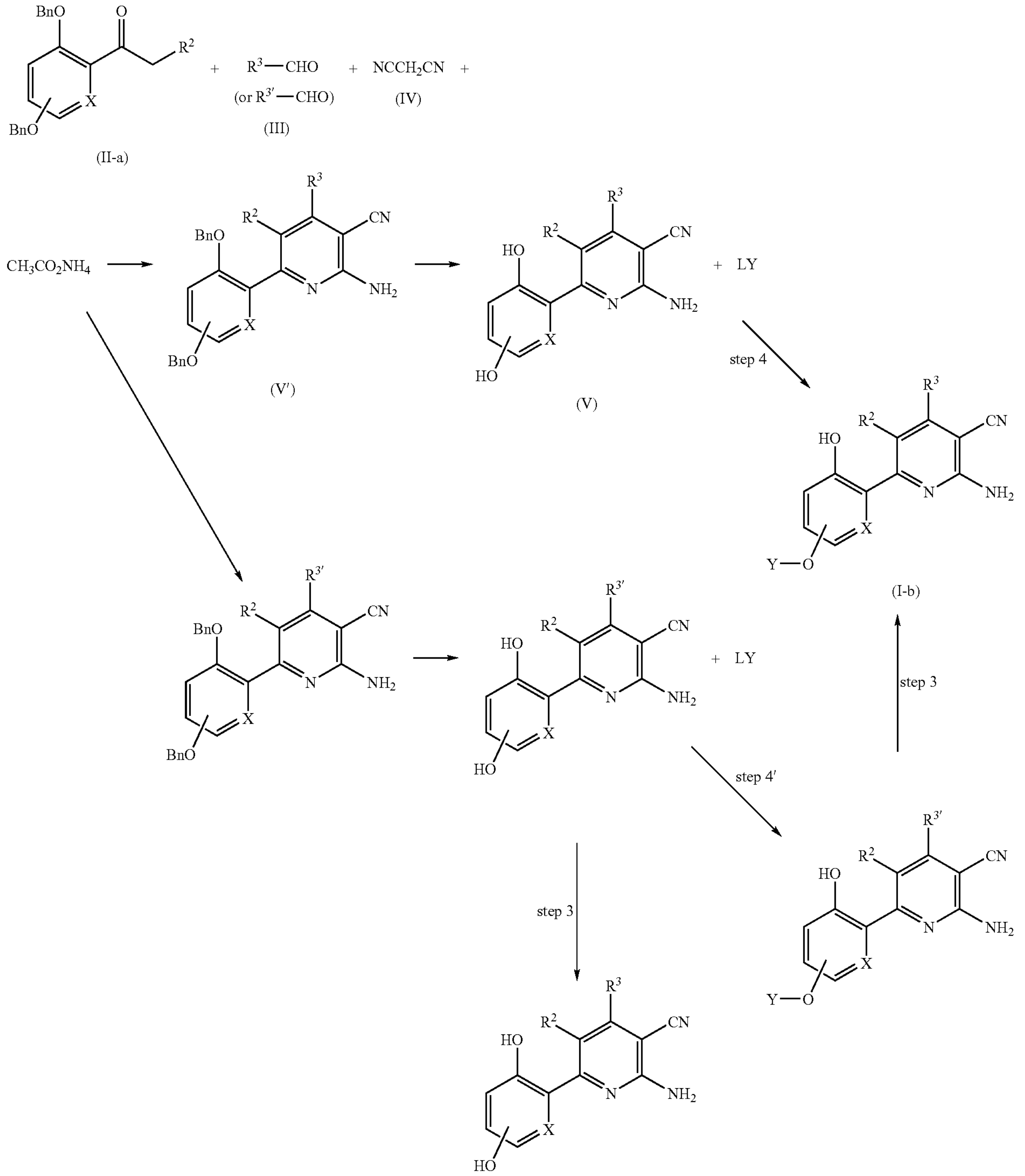
(I-b')

In reaction B, the compound of the formula (II-a) is reacted with an aldehyde (III), a nitrile (IV) and ammonium acetate under the same condition as the reaction A to obtain the compound of the formula (V'). The benzyl protecting groups in the compound of the general formula (II-a) can be replaced with any of appropriate protecting group. The protecting group is then removed after the reaction. In the step 4 of the reaction B, the compound (V) is reacted with L-Y, wherein L represents a leaving group, such as halogen atom e.g., chlorine, bromine or iodine atom; $C_6$–$C_{10}$ aryl-sulfonyloxy group e.g. benzenesulfonyloxy, polysulfonyloxy, or p-toluene-sulfonyloxy; and $C_1$–$C_4$ alkylsulfonyloxy group, e.g. methanesulfonyloxy and the like. Y represents $C_1$–$C_6$ alkyl, or —$(CH_2)_n$—$R^{111}$ (wherein $R^{111}$ is the same as defined above). The reaction with the compound (V) and L-Y can be carried out in a solvent including, for instance, alcohols such as methanol and ethanol; ethers, such as dioxane, and tetrahydrofuran (THF); nitrites such as acetonitrile; amides such as dimethylformamide (DMF) and dimethylacetamide; sulfoxides such as dimethyl sulfoxide, and others. Optionally, two or more of the solvents selected from the listed above can be mixed and used.

The reaction temperature of the reaction between compound (V) and L-Y can be optionally set depending on the compounds to be reacted. The reaction temperature is usually, but not limited to, about −10° C. to 200° C. and preferably about 10° C. to 80° C. The reaction may be carried out for, usually, 30 minutes to 48 hrs and preferably 1 to 24 hrs. The reaction can be advantageously conducted in the presence of a base. Examples of the base include an alkali metal hydride such as sodium hydride or potassium hydride; alkali metal alkoxide such as sodium methoxide or sodium ethoxide; alkali metal hydroxide such as sodium hydroxide or potassium hydroxide; carbonates such as sodium carbonate or potassium carbonate, and hydrogen carbonates such as sodium hydrogen carbonate and potassium hydrogen carbonate; organic amines such as triethylamine.

The step 3 of the reaction B is the same as that of reaction A.

Alternatively, the compound of the formula (I-c) below:

(I-c)

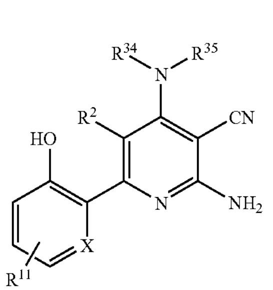

wherein X, $R^{11}$, $R^2$, $R^{34}$ and $R^{35}$ are the same as defined above, can be advantageously prepared by the following reaction C.

Reaction C:

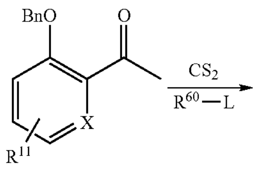

-continued

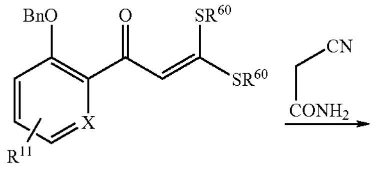

(VII)

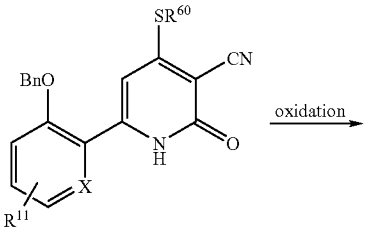

(VIII)

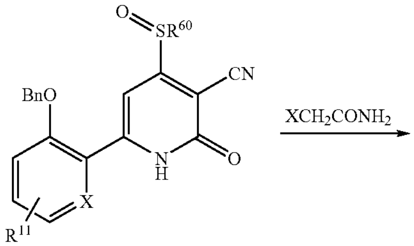

(IX)

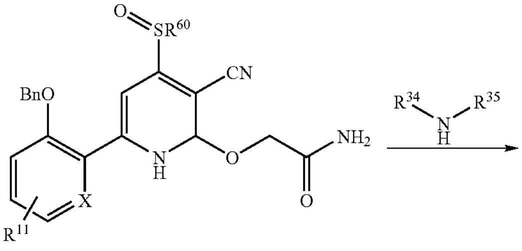

(X)

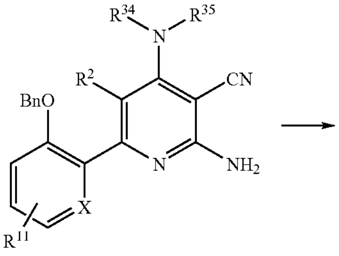

(XI)

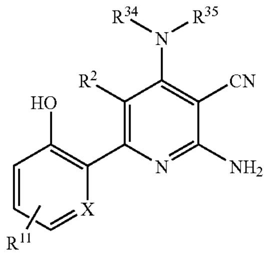

(I-c)

First, the compound of the formula (VI) may be reacted with carbon disulfide and $R^{60}$-L (wherein $R^{60}$ represents $C_{1-6}$ alkyl and L represents a leaving group as defined above)

to obtain the compound of the formula (VII). Benzyl protecting group in the compound of the formula (VI) can be replaced with any of an appropriate protecting group. This reaction may be advantageously conducted in the presence of base, such as the combination of sodium hydride and dimethyl acetamide.

The resulting compound (VII) may be reacted with cyanoacetamide in the presence of a solvent and a base. Then the compound (VIII) may be oxidized to yield the compound (IX). The compound (IX) is then reacted with halogenoacetoamide such as chloroacetamide in the presence of a base in a solvent. The resulting compound (X) is reacted with $NHR^{34}R^{35}$ ($R^{34}$ and $R^{35}$ are the same as defined above). Finally, the generated product is reacted with a base and is deprotected to obtain the compound (I-c).

The solvents used in each process of the reaction include, for instance, ethers, such as dioxane and tetrahydrofuran; aromatic hydrocarbons such as benzene, toluene and xylene; nitriles such as acetonitrile; amides such as dimethylformaide (DMF) and dimethylacetamide; sulfoxides such as dimethyl sulfoxide, and others. The above solvent may be used alone or in combination.

Examples of the base used in the reaction include an alkali metal hydride such as sodium hydride or potassium hydride; alkali metal alkoxide such as sodium methoxide or sodium ethoxide; alkali metal hydroxide such as sodium hydroxide or potassium hydroxide; carbonates such as sodium carbonate or potassium carbonate, and hydrogen carbonates such as sodium hydrogen carbonate and potassium hydrogen carbonate; organic amines such as triethylamine.

The reaction temperature can be optionally set depending on the compound to be reacted. The reaction temperature, unless otherwise stated above, is about 10° C. to 200° C. Each process of the reaction may be conducted for, usually, 30 minutes to 48 hours and preferably 1 to 24 hours.

Amino group at position 2 of the pyridine ring is, if necessary, modified according to conventional method to prepare other groups such as alkylamino, alkanoylamino, etc.

When $R^{11}$ is $C_{1-6}$ alkylsulfonylamino, $C_{1-6}$ alkylamino, di($C_{1-6}$ alkyl)amino, $C_{1-6}$ alkanoylamino, phenyl $C_{1-6}$ alkylamino, or phenylsulfonylamino, it is derived from $—NH_2$ with the use of conventional methods during the course of reaction A.

The compounds of the formulas (I-a), (I-b) and (I-c) can be further reacted to modify the substituents at position 2 and position 3 of the pyridine ring to synthesize the desired compounds in the scope of the present invention. Also, in the course of reaction A, B, and C above, the substituents at position 2 and position 3 of the pyridine ring can be modified.

The amino moiety at position 2 can be modified by the conventional methods as follows:

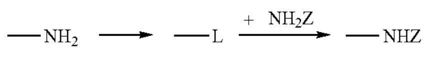

wherein L is the leaving group and the same as defined above, Z is benzyl, $C_{1-6}$ alkyl, or phenyl, or NHZ may form saturated 5–6 membered ring optionally contain NH or O as other heteroatom than the adjacent N atom.

In another embodiment, the amino moiety at position 2 can be converted to amide with the use of acid chloride.

The cyano moiety at position 3 can be converted to carbamoyl by the conventional alkaline hydrolysis.

The tertiary butoxy carbonyl at position 3 can be easily modified, by the conventional reactions of ester, to alcohol, carboxyl, and the like. Alcohol or carboxy may be further converted to another substituents by the conventional methods.

In some embodiment, the substituents of the positions 2 and 3 together form ring optionally having substituents. Any conventional method or combination of any conventional methods can be used to form the rings. The examples of forming the rings are shown below.

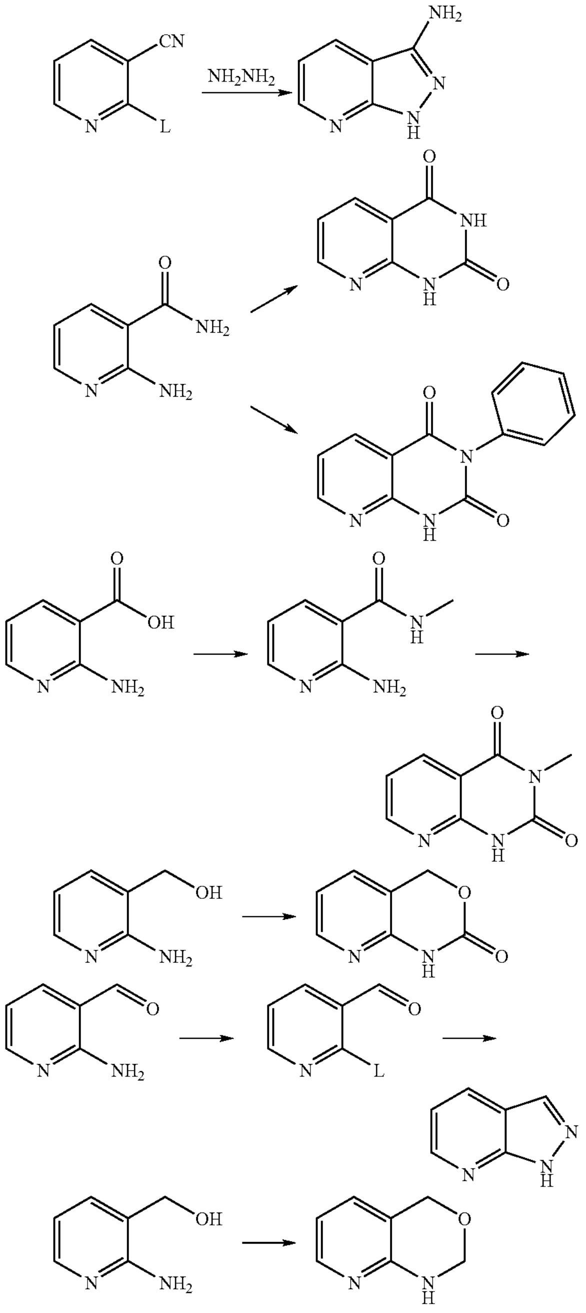

Yet, in another embodiment, the substituents of the positions 3 and 4 together form ring optionally having substituents. Any conventional method or combination of any conventional methods can be used to form the rings. The examples of forming the rings are shown below.

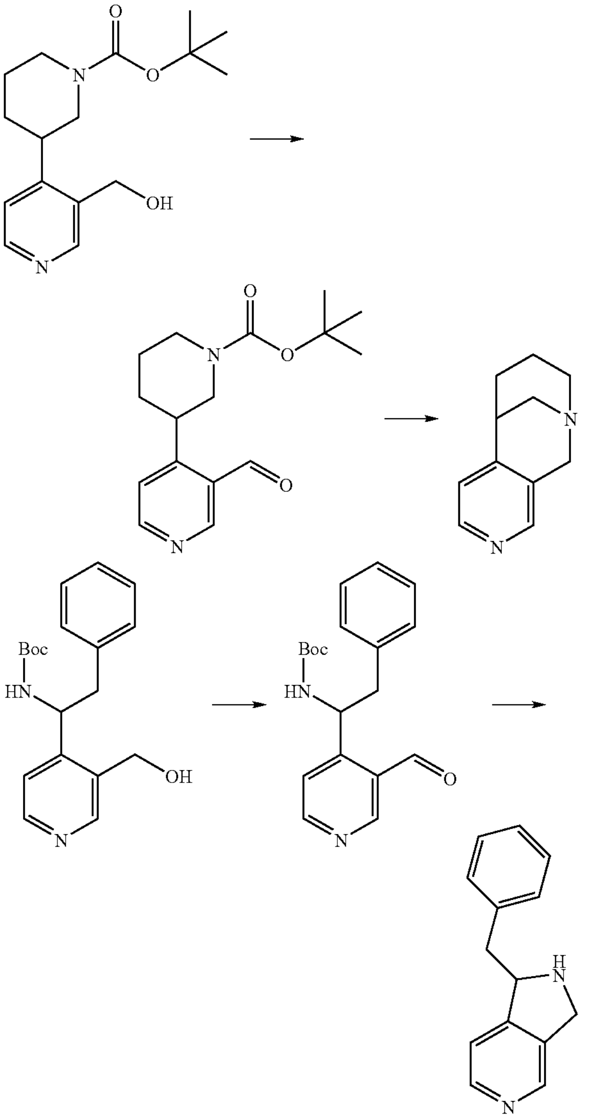

When the compound shown by the formula (I) or a salt thereof has tautomeric isomers and/or stereoisomers (e.g, geometrical isomers and conformational isomers), each of their separated isomer and mixtures are also included in the scope of the present invention.

When the compound shown by the formula (I) or a salt thereof has an asymmetric carbon in the structure, their optically active compounds and racemic mixtures are also included in the scope of the present invention.

Typical salts of the compound shown by the formula (I) include salts prepared by reaction of the compounds of the present invention with a mineral or organic acid, or an organic or inorganic base. Such salts are known as acid addition and base addition salts, respectively.

Acids to form acid addition salts include inorganic acids such as, without limitation, sulfuric acid, phosphoric acid, hydrochloric acid, hydrobromic acid, hydriodic acid and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxide, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, sodium hydroxide, potassium hydroxide, potassium carbonate, sodium carbonate, sodium bicarbonate, potassium bicarbonate, calcium hydroxide, calcium carbonate, and the like.

The compound of the present invention or a salts thereof, depending on its substituents, may be modified to form lower alkylesters or known other esters; and/or hydrates or other solvates. Those esters, hydrates, and solvates are included in the scope of the present invention.

The compound of the present invention may be administered in oral forms, such as, without limitation normal and enteric coated tablets, capsules, pills, powders, granules, elixirs, tinctures, solution, suspensions, syrups, solid and liquid aerosols and emulsions. They may also be administered in parenteral forms, such as, without limitation, intravenous, intraperitoneal, subcutaneous, intramuscular, and the like forms, well known to those of ordinary skill in the pharmaceutical arts. The compounds of the present invention can be administered in intranasal form via topical use of suitable intranasal vehicles, or via transdermal routes, using transdermal delivery systems well known to those of ordinary skilled in the art.

The dosage regimen with the use of the compounds of the present invention is selected by one of ordinary skill in the arts, in view of a variety of factors, including, without limitation, age, weight, sex, and medical condition of the recipient, the severity of the condition to be treated, the route of administration, the level of metabolic and excretory function of the recipient, the dosage form employed, the particular compound and salt thereof employed.

The compounds of the present invention are preferably formulated prior to administration together with one or more pharmaceutically acceptable excipients. Excipients are inert substances such as, without limitation carriers, diluents, flavoring agents, sweeteners, lubricants, solubilizers, suspending agents, binders, tablet disintegrating agents and encapsulating material.

Yet, another embodiment of the present invention is pharmaceutical formulation comprising a compound of the invention and one or more pharmaceutically acceptable excipients that are compatible with the other ingredients of the formulation and not deleterious to the recipient thereof. Pharmaceutical formulations of the invention are prepared by combining a therapeutically effective amount of the compounds of the invention together with one or more pharmaceutically acceptable excipients therefor. In making the compositions of the present invention, the active ingredient may be mixed with a diluent, or enclosed within a carrier, which may be in the form of a capsule, sachet, paper, or other container. The carrier may serve as a diluent, which may be solid, semi-solid, or liquid material which acts as a vehicle, or can be in the form of tablets, pills powders, lozenges, elixirs, suspensions, emulsions, solutions, syrups, aerosols, ointments, containing, for example, up to 10% by weight of the active compound, soft and hard gelatin capsules, suppositories, sterile injectable solutions and sterile packaged powders.

For oral administration, the active ingredient may be combined with an oral, and non-toxic, pharmaceutically-acceptable carrier, such as, without limitation, lactose, starch, sucrose, glucose, sodium carbonate, mannitol, sorbitol, calcium carbonate, calcium phosphate, calcium sulfate, methyl cellulose, and the like; together with, optionally, disintegrating agents, such as, without limitation, maize, starch, methyl cellulose, agar bentonite, xanthan gum, alginic acid, and the like; and optionally, binding agents, for example, without limitation, gelatin, acacia, natural sugars, beta-lactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powder forms, the carrier may be a finely divided solid, which is in admixture with the finely divided active ingredient. The active ingredient may be mixed with a carrier having binding properties in suitable proportions and compacted in the shape and size desired to produce tablets. The powders and tablets preferably contain from about 1 to about 99 weight percent of the active ingredient which is the novel composition of the present invention. Suitable solid carriers are magnesium carboxymethyl cellulose, low melting waxes, and cocoa butter.

Sterile liquid formulations include suspensions, emulsions, syrups and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in suitable oil.

The formulation may be in unit dosage form, which is a physically discrete unit containing a unit dose, suitable for administration in human or other mammals. A unit dosage form can be a capsule or tablets, or a number of capsules or tablets. A "unit dose" is a predetermined quantity of the active compound of the present invention, calculated to produce the desired therapeutic effect, in association with one or more excipients. The quantity of active ingredient in a unit dose may be varied or adjusted from about 0.1 to about 1000 milligrams or more according to the particular treatment involved.

Typical oral dosages of the present invention, when used for the indicated effects, will range from about 0.01 mg/kg/day to about 100 mg/kg/day, preferably from 0.1 mg/kg/day to 30 mg/kg/day, and most preferably from about 0.5 mg/kg/day to about 10 mg/kg/day. In the case of parenteral administration, it has generally proven advantageous to administer quantities of about 0.001 to 100 mg/kg/day, preferably from 0.01 mg/kg/day to 1 mg/kg/day. The compounds of the present invention may be administered in a single daily dose, or the total daily dose may be administered in divided doses, two, three, or more times per day. Where delivery is via transdermal forms, of course, administration is continuous.

The effect of the present compounds was examined by the following assays and pharmacological tests.

[IKK-β Kinase Inhibitory Assay]

(1) Preparation of IKK-β kinase protein.

A cDNA fragment encoding human IKK-β open reading frame was generated by PCR with the use of a pair of primers designed from the published sequence (Woronicz J D et al. (1997) Science 278, 866–869). A template was obtained from Quickclone cDNA (Clontech) using Elongase™ Amplification kit (Life Technologies). The DNA fragments generated by PCR were gel-purified and subcloned into pBluescript. The cDNA fragment cloned in pBluescript was inserted into pcDNA3.1/His C KpnI/NotI, and transferred into pVL1393 SmaI/XbaI (Pharmingen) to construct a baculovirus transfer vector. Then the vector, together with the linearized baculovirus (BaculoGold™, Pharmingen) was used to transfect Sf21 cells (Invitrogen, San Diego, Calif.). Generated recombinant baculovirus was cloned and amplified in Sf21 cells, grown in TNM-FH insect cell medium (Life Technologies, Inc.) supplemented with 10% FCS, 50 g/ml Gentamycin, 0.1% Pluronic F-68 (Life Technologies, Inc.) as suspension culture (200 ml in 1 L Erlenmeyer flask; 27° C.; 130 rpm). Sf21 cells were infected with this amplified virus with a multiplicity of infection of 5 following standard protocols (Crossen R, Gruenwald S (1997) Baculovirus Expression Vector System Instruction Manual, Pharmingen Corporation) and harvested 48 hrs later. The cells were lysed to obtain the produced chimeric protein of IKK-β kinase fused by histidine (His-tagged IKK-beta).

(2) The preparation of purified GST-IκBα fusion proteins

An expression vector containing the nucleotide sequence encoding fusion protein of GST with amino acid residues 1 to 54 of IκBα under the control of an IPTG-inducible promoter was constructed. The expression vector was introduced in *E. coli* and the transformant was cultured and lysed to obtain a GST-IκBα fusion protein. Then the resulting GST-IκBα fusion protein was purified and biotinated for kinase assay.

(3) The measurement of IKK-β kinase activity

The 96-well format kinase assay of IKK-β were performed to test the inhibitory activity of the compounds of the present invention. First, 5 μl of a test compound was put in the presence of 2.5% dimethyl sulfoxide (DMSO) in each well in a U-bottomed 96-well plate (Falcon). For control wells of background (BG) and total phosphorylation (TP), 5 μl of 2.5% DMSO was put. Recombinant IKK-β (final 0.6 μg/ml) and bio-GST-IκBα (1–54) (final 0.2 μM) were diluted in 25 μl of 2× kinase buffer β (40 mM Tris-HCl, pH 7.6, 40 mM $MgCl_2$, 40 mM β-glycerophosphate, 40 mM p-nitrophenylphosphate, 2 mM EDTA, 40 mM creatine phosphate, 2 mM DTT, 2 mM $Na_3VO_4$, 0.2 mg/ml BSA and 0.8 mM phenylmethylsulfonyl fluoride) and transferred to the 96-well plate. Bio-GST-IκBα (1–54) in 25 μl of 2× kinase buffer β without IKK-β was transferred to BG wells. Then 20 μl of 12.5 μM ATP, 62.5 μCi/ml [$\gamma$-$^{33}$P] ATP (Amersham Pharmacia Biotech) was added and the resulting mixture was incubated for 2 hrs at room temperature. The kinase reactions were terminated by the addition of 150 μl of termination buffer (100 mM EDTA, 1 mg/ml BSA, 0.2 mg $NaN_3$). One handred and fifty μl of the sample were transferred to a streptavidin-coated, white MTP (Steffens Biotechniche Analysen GmbH #08114E14.FWD) to capture the biotinylated substrates. After 1 hr of incubation, non-bound radioactivity was eliminated by washing the wells five times with 300 μl of washing buffer including 0.9% NaCl and 0.1% (w/v) Tween-20 with the use of a MW-96 plate washer (BioTec). The bound radioactivity was determined after the addition of 170 μl MicroScint-PS scintillation cocktail (Packard) using a TopCount scintillation counter.

[Syk Tyrosine Kinase Inhibitory Assay for Selectivity]

(1) Preparation of Syk protein

A cDNA fragment encoding human Syk openreading frame was cloned from total RNA of human Burkitt's lymphoma B cell lines, Raji (American Type Culture Collection), with the use of RT-PCR method. The cDNA fragment was inserted into pAcG2T (Pharmingen, San Diego, Calif.) to construct a baculovirus transfer vector. Then the vector, together with the linearized baculovirus (BaculoGold™, Pharmingen), was used to transfect Sf21 cells (Invitrogen, San Diego, Calif.).

Generated recombinant baculovirus was cloned and amplified in Sf21 cells. Sf21 cells were infected with this amplified high titer virus to produce a chimeric protein of Syk kinase fused by glutathione-S-transferase (GST).

The resulting GST-Syk was purified with the use of glutathione column (Amersham Pharmacia Biotech AB, Uppsala, Sweden) according to the manufacturer's instruction. The purity of the protein was confirmed to be more than 90% by SDS-PAGE.

(2) Synthesize of a peptide

Next, a peptide fragment of 30 residues including two tyrosine residues, KISDFGLSKALRADENYYKAQTHGKWPVKW (SEQ ID NO: 1), was synthesized by a peptide synthesizer. The N-terminal of the fragment was then biotinylated to obtain biotinylated activation loop peptide (AL).

(3) The measurement of Syk tyrosine kinase activity

All reagents were diluted with the Syk kinase assay buffer (50 mM Tris-HCl (pH 8.0), 10 mM $MgCl_2$, 0.1 mM $Na_3VO_4$, 0.1% BSA, 1 mM DTT). First, a mixture (35 μl) including 3.2 μg of GST-Syk and 0.5 μg of AL was put in each well in 96-well plates. Then 5 μl of a test compound in the presence of 2.5% dimethyl sulfoxide (DMSO) was added to each well. To this mixture was added 300 μM ATP (10 μl) to initiate the kinase reaction. The final reaction mixture (50 μl) consists of 0.65 nM GST-Syk, 3 μM AL, 30 μM ATP, a test compound, 0.25% DMSO, and a Syk kinase assay buffer.

The mixture was incubated for 1 hr at room temperature (RT), and the reaction was terminated by the addition of 120 μl of termination buffer (50 mM Tris-HCl (pH 8.0), 10 mM EDTA, 500 mM NaCl, 0.1% BSA). The mixture was transferred to streptavidin-coated plates and incubated for 30 min. at room temperature to combine biotin-AL to the plates. After washing the plates with Tris-buffered saline (TBS) (50 mM Tris-HCl (pH 8.0), 138 mM NaCl, 2.7 mM KCl) containing 0.05% Tween-20 for 3 times, 100 μl of antibody solution consisting of 50 mM Tris-HCl (pH 8.0), 138 mM NaCl, 2.7 mM KCl, 1% BSA, 60 ng/ml anti-phosphotyrosine monoclonal antibody, 4G10 (Upstate Biotechnology), which was labeled with europium by Amersham Pharmacia's kit in advance, was added and incubated at room temperature for 60 minutes. After washing, 100 μl of enhancement solution (Amersham Pharmacia Biotech) was added and then time-resolved fluorescence was measured by multi-label counter ARVO (Wallac Oy, Finland) at 340 nm for excitation and 615 nm for emission with 400 msec of delay and 400 msec of window.

[The Measurement of RANTES Production in Response to TNF-α from A549 Cells]

(1) Preparation of A549 cells

The A549 human lung epithelium cell line (ATCC #CCL-885) was maintained in Dulbecco's modified Eagle's medium (D-MEM, Nikken Biomedical Institute) supplemented with 10% FCS (Gibco), 100 U/ml penicillin, 100 μg/ml streptomycin, and 2 mM glutamine (culture medium). Forty thousand ($4\times10^4$) cells (80 μl/well) were seeded in each well of 96 well flat-bottom tissue culture plate (Falcon #3072). The plate was allowed to stand for 2 hrs, thus the cells were adhered to the bottom of each well. To the each well was added 10 μl vehicle (1% DMSO), serial dilutions of test compounds in 1% DMSO, or 5 nM Dexamethasone in 1% DMSO as a reference. The mixture (90 μl/well) was incubated for 1 hr at 37° C. After 1 hr, 1 μg/ml TNF-α (10 μl) in culture medium was added to the mixture to obtain 100 μl of reaction mixture. The reaction mixture was cultured for 24 hrs to stimulate the cells with 100 ng/ml TNF-α. Cells with vehicle without TNF-α stimulation were also prepared.

(2) Measurement of RANTES production

Then the concentration of RANTES released from the cells in the supernatants of each well was determined using a quantitative sandwich enzyme immunoassay technique. First, 2 μg/ml mouse anti-huRANTES mAb (R&D Systems, #mAb678) in PBS buffer (pH 7.4, 100 μl) was put in each well of 96-well NUNC fluoro plate (Nalge Nunc, N.Y. USA) (Final 200 ng/well) and the plate was allowed to stand for overnight at 4° C. to be coated by the antibody. Each well of the plate was then washed with 350 μl wash buffer (0.05% Tween-20, 0.85% NaCl, and 25 mM Tris/HCl pH7.4) for three times. Blocking buffer containing 1% BSA (Sigma□99% pure, 100 g), 5% sucrose (Nacalai tesque, 99% pure, 500 g), and 0.02% azide (Nacalai tesque, 100%, 500 g) were added (200 μl) to each well and then the plate was allowed to stand for 4 hours to stabilize the coated antibody. Next, 50 μl supernatants of cell culture prepared in (1) above were put in each well of the 96-well NUNC fluoro plate with coated antibody. Recombinant Human RANTES (Pepro Tech, Inc. #300-06) was used as the standard for the determination of RANTES production (linear range between 1 and 10 ng/ml). Eu-labelled mouse anti-huRANES mAb (60 ng/ml: R&D Systems, #mAb278) in PBS supplemented by 1% BSA and 0.05% Tween 20 was added (50 μl) to each well. The reaction mixtures were incubated at room temperature for 4 hrs. After washing with wash buffer (0.05% Tween-20, 0.85% NaCl, and 25 mM Tris/HCl pH7.4, 350 μl/well) for 5 times with the use of a Sera Washer (Bio-Tech, #MW-96R), the enhancement solution (DELFIA, #1244-405, 100 μl/well) was added to each well. The plate was incubated for 10 minutes at room temperature with moderate shaking. Fluorescent intensity was measured using a DELFIA fluorimeter (Wallac). Excitation was performed at 340 nm and emission was measured at 615 nm.

[The Measurement of TNF-α Production in Response to LPS from Peripheral Blood Mononuclear Cells (PBMC)]

(1) Preparation of PBMC

Human PBMC were prepared by first obtaining blood from healthy donors and isolating the cells from the blood. The isolation was done by Ficoll gradient-centrifugation method using Ficoll Pacque (Pharmacia #17-1440-02). Within three hours from donation, the isolated PBMC was used. After three times washing with PBS, PBMC were resuspended with RPMI 1640 (Nikken BioMedical Institute) supplemented with 10%

FCS (Gibco), 100 U/ml penicillin, 100 μg/ml streptomycin, and 2 mM glutamine (culture medium). The cells ($1\times10^5$ in 150 μl/well) were seeded in each well of 96 well flat-bottom tissue culture plate (Falcon #3072). To the each well was added 20 μl vehicle (1% DMSO), serial dilutions of test compounds in 1% DMSO, or 250 nM Dexamethasone in 1% DMSO as a reference. The mixture (170 μl/well) was incubated for 1 hr at 37° C. After 1 hr, 20 ng/ml LPS (30 μl) in culture medium was added to the mixture to obtain 200 μl of reaction mixture. The reaction mixture was cultured for 7 hrs to stimulate the cells with 3 ng/ml LPS. Cells with vehicle without LPS stimulation were also prepared. The supernatants of the reaction mixture were then collected.

(2) Measurement of TNF-α production

The TNF-α concentration in the supernatants was determined using a DuoSet™ ELISA Development Kit (GenzymeTechne, Minneapolis, USA) following the manufacturer's recommendations. First, 4 μg/ml of mouse anti-human TNF-α Ab in PBS buffer (100 μl) was put in each well of 96-well plate (NUNC, Maxisorp™) and the plate was allowed to stand for overnight at 4° C. to be coated with the antibody. Each well of the plate was then washed 5 times with 350 μl of wash buffer containing PBS, 0.05% Tween 20 (Nakalai tesque) using Sera Washer (Bio-Tech, #MW-96R). To each well was added 300 μl of 1% BSA (Sigma), 5% sucrose in PBS. After 2 hrs incubation at room temperature, the buffer was discarded, and 50 μl of culture medium was added. Next, 50 μl supernatant of stimulated cell culture prepared (1) above was put in each well of the 96-well plate. Recombinant human TNF-α (Genzyme Techne) was used as the standard for the determination of TNF-α production (linear range between 30 and 2,000 pg/ml). The reaction mixtures were incubated for 1 hr at room temperature. After 5 times washing, 100 μl biotinylated goat anti-human TNF-α antibody (Genzyme Techne, 300 ng/ml) in 0.1% BSA, 0.05% Tween in PBS (Reagent diluent) was added to each well, and incubated at room temperature for 1 hr. After 5 times washing, 100 μl of Streptavidin-conjugated horseradishperoxidase (Genzyme Techne, 1/100 in Reagent diluent) was added to each well. After 20 min, each well of the plate was washed 5 times with wash buffer (350 μl/well). The substrate of hourseradishperoxidase and $H_2O_2$ (TMBZ peroxidase detection kit, SUMILON #ML-1120T) were added to the mixture and the mixture was allowed to stand at room temperature. The reaction was terminated after 10 min by adding 2N $H_2SO_4$. Optical density at 450 nm was measured with the use of a microplate reader (Labosystems, Multiscan Multisoft). Quantification of TNF-α production in each sample was performed by comparison of optical densities between each sample and the standard curve.

[The Measurement of IL-2 Production in Jurkat T Cells in Response to Antibody Stimulation]

IL-2 production was measured in Jurkat T cells (E6-1 clone; ATCC # TIB-152) in response to stimulation with anti-CD3/anti-CD28 antibodies.

(1) Preparation of immobilized antibodies

First, anti-CD3 antibodies (400 ng/well Nichirei, NU-T3 4 μg/ml in 100 μl Dulbecco's PBS) were put in each well of 96-well plate (Falcon #3072) and the plate was allowed to stand for 2 hrs at room temperature to be coated with the antibody. Each well of the plate was then washed with 250 μl PBS 3 times.

(2) Preparation of Jurkat cell culture

Jurkat T cells were cultured in RPMI 1640 medium supplemented with 10% heat-inactivated fetal calf serum, 2 mM L-glutamine, 100 U/ml penicillin G, and 100 μg/ml streptomycin (culture medium). Two hundred thousand ($2\times10^5$) cells (190 μl/well) were seeded in each well of 96-well U-bottom tissue culture plates (Falcon #3077). To each well was added 10 μl vehicle (0.2% DMSO), serial dilution of compounds in 0.2% DMSO, or 25 nM cyclosporin A as a reference in 0.2% DMSO. The mixture (200 μl) was incubated for one hour at 37° C. in a humidified 5% $CO_2$ environment.

(3) Stimulation of the cell

The reaction mixture obtained in (2) (100 μl) was put in the each well of the antibody-immobilized plate prepared in (1). To this well was added anti-CD28 antibodies (Nichirei, KOLT-2, 6 μg/ml in cell culture medium, 50 μl/well) and 2.5 μg/ml goat anti-mouse kappa chain antibodies (Bethyl Laboratories, (Cat#A90-119A) 10 μg/ml in culture medium, 50 μl/well). The reaction mixture in each well was incubated for 24 hrs at 37° C. to stimulate cells with immobilized anti-CD3 antibodies (400 ng/well) and anti-CD28 antibodies (1.5 μg/ml), and then to crosslink receptors on the cells with anti-mouse kappa chain antibodies (2.5 μg/ml).

(4) Measurement of IL-2 production

The supernatants of the reaction mixture were then collected. The IL-2 concentration in the supernatants was determined using a DuoSet™ ELISA Development Kit (GenzymeTechne, Minneapolis, USA) following the manufacturer's recommendations. First, 2 μg/ml of mouse anti-huIL-2 Ab in PBS buffer (100 μl) was put in each well of 96-well plate (NUNC, Maxisorp™) and the plate was allowed to stand for overnight at 4° C. to be coated with the antibody. Each well of the plate was then washed 5 times with 350 μl of wash buffer containing PBS, 0.05% Tween 20 (Nakalai tesque) using Sera Washer (Bio-Tech, #MW-96R). To each well was added 250 μl of 1% BSA (Sigma) in PBS, 0.05% Tween 20 (dilution buffer). After 2 hrs incubation at room temperature, the buffer was discarded, and 50 μl of culture medium was added. Next, 50 μl supernatant of stimulated cell culture prepared (3) above was put in each well of the 96-well plate with coated mouse anti-huIL-2 antibody. Recombinant Human IL-2 (Genzyme Techne) was used as the standard for the determination of IL-2 production (linear range between 200 and 5,400 pg/ml). The reaction mixtures were incubated for 1 hr at room temperature. After S times washing, 100 μl biotinylated rabbit anti-huIL-2 antibody (Genzyme Techne, 1.25 μg/ml) in dilution buffer was added to each well, and incubated at room temperature for 1 hr. After 5 times washing, 100 μl of Streptavidin-conjugated horseradishperoxidase (Genzyme Techne, 1/1000 in dilution buffer) was added to each well. After 20 min, each well of the plate was washed 5 times with wash buffer (350 μl/well). Substrate and $H_2O_2$ (TMBZ peroxidase detection kit, SUMILON #ML-1120T) were added to the mixture and the mixture was allowed to stand at room temperature. The reaction was terminated after 10 min by adding 2N $H_2SO_4$. Optical density at 450 nm was measured with the use of a microplate reader (Labosystems, Multiscan Multisoft). Quantification of IL-2 production in each sample was performed by comparison of optical densities between each sample and the standard curve.

[Mouse LPS-induced TNF-α Production]

Eight weeks old BALB/c female mice were placed into two groups, a control group and a treated group. A solution containing 200 μg/mouse of LPS in 0.9% physiological salt was administered by intraperitoneal (ip) injection into the control mice. Mice in the treated group were first injected ip with compounds of the present invention 30 minutes prior to the LPS injection. Under anesthesia with pentobarbital (80 mg/kg, i.p.), blood was collected from the posterior venous cavity of the treated and control mice at 90 min post-LPS injection into 96-well plate containing 2% EDTA solution. The plasma was separated by centrifugation at 1800 rpm for 10 minutes at 4° C. and then diluted with four times volumes of phosphate buffer saline (pH 7.4) containing 1% bovine serum albumin. TNF-α concentration in the sample was determined using an ELISA kit (Pharmingen, San Diego, Calif.)

The mean TNF-α level in 5 mice from each group was determined and the percent reduction in TNF-α levels was calculated. The treated mice showed significant decrease in the level of TNF-α as compared to the control mice. The result indicates that the compounds of the present invention can restrain LPS-induced cytokine activity.

Results in vitro test and Cellular assay result (A549) are shown in Examples and tables of the Examples below. The data corresponds to the compounds as yielded by solid phase synthesis and thus to levels of purity of about 40 to 90%. For practical reasons, the compounds are grouped in four classes of activity as follows:

In vitro $IC_{50}$=A (=or <) 0.5 μM<B (=or <) 2 μM<C (=or <) 10 μM<D

Cellular $IC_{50}$=A (=or <) 1 μM<B (=or <) 10 μM<C

The compounds of the present invention also show excellent selectivity and strong activity in other cellular activity and in vivo assays.

EXAMPLES

The present invention will be described in detail below in the form of examples, but they should by no means be construed as defining the metes and bounds of the present invention.

In the examples below, all quantitative data, if not stated otherwise, relate to percentages by weight. Proton nuclear magnetic resonance (1H NMR) spectra were recorded at either 300 or 500 MHz by Bruker DRX-300

500 Bruker UltraShield™ and chemical shifts are reported in parts per million relative to tetramethylsilane (TMS). Mass spectra were obtained using electrospray (ES) ionization techniques (micromass Platform LC).

[Starting Compound 1A]

(Starting compound 1A)

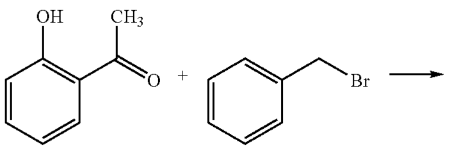

-continued

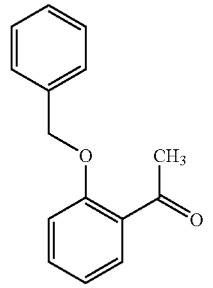

A mixture of 2'-hydroxyacetophenone (68.1 g, 0.500 mol), benzylbromide (94.1 g, 0.550 mol) and $K_2CO_3$ (103 g, 0.750 mol) in acetone (1.0 L) was heated at reflux, and the stirring was continued overnight. After cooled to room temperature, the mixture was concentrated under reduced pressure. The residue was diluted with water, and extracted with ethyl acetate. The separated organic phase was washed with brine, dried over $MgSO_4$, filtered and concentrated under reduced pressure. The crude product was purified by distillation under reduced pressure to give 1-[2-(benzyloxy)phenyl]ethanone as a colorless oil. (100 g, yield; 88%)

[Starting Compound 1B]

To a solution of 2' hydroxyacetophenone (6.79 g, 30 mmol) in ether (200 mL) was added a solution of bromine (5.00 g, 31 mmol) in ether (20 mL). After being stirred at room temperature for 30 min, the mixture was diluted with ether (100 mL), and then washed with saturated aqueous $NaHCO_3$ (100 mL) and with brine (100 mL), successively. The combined organic phase was dried over $Na_2SO_4$, filtered and concentrated under reduced pressure. The residue was washed with ether and hexane successively, and dried under reduced pressure to give 1-[2-(benzyloxy)phenyl]-2-bromoethanone. (8.42 g, yield; 92%)

(Starting compound 1B)

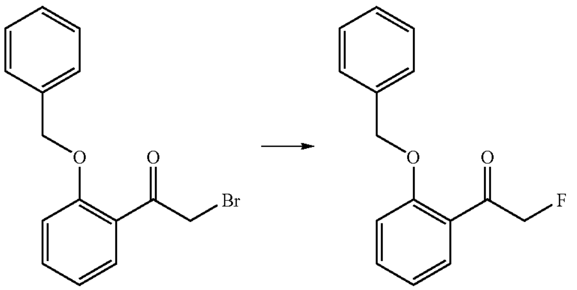

To a solution of 1-[2-(benzyloxy)phenyl]-2-bromoethanone (2.59 g, 8.5 mmol) and pyridine (1.37 mL, 17 mmol) in THF was added tetrabutylammonium hydrogen difluoride (4.78 g, 17 mmol). The reaction mixture was stirred under reflux for 22 hrs. The mixture was diluted with ether (250 mL), then washed with 1N aqueous hydrochloric acid (100 mL) and brine (100 mL), successively. The organic phase was dried over $Na_2SO_4$, filtered and concentrated under reduced pressure. The crude product was purified by column chromatography on silica gel (hexane/ethyl acetate, 4:1) to give 1-[2-(benzyloxy)phenyl]-2-fluoroethanone (688 mg, yield; 33%).

[Starting Compound 1C]

(Starting compound 1C)

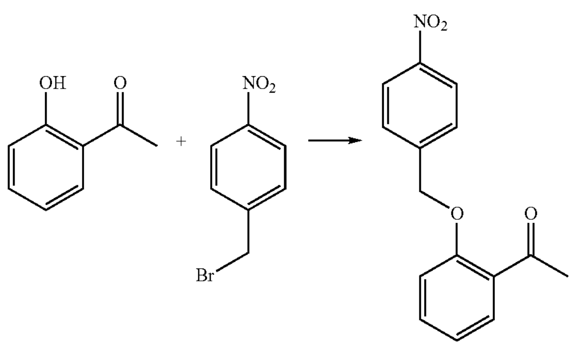

To a stirred solution of 2'-hydroxyacetophenone (5.000 g, 36.724 mmol) in acetonitrile (200 mL) was added potassium carbonate (7.613 g, 55.086 mmol). The mixture was stirred at 50 ° C. for 30 min. 4-Nitrobenzyl bromide (8.727 g, 40.396 mmol) was added to the mixture, and the stirring was continued at 50 ° C. for 12 hrs. Potassium carbonate (0.508 g, 3.672 mmol) and 4-nitrobenzyl bromide (0.793 g, 3.672 mmol) were added to the mixture and the resulting mixture was stirred at 50° C. for 12 hrs. After cooled to room temperature, the reaction mixture was concentrated under reduced pressure and diluted with ethyl acetate. The organic phase was washed with water, dried over $Na_2SO_4$, filtered, and concentrated. The resulting residue was washed with hexane to give 1-{2-[(4-nitrobenzyl)oxy]phenyl}ethanoneas a white solid. (8.900 g, yield; 89%)

[Starting Compound 1D]

In a same manner as the method to prepare starting compound 1A, except that benzylbromide was replaced with methoxybenzylchloride, methoxybenzyl-acetophenone was prepared.

(Starting compound 1D)

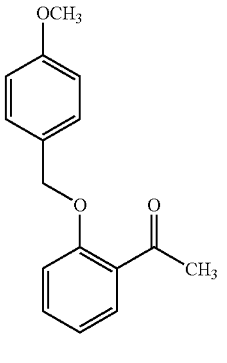

[Starting Compound 1E]

(Starting compound 1E)

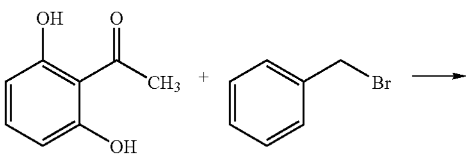

-continued

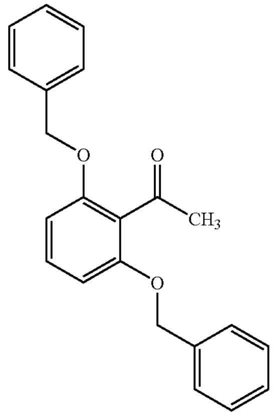

A suspension of (2',6'-dihydroxy)acetophenone (25.0 g, 164 mmol), benzyl bromide (40 mL, 337 mmol), potassium carbonate (136 g, 986 mmol) and sodium iodide (2.5 g, 16 mmol) in acetone (500 mL) was stirred at reflux overnight. The mixture was concentrated under reduced pressure, and diluted with ethyl acetate (500 mL) and water (250 mL). The separated aqueous phase was extracted with ethyl acetate (200 mL×2). The combined organic phase was washed with brine (100 mL), dried over $Na_2SO_4$, filtered and concentrated under reduced pressure. The residue was triturated with hexane, collected by filtration, washed with hexane and dried under reduced pressure to give 1-[2,6-bis(benzyloxy)phenyl]ethanone (24.9 g, yield; 46%).

[Starting Compound 1F]

A suspension of 3-hydroxypicolinonitrile (3.00 g, 25.0 mmol), which was prepared according to "Synthesis" 316 (1983) and "J. Org. Chem." 48 1375 (1983), potassium carbonate (5.40 g, 39.1 mmol) and benzyl bromide (5.10 g, 29.8 mmol) in acetone (150 mL) was stirred at room temperature for 20 hrs. The reaction mixture was filtrated and the filtrate was evaporated. The residue was purified by column chromatography on silica gel (ethyl acetate/n-hexane=1/3 to 1/2) followed by recrystallization from ethyl acetate/n-hexane=1/4 to give 3-benzyloxypicolinonitrile as a colorless solid (4.354 g, yield; 83%).

(Starting compound 1F)

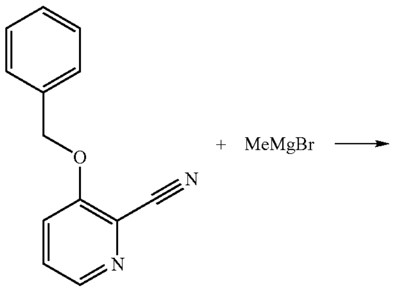

-continued

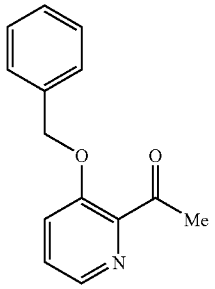

To a cold (0° C.) solution of 3-benzyloxypicolinonitrile (2.50 g, 11.9 mmmol) in tetrahydrofuran (100 mL) was added dropwise 0.92M methyl magnesium bromide in tetrahydrofuran (150 mL, 138 mmol). The mixture was stirred at 0° C. for 30 minutes and then at room temperature for 4 hrs. The reaction mixture was poured into water (2000 mL) and acidified with 10% sulfuric acid (500 mL). After being stirred for 30 min, the reaction mixture was poured into saturate aqueous $NaHCO_3$ solution slowly and extracted with ethyl acetate. The organic phase was washed with brine, dried over $Na_2SO_4$, filtrated, and evaporated. The residue was purified by column chromatography on silica gel (ethyl acetate/n-hexane=1/3) to give 1-(2-benzyloxy-phenyl)-ethanone as a colorless oil (2.49 g, yield; 92%).

[Starting Compound 1G]

To a stirred solution of 1-(2,6-dihydroxyphenyl)ethanone (50.0 g, 328 mmol) in acetone (1000 mL) was added potassium carbonate (227 g, 1643 mmol) and (bromomethyl)cyclopropane (35.1 mL, 361 mmol). The mixture was stirred at 50° C. for 2 days. The reaction mixture was filtrated on Celite®, and then the filtrate was concentrated under reduced pressure. The residue was diluted with water and extracted with ethyl acetate. The separated organic phase was washed with water and brine, dried over $MgSO_4$, filtered and concentrated under reduced pressure. The residue was suspended in hexane. Then the suspension was stirred at 80° C. for 30 min. The solution was filtered and the filtrate was allowed to cool to room temperature. The resulting white solid was collected by filtration, washed with hexane, and dried under reduced pressure to give 1-{2-[(cyclopropylmethyl)oxy]-6-hydroxyphenyl}ethanone as a pale yellow solid (56.3 g, yield; 83%).

(Starting compound 1G)

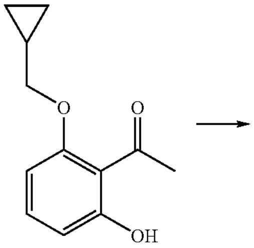

-continued

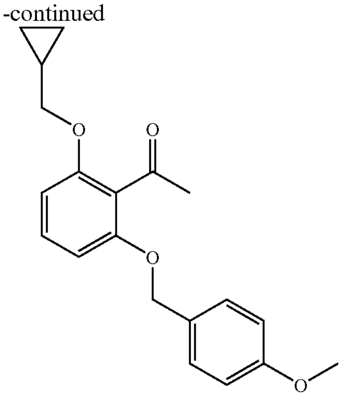

To a stirred solution of 1-{2-[(cyclopropylmethyl)oxy]-6-hydroxyphenyl} ethanone (56.3 g, 272 mmol) in acetone (1000 mL) was added potassium carbonate (188 g, 1364 mmol), 4-methoxybenzyl chloride (40.9 mL, 300 mmol) and tetrabutyl-ammonium iodide (20.2 g, 54.6 mmol). The mixture was stirred at reflux overnight. The reaction mixture was allowed to cool to room temperature, filtered on Celite®, and then the filtrate was concentrated under reduced pressure. The residue was diluted with water and extracted with ethyl acetate. The separated organic phase was washed with brine, dried over $MgSO_4$, filtered and concentrated under reduced pressure. Then the resulting white solid was recrystallized from ethanol, collected by filtration, washed with ethanol, and dried under reduced pressure to give 1-{2-(cyclopropylmethoxy)-6-[(4-methoxybenzyl)oxy] phenyl}ethanone as a white solid (79.2 g, yield; 89%).

[Starting Compound 1H]

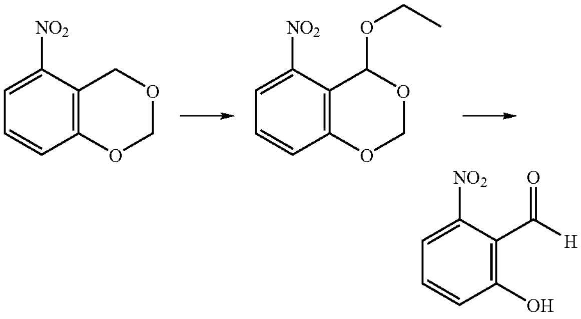

To a stirred solution of 5-nitro-4H-1,3-benzodioxine (10.0 g, 55.203 mmol) in carbon tetrachloride (70 mL) were added N-bromosuccinimide (10.808 g, 60.723 mmol) and 2,2'-azobisisobutyronitrile (0.906 g, 5.520 mmol). The mixture was stirred at 100° C. for 2 hrs. After cooled to room temperature, a solution of sodium ethoxide (4.884 g, 71.764 mmol) in ethanol (70 mL) was added to the mixture, and the stirring was continued at room temperature for 3 hrs. The reaction was quenched with water and extracted with ethyl acetate. The organic phase was washed with brine, dried over magnesium sulfate, filtered and concentrated under reduced pressure. The residue was purified by column chromatography on silica gel (hexane/ethyl acetate=9/1) to give 4-ethoxy-5-nitro-4H-1,3-benzodioxine as a pale yellow oil (10.8 g, yield; 87%).

To a stirred solution of 4-ethoxy-5-nitro-4H-1,3-benzodioxine (5.80 g, 25.755 mmol) in ethanol (15 mL) and THF (10 mL) was added 4N HCl in 1,4-dioxane (20 mL). The mixture was stirred at 60° C. for 6 hrs and 90° C. for 6 hrs. After cooled to room temperature, the reaction mixture was diluted with water and extracted with ethyl acetate. The organic phase was dried over magnesium sulfate, filtered and concentrated under reduced pressure. The residue was purified by column chromatography on silica gel (hexane/ethyl acetate=9/1) to give 2-hydroxy-6-nitrobenzaldehyde as a pale yellow oil (4.450 g, yield; quant.).

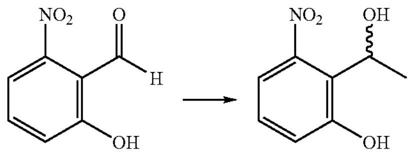

To a stirred solution of 2-hydroxy-6-nitrobenzaldehyde (4.5 g, 26.926 mmol) was added dropwise trimethylaluminum (2M in toluene, 27 mL) under an argon atmosphere. The mixture was stirred at room temperature for 1 hr. The reaction mixture was poured into a cold (0° C.) aqueous 1N hydrochloric acid and extracted with ethyl acetate. The organic phase was washed with brine and dried over $Na_2SO_4$, filtered and concentrated. The residue was purified by column chromatography on silica gel (hexane/ethyl acetate=9/1) to give 2-(1-hydroxyethyl)-3-nitrophenol as an orange oil (4.660 g, yield; 95%).

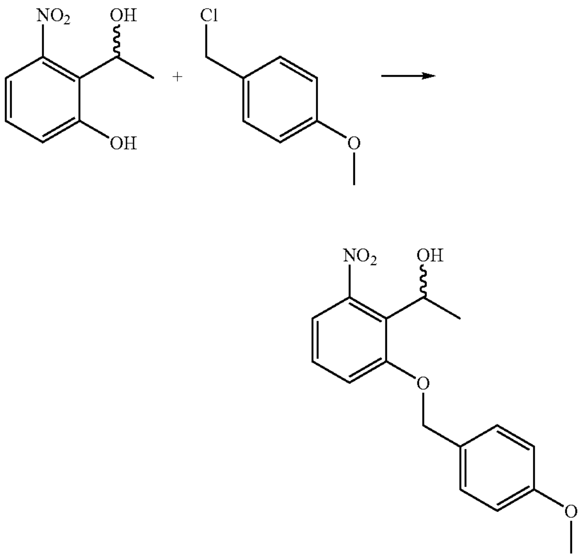

To a stirred solution of 2-(1-hydroxyethyl)-3-nitrophenol (0.300 g, 1.638 mmol) in acetone (5 mL) was added potassium carbonate (0.25 g, 1.802 mmol). The mixture was stirred at room temperature for 15 min, and 4-methoxybenzyl chloride (0.22 mL, 1.638 mmol) was added to the mixture. The mixture was stirred at room temperature for 2 hrs and at 60° C. for 3 hrs. The reaction was quenched with saturated aqueous ammonium chloride solution and extracted with ethyl acetate. The organic phase was dried over $Na_2SO_4$, filtered and concentrated. The residue was purified by column chromatography on silica gel (hexane/ethyl acetate=4/1). The purified compound was washed with diisopropyl ether to give 1-{2-[(4-methoxybenzyl)oxy]-6-nitrophenyl}ethanol as a white solid (0.201 g, yield; 41%).

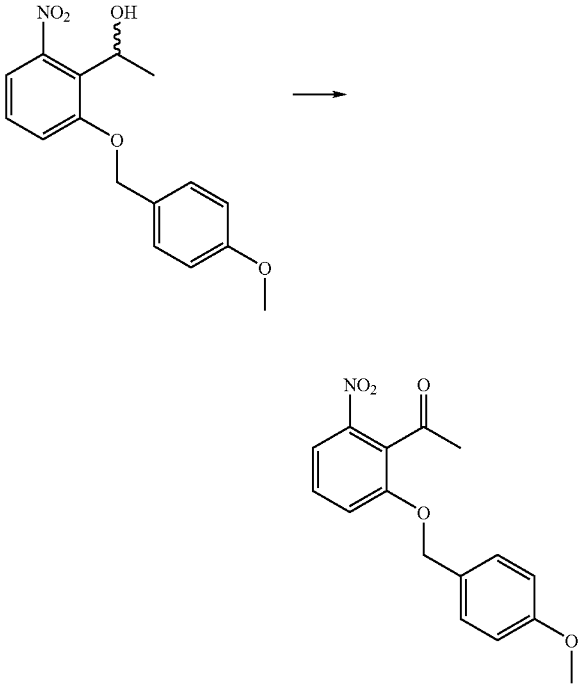

To a cooled (0° C.), stirred solution of 1-{2-[(4-methoxybenzyl)oxy]-6-nitro-phenyl}ethanol (0.20 g, 0.659 mmol) in dichloromethane (20 mL) were added molecular sieves 4A (1 g), N-methylmorpholine N-oxide (0.15 g, 1.319 mmol) and tetra-n-propylammonium perruthenate (0.01 g). The mixture was stirred at room temperature for 12 hrs. The reaction mixture was filtered on Celite®, and the filtrate was diluted with ethyl acetate. The organic phase was washed with saturated aqueous ammonium chloride solution and dried over $Na_2SO_4$, filtered and concentrated under reduced pressure to give 1-{2-[(4-methoxybenzyl)oxy]-6-nitrophenyl}ethanone as a white solid (0.159 g, yield; 80%). The residue was used for the next step without further purification.

(Starting compound 1H)

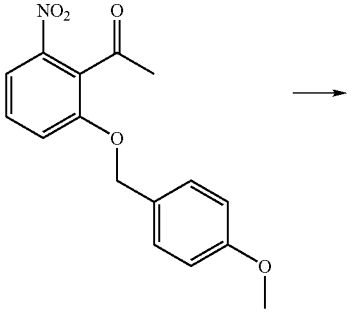

-continued

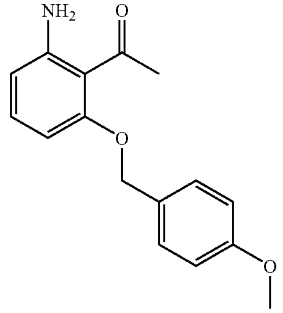

To a stirred suspension of 1-{2-[(4-methoxybenzyl)oxy]-6-nitrophenyl}ethanone (0.50 g, 1.659 mmol) in ethanol was added a solution of ammonium chloride (0.10 g, 1.825 mmol) in water (5 mL) followed by iron powder (0.75 g). The mixture was stirred at 100° C. for 1 hr. The reaction mixture was filtrated on Celite®. The filtrate was diluted with ethyl acetate and washed with water. The separated organic phase was washed with brine and dried over $Na_2SO_4$, filtrated and concentrated under reduced pressure to give 1-{2-amino-6-[(4-methoxybenzyl)oxy]phenyl}ethanone as a yellow solid (0.790 g, yield; 108%). The residue was used for the next step without further purification.

[Starting Compound 1I]

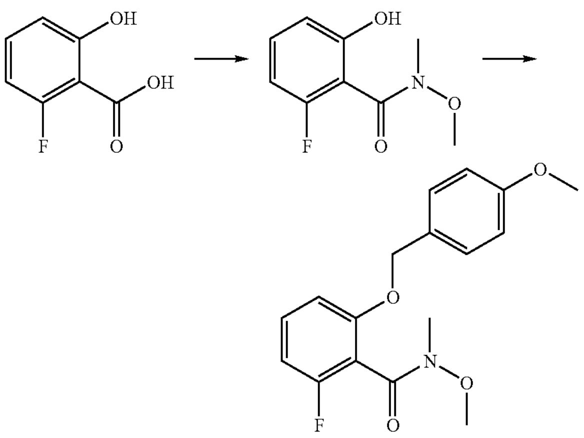

To a cold (0° C.) solution of 2-fluoro-6-hydroxybenzoic acid (5.00 g, 32.029 mmol) in dimethyl formamide (200 mL) were added N,O-dimethylhydroxylamine hydro-chloride (6.25 g, 64.057 mmol), 1-ethyl-3-(3-dimethylaminopropyl) carbodiimide hydrochloride (9.82 g, 48.043 mmol), 1-hydroxybenzotriazole (5.19 g, 38.435 mmol), and triethylamine (8.93 mL, 64.057 mmol). The mixture was stirred at room temperature for 15 hrs. The reaction mixture was extracted with ethyl acetate and water. The separated organic phase was washed with brine, dried over $Na_2SO_4$, filtered and concentrated under reduced pressure. The resulting residue was purified by column chromatography on silica gel (ethyl acetate/hexane=2/1) to give 2-fluoro-6-hydroxy-N-methoxy-N-methylbenzamide as an orange solid (4.320 g, yield; 68%).

To a stirred solution of 2-fluoro-6-hydroxy-N-methoxy-N-methylbenzamide (4.320 g, 21.689 mmol) in acetone (50 mL) were added 4-methoxy benzylchloride (3.74 g, 23.858 mmol), potassium carbonate (4.50 g, 32.534 mmol), and potassium iodide (360 mg, 2.169 mmol). The mixture was stirred at reflux for 15 hrs. After cooled to room temperature, the reaction mixture was filtered, and the filtrate was concentrated under reduced pressure. The residue was extracted with ethyl acetate and water. The separated organic phase was washed with brine, dried over $Na_2SO_4$, filtered and concentrated under reduced pressure. The resulting residue was purified by column chromatography on silica gel (hexane/ethyl acetate=2/1) to give 2-fluoro-N-methoxy-6-[(4-methoxybenzyl)oxy]-N-methylbenzamide as a pale yellow oil (6.926 g, yield; quant.).

(Starting compound 1I)

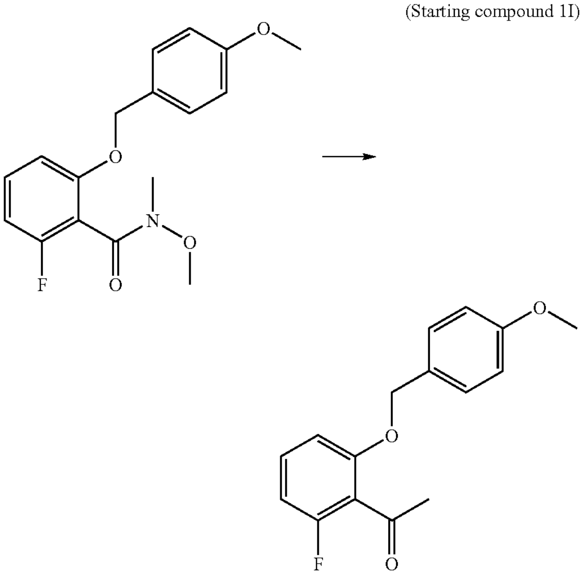

To a cold (0° C.) solution of 2-fluoro-N-methoxy-6-[(4-methoxybenzyl)oxy]-N-methylbenzamide (6.926 g, 21.70 mmol) in tetrahydrofuran (10 mL) was added 1N methyl magnesium bromide in tetrahydrofuran (43.40 mL, 43.40 mmol). The reaction mixture was stirred at reflux for 4 hrs. After cooled to room temperature, the reaction mixture was quenched with saturated aqueous $NaHCO_3$ solution, and extracted with ethyl acetate. The separated organic phase was washed with water and brine, dried over $Na_2SO_4$, filtered, and concentrated under reduced pressure. The resulting residue was purified by column chromatography on silica gel (hexane:ethyl acetate, 3/1) to give 1-{2-fluoro-6-[(4-methoxybenzyl)oxy]phenyl}ethanone as a pale yellow solid (1.21 g, yield; 20%).

[Starting Compound 1J]

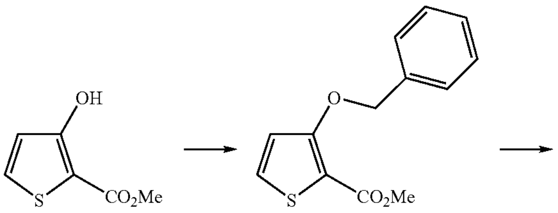

-continued

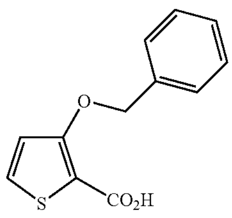

A mixture of methyl 3-hydroxy-2-thiophenecarboxylate (5.00 g, 31.61 mmol), benzyl bromide (3.76 mL, 31.61 mmol), and $K_2CO_3$ (4.81 g, 34.77 g) in acetone (50 mL) was stirred at reflux for 1.5 hrs. After cooled to room temperature, the mixture was filtered, and the filtrate was concentrated under reduced pressure. The residue was purified by column chromatography on silica gel (hexane:ethyl acetate=15/1 to 9/1) to give methyl 3-(benzyloxy)-2-thiophenecarboxylate as a pale yellow oil (7.91 g, yield: quant.).

To a solution of methyl 3-(benzyloxy)-2-thiophenecarboxylate (7.85 g, 31.61 mmol) in MeOH (32 mL) and THF (16 mL) was added 2 N NaOH (21 ML), and the mixture was stirred at reflux for 10 hrs, and then concentrated under reduced pressure. The residue was diluted with water, washed with ether. The separated aqueous phase was acidified with 5N HCl. The precipitated solid was collected by filtration, washed with hexane, and dried under reduced pressure at 60° C. to give 3-(benzyloxy)-2-thiophenecarboxylic acid as a yellow solid (6.76 g, yield; 91%).

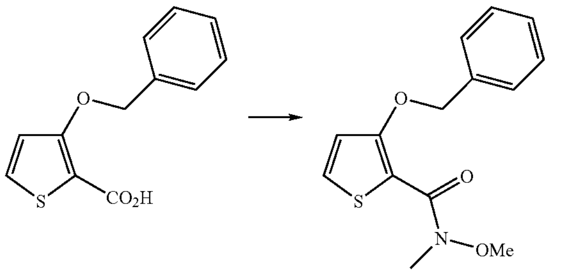

To a solution of 3-(benzyloxy)-2-thiophenecarboxylic acid (3.00 g, 12.81 mmol) in $CH_2Cl_2$ (30 mL) were added oxalyl chloride (1.34 mL, 15.4 mmol) and DMF (0.05 mL). The mixture was stirred at room temperature for 1 hr, and concentrated under reduced pressure. The residue was dissolved in ethyl acetate (10 mL). Then the solution was added to a mixture of N,O-dimethylhydroxyamine hydrochloride (1.50 g, 15.37 mmol) and $K_2CO_3$ (3.54 g, 25.62 mmol) in ethyl acetate (30 mL) and water (30 mL) at 0° C. The mixture was vigorously stirred at 0° C. for 0.5 hrs, and at room temperature for 1.5 hrs. The organic phase was separated, washed with 1 N HCl, saturated $NaHCO_3$, and brine, dried over $Na_2SO_4$, filtered, and evaporated. The residue was purified by column chromatography on silica gel (n-hexane/ethyl acetate=2/1) to give 3-(benzyloxy)-N-methoxy-N-methyl-2-thiophenecarboxamide as a pale yellow solid (3.473 g, yield; 98%).

(Starting compound 1J)

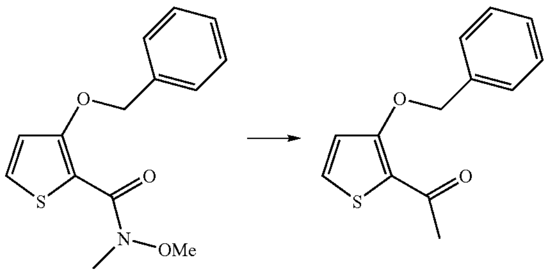

To a cold (0° C.) solution of 3-(benzyloxy)-N-methoxy-N-methyl-2-thiophene-carboxamide (3.47 g, 12.50 mmol) in THF (50 mL) was added a solution of methyl-magnesium bromide in THF (1 M, 35 mL). After being stirred at 0° C. for 1 hr, the reaction mixture was quenched with saturated aqueous $NH_4Cl$ solution, diluted with water, and extracted with ethyl acetate. The separated organic phase was washed with brine, dried over $Na_2SO_4$, filtered and evaporated. The residue was purified by column chromatography on silica gel (hexane/ethyl acetate/$CH_2Cl_2$=3/1/1) followed by recrystallization from n-hexane/ethyl acetate to give 1-[3-(benzyloxy)-2-thienyl]ethanone as a white solid (2.592 g, yield; 89%).

[Starting Compound 2A]

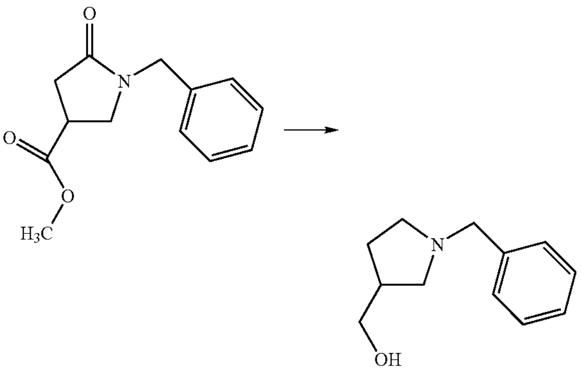

To a cold (0° C.) suspension of lithium aluminum hydride (2.44 g, 64 mmol) in THF (40 mL) was added methyl 1-benzyl-5-oxo-3-pyrrolidinecarboxylate (5.00 g, 21 mmol). The reaction mixture was stirred at room temperature for 5 hrs. To the reaction mixture were added water (2.5 mL), 15% aqueous sodium hydroxide solution (2.5 mL), and water (7.5 mL), successively. The mixture was filtered through Celite®. The filtrate was concentrated under reduced pressure to give (1-benzyl-3-pyrrolidinyl)methanol. (4.16 g, yield; quant.)

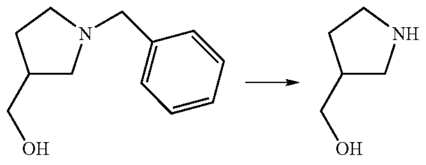

To a suspension of $Pd(OH)_2$ (0.4 g) in methanol (30 mL) was added (1-benzyl-3-pyrrolidinyl)methanol (4.16 g, 21 mmol). The reaction mixture was stirred under a hydrogen atmosphere for 24 hours. The reaction mixture was diluted with ethyl acetate (200 mL), then filtered through a Celite®. The filtrate was concentrated under reduced pressure to give 3-pyrrolidinylmethanol (2.33 g, yield; quant.).

(Starting compound 2A)

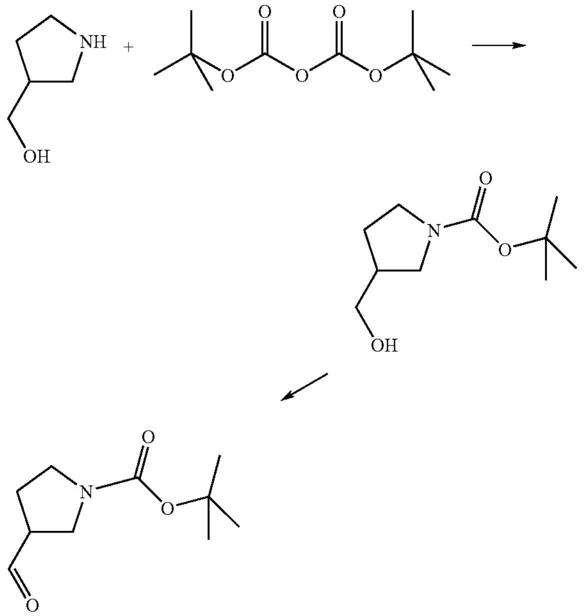

To a solution of 3-pyrrolidinylmethanol (2.33 g, 21 mmol) and triethylamine (4.8 mL, 35 mmol) in dichloromethane (60 mL) was added di(tert-butyl) dicarbonate (5.3 g, 24 mmol) at 0° C. The reaction mixture was stirred at room temperature for 26 hrs. The mixture was diluted with ethyl acetate (200 mL), and washed with 1N HCl (100 mL), with a saturated aqueous $NaHCO_3$ solution (100 mL) and with brine (100 mL), successively. The organic phase was dried over $Na_2SO_4$, filtered, and concentrated under reduced pressure to give tert-butyl 3-(hydroxymethyl)-1-pyrrolidinecarboxylate (4.06 g, yield; 96%).

To a cold (0° C.) mixture of tert-butyl 3-(hydroxymethyl)-1-pyrrolidinecarboxylate (4.0 g, 20 mmol), dichloromethane (100 mL), dimethyl sulfoxide (20 mL) and tri-ethylamine (16.9 mL, 121 mmol) under an argon atmosphere was added sulfur trioxide-pyridine complex (9.63 g, 60 mmol). The reaction mixture was allowed to warm to room temperature, and the stirring was continued for 1 hr. The mixture was extracted with ether (200 mL) and a saturated aqueous $NaHCO_3$ solution (100 mL). The separated aqueous phase was further extracted with ether (100 mL×2). The combined organic phase was washed with a 1N aqueous HCl solution (100 mL), a saturated aqueous $NaHCO_3$ solution (100 mL), and brine (100 mL), successively. The organic phase was dried over $Na_2SO_4$, filtered and concentrated under reduced pressure (5.32 g, yield; quant.).

[Starting Compound 2B]

To a cooled (0° C.), stirred solution of 3-piperidinecarboxylic acid (100.000 g, 774.233 mmol) in dioxane (400 mL) were added 2N NaOH (400 mL, 800 mmol) and di-tert-butyl dicarbonate (168.978 g, 774.233 mmol). The mixture was allowed to warm to room temperature, and the stirring was continued for 12 hrs. The mixture was concentrated under reduced pressure. The residue was diluted with water and acidified (pH 3–4) with aqueous 1N HCl solution. The resulting solid was collected by filtration. The white solid was dissolved in ethyl acetate and washed with water. The separated organic phase was dried over $Na_2SO_4$, filtered, and concentrated. The resulting solid was suspended in hexane and collected by filtration, and dried under reduced pressure to give 1-(tert-butoxycarbonyl)-3-piperidine carboxylic acid as a white solid. (156 g, yield; 88%)

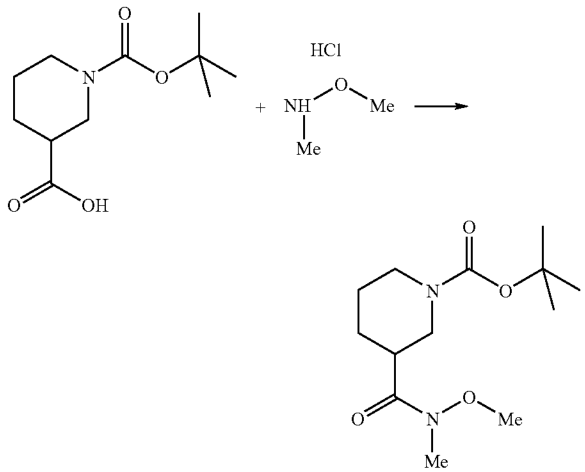

To a cold (0° C.) solution of 1-(tert-butoxycarbonyl)-3-piperidine carboxylic acid (7.000 g, 30.531 mmol) in dichloromethane (200 mL) including triethylamine (4.681 mL, 33.584 mmol) were added benzotriazole-1-yl-oxy-tris-pyrrolidino-phosphonium hexafluorophosphate (15.885 g, 30.531 mmol), N,O-dimethylhydroxyamine (3.276 g, 33.584 mmol) and triethylamine (4.255 mL, 30.531 mmol) successively. The mixture was allowed to warm to room temperature, and the stirring was continued for 12 hrs. The reaction mixture was diluted with dichloromethane and washed with an aqueous 1N HCl solution, saturated aqueous $NaHCO_3$ solution, and brine, successively. The organic phase was dried over $Na_2SO_4$, filtered, and concentrated. The resulting residue was purified by column chromatography on silica gel (chloroform/ethyl acetate=10/1-9/1) to give 3-{[methoxy(methyl)amino]carbonyl}-1-piperidine-carboxylic acid tert-butyl ester as a white solid. (8.050 g, yield;96%)

(Starting compound 2B)

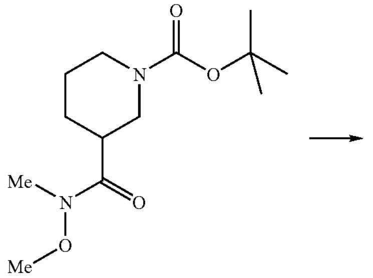

-continued

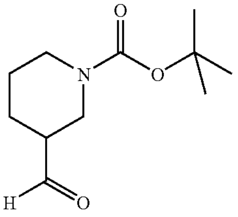

To a cooled (−15° C.), stirred suspension of lithium aluminum hydride (4.355 g, 114.743 mmol) in diethyl ether (500 mL) was added dropwise a solution of 3-{[methoxy(methyl)amino]carbonyl}-1-piperidine-carboxylic acid tert-butyl ester (25.000 g, 91.795 mmol) in THF (150 mL) over 30 min. The reaction mixture was quenched with aqueous 1N potassium hydrogen sulfate (300 mL), and extracted with a 1:1 mixture of diethyl ether and ethyl acetate. The organic phase was dried over $MgSO_4$, filtered, and concentrated under reduced pressure to give 3-formyl-piperidine-1-carboxylic acid tert-butyl ester, which was used for the next steps without further purification. (22.56 g, yield; quant.)

[Starting Compound 2C]

To a cooled (0° C.) and stirred solution of nipecotinic acid (3.0 g, 23.3 mmol) in 1,4-dioxane (12 mL) was added 2N NaOH solution (24.0 mL, 48.0 mmol) followed by a solution of benzyl chloroformate (3.96 g, 23.2 mmol) in 1,4-dioxane (12 mL). The reaction mixture was allowed to warm to room temperature, and the stirring was continued for 3 hrs. The mixture was concentrated under reduced pressure. The residue was diluted with water and acidified with 1H HCl (pH 3–4). The mixture was extracted with ethyl acetate, and the separated organic phase was washed with brine, dried over $Na_2SO_4$, filtered, and evaporated. The resulting white solid was suspended in hexane, collected by filtration, washed with hexane, and dried under reduced pressure to give 1-[(benzyloxy)carbonyl]-3-piperidinecarboxylic acid as a white solid (4.4 g, yield; 71%).

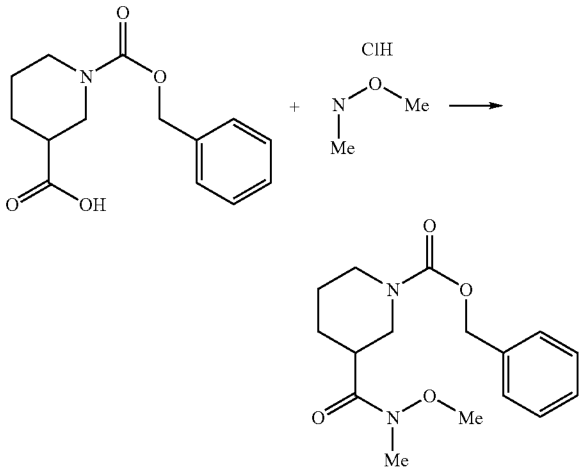

To a cooled (−15° C. to −20° C.) and stirred solution of 1-[(benzyloxy)carbonyl]-3-piperidinecarboxylic acid (4.0 g, 15.2 mmol) in dry THF (50 mL) including methylmorpholine (2 mL) was added dropwise a solution of isobutyl chloroformate (2.28 g, 16.7 mmol) in THF (10 mL). After the mixture was stirred at the same temperature for 20 min, a solution of N,O-dimethylhydroxylamine hydrochloride (1.63 g, 16.7 mmol) in THF (20 mL) including methylmorpholine (2 mL) was added. The reaction mixture was allowed to warm to room temperature, and then stirred for 16 hrs. The reaction mixture was concentrated under reduced pressure and partitioned between ethyl acetate and water. The separated organic phase was washed with 1N HCl, saturated $NaHCO_3$, and brine, successively. The organic phase was dried over $Na_2SO_4$, filtered, and concentrated under reduced pressure to give benzyl 3-{[methoxy(methyl)amino]carbonyl}-1-piperidinecarboxylate as a colorless oil (4.7 g, yield; quant.).

(Starting compound 2C)

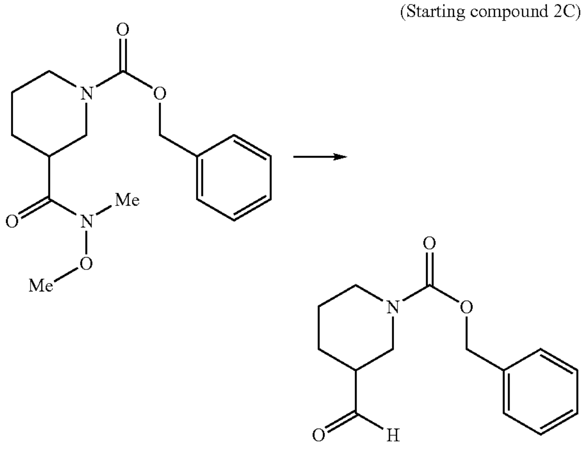

To a cooled (−78° C.) suspension of lithium aluminum hydride (0.70 g, 18.4 mmol) in dry THF (100 mL) under an argon atmosphere was added dropwise a solution of benzyl 3-{[methoxy(methyl)amino]carbonyl}-1-piperidinecarboxylate (4.5 g, 14.7 mmol) in THF (30 mL), and the stirring was continued at −78° C. for 45 min. The reaction mixture was quenched with 0.5N $KHSO_4$ (130 mL), and then extracted with ether. The separated organic phase was dried over $MgSO_4$, filtered, and concentrated under reduced pressure to give benzyl 3-formyl-1-piperidinecarboxylate as a colorless oil (0.54 g, yield; 82%).

[Starting Compound 2D]

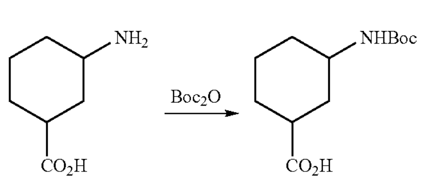

To a cold (0° C.) mixture of 3-aminocyclohexane-carboxylic acid (10.0 g, 69.8 mmol) in 1,4-dioxane (100 mL) and 2N NaOH (100 mL) was added di(tert-butyl) dicarbonate (15.2 g, 69.8 mmol). The mixture was stirred at room temperature for 1.5 hrs, and then neutralized with 2N HCl. The resulting mixture was concentrated under reduced pressure. The residue was acidified with 2N HCl and extracted with ethyl acetate. The separated organic phase was washed with brine, dried over $Na_2SO_4$, filtered and evaporated. The residual solid was triturated with hexane, collected by filtration, and dried under reduced pressure to give 3-[(tert-butoxycarbonyl)amino]cyclohexanecarboxylic acid as a white solid (8.00 g, yield; 47%).

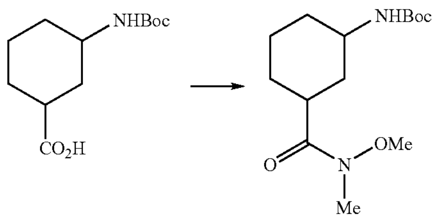

To a cold (0° C.) solution of 3-[(tert-butoxycarbonyl)amino]-cyclohexanecarboxylic acid (5.00 g, 20.6 mmol) in $CH_2Cl_2$ (50 mL) including triethylamine (3.1 mL, 22.2 mmol) were added benzotriazol-1-yloxytris(pyrrolidino)phosphonium hexa-fluorophosphate (10.7 g, 20.6 mmol), N,O-dimethylhydroxyamine hydrochloride (2.21 g, 20.6 mmol) and $Et_3N$ (3.2 mL, 23.0 mmol) successively. The resulting mixture was allowed to warm to room temperature, and the stirring was continued for 18 hrs. The reaction mixture was diluted with $CH_2Cl_2$ and washed with 1N HCl, saturated aqueous $NaHCO_3$ solution, and brine, successively. The organic phase was dried over $Na_2SO_4$, filtered, and evaporated. The residue was purified by column chromatography on silica gel (hexane/ethyl acetate=1:1) to give tert-butyl 3-{[methoxy(methyl)amino]carbonyl}cyclohexylcarbamate as a colorless oil (5.39 g, yield; 92%).

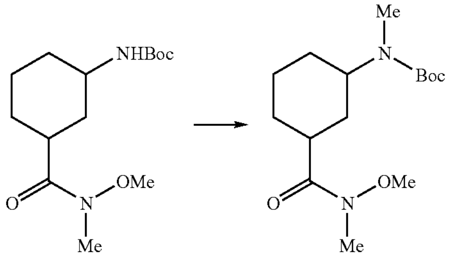

To a suspension of NaH (60%, 340 mg, 8.38 mmol) in THF (10 mL) was added dropwise a solution of tert-butyl 3-{[methoxy(methyl)amino]carbonyl}cyclo-hexylcarbamate (2.00 g, 6.98 mmol) in THF (10 mL) followed by methyl iodide (1.09 g, 7.68 mmol). The mixture was stirred at 60° C. for 0.5 hr. After cooled to room temperature, the mixture was poured into water and extracted with ethyl acetate. The organic phase was washed with brine, dried over $Na_2SO_4$, filtered and evaporated. The residue was purified by column chromatography on silica gel (hexane/ethyl acetate=1/1) to give tert-butyl N-[3-(N-methoxy-N-methyl-carbamoyl)cyclohexyl]-N-methylcarbamate as a colorless oil (1.94 g, yield; 93%).

(Starting compound 2D)

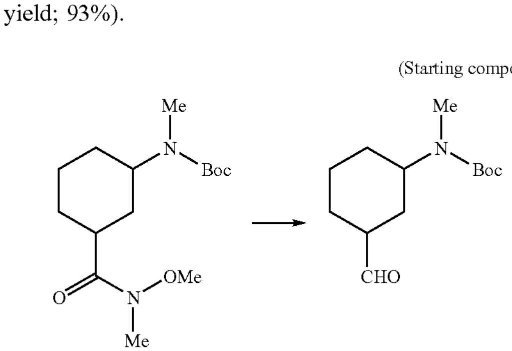

To a cold (0° C.) suspension of $LiAlH_4$ (380 mg, 9.9 mmol) in $Et_2O$ (40 mL) was added dropwise a solution of tert-butyl N-[3-(N-methoxy-N-methylcarbamoyl)cyclohexyl]-N-methylcarbamate (2.38 g, 7.92 mmol) in $Et_2O$ (40 mL) over 10 min. The reaction mixture was stirred at 0° C. for 0.5 hr, and quenched with 1N $KHSO_4$ (100 mL). The organic phase was separated, dried over $MgSO_4$ and evaporated to give tert-butyl 3-formylcyclohexyl(methyl)carbamate as a colorless oil, which was used for next step without purification (1.66 g, yield;87%).

[Starting Compound 2E]

To a cold (0° C.) solution of ethyl nipecotate (7.86 g, 50 mmol) in $CH_2Cl_2$ (120 mL) was added di-tert-butyl dicarbonate (11.46 g, 52.5 mmol). The resulting mixture was stirred at room temperature for 4 hrs. The reaction mixture was diluted with a 5% aqueous $NaHCO_3$ solution. The organic phase was separated, dried over $MgSO_4$, filtered and evaporated under reduced pressure to give 1-tert-butyl 3-ethyl 1,3-piperidinedicarboxylate (12.8 g, yield; quant.).

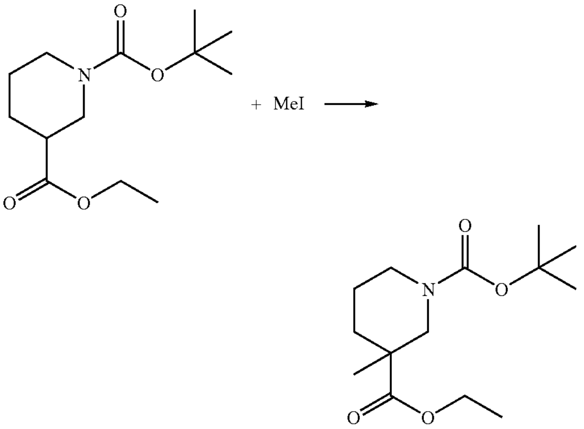

To a cold (−78° C.) solution of lithium diisopropylamide (LDA) (23.3 mmol) in THF (10 mL) under an argon atmosphere was added dropwise a solution of 1-tert-butyl 3-ethyl 1,3-piperidinedicarboxylate (3.0 g, 11.6 mmol) in THF (5 mL), then stirred at −50° C. for 2 hrs. To the resulting mixture was added a solution of MeI (1.98 g, 14 mmol) in THF at −50° C. The reaction mixture was allowed to warm to room temperature, and quenched with saturated aqueous $NH_4Cl$ solution. The mixture was concentrated under reduced pressure, and the residue was partitioned between ethyl acetate and water. The organic phase was separated, dried over $MgSO_4$, filtered and concentrated under reduced pressure. The crude product was purified by column chromatography on silica gel (hexane:ethyl acetate, 9:1) to give 1-tert-butyl 3-ethyl 3-methyl-1,3-piperidinedicarboxylate as a pale yellow oil (2.27 g, yield; 72%).

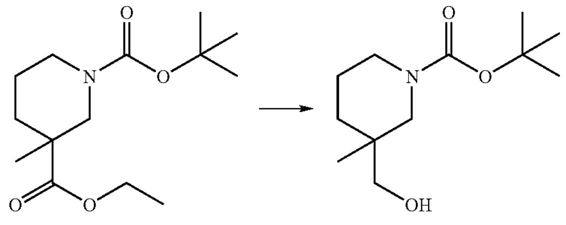

To a cold (−20° C.) solution of 1-tert-butyl 3-ethyl 3-methyl-1,3-piperidinedicarboxylate (2.3 g, 8.48 mmol) in dry THF was added $LiBH_4$ (2M in THF, 10.6 mmol), and the stirring was continued overnight. The reaction mixture was allowed to warm to room temperature. The reaction mixture was cooled by ice water and acidified (pH 5–6) with aqueous 1N HCl. The mixture was concentrated under reduced pressure, then extracted with ethyl acetate. The organic phase was separated, dried over $MgSO_4$, filtered, and evaporated. The crude product was purified by column chromatography on silica gel (hexane: ethyl acetate, 4:1-3:1) to give tert-butyl 3-(hydroxymethyl)-3-methyl-1-piperidinecarboxylate as a colorless oil form (1.5 g, yield; 78%).

(Starting compound 2E)

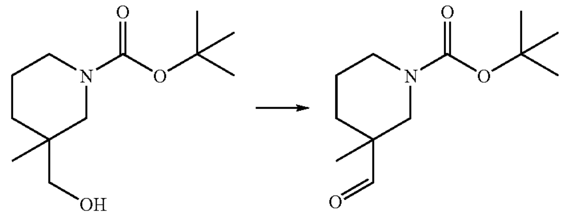

To an ice water cooled solution of tert-butyl 3-(hydroxymethyl)-3-methyl-1-piperidinecarboxylate (1.5 g, 6.6 mmol) in $CH_2Cl_2$ were added DMSO (7.1 g, 91.6 mmol), $Et_3N$ (5.5 mL, 39.8 mmol), and sulfur trioxide-Pyridine complex (3.1 g, 19.9 mmol) successively. The mixture was stirred at room temperature for 1 hr. The reaction mixture was diluted with ether, purified by column chromatography on silica gel (hexane:ethyl acetate, 5:1-4:1) to give tert-butyl 3-formyl-3-methyl-1-piperidinecarboxylate as a colorless oil form (1.3 g, yield; 86%).

[Starting Compound 2F]

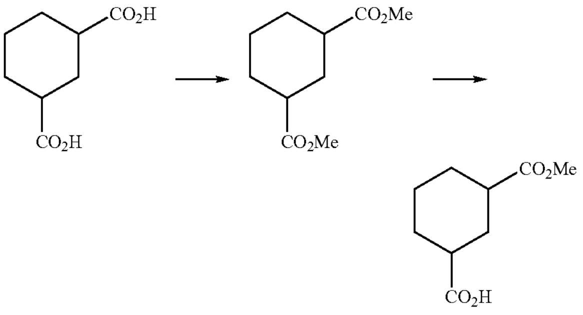

To a solution of 1,3-cyclohexanedicarboxylic acid (10 g, 58 mmol) in MeOH (50 mL) was added conc. $H_2SO_4$ (2 mL). Then the mixture was stirred at room temperature for 4 hrs. The mixture was concentrated under reduced pressure, and then partitioned between ethyl acetate and a saturated aqueous $NaHCO_3$ solution. The organic phase was washed with brine, dried over $Na_2SO_4$, and evaporated to give dimethyl 1,3-cyclohexanedicarboxylate as a colorless oil (11.6 g, yield; quant.). To a solution of dimethyl 1,3-cyclohexanedicarboxylate (11.6 g, 57.9 mmol) in MeOH (58 mL) was added a 1N NaOH solution (58 mL) dropwise over 1 hr at 0° C. The resulting mixture was stirred at 0° C. for 0.5 hrs, and at room temperature for 2 hrs. The mixture was concentrated under reduced pressure, and the residual solution was partitioned between ethyl acetate and water. The aqueous phase was separated, acidified with conc. HCl (15 mL), saturated with NaCl, and then extracted with ethyl acetate. The extract was dried over $Na_2SO_4$, filtered and concentrated under reduced pressure to give 3-(methoxycarbonyl)cyclohexanecarboxylic acid as a colorless oil (6.16 g, yield; 57%).

(Starting compound 2F)

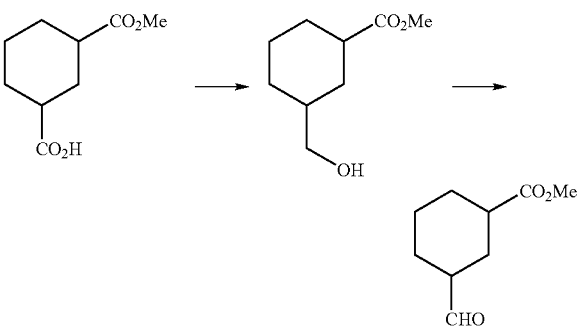

To a cold (−78° C.) solution of 3-(methoxycarbonyl)cyclohexanecarboxylic acid (1.25 g, 6.71 mmol) in THF (20 mL) was added $BH_3.Me_2S$ (0.7 mL, 7.38 mmol). The resulting mixture was stirred at −78° C. to room temperature overnight. The reaction mixture was quenched with a saturated aqueous $NH_4Cl$ solution and extracted with ethyl acetate. The organic phase was washed with brine, dried over $Na_2SO_4$, and evaporated. The residue was purified by column chromatography on silica gel (n-hexane/ethyl acetate=2/1) to give methyl 3-(hydroxymethyl)cyclo-hexanecarboxylate as a colorless oil (845 mg, yield; 73%). To a solution of methyl 3-(hydroxymethyl)cyclohexanecarboxylate (840 mg, 4.88 mmol) in $Et_3N$ (4.4 mL, 32 mmol) and DMSO (10 mL) was added sulfur trioxide-pyridine complex (2.56 g, 16.1 mmol). The mixture was stirred at room temperature for 1 hr. The reaction mixture was partitioned between ethyl acetate and water. The organic phase was washed with brine, dried over $Na_2SO_4$, filtered and evaporated. The residue was purified by column chromatography on silica gel (n-hexane/ethyl acetate=2/1) to give methyl 3-formylcyclohexanecarboxylate as a pale yellow oil (795 mg, yield; 96%).

[Starting Compound 2G]

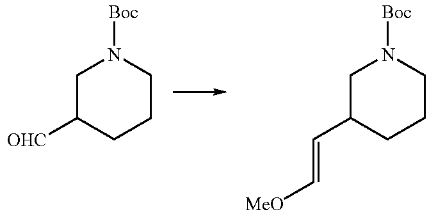

To a suspension of methoxymethylphosphonium chloride (5.14 g, 15 mmol) in THF (18 mL) was added potassium tert-butoxide (1.98 g, 15 mmol) at 0° C., and the mixture was stirred at 0° C. for 0.5 hr. A solution of tert-butyl 3-formyl-1-piperidinecarboxylate (2.13 g, 10 mmol) in THF (8 mL) was added dropwise at −20° C., and the resulting mixture was stirred at 0° C. to room temperature overnight. The mixture was partitioned between toluene and water. The separated organic phase was washed with brine, dried over $Na_2SO_4$, filtered, and evaporated. Purification by column chromatography on silica gel (hexane/ethyl acetate=5/1) gave tert-butyl 3-(2-methoxyethenyl)-1-piperidinecarboxylate as a colorless oil (1.16 g, yield; 48%).

(Starting compound 2G)

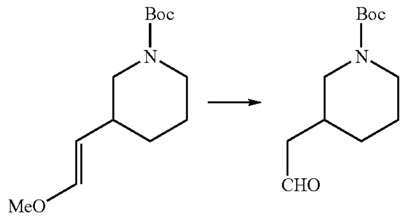

tert-Butyl 3-(2-methoxyethenyl)-1-piperidinecarboxylate (1.16 g, 4.81 mmol) was dissolved in 90% formic acid (2 mL). The mixture was stiffed at room temperature for 40 min. The mixture was then partitioned between ethyl acetate and saturated aqueous $NaHCO_3$ solution. The separated organic phase was washed with brine, dried over $Na_2SO_4$, filtered and evaporated. Purification by column chromatography (hexane/ethyl acetate=4/1) gave tert-butyl 3-(2-oxoethyl)-1-piperidinecarboxylate as a colorless oil (652 mg, yield; 60%).

[Starting Compound 2H]

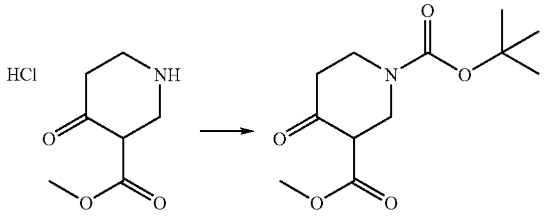

To a cold (0° C.) mixture of 3-methoxycarbonyl 4-piperidone HCl (10 g, 51.6 mmol) and triethylamine (10.8 mL, 77.5 mmol) in dichloromethane (100 mL) was added a solution of di-tert-butyl dicarbonate (11.8 g, 54.2 mmol) in dichloromethane (100 mL). The mixture was stirred at room temperature for 2 hrs and concentrated under reduced pressure. The residue was quenched with water, extracted with ether, dried over $MgSO_4$, filtered, and evaporated to give 1-tert-butyl 3-methyl 4-oxo-1,3-piperidinedicarboxylate, which was used for the next reaction without further purification. (14.9 g, yield; quant.)

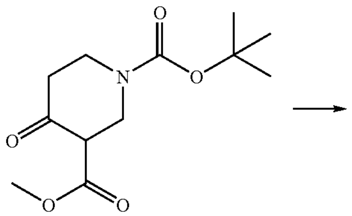

-continued

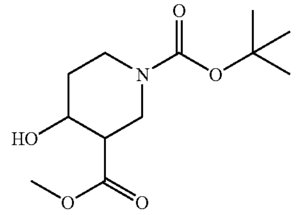

To a cold (0° C.) solution of 1-tert-butyl 3-methyl 4-oxo-1,3-piperidinedicarboxylate (134.0 g, 520.8 mmol) in methanol (800 mL) was added $NaBH_4$ (9.85 g, 260.4 mmol) portionwise. The resulting mixture was stirred overnight to be allowed to warm to room temperature. The solvent was removed under reduced pressure, the residue was dissolved into ethyl acetate, washed with brine, dried over $MgSO_4$, filterd, and concentrated under reduced pressure to give 1-tert-butyl 3-methyl 4-hydroxy-1,3-piperidinedicarboxylate, which was used for the next reaction without further purification. (120.8 g, yield 90%)

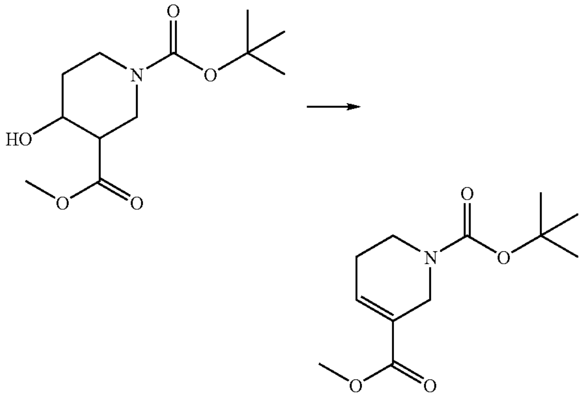

To a cold (0° C.) solution of 1-tert-butyl 3-methyl 4-hydroxy-1,3-piperidine-dicarboxylate (1,64 g, 6.32 mmol), 4-dimethylaminopyridine (16.0 mg, 0.13 mmol), and triethylamine (2.64 mL, 19.0 mmol) in dichloromethane (25 mL) was added dropwise trifluoroacetic anhydride (1.12 mL, 7.91 mmol). The reaction mixture was stirred at room temperature for 40 hrs. The reaction was quenched with 10% $K_2CO_3$ solution, extracted with $CHCl_3$. The separated organic phase was washed with brine, dried over $MgSO_4$, filtered and evaporated under reduced pressure. The crude product was purified by silica gel column chromatography (hexane: ethyl acetate=5:1) to give 1-tert-butyl 3-methyl 5,6-dihydro-1,3(2H)-pyridinedicarboxylate as a pale yellow oil. (707.4 mg, yield 46%)

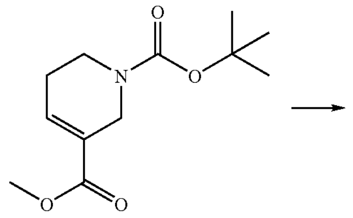

-continued

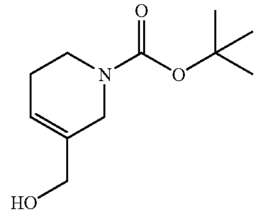

To a cold (−20° C.) solution of 1-tert-butyl 3-methyl 5,6-dihydro-1,3(2H)-pyridinedicarboxylate (700.0 mg, 2.90 mmol) in dry toluene (40 mL) was added a solution of diisobutylaluminum hydride in toluene (1.5M, 4.83 mL, 7.25 mmol) dropwise under an argon atmosphere. The reaction mixture was stirred at 0° C. for 30 min and then stirred at room temperature. The reaction was quenched by an addition of water and the stirring was continued for additional 1 hr. The precipitated aluminum salts were filtered off. The filtrate was diluted with saturated $NH_4Cl$ solution, extracted with ethyl acetate. The separated organic phase was washed with brine, dried over $MgSO_4$, filtered and evaporated to give tert-butyl 5-(hydroxymethyl)-3,6-dihydro-1(2H)-pyridinecarboxylate, which was used for the next reaction without further purification. (580.0 mg, yield 94%)

(Starting compound 2H)

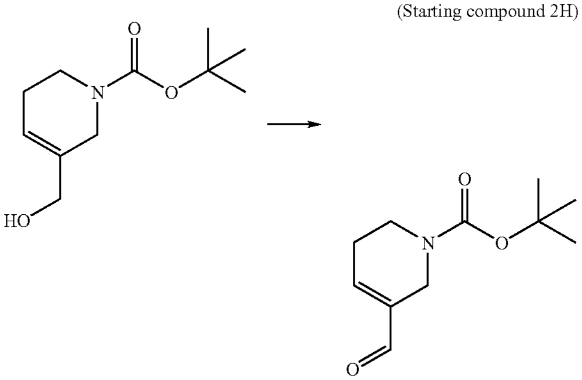

To a solution of tert-butyl 5-(hydroxymethyl)-3,6-dihydro-1(2H)-pyridinecarboxylate (14.65 g, 68.69 mmol) in dichloromethane was added $MnO_2$ (89.58 g, 1030.36 mmol), then stirred overnight at room temperature. The reaction mixture was filtered through Celite®, the filtrate was concentrated under reduced pressure to give tert-butyl 5-formyl-3,6-dihydro-1(2H)-pyridinecarboxylate, which was pure enough to be used for the next reaction. (13.55 g, yield 94%)

Example 1-1

(1) A mixture of 2'-benzyloxyacetophenone (starting compound 1A) (10.00 g, 44.19 mmol), tert-butyl 3-formyl-1-piperidine carboxylate (starting compound 2B) (10.37 g, 44.61 mmol), malononitrile (3.21 g, 48.61 mmol), and ammonium acetate (17.03 g, 220.97 mmol) in toluene (50 mL) was stirred at 150° C. for 2 hrs. After cooled to room temperature, the reaction mixture was diluted with ethyl acetate. The organic phase was washed with water and saturated brine, dried over $Na_2SO_4$, filtered and concentrated. The residue was purified by column chromatography on silica gel (hexane/ethyl acetate=2/1). The purified compound (yellow oil) was recrystallized from ethanol to give tert-butyl 3-{2-amino-6-[2-(benzyloxy)phenyl]-3-cyano-4-pyridinyl}-1-piperidinecarboxylate as a white solid. (5.83 g, yield; 27%).

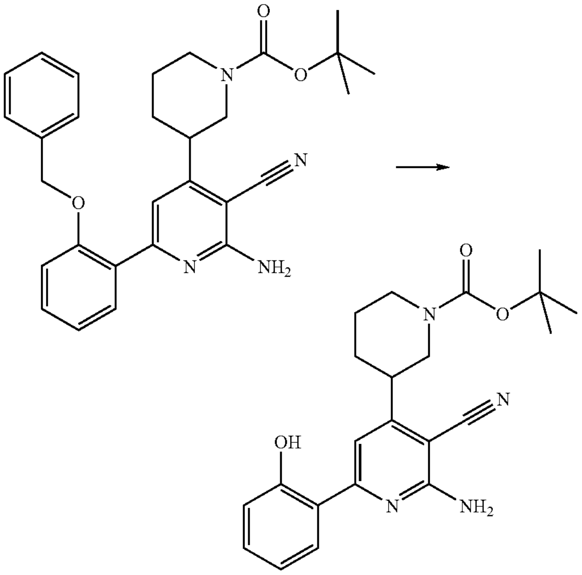

(2) A mixture of tert-butyl 3-{2-amino-6-[2-(benzyloxy)phenyl]-3-cyano-4-pyridinyl}-1-piperidinecarboxylate (2.160 g, 4.457 mmol) and 10% Pd—C (0.720 g) in ethyl acetate (30 mL) was stirred at room temperature for 2 days under a hydrogen atmosphere (3 atm). The mixture was filtrated with Celite® and the filtrate was concentrated under reduced pressure. The residue was recrystallized from diethyl ether to give tert-butyl 3-[2-amino-3-cyano-6-(2-hydroxyphenyl)-4-pyridinyl]-1-piperidinecarboxylate as a white solid. (0.180 g, yield; 10%)

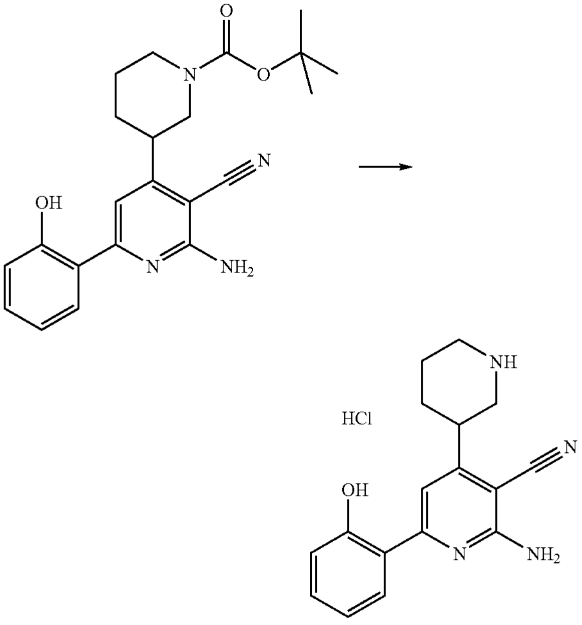

(3) To a stirred solution of tert-butyl 3-[2-amino-3-cyano-6-(2-hydroxyphenyl)-4-pyridinyl]-1-piperidinecarboxylate (0.170 g, 0.431 mmol) in dioxane (30 mL) was added 4N HCl in dioxane (3 mL). The mixture was stirred at room temperature for 12 hrs. The resulting precipitates were collected by filtration and the filtrate was washed with dioxane to give 2-amino-6-(2-hydroxyphenyl)-4-(3-piperidinyl)nicotino-nitrile hydrochloride(0.075 g, yield; 53%).

Molecular weight: 330.82

Mass spectrometry: 295 $(M+H)^+$

In vitro activity grade: A

Cellular activity grade: (A549)-A/(Jurkat)-A $^1$H-NMR(300 MHz, DMSO-d6): 1.81–1.89 (4H, m), 2.88–2.92 (1H, m), 3.31–3.40 (4H, m), 6.89–6.94 (2H, m), 7.32–7.38 (1H, m), 7.43 (1H, s), 8.05 (1H, d, J=7.4 Hz), 8.83–8.85 (1H, br s), 9.45–9.47 (1H, br s).

Example 1-2

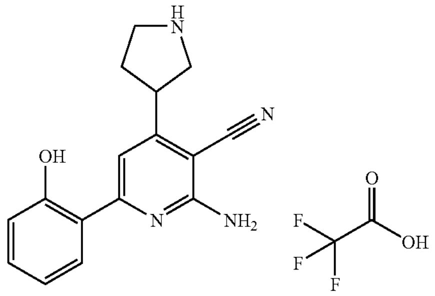

With the use of starting compound 2A instead of 2B, 2-amino-6-(2-hydroxyphenyl)-4-(3-pirrolidinyl)nicotinonitrile trifluoroacetate was prepared in a similar manner as described in Example 1-1.

Molecular weight: 394.36

Mass spectrometry: 281 $(M+H)^+$

In vitro activity grade: A

Cellular activity grade: (A594)-A/(Jurkat)-B $^1$H-NMR(500 MHz, DMSO-d6): 2.10 (1H, m), 3.60–3.70 (2H, m), 6.91 (2H, m), 7.36–7.44 (4H, m), 8.05 (1H, d, J=8.2 Hz), 9.00 (2H, br), 13.35 (1H, s).

Example 1-3

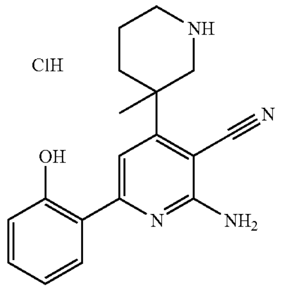

With the use of starting compound 2E instead of 2B, 2-amino-6-(2-hydroxyphenyl)-4-(3-methylpiperidin-3-yl)-nicotinonitrile hydrochloride was prepared in a similar manner as described in Example 1-1.

Molecular weight: 344.85

Mass spectrometry: 309 $(M+H)^+$

In vitro activity grade: B

Cellular activity grade: (A594)-B $^1$H-NMR(500 MHz, DMSO-d6): 1.52 (3H, s), 1.78 (2H, br d, J=38.1 Hz), 1.97–2.04 (1H, m), 2.37–2.44 (1H, m), 2.99 (2H, br d, J=31.7 Hz), 3.34 (1H, dd, J=5.5, 12.5 Hz), 3.75 (1H, dd, J=5.5, 12.5 Hz), 6.92–6.96 (2H, m), 7.22 (1H, s), 7.33–7.39 (2H, m), 8.05–8.08 (1H, m), 9.02 (1H, br s), 9.42 (1H, br s).

Example 1-4

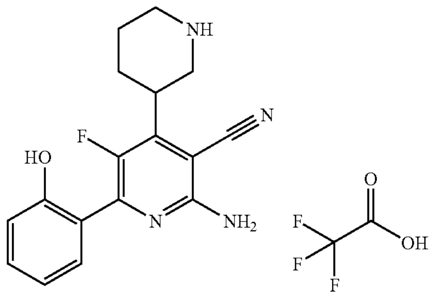

With the use of the starting compound 1B instead of 1A, 2-amino-5-fluoro-6-(2-hydroxyphenyl)-4-(3-piperidinyl)-nicotinonitrile trifluoroacetate was prepared in a similar manner as described in Example 1-1.

Molecular weight: 426.37

Mass spectrometry: 313 $(M+H)^+$

In vitro activity grade: A

Cellular activity grade: (A594)-B/(Jurkat)-B $^1$H-NMR(500 MHz, DMSO-d6): 1.77 (2H, m), 1.95 (3H, m), 2.94 (1H, t, J=10.7 Hz), 3.25–3.37 (2H, m), 3.50 (1H, d, J=12.0 Hz), 6.90 (1H, dt, J=1.0, 8.2 Hz), 6.93 (1H, d, J=8.2 Hz), 7.03 (2H, br), 7.32 (1H, dt, J=1.6, 8.5 Hz), 7.47 (1H, dd, J=1.6, 7.9 Hz), 8.73 (2H, br), 10.72 (1H, s).

Example 1-5

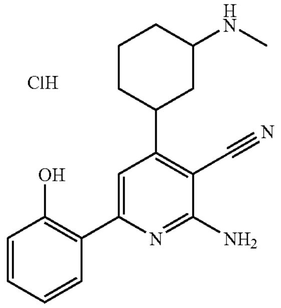

With the use of the starting compound 2D instead of 2B, 2-amino-6-(2-hydroxyphenyl)-4-[3-methylamino]cyclohexyl]nicotinonitrile hydrochloride was prepared in a same manner as described in Example 1-1.

Molecular weight: 358.87

Mass spectrometry: 323 $(M+H)^+$

In vitro activity grade: A

Cellular activity grade: (A594)-B $^1$H-NMR(300 MHz, DMSO-d6): 1.34–1.86 (5H, m), 1.86–2.04 (1H, m), 2.04–2.30 (2H, m), 2.50–2.60 (3H, m), 2.76–2.95 (1H, m), 3.17 (1H, br s), 6.85–6.96 (2H, m), 7.20–7.40 (3H, m), 7.99 (1H, d, J=8.1 Hz), 9.11 (2H, br s).

Example 1-6

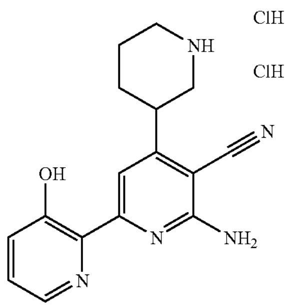

With the use of starting compound 1F instead of 1A, 6-amino-3'-hydroxy-4-(3-piperidinyl)-2,2'-bipyridine-5-carbonitrile hydrochloride was prepared in a same manner as described in Example 1-1.

Molecular weight: 368.27

Mass spectrometry: 337 $(M+H)^+$

In vitro activity grade: A

Cellular activity grade: (A594)-A $^1$H-NMR (500 MHz, DMSO-d6): 1.78–1.82 (2H, m), 1.93–1.95 (2H, m), 3.03–3.07 (1H, m), 3.27–3.37 (3H, m), 3.56 (1H, m), 7.39 (1H, dd, J=1.6, 8.5 Hz), 7.43 (1H, dd, J=4.1, 8.5 Hz), 7.56 (1H, br), 7.76 (1H, s), 8.23 (1H, dd, J=1.6, 4.1 Hz), 8.78 (1H, br), 9.18 (1H, br).

Example 1-7

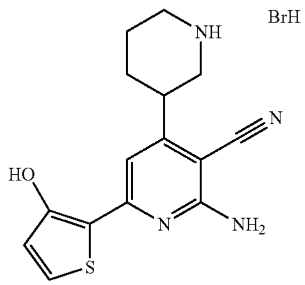

With the use of the starting compound 1J instead of 1A, 2-amino-6-(3-hydroxy-2-thienyl)-4-(3-piperidinyl)nicotinonitrile hydrobromide was prepared in a same manner as described in Example 1-1.

Molecular weight: 381.30

Mass spectrometry: 301 $(M+H)^+$

In vitro activity grade: A

Cellular activity grade: (A594)-A $^1$H-NMR (500 MHz, DMSO-d6): 1.69–1.84 (2H, m), 1.84–2.00 (2H, m), 2.94–3.06 (1H, m), 3.12–3.28 (2H, m), 3.28–3.40 (2H, m), 6.82 (2H, d, J=5.4 Hz), 6.83 (1H, s), 7.63 (2H, d, J=5.4 Hz), 8.55–8.70 (1H, m), 8.85–9.00 (1H, m).

Example 1-8

With the use of the starting compound 2F instead of 2B, methyl 3-[2-amino-3-cyano-6-(2-hydroxyphenyl)-4-pyridinyl]-cyclohexanecarboxylate was prepared in a similar manner as described in Example 1-1.

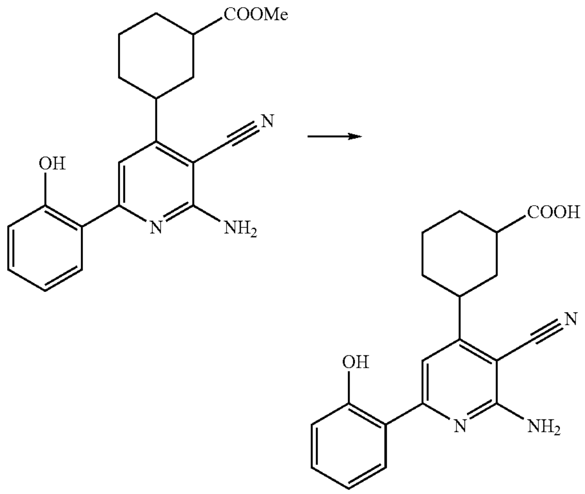

A suspension of methyl 3-[2-amino-3-cyano-6-(2-hydroxyphenyl)-4-pyridinyl]cyclo-hexanecarboxylate (151 mg, 0.43 mmol) in 2N NaOH (1 mL) and THF (2 mL) was stirred at 60° C. for 4 hrs. The reaction mixture was neutralized with 1N HCl (2 mL), and then diluted with water. The resulting precipitates were collected by filtration, washed with EtOH, and dried (60° C., 2 hrs, under reduced pressure) to give 3-[2-amino-3-cyano-6-(2-hydroxyphenyl)-4-pyridinyl]cyclohexanecarboxylic acid as a yellow solid (105 mg, yield; 72%).

Molecular weight: 337.38

Mass spectrometry: 338 $(M+H)^+$

In vitro activity grade: B

Cellular activity grade: (A594)-C $^1$H-NMR (300 MHz, DMSO-d6): 1.30–2.14 (8H, m), 2.30–2.59 (1H, m), 2.70–2.89 (1H, m), 6.83–6.93 (2H, m), 7.24–7.38 (4H, m), 8.00–8.10 (1H, m), 12.41 (1H, s), 13.47 (1H, s).

Examples 1-9

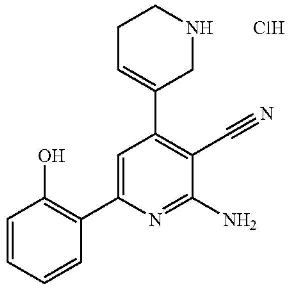

With the use of the starting compound 1D instead of 1A and the starting compound 2H instead of 2B, 2'-amino-6'-

(2-hydroxyphenyl)-1,2,5,6-tetrahydro-3,4'-bipyridine-3'-carbonitrile hydrochloride was prepared in a same manner as described in Example 1-1.

Molecular weight: 328.80

Mass spectrometry: 293 $(M+H)^+$

In vitro activity grade: A

Cellular activity grade: (A594)-A $^1$H-NMR (500 MHz, DMSO-d6): 2.52 (2H, br s), 3.24 (2H, br s), 4.05(2H, br s), 6.45 (1H, s), 6.90–6.93 (2H, m), 7.35–7.46 (4H, m), 8.01–8.02 (1H, m), 9.37 (1H, br s).

Examples 1-10

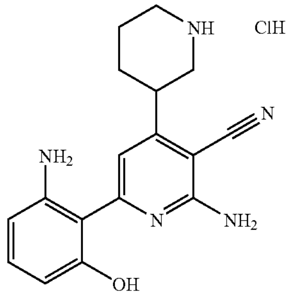

With the use of starting compound 1H instead of 1A, 2-amino-6-(2-amino-6-hydroxyphenyl)-4-(3-piperidinyl) nicotinonitrile hydrochloride was prepared in a same manner as described in Example 1-1.

Molecular weight: 345.83

Mass spectrometry: 310 $(M+H)^+$

In vitro activity grade: C

Cellular activity grade: (A594)-C $^1$H-NMR (500 MHz, DMSO-d6): 1.81–1.92 (3H, m), 2.89–2.93 (1H, m), 3.28–3.32 (3H, m), 6.97 (2H, dd, j=11.7, 8.2Hz), 7.30 (2H, t, J=8.2Hz), 9.01 (1H, m), 9.59 (1H, m).

Examples 1-11

(1) With the use of the starting compound 1H instead of 1A, tert-butyl 3-(2-amino-6-{2-amino-6-[(4-methoxybenzyl) oxy]phenyl}-3-cyano-4-pyridinyl)-1-piperidinecarboxylate was prepared in a same manner as described in the step (1) of Example 1-1.

(2) To a cooled (0° C.), stirred solution of tert-butyl 3-(2-amino-6-{2-amino-6-[(4-methoxybenzyl)oxy]phenyl}-3-cyano-4-pyridinyl)-1-piperidinecarboxylate (0.30 g, 0.566 mmol) in methanol (10 mL) including acetic acid (0.03 g, 0.566 mmol) was added benzaldehyde (0.08 mL, 1.133 mmol) followed by sodium cyanoborohydride (0.04 g, 0.566 mmol), and the stirring was continued at 0° C. for 3 hrs. The reaction was quenched with water and extracted with ethyl acetate. The organic phase was dried over sodium sulfate, filtered and concentrated under reduced pressure. The residue was purified by silica gel column chromatography (hexane/ethyl acetate=4/1) to give tert-butyl 3-(2-amino-6-{2-(benzylamino)-6-[(4-methoxybenzyl)oxy]-phenyl}-3-cyano-4-pyridinyl)-1-piperidinecarboxylate as a yellow amorphous (0.299 g, yield; 85%).

(3) Then the yellow amorphous was treated under acidic conditions in the similar manner as that of the step (3) in Example 1-1 to give 2-amino-6-[2-(benzylamino)-6-hydroxyphenyl]-4-(3-piperidinyl)-1-nicotinonitrile hydrochloride.

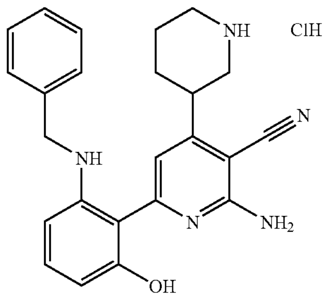

Molecular weight: 435.96

Mass spectrometry: 400 $(M+H)^+$

In vitro activity grade: B

Cellular activity grade: (A594) C $^1$H-NMR (500 MHz, DMSO-d6): 1.69–1.83 (2H, m), 1.90–1.92 (2H, m), 2.89–2.92 (1H, m), 3.15–3.18 (1H, m), 3.28–3.33 (3H. m), 4.28 (2H, s), 6.17 (1H, d, J=8.2 Hz), 6.32 (1H, d, J=8.2 Hz), 7.00 (1H, t, J=8.2 Hz), 7.09 (1H, s), 7.20–7.23 (1H, m), 7.28–7.33 (4H, m), 8.97 (1H, m), 9.47 (1H, m).

Example 1-12

To a cooled (0° C.), stirred solution of tert-butyl 3-(2-amino-6-{2-amino-6-[(4-methoxybenzyl)oxy]phenyl}-3-cyano-4-pyridinyl)-1-piperidinecarboxylate (0.10 g, 0.189 mmol) obtained in the step (1) of Example 1-11 in dichloromethane (10 mL) including triethylamine (0.02 g, 0.227 mmol) was added acetic anhydride (0.08 g, 0.889 mmol) .The stirring was continued at 0° C. for 5 hrs. The mixture was allowed to warm to room temperature, and the stirring was continued for 30 min. The reaction was quenched with water and extracted with ethyl acetate. The organic phase was washed with brine and dried over $Na_2SO_4$, filtered and concentrated under reduced pressure. The residue was purified by silica gel column chromatography (hexane/ethyl acetate=2/1-1/1-1/2) to give tert-butyl 3-(6-{2-(acetylamino)-6-[(4-methoxybenzyl)oxy]phenyl}-2-amino-3-cyano-4-pyridinyl)-1-piperidine-carboxylate as a pale yellow oil (0.102 g, yield; 94.5%).

Then the yellow oil was treated with acids in the same manner as in the step (2) in Example 1-1 to give N-{2-[6-amino-5-cyano-4-(3-piperidinyl)-2-pyridinyl]-3-hydroxyphenyl}acetamide hydrochloride.

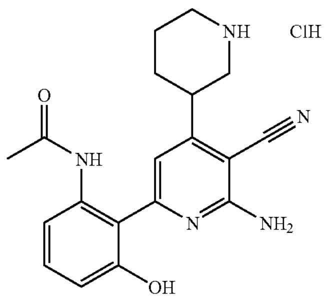

Molecular weight: 387.87

Mass spectrometry: 352 $(M+H)^+$

In vitro activity grade: C

Cellular activity grade: (A594) C

$^1$H-NMR (500 MHz, DMSO-d6): 1.60–1.86 (4H, m), 1.90 (3H, s), 2.88–2.95 (1H, m), 3.12–3.26 (4H, m), 6.78 (1H, d, J=8.2 Hz), 7.02 (1H, s), 7.23 (1H, t, J=8.2 Hz), 7.28–7.30 (1H, m), 8.90–8.92 (1H, m), 9.40–9.42 (1H, m), 9.90 (1H, br s).

Examples 1-13 to 1-44

In similar manners as described in Example 1-1 to Example 1-12 above, compounds in Examples 1-13 to 1-44 as shown in Table 1 were synthesized.

TABLE 1

| Ex. No | Structure | Mol weight | Mass | in vitro | A549 | NMR |
|---|---|---|---|---|---|---|
| 1-13 | 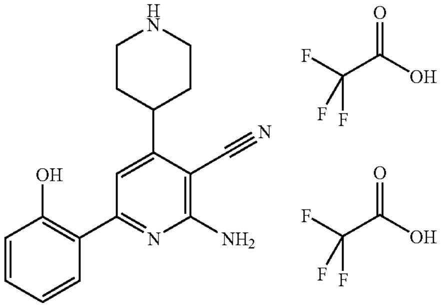 | 522.41 | 295 | A | A | (300MHz, DMSO-d6): 1.99(4H, m), 3.11(3H, m), 3.43(2H, d, J=13.2 Hz), 6.91(2H, m), 7.20(1H, s), 7.35 3H, m), 7.94(1H, d, J=8.5 Hz), 8.46(1H, br), 8.76(1H, br), 13.20 1H, br). |
| 1-14 | 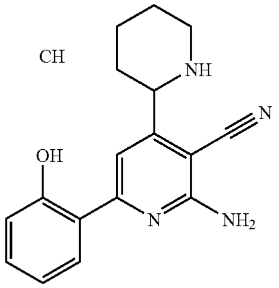 | 330.82 | 295 | B | B | (300MHz, DMSO-d6): 1.67–2.05 6H, m), 3.19–3.26(1H, m), 3.42–3.51(1H, m), 4.30–4.33(1H, m), 6.91–6.95(2H, m), 7.35–7.40(1H, m), 7.65(1H, br s), 8.07(1H, s), 8.18 1H, d, J=7.3 Hz), 9.41–9.45(1H, m), 10.27–10.30(1H, m). |
| 1-15 | 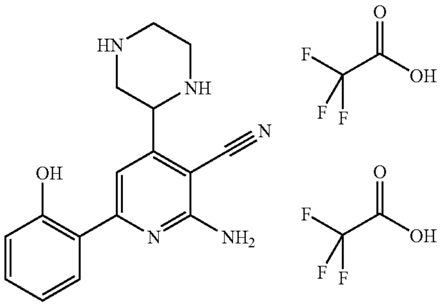 | 523.40 | 296 | B | B | (300MHz, DMSO-d6): 3.00(3H, m), 3.69(3H, m), 4.06(1H, m), 4.55(1H, d, J=3.7 Hz), 5.14(1H, dd, J=4.0, 11.7 Hz), 6.95(2H, m), 7.38(1H, t, J=8.3 Hz), 7.81(3H, m), 7.98(1H, d, J=8.3 Hz), 9.40(3H, br), 13.5 Hz, 1H, s). |
| 1-16 | 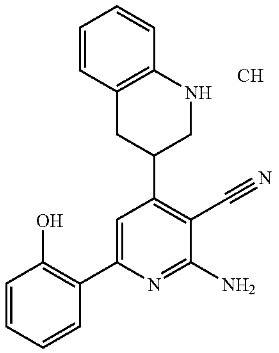 | 378.86 | 343 | D | | (500MHz, DMSO-d6): 2.89(1H, d, J=14.8Hz), 2.92–3.19(2H, m), 3.38–3.41(2H, m), 6.54(1H, m), 6.59 1H, d, J=7.9Hz), 6.84–6.90(2H, m), 6.94–6.97(2H, m), 7.30–7.37 4H, m), 7.96(1H, d, J=8.2Hz), 13.45(1H, br). |

TABLE 1-continued

| Ex. No | Structure | Mol weight | Mass | in vitro | A549 | NMR |
|---|---|---|---|---|---|---|
| 1-17 | 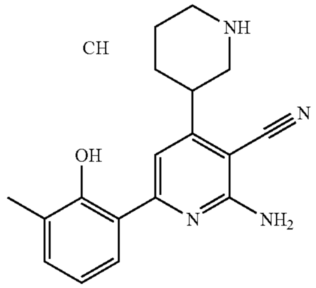 | 344.85 | 309 | B | B | (300MHz, DMSO-d6): 1.78–1.96 4H, m), 2.20(3H, s), 2.87–2.93(1H, m), 3.23–3.43(4H, m), 6.32(0.7H, br s), 6.82(1H, t, J=7.5Hz), 7.25 1H, d, J=7.2Hz), 7.42(3H, br s), 7.91(1H, d, J=8.3Hz), 13.88(1H, br s). |
| 1-18 | 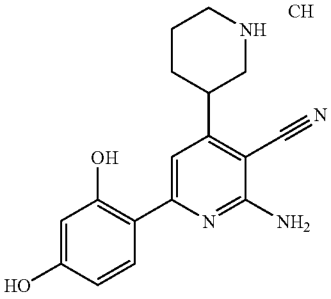 | 346.82 | 311 | B | B | (300MHz, DMSO-d6): 1.76–1.95(4H, m), 2.89(1H, m), 3.22(1H, m), 3.31–3.39(3H, m), 6.26(1H, d, J=2.3Hz), 6.36(1H, dd, J=2.3, 8.7 Hz), 7.24(1H, s), 7.31(1H, br s), 7.87(1H, d, J=8.7Hz), 8.77(1H, br s), 9.36(1H, br s). |
| 1-19 | 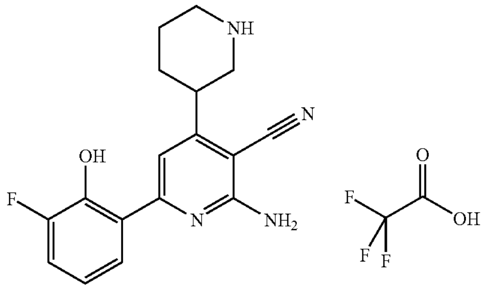 | 426.37 | 313 | A | A | (500MHz, DMSO-d6): 1.76–1.97 4H, m), 2.88–2.90(1H, m), 3.22–3.27(4H, m), 6.88–6.94(1H, m), 7.30–7.35(1H, m), 7.44(1H, s), 7.55(2H, br s), 7.88(1H, d, J=8.5 Hz), 8.60(1H, br s), 8.99(1H, br s), 13.83(1H, br s). |
| 1-20 | 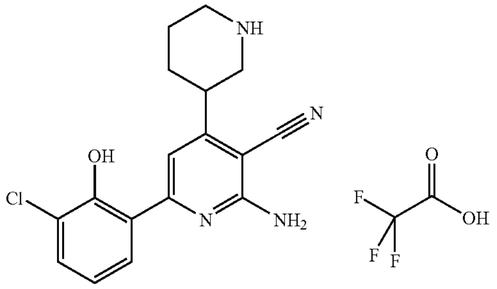 | 442.83 | 329 | A | A | (500MHz, DMSO-d6): 1.74–1.97 4H, m), 2.86–2.92(1H, m), 3.23–3.45(4H, m), 6.94(1H, t, J=7.8Hz), 7.47(1H, br s), 7.55(1H, dd, J=7.6, 1.4Hz), 7.59(2H, br s), 8.07(1H, dd, 8.5, 1.4Hz), 8.60(1H, br s), 8.99 1H, br s), 14.58(1H, br s). |
| 1-21 | 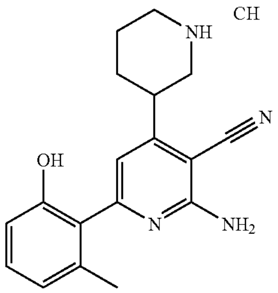 | 344.85 | 309 | C | B | (500MHz, DMSO-d6): 1.79–1.95 4H, m), 2.20(3H, s), 2.90(1H, dd, J=10.4, 11.3Hz), 3.23–3.42(4H, m), 6.82(1H, t, J=7.6Hz), 7.26(1H, d, J=7.6Hz), 7.43(2H, br s), 7.43(1H, s), 7.91(1H, d, J=7.6Hz), 8.86(1H, br), 9.51(1H, br), 13.91(1H, br). |

TABLE 1-continued
| Ex. No | Structure | Mol weight | Mass | in vitro | A549 | NMR |
|---|---|---|---|---|---|---|
| 1-22 | 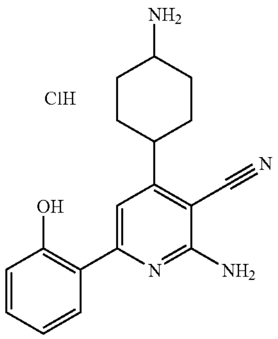 | 344.85 | 309 | A | A | (300MHz, DMSO-d6): 1.40–2.20 8H, m), 2.60–2.88(1H, m), 3.10 and 3.48(1H, br s), 6.75–6.95(2H, m), 7.00–7.85(3H, m), 7.85–8.25 1H, m), 8.14(1H, br s), 8.37(1H, br s). |
| 1-23 | 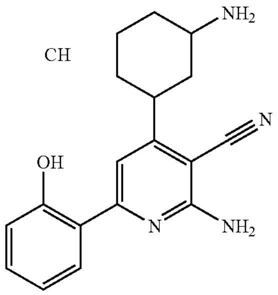 | 344.85 | 309 | A | A | (300MHz, DMSO-d6): 1.27–2.17 8H, m), 2.75–3.00(1H, m), 3.19 1H, br s), 6.70–7.00(2H, m), 7.00–7.80(3H, m), 7.80–8.40(3H, m). |
| 1-24 | 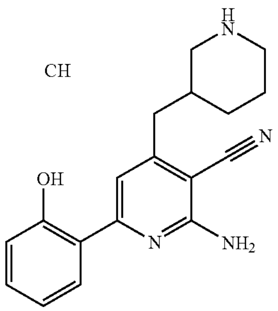 | 344.85 | 309 | A | B | (500MHz, DMSO-d6): 1.25–1.38 1H, m), 1.58–1.70(1H, m), 1.72–1.84(2H, m), 2.15–2.25(1H, m), 2.60–2.85(4H, m), 3.10–3.22(2H, m), 6.88–6.94(2H, m), 7.34(1H, t, J=7.7Hz), 7.38(1H, s), 7.45(2H, br), 7.95(1H, d, J=8.5Hz), 8.70(1H, br), 9.05(1H, br). |
| 1-25 | 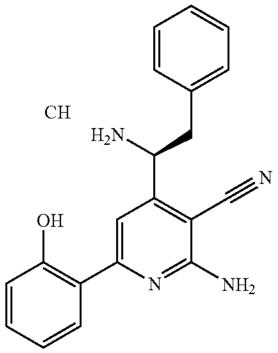 | 366.85 | 331 | A | B | (300MHz, DMSO-d6): 3.20(1H, dd, J=9.5, 13.2Hz), 3.22(1H, dd, J=5.7, 13.2Hz), 4.54(1H, br), 6.90–6.95 2H, m), 7.10–7.13(2H, m), 7.22–7.51(7H, m), 8.09(1H, s), 8.12(1H, d, J=7.9Hz), 9.00(3H, br). |

TABLE 1-continued
| Ex. No | Structure | Mol weight | Mass | in vitro | A549 | NMR |
|---|---|---|---|---|---|---|
| 1-26 | 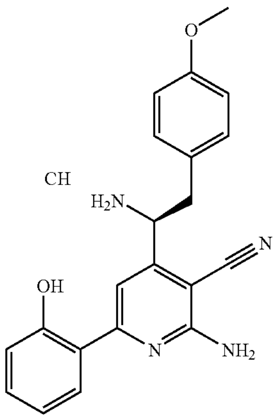 | 396.88 | 361 | A | B | (500MHz, DMSO-d6): 3.11–3.24 1H, m), 3.27–3.45(1H, m), 3.68 3H, s), 5.24(1H, br s), 6.79(2H, d, J=8.8Hz), 6.88–6.99(2H, m), 7.08 2H, d, J=8.8Hz), 7.33–7.41(3H, m), 7.63(1H, s), 8.00(1H, dd, J=1.3, 8.2Hz), 10.14(1H, s). |
| 1-27 | 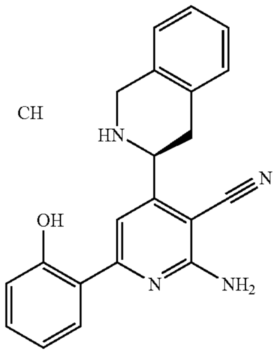 | 378.86 | 343 | C | | (300MHz, DMSO-d6): 2.77–2.86 1H, m), 4.82(1H, d, J=17.4Hz), 5.08(1H, dd, J=4.2, 11.9Hz), 5.20 1H, d, J=17.4Hz), 6.93–7.00(2H, m), 7.28–7.51(4H, m)7.83(1H, s), 7.94(1H, br s), 8.07(1H, dd, J=7.2, 14.9Hz), 9.53(1H, s). |
| 1-28 | 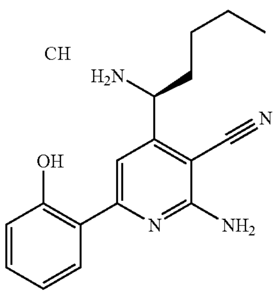 | 332.84 | 297 | A | C | (300MHz, DMSO-d6): 0.85(3H, t, J=6.7Hz), 1.17–1.30(4H, m), 1.88–1.94(1H, m), 1.97–2.12(1H, m), 4.29(1H, br s), 6.93(2H, t, J=6.5 Hz), 7.37(1H, t, J=7.6Hz), 7.60 1H, br s), 7.92(1H, s), 8.07(1H, dd, J=7.8, 14.5Hz), 8.99(2H, s). |
| 1-29 | 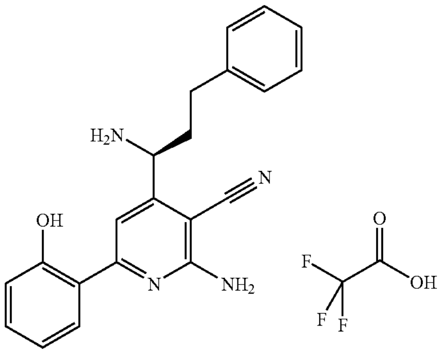 | 458.44 | 345 | B | C | (300MHz, DMSO-d6): 2.08(1H, m), 5.03(1H, dd, J=4.1, 6.8Hz), 6.92 2H, m), 7.15–7.39(6H, m), 7.70 3H, d, J=5.6Hz), 8.06(1H, dd, J=1.3, 8.3Hz), 8.87(1H, br), 9.25(1H, m), 10.34(1H, m), 13.69(1H, s). |

TABLE 1-continued
| Ex. No | Structure | Mol weight | Mass | in vitro | A549 | NMR |
|---|---|---|---|---|---|---|
| 1-30 | 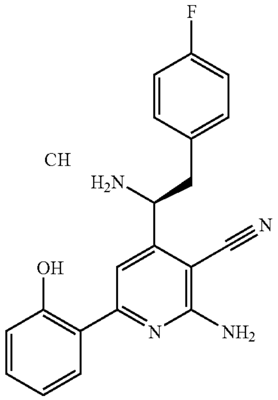 | 384.84 | 349 | A | B | (300MHz, DMSO-d6): 3.15–3.23 1H, m), 3.47–3.53(1H, m), 4.47–4.51(1H, m), 6.91–6.98(2H, m), 7.06–7.20(4H, m), 7.35–7.48(1H, m), 8.11(1H, s), 8.13–8.17(1H, m), 9.10(2H, br s). |
| 1-31 | 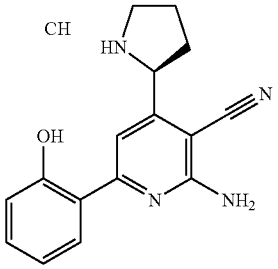 | 316.79 | 281 | B | B | (300MHz, DMSO-d6): 1.34–1.53 1H, m), 2.30–2.47(3H, m), 3.40–3.67(2H, m), 5.03–5.14(1H, m), 6.82–7.00(2H, m), 7.28–7.44(1H, m), 7.65(1H, s), 7.97(1H, d, J=8.2 Hz), 8.10(3H, br), 9.85(1H, br s), 10.02(1H, br s). |
| 1-32 | 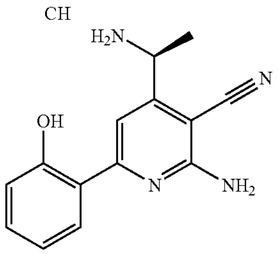 | 290.75 | 255 | A | B | (300MHz, DMSO-d6): 1.58(3H, d, J=6.9Hz), 4.45(1H, m), 6.91–6.96 2H, m), 7.34–7.40(1H, m), 7.90 1H, s), 8.06(1H, d, J=8.0Hz), 8.94 1H, br s). |
| 1-33 | 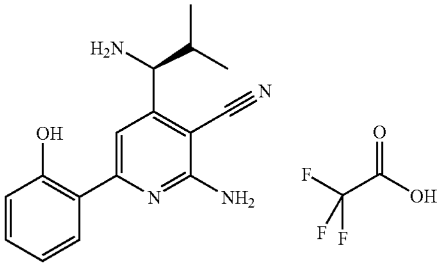 | 396.37 | 283 | A | B | (300MHz, DMSO-d6): 0.64(3H, d, J=6.8Hz), 1.08(3H, d, J=6.9Hz), 4.96(1H, s), 6.90–6.95(2H, m), 7.36(1H, t, J=8.4Hz), 7.61(1H, s), 7.72(2H, br s), 8.05(1H, d, J=7.0 Hz), 10.21(1H, s), 13.65(1H, s). |

TABLE 1-continued
| Ex. No | Structure | Mol weight | Mass | in vitro | A549 | NMR |
|---|---|---|---|---|---|---|
| 1-34 | 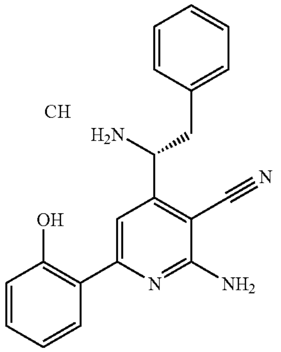 | 366.85 | 331 | A | B | (300MHz, DMSO-d6): 3.18(1H, dd, J=9.4, 13.2Hz), 3.21(1H, dd, J=5.7, 13.2Hz), 4.54(1H, br), 6.91–6.99(2H, m), 7.10–7.13(2H, m), 7.22–7.29(4H, m), 7.35–7.55(3H, m), 8.06(1H, s), 8.12(1H, d, J=7.9 Hz), 9.02(3H, br). |
| 1-35 | 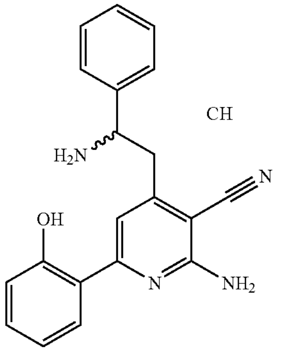 | 366.85 | no peak | A | B | (300MHz, DMSO-d6): 3.26–3.34 1H, m), 3.48–3.57(1H, m), 4.02–4.80(1H, m), 6.87–6.93(2H, m), 7.30–7.43(1H., m), 7.53(2H, d, J=6.4Hz), 7.89(1H, d, J=8.8Hz), 8.79(2H, br s). |
| 1-36 | 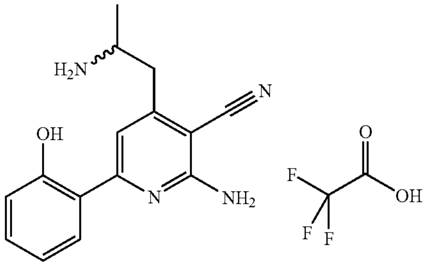 | 382.35 | 269 | A | B | (300MHz, DMSO-d6): 1.21(3H, d, J=6.4Hz), 2.88–3.08(2H, m), 3.73 1H, br s), 6.89(1H, s), 6.92(1H, br s), 7.35(2H, t, J=6.8Hz), 7.43(1H, br s), 7.95(3H, br s), 13.36(1H, s). |
| 1-37 | 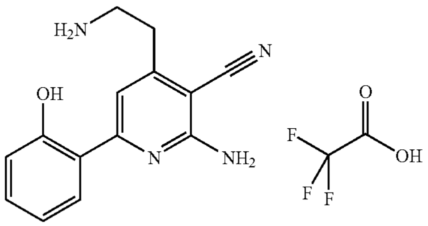 | 368.32 | 255 | A | A | (500MHz, DMSO-d6): 3.03(2H, t, J=7.5Hz), 3.23(2H, t, J=7.7Hz), 6.89–6.99(2H, m), 7.35(2H, t, J=7.1Hz), 7.41(2H, br s), 7.88–7.98 4H, m), 13.38 1H, s). |

TABLE 1-continued
| Ex. No | Structure | Mol weight | Mass | in vi-tro | A549 | NMR |
|---|---|---|---|---|---|---|
| 1-38 | 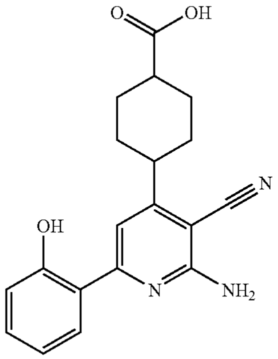 | 337.38 | 338 | A | B | (500MHz, DMSO-d6): 1.47(2H, dq, J=3.0, 12.8Hz), 1.72(2H, dq, J=3.0, 12.8Hz), 1.84(2H, dd, J=3.0, 12.8Hz), 2.05(2H, dd, J=3.0, 12.8 Hz), 2.33(2H, tt, J=3.3, 12.3Hz), 2.73(2H, tt, J=3.2, 12.0Hz), 6.86–6.93(2H, m), 7.23–7.38(4H, m), 8.04(1H, d, J=7.9Hz), 12.14(1H, br s), 13.51(1H, br s). |
| 1-39 | 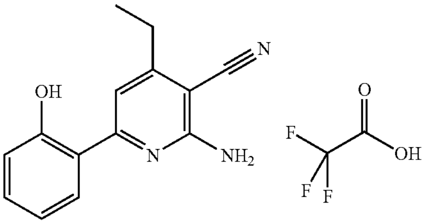 | 353.30 | | C | C | |
| 1-40 | 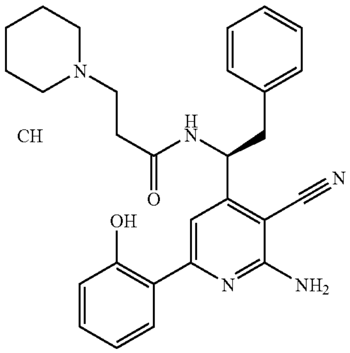 | 506.05 | 470 | B | B | (300MHz, DMSO-d6): 1.25(1H, br), 1.60(5H, br m), 2.69–2.80(4H, m), 3.04(2H, d, J=7.5Hz), 3.12–3.20 2H, m), 5.19(1H, dd, J=7.4, 15.4 Hz), 6.91–6.97(2H, m), 7.21–7.45 8H, m), 7.56(1H, s), 7.96–7.99 1H, m), 9.14(1H, d, J=8.1Hz), 9.58(1H, br), 13.33(1H, br s). |
| 1-41 | 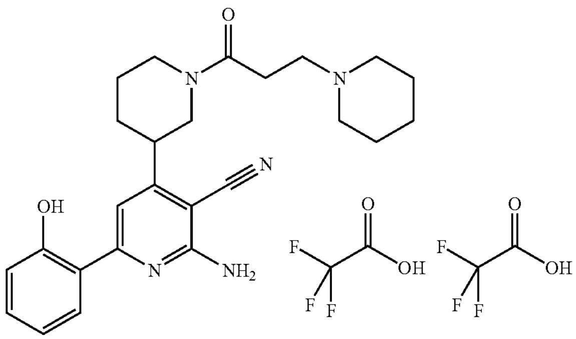 | 661.61 | | B | B | |

TABLE 1-continued

| Ex. No | Structure | Mol weight | Mass | in vitro | A549 | NMR |
|---|---|---|---|---|---|---|
| 1-42 | 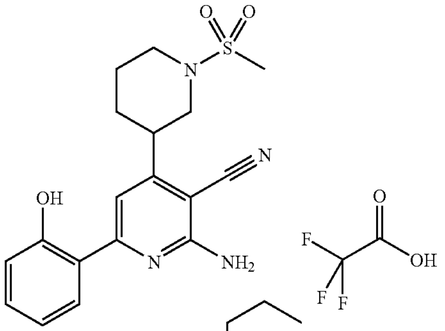 | 486.47 | 373 | C | B | (300MHz, DMSO-d6): 1.85(4H, m), 3.00(5H, m), 3.62(3H, d, J=11.2 Hz), 6.90(2H, m), 7.37(3H, m), 8.02(1H, dd, J=1.4, 8.4Hz), 13.4 1H, s). |
| 1-43 | 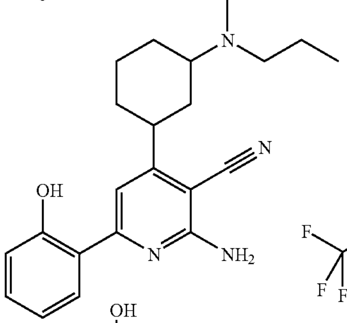 | 506.57 | 393 | A | A | (500MHz, DMSO-d6): 0.93(6H, m), 1.68(8H, m), 2.01(4H, m), 3.00(5H, m), 6.92(2H, m), 7.35(4H, m), 8.02 1H, d, J=13.2Hz), 8.84(1H, br), 13.4(1H, s). |
| 1-44 | 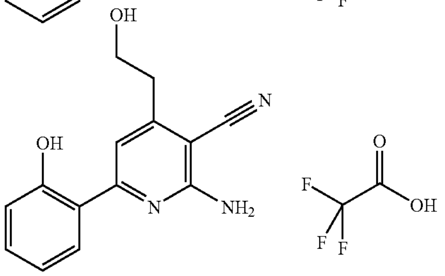 | 369.30 | 256 | B | B | (300MHz, DMSO-d6): 3.18(2H, t, J=6.2Hz), 4.76(2H, t, J=6.2Hz), 6.90(2H, m), 7.23–7.82(4H, m), 7.95 1H, dd, J=1.6, 8.4Hz), 13.39(1H, s). |

Example 2-1

(1) With the use of starting compound 1E instead of 1A, tert-butyl 3-{2-amino-6-[2,6-bis(benzyloxy)phenyl]-3-cyano-4-pyridinyl}-1-piperidinecarboxylate (3.54 g, yield; 30%) was prepared in a similar manner as described in step (1) in Example 1-1.

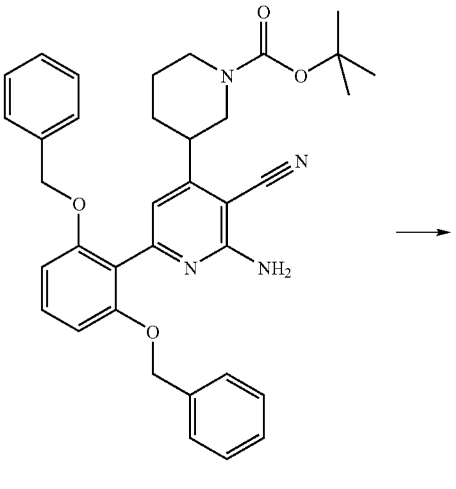

-continued

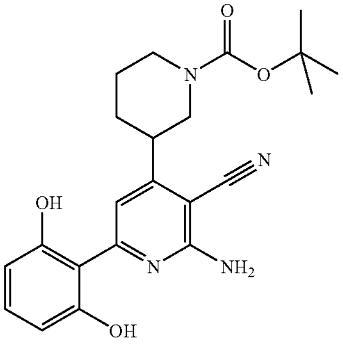

(2) A suspension of tert-butyl 3-{2-amino-6-[2,6-bis(benzyloxy)phenyl]-3-cyano-4-pyridinyl}-1-piperidinecarboxylate (3.46 g, 5.9 mmol) and Pd/C (10%, 600 mg) in ethyl acetate (50 mL) including acetic acid (5 mL) was stirred for 2 days at room temperature under a hydrogen atmosphere. The reaction mixture was diluted with THF (200 mL) and filtered through Celite®. The filtrate was concentrated under reduced pressure. The residue was washed with ethyl acetate and hexane, and dried under reduced pressure to give tert-butyl 3-[2-amino-3-cyano-6-(2,6-dihydroxy-phenyl)-4-pyridinyl]-1-piperidinecarboxylate (1.82 g, yield; 76%).

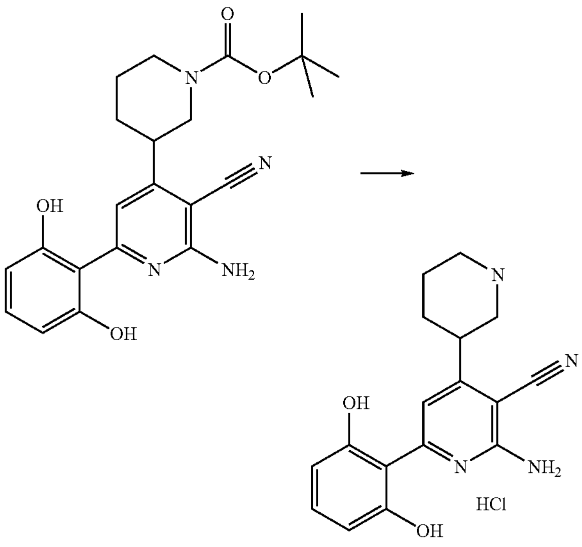

(3) tert-butyl 3-[2-amino-3-cyano-6-(2,6-dihydroxyphenyl)-4-pyridinyl]-1-piperidine-carboxylate (200 mg, 0.49 mmol) was treated under acidic conditions in a similar manner as described in the step (3) of Example 1-1. The resulting precipitate was collected by filtration, washed with ethyl acetate and hexane, and dried under reduced pressure to give 2-amino-6-(2,6-dihydroxyphenyl)-4-(3-piperidinyl) nicotinonitrile hydrochloride (123 mg, yield; 73%).

Molecular weight: 346.82

Mass spectrometry: 311 $(M+H)^+$

In vitro activity grade: A

Cellular activity grade: (A549)-A $^1$H-NMR (500 MHz, DMSO-d6): 1.66–1.99 (5H, m), 2.91–3.20 (2H, m), 3.23–3.42 (3H, m), 6.41 (2H, d, J=7.9 Hz), 7.08 (1H, t, J=7.9 Hz), 7.28 (2H, br d), 7.65 (1H, s), 8.82 (1H, br d), 9.17 (1H, br d).

Example 2-2

A suspension of tert-butyl 3-[2-amino-3-cyano-6-(2,6-dihydroxyphenyl)-4-pyridinyl]-1-piperidinecarboxylate (300 mg, 0.73 mmol) obtained in the step (2) of Example 2-1, benzyl bromide (0.1 mL, 0.80 mmol) and potassium carbonate (303 mg, 2.19 mmol) in a solution of acetone (15 mL) and THF (15 mL) was stirred for 2 days at room temperature. The reaction mixture was concentrated under reduced pressure, then dissolved in ethyl acetate (100 mL) and water (100 mL). The separated aqueous phase was extracted with ethyl acetate (100 mL×2). The combined organic phase was washed with brine (100 mL), dried over $Na_2SO_4$, filtered, and concentrated under reduced pressure. The crude product was purified by column chromatography on silica gel (hexane/ethyl acetate, 4:1-2:1-1:1) to give tert-butyl 3-{2-amino-6-[2-(benzyloxy)-6-hydroxyphenyl]-3-cyano-4-pyridinyl}-1-piperidinecarboxylate (239 mg, yield; 65%).

To a solution of tert-butyl 3-{2-amino-6-[2-(benzyloxy)-6-hydroxyphenyl]-3-cyano-4-pyridinyl}-1-piperidinecarboxylate (239 mg, 0.48 mmol) in dioxane (25 mL) was added 4N HCl/dioxane (25 mL). The reaction mixture was stirred at room temperature overnight. The resulting precipitate was collected by filtration, washed with ethyl acetate and hexane, dried under reduced pressure to give 2-amino-6-[2,-(benzyloxy)-6-hydroxyphenyl]-4-(3-piperidinyl)nicotinonitrile hydrochloride (184 mg, yield; 88%).

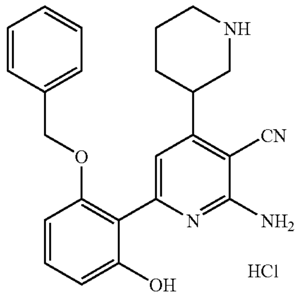

Molecular weight: 436.95

Mass spectrometry: 401 $(M+H)^+$

In vitro activity grade: A

Cellular activity grade: (A549)-A $^1$H-NMR (500 MHz, DMSO-d6): 1.07–1.14 (1H, m), 1.65–1.74 (3H, m), 2.57–2.73 (2H, m), 3.07–3.12 (1H, m), 3.17–3.23 (2H, m), 5.07 (1H, d, J=11.3 Hz), 5.12 (1H, d, J=11.3 Hz), 6.57 (1H, d, J=8.3 Hz), 6.73 (1H, d, J=8.3 Hz), 7.24–7.49 (8H, m), 8.72 (1H, br d), 9.01 (1H, br d), 12.54 (1H, s).

Example 2-3

With the use of the starting compound 1G instead of 1A and 4-formyl-piperidine-1-carboxylic acid tert-butyl ester prepared in a similar manner as that of the starting compound 2B, tert-butyl 4-(2-amino-3-cyano-6-{2-(cyclopropylmethoxy)-6-[(4-methoxybenzyl)oxy]phenyl}-4-pyridinyl)-1-piperidinecarboxylate was prepared in a similar manner as that of step (1) of Example 1-1.

To a stirred solution of tert-butyl 4-(2-amino-3-cyano-6-{2-(cyclopropylmethoxy)-6-[(4-methoxybenzyl)oxy]phenyl}-4-pyridinyl)-1-piperidinecarboxylate (0.63 g, 1.077 mmol) in 1,4-dioxane (25 mL) was added 4N HCl in 1,4-dioxane (25 mL). The mixture was stirred at room temperature for 12 hrs. The resulting solid was collected with filtration and washed with diisopropyl ether to give 2-amino-6-[2-(cyclopropylmethoxy)-6-hydroxyphenyl]-4-(3-piperidinyl)nicotinonitrile hydrochloride as a yellow solid (0.340 g, yield; 79%).

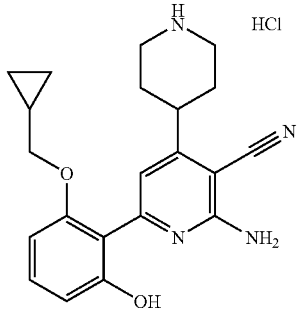

Molecular weight: 400.91
Mass spectrometry: 365 $(M+H)^+$
In vitro activity grade: A
Cellular activity grade: (A549)A $^1$H-NMR (500 MHz, DMSO-d6): 0.31–0.34 (2H, m), 0.55–0.59 (2H, m), 1.03–1.04 (1H, m), 1.91–1.99 (4H, m), 3.06–3.14 (3H, m), 3.37–3.39 (2H, m), 3.87 (2H, d, J=7.3 Hz), 6.55 (2H, dd, J=9.9, 8.2 Hz), 7.23 (1H, t, J=8.2 Hz), 9.19–9.11 (1H, m), 9.20–9.23 (1H, m).

Examples 2-4 to 2-87

According to the similar synthetic procedure of Examples 2-1 to 2-3, compounds shown in Tables 2 were prepared.

TABLE 2

| Ex. No | Structure | Mol weight | Mass | in vitro | A549 | NMR |
|---|---|---|---|---|---|---|
| 2-04 | 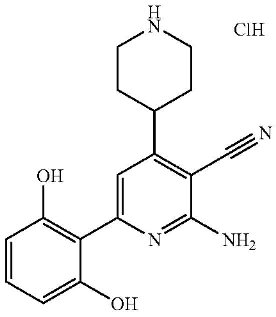 | 346.82 | 311 | | | (500MHz, DMSO-d6): 1.88–1.98(4H, m), 3.05–3.10(3H, m), 3.38–3.57(2H, m), 6.43(2H, d, J=8.2Hz), 7.09(1H, t, J=8.2Hz), 7.56–7.60(1H, br s), 7.60 1H, s), 8.94–9.01(2H, m). |
| 2-05 | 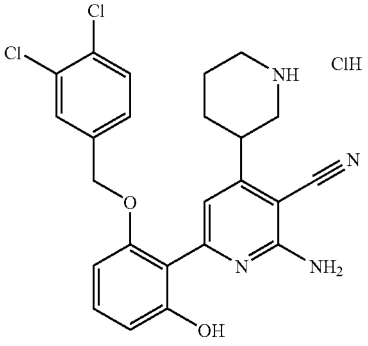 | 505.84 | 470 | A | B | (500MHz, DMSO-d6): 1.26(1H, br), 1.75 3H, m), 2.71(1H, br), 2.88(1H, br), 3.18 1H, br), 3.28(1H, br), 5.07(1H, d, J=11.7Hz), 5.12(1H, d, J=11.7Hz), 6.59 1H, m), 6.69(1H, d, J=8.5Hz), 7.15 1H, d, J=8.2Hz), 7.26(2H, m), 7.45 1H, dd, J=1.9, 8.2Hz), 7.69(1H, d, J=8.2Hz), 8.76(1H, br), 8.92(1H, br), 9.09 1H, br), 9.40(1H, br s). |
| 2-06 | 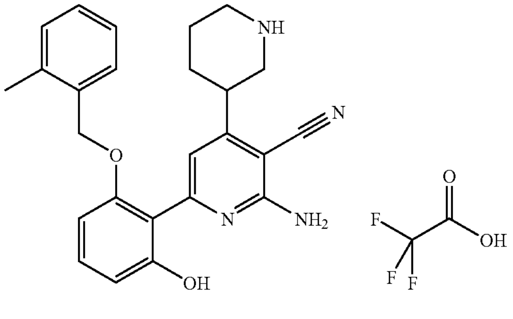 | 528.54 | 415 | A | B | (500MHz, DMSO-d6): 0.92(1H, ddd, J=3.5, 3.5, 12.3Hz), 1.58–1.72(3H, m), 2.27(3H, s), 2.30–2.70(3H, m), 3.06 1H, t, J=12.0Hz), 3.25(1H, m), 5.08 1H, d, J=11.0Hz), 5.13(1H, d, J=10.8 Hz), 6.56(1H, d, J=8.2Hz), 6.77(1H, d, J=8.2Hz), 7.23–7.31(6H, m), 7.43(1H, d, J=7.6Hz), 8.59(1H, br), 8.74(1H, br), 12.82(1H, br). |
| 2-07 | 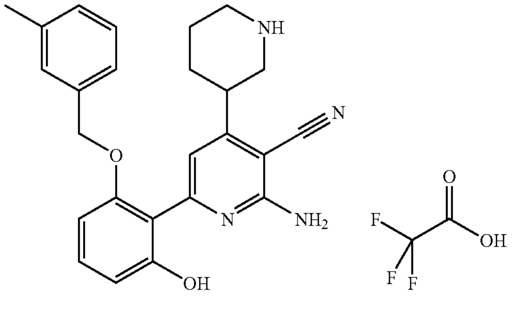 | 528.54 | 415 | A | B | (500MHz, DMSO-d6): 0.92(1H, ddd, J=3.8, 4.1, 12.6Hz), 1.58–1.72(3H, m), 2.27(3H, s), 2.30–2.70(3H, m), 3.07 1H, m), 3.25(1H, t, J=9.5Hz), 5.08 1H, d, J=10.7Hz), 5.13(1H, d, J=10.7 Hz), 6.56(1H, dd, J=1.0, 8.2Hz), 6.77 1H, d, J=8.2Hz), 7.23–7.31(6H, m), 7.43(1H, d, J=7.3Hz), 8.59(1H, br), 8.75(1H, br), 12.83(1H, br). |

TABLE 2-continued

| Ex. No | Structure | Mol weight | Mass | in vitro | A549 | NMR |
|---|---|---|---|---|---|---|
| 2-08 | 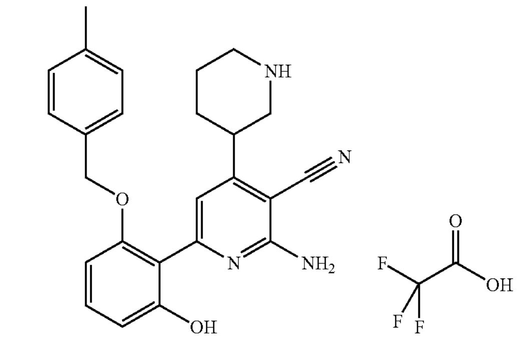 | 528.54 | 415 | A | A | (500MHz, DMSO-d6): 0.85(1H, m), 1.62–1.95(3H, m), 2.31(3H, s), 2.30–2.70 3H, m), 3.08(1H, m), 3.20–3.50(1H, m), 5.02(1H, d, J=10.7Hz), 5.07(1H, d, J=10.7Hz), 6.55(1H, dd, J=1.0, 8.2Hz), 6.72(1H, d, J=8.2Hz), 7.22–7.27(6H, m), 7.37(1H, d, J=7.9Hz), 8.58(1H, br), 8.76(1H, br), 12.68(1H, br). |
| 2-09 | 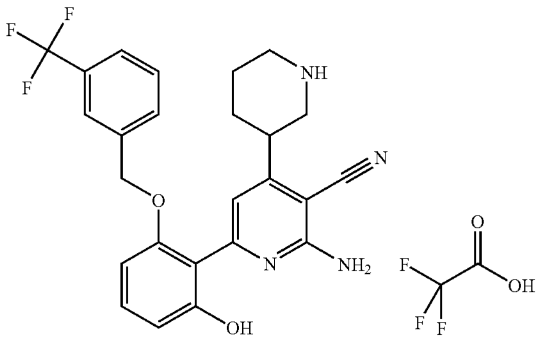 | 582.51 | 469 | A | B | (500MHz, DMSO-d6): 1.17–1.24(1H, m), 1.64–1.72(3H, m), 2.30–2.50(2H, m), 2.63–2.68(1H, m), 2.81(1H, br t, J=11.7Hz), 3.12(1H, m), 5.17(1H, d, J=11.7Hz), 5.22(1H, d, J=11.7Hz), 6.58 1H, d, J=8.2Hz), 6.71(1H, d, J=8.2 Hz), 7.11(1H, s), 7.17(2H, br s), 7.25 1H, t, J=8.2Hz), 7.64(1H, dd, J=7.9, 8.2Hz), 7.71(2H, m), 7.75(1H, d, J=7.9Hz), 8.60(1H, br), 8.80(1H, br), 11.9 1H, br). |
| 2-10 | 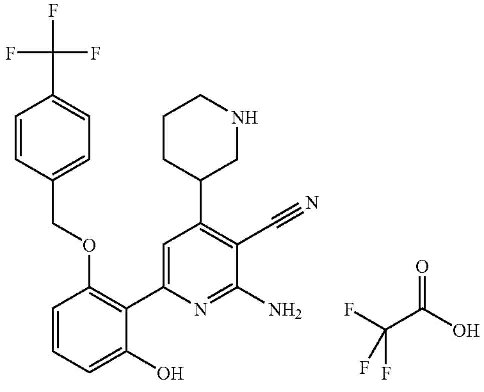 | 582.51 | 469 | A | B | (500MHz, DMSO-d6): 1.24–1.31(1H, m), 1.71(3H, m), 2.60(2H, m), 2.69(1H, m), 2.88(1H, br t, J=12.3Hz), 3.13(1H, m), 5.19(1H, d, J=12.3Hz), 5.24(1H, d, J=12.3Hz), 6.57(1H, d, J=8.2Hz), 6.70(1H, d, J=8.2Hz), 7.17(1H, s), 7.19(2H, br s), 7.24(1H, t, J=8.2Hz), 7.66(2H, d, J=7.9Hz), 7.77(2H, d, J=7.9Hz), 8.66(2H, br), 11.95(1H, s). |
| 2-11 | 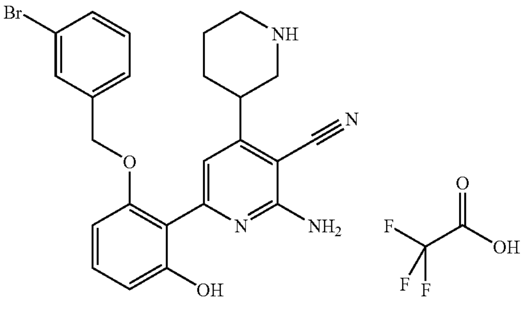 | 593.40 | no peak | A | B | (500MHz, DMSO-d6): 1.22(1H, m), 1.74 3H, m), 2.69–2.81(2H, m), 3.13(1H, t, J=12.3Hz), 5.07(1H, d, J=11.4Hz), 5.12(1H, d, J=11.4Hz), 6.57(1H, d, J=8.5Hz), 6.69(1H, d, J=8.5Hz), 7.16 1H, s), 7.19(2H, br s), 7.25(1H, t, J=8.5Hz), 7.37(1H, t, J=7.9Hz), 7.46 (1H, d, J=7.9Hz), 7.55(1H, d, J=7.9 Hz), 7.61(1H, br s), 8.59(1H, br s), 8.79 1H, br s), 12.10(1H, br). |

TABLE 2-continued

| Ex. No | Structure | Mol weight | Mass | in vitro | A549 | NMR |
|---|---|---|---|---|---|---|
| 2-12 | 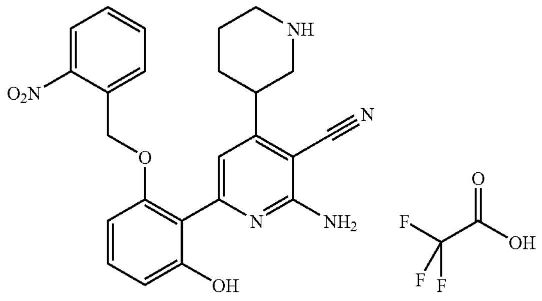 | 559.51 | 446 | A | B | (500MHz, DMSO-d6): 1.24(1H, m), 1.73 3H, m), 2.30–2.70(3H, m), 2.80(1H, m), 3.14(1H, m), 5.42(1H, d, 13.2 Hz), 5.46(1H, d, J=13.2Hz), 6.58(1H, d, J=8.2Hz), 6.67(1H, d, J=8.2Hz), 7.10(1H, s), 7.19(2H, br s), 7.24(1H, t, J=8.2Hz), 7.64(1H, dt, J=1.3, 8.2Hz), 7.71(1H, d, J=7.6Hz), 7.78(1H, d, J=7.6Hz), 8.11(2H, d, J=8.2Hz), 8.56 1H, br), 8.74(1H, br), 11.94(1H, br). |
| 2-13 | 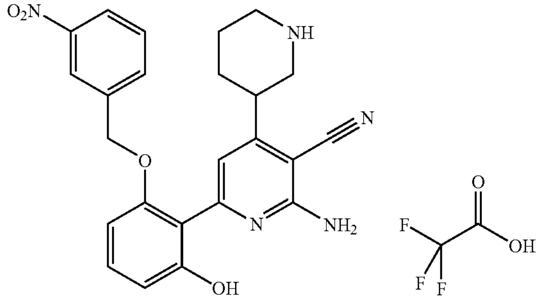 | 559.51 | 446 | A | B | (500MHz, DMSO-d6): 1.29(1H, m), 1.71 3H, m), 2.30–2.50(2H, m), 2.69(1H, m), 2.84(1H, dd, J=11.4, 11.6Hz), 3.14 1H, m), 5.23(1H, d, J=12.3Hz), 5.28 1H, d, J=12.3Hz), 6.59(1H, dd, J=1.0, 8.5Hz), 6.71(1H, d, J=8.5Hz), 7.12(1H, s), 7.16(2H, br s), 7.25(1H, t, J=8.5Hz), 7.71(1H, t, J=7.9Hz), 7.89 (1H, d, J=7.6Hz), 8.20(1H, dd, J=1.3, 8.2Hz), 8.24(1H, s), 8.58(1H, br), 8.82 1H, br). |
| 2-14 | 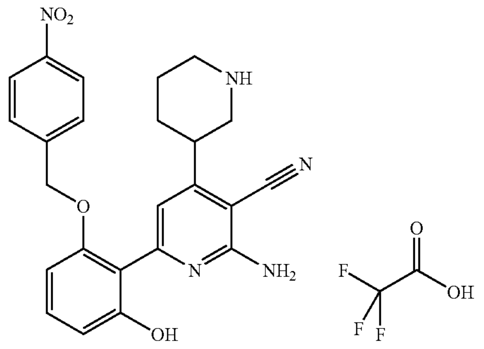 | 559.51 | 446 | A | A | (500MHz, DMSO-d6): 1.38(1H, m), 1.75 3H, m), 2.30–2.50(1H, m), 2.73(1H, dd, J=10.7, 12.0Hz), 2.88(1H, dd, J=10.7, 11.6Hz), 3.14(1H, m), 3.29(1H, m), 5.27(2H, dd, J=12.9, 16.1Hz), 6.58 1H, dd, J=1.0, 8.2Hz), 6.69(1H, d, J=8.5Hz), 7.13(1H, s), 7.19(2H, br s), 7.24(1H, t, J=8.2Hz), 7.69(1H, t, J=8.8Hz), 8.26(1H, d, J=8.8Hz), 8.54 1H, s), 8.79(1H, br), 11.8(1H, br). |
| 2-15 | 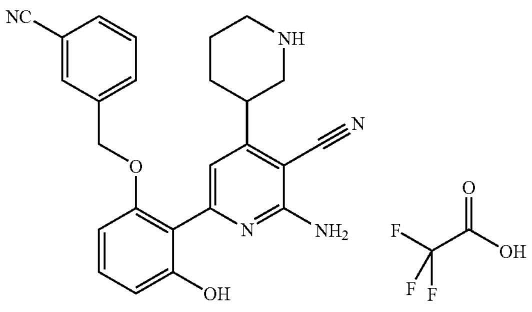 | 539.52 | 426 | A | A | (500MHz, DMSO-d6): 1.24(1H, m), 1.68–1.81(3H, m), 2.30–2.50(2H, m), 2.72 1H, dd, J=10.1, 12.3Hz), 2.82(1H, dd, J=10.4, 12.0Hz), 3.13(1H, m), 5.12 1H, d, J=11.7Hz), 5.18(1H, d, J=11.7 Hz), 6.58(1H, d, J=8.5Hz), 6.71(1H, d, J=8.5Hz), 7.13(1H, s), 7.18(2H, br s), 7.26(1H, t, J=8.5Hz), 7.62(1H, t, J=7.9Hz), 7.79(1H, d, J=7.9Hz), 7.84 1H, d, J=7.9Hz), 7.88(1H, s), 8.59 1H, br), 8.76(1H, br), 11.95(1H, br). |

TABLE 2-continued

| Ex. No | Structure | Mol weight | Mass | in vitro | A549 | NMR |
|---|---|---|---|---|---|---|
| 2-16 | 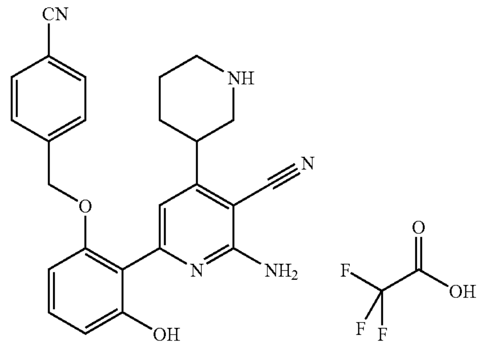 | 539.52 | 426 | A | A | (500MHz, DMSO-d6): 1.31(1H, m), 1.68–1.91(3H, m), 2.30–2.50(2H, m), 2.73 1H, m), 2.87(1H, dd, J=11.4, 12.3Hz), 3.14(1H, t, J=12.3Hz), 5.19(1H, d, J=12.6Hz), 5.22(1H, d, J=12.6Hz), 6.57 1H, d, J=8.2Hz), 6.68(1H, d, J=8.2 Hz), 7.13(1H, s), 7.18(2H, br s), 7.24 1H, t, J=8.2Hz), 7.62(1H, t, J=8.2 Hz), 7.88(1H, d, J=8.2Hz), 8.58(1H, br), 8.80(1H, br), 11.84(1H, br s). |
| 2-17 | 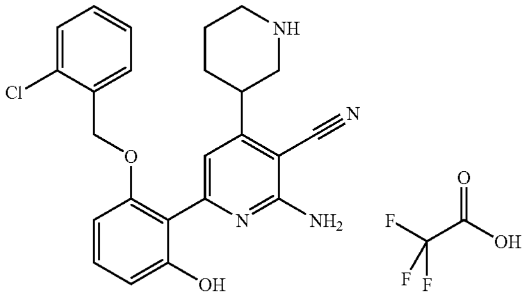 | 548.95 | 435 | A | B | (500MHz, DMSO-d6): 1.06(1H, m), 1.60–1.80(3H, m), 2.50–2.70(m, 4H), 3.10 1H, m), 5.13(1H, d, J=11.4Hz), 5.21 1H, d, J=11.4Hz), 6.58(1H, dd, J=0.9, 8.2Hz), 6.74(1H, d, J=8.2Hz), 7.21(1H, s), 7.24(2H, br), 7.28(1H, t, J=8.2Hz), 7.41(1H, dt, J=1.6, 7.3Hz), 7.44(1H, dt, J=1.9, 7.6Hz), 7.57(1H, dd, J=1.6, 7.9Hz), 7.61(1H, dd, J=1.9, 7.3Hz), 8.61(1H, br), 8.77(1H, br). |
| 2-18 | 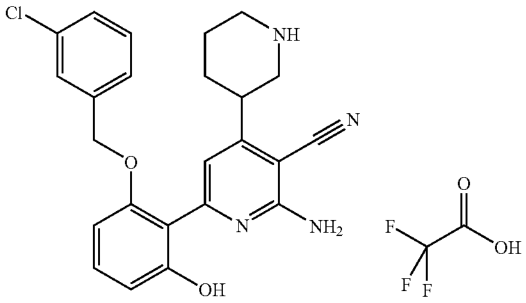 | 548.95 | 435 | A | B | (500MHz, DMSO-d6): 1.22(1H, m), 1.74 3H, m), 2.71(2H, m), 3.13(1H, t, J=12.3Hz), 5.08(1H, d, J=11.3Hz), 5.13 1H, d, J=11.3Hz), 6.57(1H, d, J=8.2 Hz), 6.70(1H, d, J=8.2Hz), 7.17(1H, s), 7.20(2H, br), 7.25(1H, t, J=8.2Hz), 7.42(3H, m), 7.48(1H, s), 8.62(1H, br), 8.82(1H, br). |
| 2-19 | 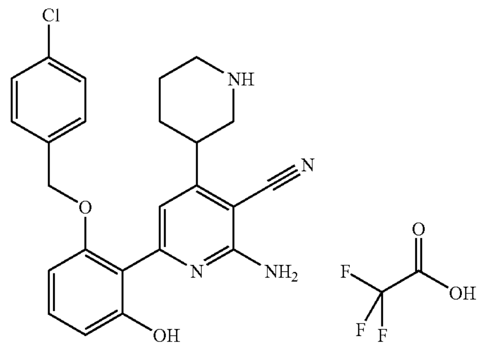 | 548.95 | 435 | A | A | (500MHz, DMSO-d6): 1.13(1H, m), 1.73 3H, m), 2.50–2.80(3H, m), 3.11(1H, t, J=12.3Hz), 5.07(1H, d, J=11.0Hz), 5.12(1H, d, J=11.0Hz), 6.56(1H, d, J=8.2Hz), 6.70(1H, d, J=8.2Hz), 7.19 1H, s), 7.21(2H, br), 7.25(1H, t, J=8.2 Hz), 7.49(4H, dt, J=2.5, 8.8Hz), 8.61 1H, br), 8.80(1H, br), 12.33(1H, br). |

TABLE 2-continued

| Ex. No | Structure | Mol weight | Mass | in vitro | A549 | NMR |
|---|---|---|---|---|---|---|
| 2-20 | 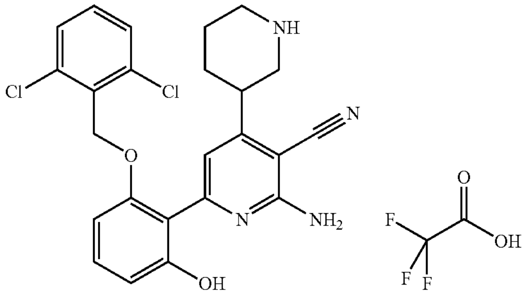 | 583.40 | 470 | A | B | (500MHz, DMSO-d6): 0.85(1H, m), 1.53 (1H, d, J=12.6), 1.69(2H, m), 3.07 1H, m), 5.24(1H, d, J=10.4Hz), 5.33 1H, d, J=12.6Hz), 1.69(2H, m), 3.07 1H, d, J=10.4Hz), 6.60(1H, dd, J= 0.9, 8.2Hz), 6.84(1H, d, J=8.5Hz), 7.14(1H, s), 7.29(2H, br), 7.32(1H, t, J= 8.2Hz), 7.51(4H, dd, J=7.6, 8.8Hz), 7.63(2H, d, J=7.9Hz), 8.64(1H, br), 8.77(1H, br), 12.95(1H, br). |
| 2-21 | 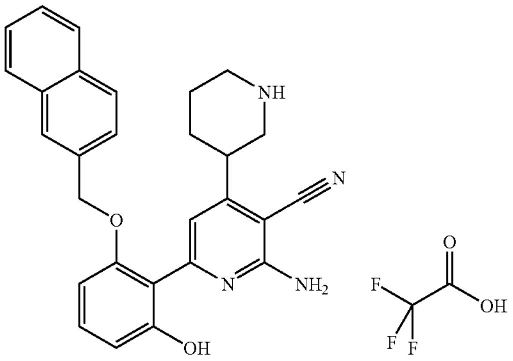 | 564.57 | 451 | A | A | (500MHz, DMSO-d6): 0.82(1H, m), 1.09 1H, m), 1.41(2H, m), 2.08(1H, m), 2.99 2H, m), 5.24(1H, d, J=10.7Hz), 5.30 1H, d, J=10.7Hz), 6.57(1H, dd, J= 1.0, 8.2Hz), 6.80(1H, d, J=8.2Hz), 7.23(2H, br), 7.26(1H, s), 7.29(1H, t, J= 8.2Hz), 7.55(2H, m), 7.62(1H, dd, J= 1.6, 8.2Hz), 7.95(3H, m), 8.03(1H, s), 8.55(1H, br), 12.65(1H, s). |
| 2-22 | 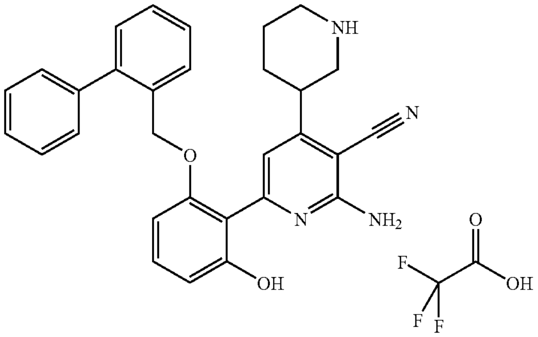 | 590.61 | 477 | A | B | (500MHz, DMSO-d6): 0.94(1H, m), 1.63 3H, m), 3.07(1H, t, J=11.4Hz), 4.90 1H, d, J=10.4Hz), 4.99(1H, d, J=10.4 Hz), 6.51(1H, d, J=8.2Hz), 6.53(1H, d, J=8.2Hz), 7.19(1H, t, J=8.2Hz), 7.26 2H, br), 7.35(6H, m), 7.48(2H, m), 7.66 1H, d, J=7.3Hz), 8.60(1H, br), 8.76 1H, br). |
| 2-23 | 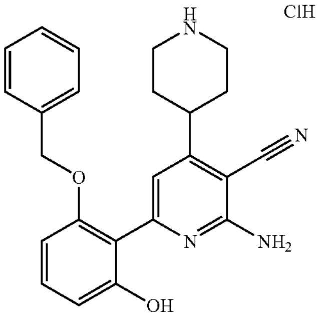 | 436.95 | 401 | A | B | (500MHz, DMSO-d6): 1.65–1.89(4H, m), 2.93–3.10(3H, m), 3.29(2H, d, J= 12.3Hz), 5.13(2H, s), 6.62(1H, d, J= 8.2Hz), 6.72(1H, d, J=8.2Hz), 7.13 1H, s), 7.28(1H, t, J=8.2Hz), 7.33(1H, t, J=7.4Hz), 7.40(2H, t, J=7.4Hz), 7.46(2H, t, J=7.4Hz), 7.72(2H, br), 9.10(1H, br s). |

TABLE 2-continued

| Ex. No | Structure | Mol weight | Mass | in vi-tro | A549 | NMR |
|---|---|---|---|---|---|---|
| 2-24 | 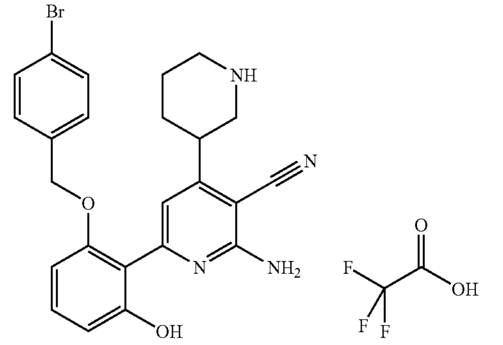 | 593.40 | 480 | A | A | (500MHz, DMSO-d6): 1.14(1H, m), 1.74 3H, m), 2.69(2H, m), 3.11(1H, t, J=12.0Hz), 5.05(1H, d, J=11.4Hz), 5.10 1H, d, J=11.4Hz), 6.56(1H, d, J=8.2 7.44(2H, d, J=8.2Hz), 7.61(2H, d, J=Hz), 6.70(1H, d, J=8.2Hz), 7.19(1H, s), 7.22(2H, br), 7.25(1H, t, J=8.2Hz), 7.44(2H, d, J=8.2Hz), 7.61(2H, d, J=8.2Hz), 8.60(1H, br), 8.81(1H, br), 12.36(1H, br). |
| 2-25 | 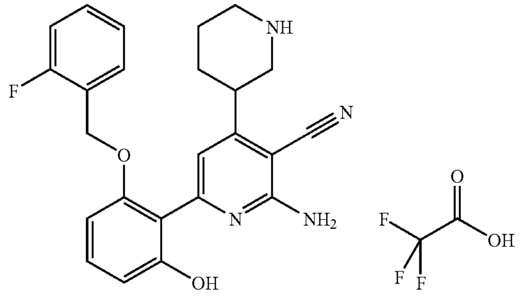 | 532.50 | 419 | A | A | (500MHz, DMSO-d6): 1.09(1H, m), 1.71 3H, m), 2.64(2H, m), 3.10(1H, t, J=12.3Hz), 3.28(2H, t, J=10.4Hz), 5.13 1H, d, J=11.0Hz), 5.18(1H, d, J=11.0 Hz), 6.58(1H, d, J=8.5Hz), 6.76(1H, d, J=8.5Hz), 7.20(1H, s), 7.26(4H, m), 7.47(1H, m), 7.58(1H, t, J=7.6Hz), 8.63(1H, br), 8.82(1H, br). |
| 2-26 | 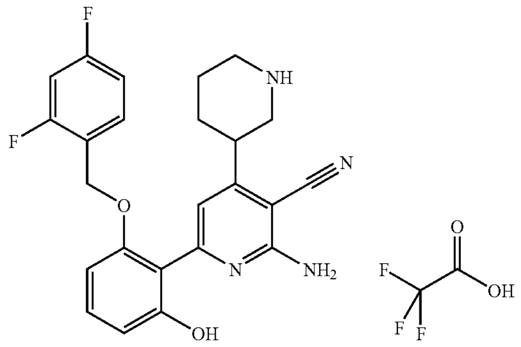 | 550.49 | | A | A | (500MHz, DMSO-d6): 1.09(1H, m), 1.71 3H, m), 2.64(2H, m), 3.10(1H, t, J=12.3Hz), 3.28(2H, t, J=10.4Hz), 5.13 1H, d, J=11.0Hz), 5.18(1H, d, J=11.0 Hz), 6.58(1H, d, J=8.5Hz), 6.76(1H, d, J=8.5Hz), 7.20(1H, s), 7.26(4H, m), 7.47(1H, m), 7.58(1H, t, J=7.6Hz), 8.63(1H, br), 8.82(1H, br). |
| 2-27 | 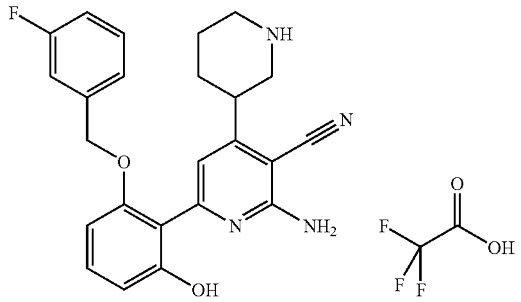 | 532.50 | 419 | A | A | (500MHz, DMSO-d6): 1.25(1H, m), 1.73 3H, m), 2.69(1H, dd, J=10.8, 11.7Hz), 2.78(1H, dd, J=11.7, 11.7Hz), 3.13 1H, t, J=12.3Hz), 5.08(1H, d, J=11.7 Hz), 5.14(1H, d, J=11.7Hz), 6.57(1H, d, J=8.2Hz), 6.70(1H, d, J=8.2Hz), 7.26(6H, m), 7.45(1H, m), 8.60(1H, br), 8.81(1H, br), 12.19(1H, br). |

TABLE 2-continued

| Ex. No | Structure | Mol weight | Mass | in vitro | A549 | NMR |
|---|---|---|---|---|---|---|
| 2-28 | 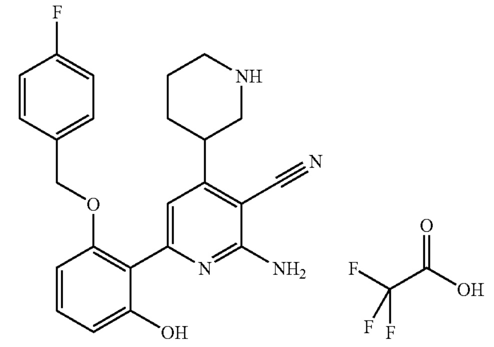 | 532.50 | 419 | A | A | (500MHz, DMSO-d6): 1.14(1H, m), 1.71 3H, m), 2.69(3H, m), 3.10(1H, t, J=12.3Hz), 5.06(1H, d, J=11.0Hz), 5.10 1H, d, J=11.0Hz), 6.56(1H, d, J=8.5 Hz), 6.72(1H, d, J=8.5Hz), 7.21(1H, s), 7.25(5H, m), 7.53(2H, dd, J=5.7, 8.5Hz), 8.59(1H, br), 8.81(1H, br). |
| 2-29 | 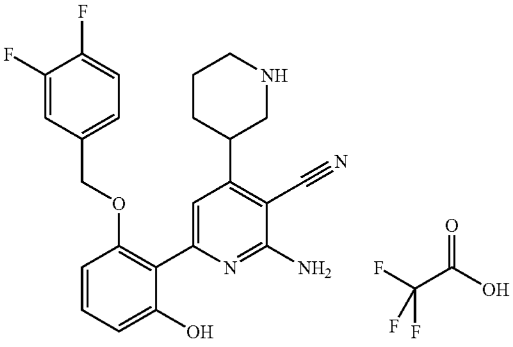 | 550.49 | 437 | A | B | (500MHz, DMSO-d6): 1.28(1H, m), 1.73 3H, m), 2.69(1H, m), 2.84(1H, dd, J=11.4, 11.4Hz), 3.13(1H, t, J=12.3Hz), 5.05(1H, d, J=11.4Hz), 5.10(1H, d, J=11.4Hz), 6.57(1H, d, J=8.2Hz), 6.69 1H, d, J=8.2Hz), 7.17(1H, s), 7.20 2H, br), 7.25(1H, t, J=8.2Hz), 7.33 1H, br), 7.50(2H, m), 8.60(1H, br), 8.82 1H, br), 12.07(1H, br). |
| 2-30 | 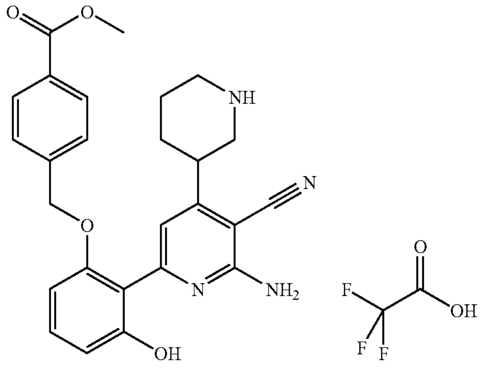 | 572.55 | 459 | A | A | (500MHz, DMSO-d6): 1.22(1H, m), 1.70 3H, m), 2.65(1H, m), 2.79(1H, dd, J=11.4, 11.4Hz), 3.12(1H, t, J=12.3Hz), 3.29(2H, br), 5.17(1H, d, J=12.0Hz), 5.22(1H, d, J=12.0Hz), 6.57(1H, d, J=8.2Hz), 6.69(1H, d, J=8.2Hz), 7.17 1H, s), 7.22(2H, br), 7.25(1H, t, J=8.2 Hz), 7.59(2H, d, J=8.2Hz), 7.99(2H, d, J=8.2Hz), 8.58(1H, br), 8.80(1H, br). |
| 2-31 | 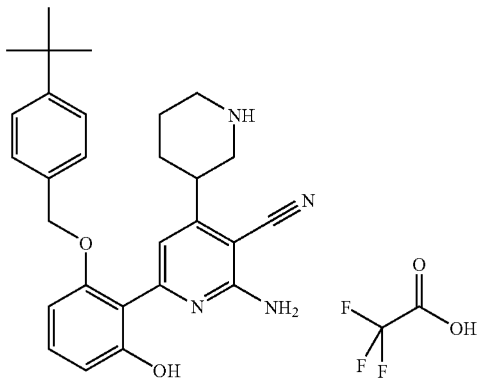 | 570.62 | 457 | A | A | (500MHz, DMSO-d6): 1.67–1.78(3H, m), 2.71(1H, dd, J=10.4, 11.4Hz), 2.89 1H, dd, J=11.4, 11.7Hz), 3.13(1H, t, J=12.3Hz), 5.04(1H, d, J=11.4Hz), 5.10(1H, d, J=11.4Hz), 6.55(1H, d, J=8.2Hz), 6.72(1H, d, J=8.2Hz), 7.22 2H, br s), 7.24(1H, t, J=8.2Hz), 7.27 1H, s), 7.37(2H, d, J=8.2Hz), 7.41 (2H, d, J=8.2Hz), 8.61(1H, br), 8.84 1H, br), 12.20(1H, br). |

TABLE 2-continued

| Ex. No | Structure | Mol weight | Mass | in vitro | A549 | NMR |
|---|---|---|---|---|---|---|
| 2-32 | 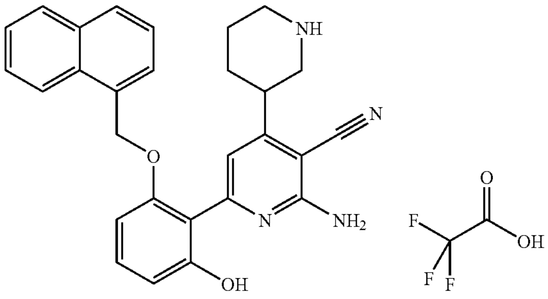 | 564.57 | 451 | A | B | (500MHz, DMSO-d6): 0.24(1H, m), 1.13 1H, d, J=13.9Hz), 1.42–1.52(2H, m), 2.04(1H, dd, J=11.0, 12.0Hz), 2.19 1H, dd, J=11.0, 12.0Hz), 2.87(1H, t, J=12.0Hz), 3.08(1H, d, J=11.4Hz), 3.15(1H, d, J=12.0Hz), 5.54(1H, d, J=11.0Hz), 5.59(1H, d, J=11.0Hz), 6.60 1H, d, J=8.2Hz), 6.95(1H, d, J=8.2 Hz), 7.10(1H, s), 7.23(2H, br s), 7.34 1H, t, J=8.2Hz), 7.56(3H, m), 7.71 1H, d, J=6.9Hz), 8.00(3H, m), 8.46 1H, br), 8.60(1H, br). |
| 2-33 | 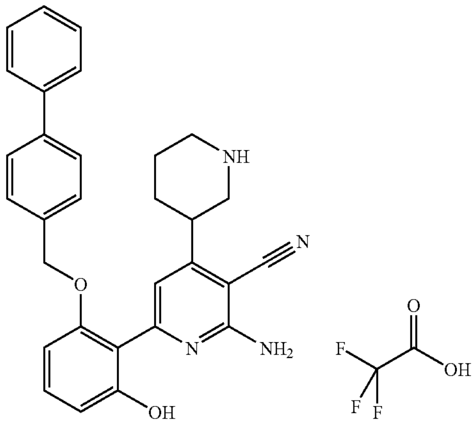 | 590.61 | 477 | A | B | (500MHz, DMSO-d6): 1.17(1H, m), 1.59–1.68(3H, m), 2.76(1H, dd, J=11.4, 11.7Hz), 3.07–3.17(3H, m), 5.13(1H, d, J=11.4Hz), 5.18(1H, d, J=11.4Hz), 6.57(1H, d, J=8.2Hz), 6.76(1H, d, J=8.2Hz), 7.24–7.94(4H, m), 7.39(1H, t, J=7.6Hz), 7.48(1H, t, J=7.6Hz), 7.56 2H, d, J=8.2Hz), 7.69(2H, d, J=7.9 Hz), 7.73(2H, d, J=7.9Hz), 8.55(1H, br d), 8.77(1H, br d), 12.47(1H, br). |
| 2-34 | 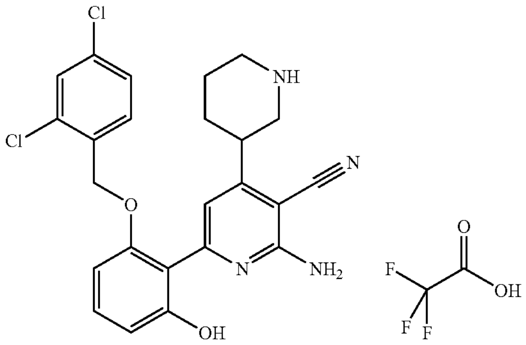 | 583.40 | 470 | A | B | (500MHz, DMSO-d6): 1.08(1H, m), 1.64–1.78(3H, m), 3.12(1H, t, J=12.3Hz), 3.32(2H, t, J=12.9Hz), 5.11(1H, d, J=11.4Hz), 5.20(1H, d, J=11.4Hz), 6.59 1H, d, J=8.2Hz), 6.73(1H, d, J=8.2 Hz), 7.16(1H, s), 7.25(2H, br), 7.27(1H, t, J=8.2Hz), 7.51(1H, dd, J=1.9, 8.2 Hz), 7.62(1H, d, J=8.2Hz), 7.76(1H, d, J=1.9Hz), 8.63(1H, br), 8.81(1H, br). |
| 2-35 | 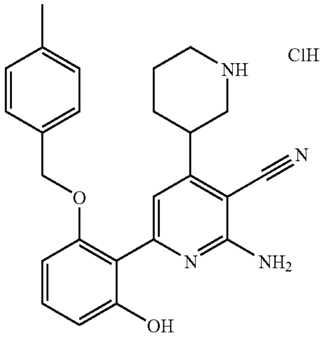 | 450.97 | 415 | A | A | (500MHz, DMSO-d6): 1.09(1H, m), 1.68 3H, m), 2.32(3H, s), 3.08–3.31(4H, m), 5.02(1H, d, J=10.6Hz), 5.07(1H, d, J=10.6Hz), 6.56(1H, d, J=8.3Hz), 6.72 1H, d, J=8.3Hz), 7.22–7.29(6H, m), 7.36(2H, d, J=7.5Hz), 8.79(1H, br), 9.16(1H, br). |

TABLE 2-continued

| Ex. No | Structure | Mol weight | Mass | in vitro | A549 | NMR |
|---|---|---|---|---|---|---|
| 2-36 | 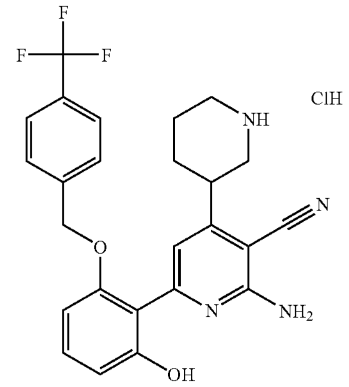 | 504.94 | 469 | A | A | (500MHz, DMSO-d6): 1.29(1H, m), 1.72 3H, m), 2.92(1H, m), 3.17–3.37(3H, m), 5.18(1H, d, J=12.4Hz), 5.24(1H, d, J=12.4Hz), 6.59(1H, dd, J=2.3, 8.3 Hz), 6.70(1H, d, J=8.3Hz), 7.18(1H, d, J=2.3Hz), 7.25(1H, dt, J=7.9, 8.3 Hz), 7.66(2H, d, J=8.3Hz), 7.78(2H, d, J=8.3Hz), 8.78(1H, br), 9.21(1H, br). |
| 2-37 | 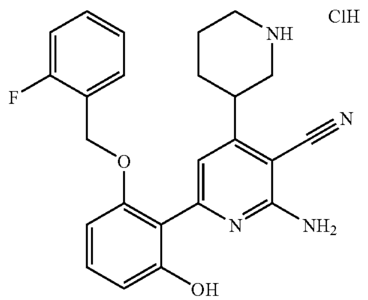 | 454.94 | 419 | A | A | (500MHz, DMSO-d6): 1.15–1.20(1H, m), 1.66–1.77(3H, m), 2.52–2.73(2H, m), 3.15–3.28(3H, m), 5.14(1H, d, J=11.0Hz), 5.18(1H, d, J=11.0Hz), 6.62 1H, d, J=8.2Hz), 6.78(1H, d, J=8.2 Hz), 7.20(1H, s), 7.26–7.33(3H, m), 7.46(2H, m), 7.58(2H, dt, J=1.6, 7.6 Hz), 9.00(1H, br d), 9.50(1H, br d). |
| 2-38 | 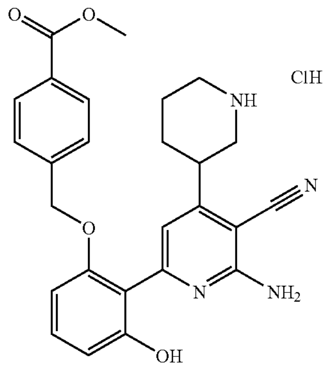 | 494.98 | 459 | A | A | (500MHz, DMSO-d6): 1.29(1H, m), 1.73 3H, m), 2.64(1H, m), 2.89(1H, dd, J=1.4, 12.7Hz), 3.24(3H, m), 3.86(3H, s), 5.17(1H, d, J=12.0Hz), 5.22(1H, d, J=12.0Hz), 6.62(1H, d, J=8.2Hz), 6.71 1H, d, J=8.5Hz), 7.20(1H, s), 7.27 1H, dd, J=8.2, 8.5Hz), 7.59(2H, d, J=8.2Hz), 7.99(2H, d, J=8.2Hz), 8.95 1H, br d), 9.41(1H, br d). |
| 2-39 | 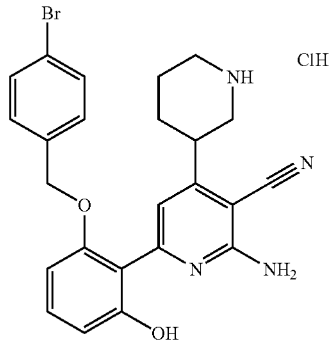 | 515.84 | 479 | A | A | (500MHz, DMSO-d6): 1.12(1H, m), 1.73 3H, m), 2.66(1H, m), 2.75(1H, t, J=12.3Hz), 3.13(1H, m), 5.05(1H, d, J=11.0Hz), 5.10(1H, d, J=11.0Hz), 6.56 1H, d, J=8.2Hz), 6.70(1H, d, J=8.2 Hz), 7.19(1H, s), 7.21(2H, br s), 7.25 1H, t, J=8.2Hz), 7.44(2H, d, J=8.5 Hz), 7.63(2H, d, J=8.5Hz), 9.03(2H, br), 12.37(1H, s). |

TABLE 2-continued

| Ex. No | Structure | Mol weight | Mass | in vitro | A549 | NMR |
|---|---|---|---|---|---|---|
| 2-40 | 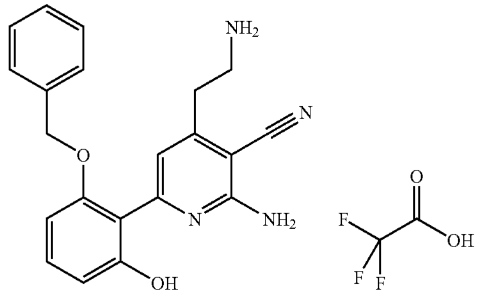 | 474.44 | 361 | A | A | (500MHz, DMSO-d6): 2.92(4H, br s), 5.15(2H, s), 6.55(1H, d, J=7.2Hz), 6.68(1H, d, J=8.5Hz), 7.22–7.25(3H, m), 7.30(1H, s), 7.33–7.35(1H, m), 7.40–7.45(4H, m), 7.95(1H, br s). |
| 2-41 | 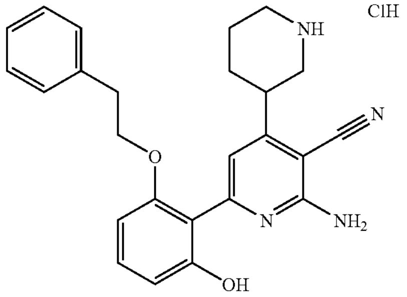 | 450.97 | 415 | A | A | (500MHz, DMSO-d6): 1.63(1H, m), 1.78–1.90(3H, m), 2.85(1H, m), 3.03(2H, dd, J=6.6, 6.9Hz), 3.12(1H, m), 3.26–3.36(3H, m), 4.20(2H, dd, J=6.6, 6.9 Hz), 6.62(1H, d, J=8.2Hz), 6.63(1H, d, J=8.5Hz), 7.18–7.24(5H, m), 7.23 1H, s), 7.26(1H, dd, J=8.2, 8.5Hz), 7.95(1H, br s), 9.11(1H, br s), 9.65(1H, br s). |
| 2-42 | 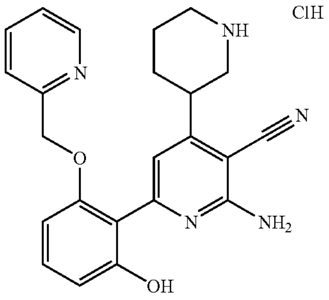 | 437.93 | 402 | A | B | (500MHz, DMSO-d6): 1.42–1.86(4H, m), 2.80–3.29(5H, m), 5.27–5.36(2H, m), 6.64(1H, d, J=8.2Hz), 6.72(1H, d, J=8.5Hz), 7.26–7.32(2H, m), 7.51–7.73(3H, m), 8.15–8.18(1H, t, J=7.5 Hz), 8.77–8.93(2H, m), 9.47(1H, br d, J=10.4Hz). |
| 2-43 | 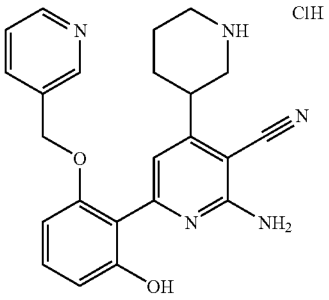 | 437.93 | 402 | A | A | (500MHz, DMSO-d6): 1.33–1.36(2H, m), 1.73–1.82(4H, m), 2.80–3.27(3H, m), 5.30(2H, s), 6.64(1H, d, J=8.2Hz), 6.74(1H, d, J=8.5Hz), 7.13(1H, s), 7.29(1H, t, J=8.2Hz), 7.48(1H, br s), 7.98(1H, m), 8.46(1H, d, J=7.6Hz), 8.84(1H, d, 5.4Hz), 8.89–8.91(1H, m), 8.95(1H, s), 9.45(1H, br d, J=10.1Hz). |
| 2-44 | 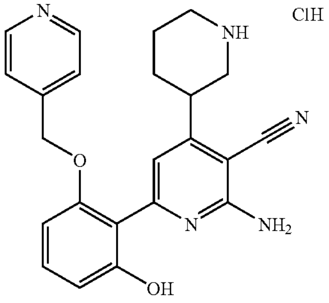 | 437.93 | 402 | A | A | (500MHz, DMSO-d6): 1.52–1.86(3H, m), 2.79–3.33(6H, m), 5.42(2H, s), 6.63(1H, d, J=8.2Hz), 6.65(1H, d, J=8.5Hz), 7.10(1H, s), 7.22–7.38(3H, m), 7.90(2H, d, J=5.7Hz), 8.82–8.89(3H, m), 9.42(1H, br d, J=10.4Hz). |

TABLE 2-continued
| Ex. No | Structure | Mol weight | Mass | in vitro | A549 | NMR |
| --- | --- | --- | --- | --- | --- | --- |
| 2-45 | 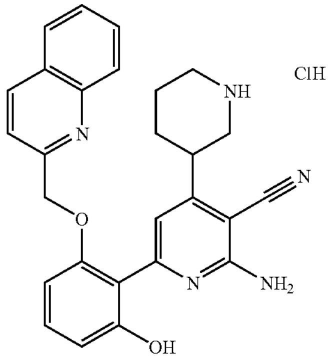 | 487.99 | 452 | A | A | (500MHz, DMSO-d6): 1.27–1.29(1H, m), 1.49–1.67(3H, m), 2.90–3.30(4H, m), 4.61(2H, br s), 5.41–5.42(2H, m), 6.63(1H, d, J=8.2Hz), 6.75(1H, d, J=8.5Hz), 7.25–7.29(2H, m), 7.66–7.71 2H, m), 7.85(1H, t, J=7.6Hz), 8.08 2H, t, J=9.3Hz), 8.57(1H, d, J=8.5 Hz), 8.81–8.83(1H, m), 9.29(1H, br d, J=9.8Hz). |
| 2-46 | 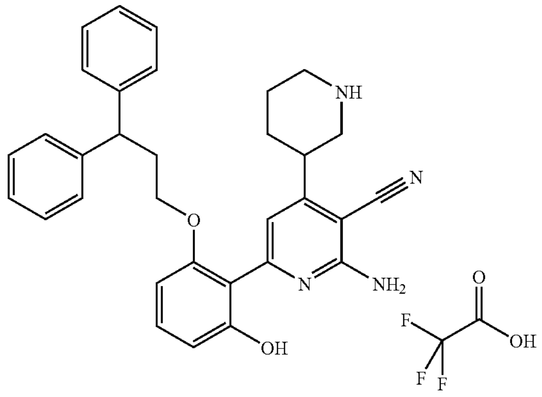 | 618.66 | 505 | A | B | (500MHz, DMSO-d6): 1.53–1.66(3H, m), 1.81(1H, m), 3.02(1H, m), 3.15–3.42(4H, m), 3.73–3.81(2H, m), 3.90–4.00(2H, m), 4.04(1H, m), 6.40(1H, d, J=8.2Hz), 6.51(1H, d, J=8.5Hz), 7.14 1H, dd, J=8.2, 8.5Hz), 7.19–7.28 10H, m), 7.36(1H, s), 8.60(1H, br s), 8.83(1H, br s). |
| 2-47 | 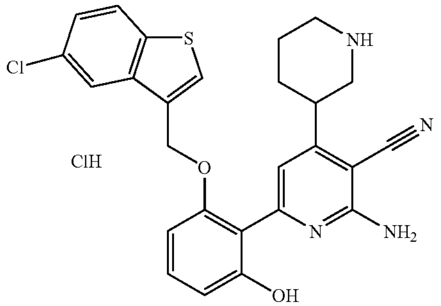 | 527.48 | 490 | A | B | (500MHz, DMSO-d6): 0.76–0.86(1H, m), 1.38(1H, br d, J=12.3Hz), 3.05 1H, t, J=10.4Hz), 3.81(2H, dd, J=12.0, 29.6Hz), 5.39(2H, dd, J=11.7, 40.0Hz), 6.60(1H, d, J=8.2Hz), 6.86 1H, d, J=8.5Hz), 7.15(1H, s), 7.29–7.44(4H, m), 7.79(1H, d, J=1.9Hz), 7.99(1H, s), 8.07(1H, d, J=8.8Hz), 8.70–8.80(1H, m), 9.07(1H, d, J=10.7 Hz). |
| 2-48 | 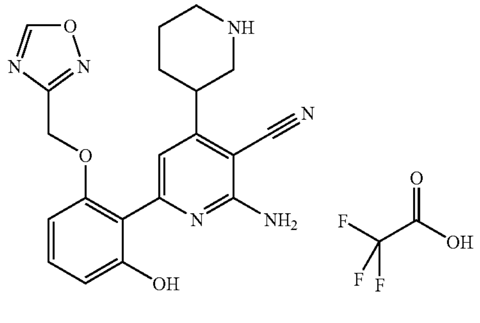 | 506.45 | 393 | A | A | (500MHz, DMSO-d6): 1.62–1.95(4H, m), 2.87–3.21(5H, m), 5.41(2H, s), 6.60(1H, d, J=8.2Hz), 6.76(1H, d, J=8.5Hz), 7.26–7.30(2H, m), 7.46(1H, s), 8.61–8.63(1H, m), 8.85(1H, br d, J=10.4Hz), 9.74(1H, s). |

TABLE 2-continued
| Ex. No | Structure | Mol weight | Mass | in vitro | A549 | NMR |
|---|---|---|---|---|---|---|
| 2-49 | 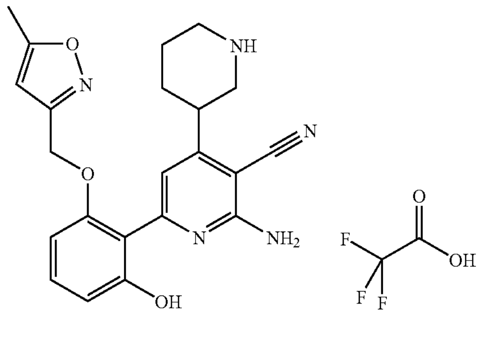 | 519.48 | 406 | A | A | (500MHz, DMSO-d6): 1.52–1.91(4H, m), 2.42(3H, s), 2.87–3.39(5H, m), 5.12–5.26(2H, m), 6.31(1H, s), 6.58 1H, d, J=8.2Hz), 6.71(1H, d, J=8.5 Hz), 7.24–7.28(3H, m), 7.36(1H, s), 8.63–8.65(1H, m), 8.90–8.93(1H, br d, J=10.4Hz). |
| 2-50 | 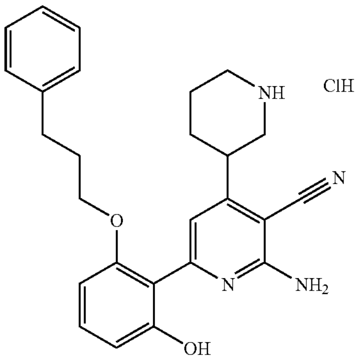 | 465.00 | 429 | A | A | (500MHz, DMSO-d6): 1.64–1.76(3H, m), 1.90(1H, m), 2.03–2.08(2H, m), 2.67(2H, t, J=7.6Hz), 2.78(1H, m), 3.06(1H, m), 3.21–3.27(2H, m), 3.35 1H, m), 3.98(12H, ddd, J=4.1, 6.3, 9.5 Hz), 6.53(1H, d, J=8.2Hz), 6.54(1H, d, J=8.2Hz), 7.15–7.28(5H, m), 7.21 1H, t, J=8.2Hz), 7.31(1H, br s), 7.33 1H, s), 8.74(1H, br s), 9.10(1H, br s). |
| 2-51 | 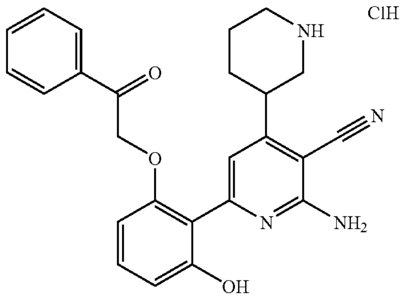 | 464.96 | 429 | A | A | (500MHz, DMSO-d6): 1.91(3H, m), 3.03 1H, m), 5.68(2H, s), 6.58(1H, d, J=8.3 Hz), 6.76(1H, d, J=8.3Hz), 7.27(1H, t, J=8.3Hz), 7.37(1H, br), 7.60(2H, t, J= 7.2Hz), 7.73(1H, t, J=7.2Hz), 8.11 2H, d, J=7.2Hz), 8.18(1H, br), 8.92 1H, br), 9.34(1H, br). |
| 2-52 | 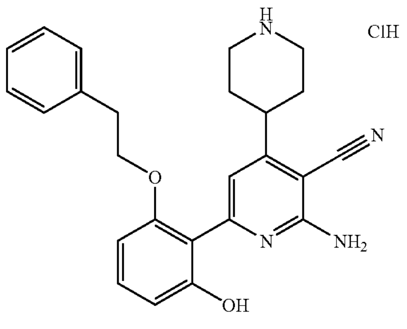 | 450.97 | 415 | A | A | (300MHz, DMSO-d6): 1.91–1.92(4H, m), 3.07–3.11(2H, m), 3.09(3H, t, J= 7.2Hz), 3.36–3.40(2H, m), 4.22(2H, t, J=7.2Hz), 6.55(1H, d, J=8.3Hz), 6.61 1H, d, J=7.9Hz), 7.20(1H, dd, J=7.9, 8.3Hz), 7.22–7.24(5H, m), 7.25(1H, s), 7.28(1H, br s), 8.86(2H, br s). |

TABLE 2-continued

| Ex. No | Structure | Mol weight | Mass | in vi-tro | A549 | NMR |
|---|---|---|---|---|---|---|
| 2-53 | 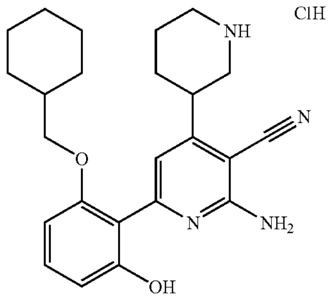 | 442.99 | 407 | A | A | (300MHz, DMSO-d6): 1.09–1.17(2H, m), 1.21–1.25(4H, m), 1.66–1.75(5H, m), 1.81–1.96(3H, m), 2.84–2.99(2H, m), 3.03–3.16(2H, m), 3.31–3.48(2H, m), 3.67–3.85(2H, m), 6.55(1H, d, J=7.9Hz), 6.57(1H, d, J=8.3Hz), 7.22 1H. dd. J=7.9, 8.3Hz), 7.27(1H, s), 7.45(1H, br s), 8.98(1H, br s), 9.44(1H, br s). |
| 2-54 | 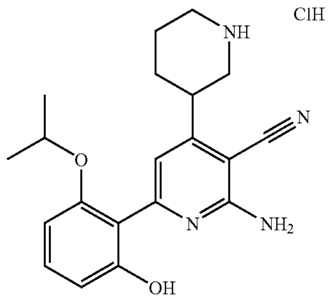 | 388.90 | 353 | A | A | (300MHz, DMSO-d6): 1.29(6H, d, J=6.0Hz), 1.61–1.95(4H, m), 2.88–3.10 2H, m), 3.28–3.49(3H, m), 4.65(1H, sep, J=6.0Hz), 6.51(1H, d, J=7.9Hz), 6.60(1H, d, J=8.7Hz), 7.22(1H, dd, J=7.9, 8.7Hz), 7.33(1H, s), 7.42(1H, br s), 8.87(1H, br s), 9.24(1H, br s). |
| 2-55 | 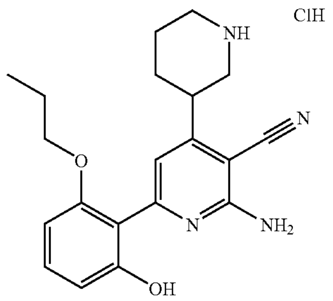 | 388.90 | 353 | A | A | (500MHz, DMSO-d6): 0.94(3H, t, J=7.3Hz), 1.67(1H, m), 1.78(1H, m), 1.76–1.85(2H, m), 1.91–1.99(2H, m), 2.88 1H, m), 3.06(1H, m), 3.27(1H, m), 3.30–3.32(3H, m), 3.38(1H, m), 3.96(2H, t, J=6.0Hz), 6.54(1H, d, J=8.2Hz), 6.58 1H, d, J=8.2Hz), 7.23(1H, t, J=8.2 Hz), 7.34(1H, s), 8.88(1H, br s), 9.31 1H, br s). |
| 2-56 | 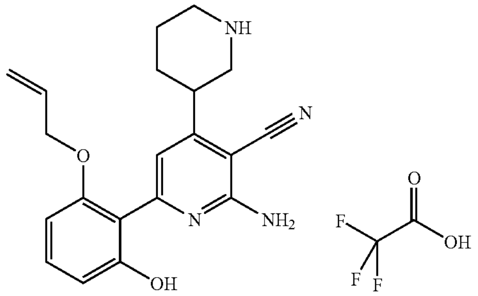 | 464.45 | 351 | A | A | (500MHz, DMSO-d6): 1.65(1H, m), 1.78 1H, m), 1.93(2H, d, J=11.4Hz), 2.88 1H, m), 3.03(1H, m), 3.21(1H, m), 3.35 2H, dd, J=10, 25Hz), 4.57(2H, d, J=5.7Hz), 5.33(2H, m), 6.08(1H, m), 6.56 2H, dd, J=8.3, 26Hz), 7.29(3H, m), 8.65(1H, br), 8.97(1H, br). |
| 2-57 | 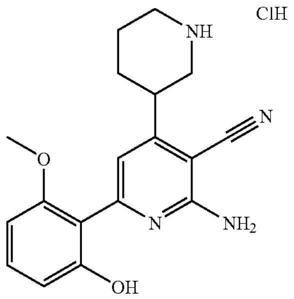 | 360.85 | 325 | A | A | (500MHz, DMSO-d6): 1.67–1.96(5H, m), 2.72–3.42(6H, m), 3.79(3H, s), 6.55(1H, d, J=8.3Hz), 6.58(1H, d, J=8.3Hz), 7.22(1H, s), 7.23(1H, t, J=8.3 Hz), 8.79(1H, br d), 9.13(1H, br d). |

TABLE 2-continued

| Ex. No | Structure | Mol weight | Mass | in vitro | A549 | NMR |
|---|---|---|---|---|---|---|
| 2-58 | 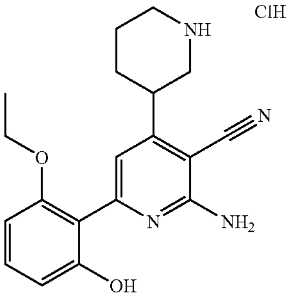 | 374.87 | 339 | A | A | (500MHz, DMSO-d6): 1.37(3H, t, J=6.9Hz), 1.68(1H, m), 1.82(1H, m), 1.92–1.96(2H, m), 2.91(1H, m), 3.08(1H, m), 3.23–3.32(2H, m), 3.39(1H, m), 4.06(2H, q, J=6.6Hz), 6.54(1H, d, J=8.2Hz), 6.58(1H, d, J=8.5Hz), 7.24 1H, dd, J=8.2, 8.5Hz), 7.40(1H, s), 7.46(1H, br s), 8.81(1H, br s), 9.22(1H, br s). |
| 2-59 | 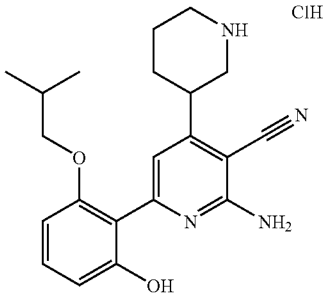 | 402.93 | 367 | A | A | (500MHz, DMSO-d6): 0.92(6H, d, J=6.6Hz), 1.68(1H, m), 1.80(1H, m), 1.91–1.94(2H, m), 2.04(1H, sep, J=6.6 Hz), 2.86(1H, m), 3.07(1H, m), 3.27–3.36(3H, m), 3.76(2H, d, J=6.6Hz), 6.56(1H, d, J=7.3Hz), 6.57(1H, d, J=8.2Hz), 7.23(1H, dd, J=7.3, 8.2Hz), 7.28(1H, s), 7.56(1H, br s), 8.95(1H, br s), 9.45(1H, br s). |
| 2-60 | 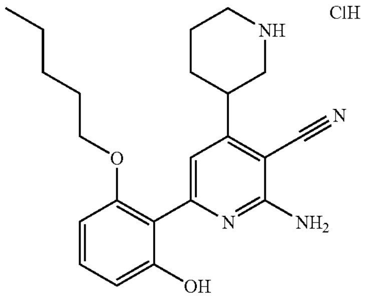 | 416.96 | 381 | A | A | (500MHz, DMSO-d6): 0.84–0.86(2H, m), 1.29–1.30(4H, m), 1.69–1.73(2H, m), 1.80–1.95(3H, m), 2.87(1H, m), 3.10(1H, m), 3.29–3.35(3H, m), 3.48 1H, m), 3.70(1H, m), 3.97(2H, q, J=6.3Hz), 6.59(2H, d, J=8.2Hz), 7.25 1H, t, J=8.2Hz), 7.31(1H, s), 7.75(1H, br s), 9.07(1H, br s), 9.60(1H, br s). |
| 2-61 | 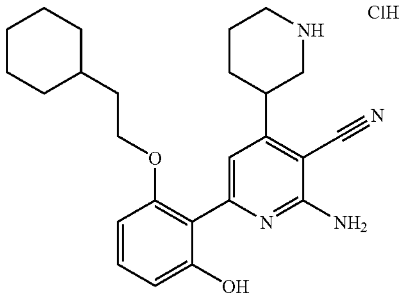 | 457.02 | 421 | A | A | (500MHz, DMSO-d6): 0.85–0.93(2H, m), 1.09–1.18(3H, m), 1.32(1H, m), 1.60–1.64(7H, m), 1.71(1H, m), 1.84 1H, m), 1.90–1.95(2H, m), 2.87(1H, m), 3.09(1H, m), 3.28(1H, m), 3.30–3.34(2H, m), 3.99(1H, dd, J=6.6, 9.5 Hz), 4.04(1H, dd, J=6.6, 9.5Hz), 6.56 1H, d, J=8.2Hz), 6.60(1H, d, J=8.5 Hz), 7.23(1H, dd, J=8.2, 8.5Hz), 7.30 1H, s), 7.59(1H, br s), 8.99(1H, br s), 9.46(1H, br s). |
| 2-62 | 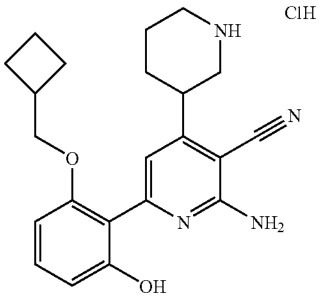 | 414.94 | 379 | A | A | (500MHz, DMSO-d6): 1.63–1.78(4H, m), 1.81–1.99(5H, m), 2.02–2.09(2H, m), 2.73(1H, m), 2.88(1H, m), 3.05(1H, m), 3.22–3.38(2H, m), 3.99(2H, d, J=6.6Hz), 6.53(1H, d, J=8.5Hz), 6.59 1H, d, J=8.2Hz), 7.22(1H, t, 8.2Hz), 7.27(1H, s), 7.28(1H, br s), 8.76(1H, br s), 9.11(1H, br s). |

TABLE 2-continued

| Ex. No | Structure | Mol weight | Mass | in vitro | A549 | NMR |
|---|---|---|---|---|---|---|
| 2-63 | 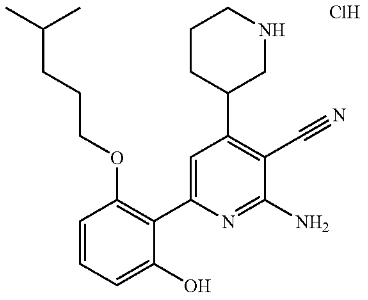 | 430.98 | 395 | A | A | (500MHz, DMSO-d6): 0.84(6H, d, J=6.6Hz), 1.17–1.25(2H, m), 1.52(1H, sep, J=6.6Hz), 1.67–1.75(3H, m), 1.80(1H, m), 1.86–1.96(2H, m), 2.87 1H, m), 3.07(1H, m), 3.24–3.39(3H, m), 3.87–4.13(2H, m), 6.54(1H, d, J=8.2Hz), 6.57(1H, d, J=8.2Hz), 7.22 1H, t, J=8.2Hz), 7.28(1H, s), 7.43, 1H, br s), 8.87(1H, br s), 9.27(1H, br s). |
| 2-64 | 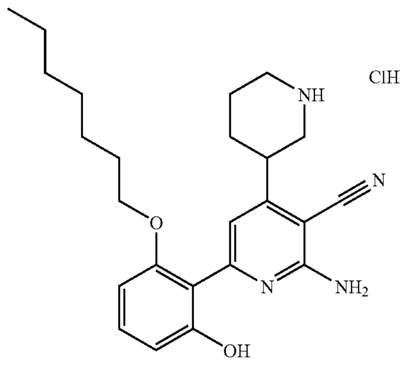 | 445.01 | 409 | A | B | (500MHz, DMSO-d6): 0.84(2H, d, J=6.9Hz), 0.85(2H, d, J=6.6Hz), 1.20–1.33(3H, m), 1.66–1.74(3H, m), 1.75–1.95(5H, m), 2.87(1H, m), 3.10(1H, m), 3.22–3.47(4H, m), 3.90(1H, d, J=6.3 Hz), 3.94–4.02(2H, m), 6.55(1H, d, J=8.2Hz), 6.58(1H, d, J=8.2Hz), 7.23 1H, t, J=8.2Hz), 7.32(1H, s), 7.48(1H, br s), 8.98(1H, m), 9.24(1H, m). |
| 2-65 | 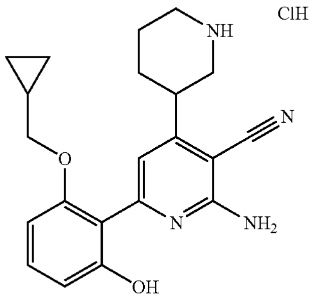 | 400.91 | 365 | A | A | (500MHz, DMSO-d6): 0.33–0.37(2H, m), 0.62–0.59(2H, m), 1.30(1H, m), 1.67(1H, m), 1.82(1H, m), 1.91–1.98 2H, m), 2.07(1H, m), 2.88(1H, m), 3.11 1H, m), 3.26–3.32(2H, m), 3.85(2H, d, J=6.9Hz), 6.53(1H, d, J=8.5Hz), 6.54 1H. d, J=8.2Hz), 7.23(1H, dd, J=8.2, 8.5Hz), 7.37(1H, br s), 7.54(1H, s), 8.94(1H, m), 9.43(1H, m). |
| 2-66 | 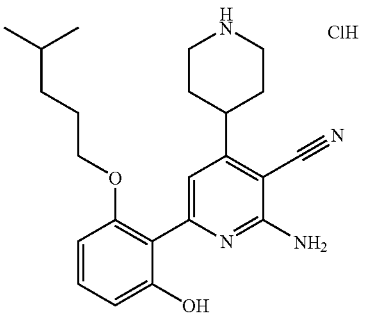 | 430.98 | 395 | A | A | (500MHz, DMSO-d6): 0.83(6H, d, J=6.6Hz), 1.03(2H, d, J=6.6Hz) 1.18–1.22(2H, m), 1.51–1.53(1H, m), 1.72–1.77(3H, m), 1.93–1.95(4H, m), 2.84–2.85(1H, m), 3.06–3.22(3H, m), 3.34–3.37(2H, m), 3.99(1H, t, J=6.6Hz), 6.55–6.59(2H, m), 7.21–7.26(2H, m), 9.03–9.12(1H, br s). |

TABLE 2-continued
| Ex. No | Structure | Mol weight | Mass | in vitro | A549 | NMR |
|---|---|---|---|---|---|---|
| 2-67 | 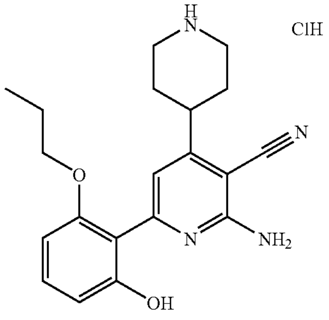 | 388.90 | 353 | A | A | (500MHz, DMSO-d6): 0.92(3H, t, J=7.25Hz), 1.77(2H, m), 1.90–1.98(2H, m), 3.06–3.13(3H, m), 3.38–3.40(2H, m), 3.97(2H, t, J=6.3Hz), 6.57(2H, dd, J=10.0, 8.3Hz), 7.23–7.27(2H, m), 9.06(2H, br s). |
| 2-68 | 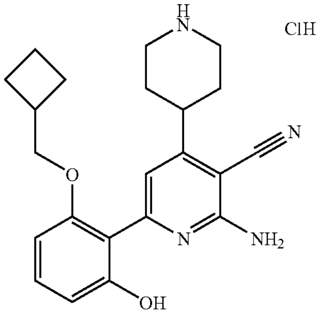 | 414.94 | 379 | A | A | (500MHz, DMSO-d6): 1.70–1.76(2H, m), 1.79–1.92(4H, m), 1.95–1.98(2H, m), 2.00–2.07(2H, m), 2.77(1H, m), 3.07–3.14(3H, m), 3.39–3.41(2H, m), 4.00(2H, d, J=6.6Hz), 6.56(1H, d, J=8.2Hz), 6.60(1H, d, J=8.2Hz), 7.19 1H, s), 7.24(1H, t, J=8.2Hz), 7.51(1H, br s), 9.03(2H, br s). |
| 2-69 | 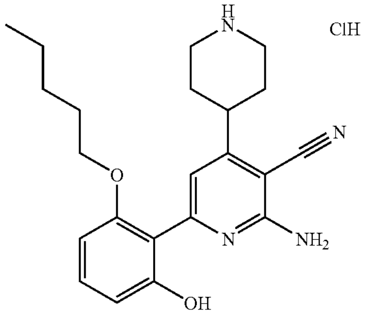 | 416.96 | 381 | A | A | (500MHz, DMSO-d6): 0.85(3H, dd, J=6.6, 7.2Hz), 1.31–1.33(4H, m), 1.74–1.78(2H, m), 1.83–1.91(2H, m), 1.94–1.99(2H, m), 3.08–3.12(3H, m), 3.37–3.39(2H, m), 4.00(2H, dd, J=6.3, 6.6 Hz), 6.53(1H, d, J=8.2Hz), 6.58(1H, d, J=8.5Hz), 7.22(1H, dd, J=8.2, 8.5 Hz), 7.29(1H, s), 7.30(1H, br s), 8.75 1H, br s), 8.83(1H, br s). |
| 2-70 | 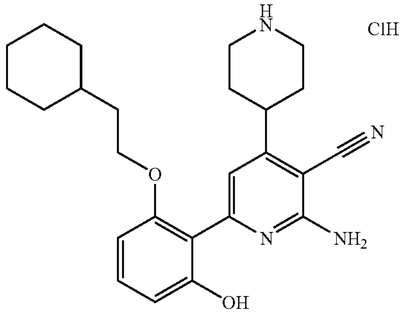 | 457.02 | 421 | A | A | (500MHz, DMSO-d6): 0.86–0.93(2H, m), 1.09–1.23(3H, m), 1.34(1H, m), 1.59–1.67(7H, m), 1.86–1.99(4H, m), 3.08–3.13(3H, m), 3.36–3.38(2H, m), 4.04(2H, dd, J=6.6, 6.9Hz), 6.54(1H, d, J=8.2Hz), 6.60(1H, d, J=8.5Hz), 7.23(1H, dd, J=8.2, 8.5Hz), 7.24(1H, s), 7.36(1H, br s), 8.91(2H, br s). |

TABLE 2-continued

| Ex. No | Structure | Mol weight | Mass | in vitro | A549 | NMR |
|---|---|---|---|---|---|---|
| 2-71 | 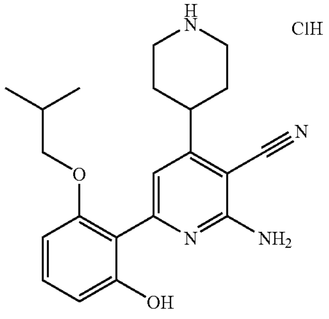 | 402.93 | 367 | A | A | (500MHz, DMSO-d6): 0.92(6H, d, J=6.6Hz), 1.83–1.92(2H, m), 1.94–1.97 2H, m), 2.08(1H, dq, J=6.6Hz), 3.04–3.13(3H, m), 3.38–3.41(2H, m), 3.78 2H, d, J=6.6Hz), 6.54(1H, d, J=8.2 Hz), 6.57(1H, d, J=8.5Hz), 7.22(1H, s), 7.23(1H, dd, J=8.2, 8.5Hz), 7.38 1H, br s), 8.86(1H, br s), 8.95(1H, br s). |
| 2-72 | 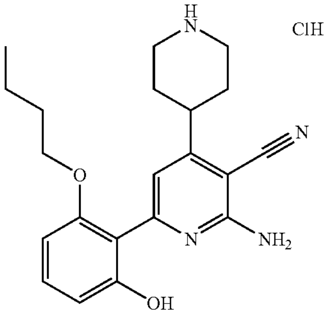 | 402.93 | 367 | A | | (500MHz, DMSO-d6): 0.89(3H, dd, J=7.3, 7.6Hz), 1.37(2H, dq, J=7.3, 7.6 Hz), 1.75(2H, dd, J=6.6, 6.9Hz), 1.86–1.97(4H, m), 3.06–3.13(3H, m), 3.37–3.40(2H, m), 4.02(2H, t, J=6.6Hz), 6.54(1H, d, J=8.2Hz), 6.59(1H, d, J=8.2Hz), 7.23(1H, t, J=8.2Hz), 7.28 1H, s), 7.47(1H, br s), 8.96(2H, br s). |
| 2-73 | 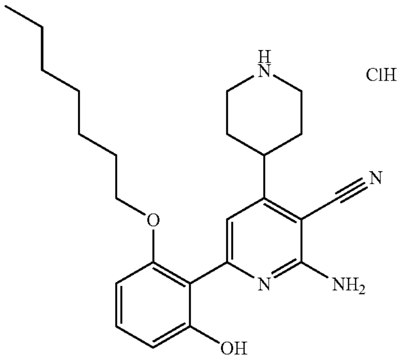 | 445.01 | 409 | A | A | (300MHz, DMSO-d6): 0.84(3H, t, J=6.8Hz), 1.22–1.27(8H, m), 1.73–1.78 2H, m), 1.87–1.94(4H, m), 3.07–3.11 3H, m), 3.35–3.40(2H, m), 4.01(2H, t, J=6.4Hz), 6.54(1H, d, J=8.3Hz), 6.58 1H, d, J=7.9Hz), 7.23(1H, dd, J=7.9, 8.3Hz), 7.28(1H, s), 7.33(1H, br s), 8.90(2H, br s). |
| 2-74 | 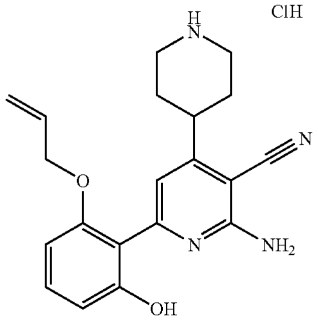 | 386.88 | 351 | A | A | (300MHz, DMSO-d6): 1.78–1.98(4H, m), 3.06–3.10(3H, m), 3.38–3.42(2H, m), 4.61(2H, d, J=5.3Hz), 5.29(1H, dd, J=1.5, 10.6Hz), 5.36(1H, dd, J=1.5, 17.3Hz), 6.11(1H, ddt, J=5.3, 10.6, 17.3Hz), 6.55(1H, d, J=8.3Hz), 6.59(1H, d, J=7.9Hz), 7.23(1H, dd, J=7.9, 8.3Hz), 7.27(1H, s), 7.33(1H, br s), 8.74(2H, br s). |

TABLE 2-continued
| Ex. No | Structure | Mol weight | Mass | in vitro | A549 | NMR |
|---|---|---|---|---|---|---|
| 2-75 | 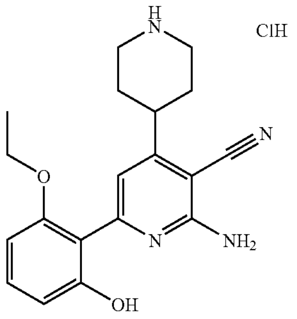 | 374.87 | 339 | A | A | (300MHz, DMSO-d6): 1.40(3H, t, J=7.2Hz), 1.80–2.01(4H, m), 3.08–3.10 3H, m), 3.39–3.43(2H, m), 4.08(2H, q, J=6.8Hz), 6.53(1H, d, J=7.9Hz), 6.57 1H, d, J=8.3Hz), 7.23(1H, dd, J=7.9, 8.3Hz), 7.34(1H, br s), 7.40(1H, s), 8.80(2H, br s). |
| 2-76 | 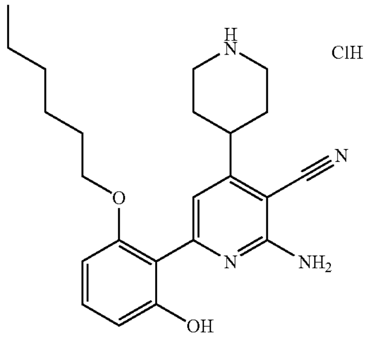 | 430.98 | 395 | A | A | (300MHz, DMSO-d6): 0.36(3H, t, J=6.8Hz), 1.25–1.34(7H, m), 1.71–1.78 2H, m), 1.82–1.91(2H, m), 1.94–1.98 2H, m), 3.05–3.37(4H, m), 4.01(2H, t, J=6.4Hz), 6.52(1H, d, J=8.3Hz), 6.58 1H, d, J=7.9Hz), 7.20(1H, br s), 7.22 1H, dd, J=7.9, 8.3Hz), 7.30(1H, s), 8.61(1H, br s), 8.75(1H, br s). |
| 2-77 | 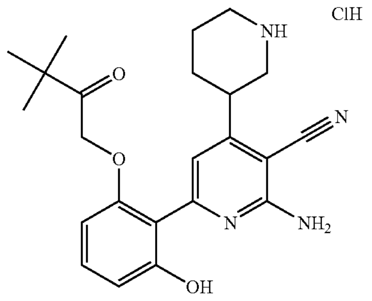 | 444.97 | 409 | A | A | (500MHz, DMSO-d6): 1.20(9H, s), 1.81–1.97(5H, m), 2.98(1H, m), 3.26–3.31 2H, m), 3.42(1H, m), 5.20(2H, s), 6.55 1H, d, J=8.2Hz), 6.61(1H, d, J=8.2 Hz), 7.25(1H, t, J=8.2Hz), 7.36(2H, br s), 8.13(1H, s), 8.81(1H, br s), 9.27(1H, br s). |
| 2-78 | 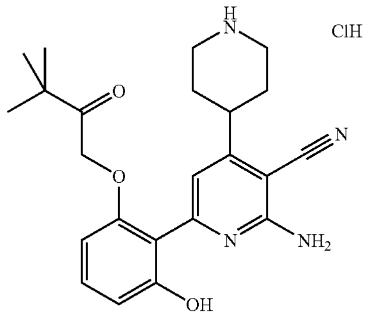 | 444.97 | 409 | A | A | (300MHz, DMSO-d6): 1.17(9H, s), 1.86–1.95(4H, m), 3.07–3.10(3H, m), 3.35–3.40(2H, m), 5.22(2H, s), 6.44(1H, d, J=8.3Hz), 6.53(1H, d, J=8.3Hz), 7.18 1H, t, J=8.3Hz), 7.21(1H, br s), 7.46 1H, br s), 8.77(1H, br s). |

TABLE 2-continued

| Ex. No | Structure | Mol weight | Mass | in vitro | A549 | NMR |
|---|---|---|---|---|---|---|
| 2-79 | 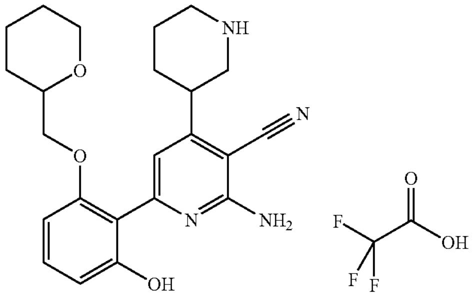 | 522.53 | 409 | A | A | (500MHz, DMSO-d6): 1.21–1.30(2H, m), 1.43–1.51(3H, m), 1.61(1H, m), 1.67–1.82(4H, m), 1.91–1.97(2H, m), 2.89(1H, m), 3.05(1H, m), 3.22(1H, m), 3.35–3.43(3H, m), 3.91(1H, m), 3.96 1H, m), 6.52(1H, d, J=8.5Hz), 6.58 1H, d, J=8.5Hz), 7.22(1H, t, J=8.2 Hz), 7.28(2H, br s), 7.38(1H, s), 8.67 1H, br s), 8.88(1H, br s). |
| 2-80 | 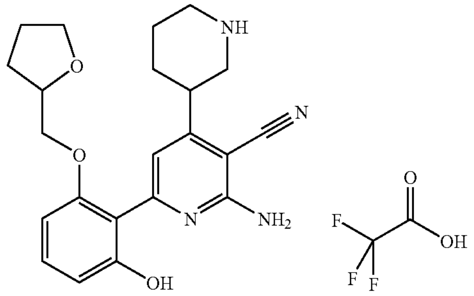 | 508.50 | 395 | A | A | (500MHz, DMSO-d6): 1.61(1H, m), 1.66–1.81(4H, m), 1.85(1H, m), 1.90–2.04 4H, m), 2.80(1H, m), 3.12(1H, m), 3.23 1H, m), 3.40(1H, m), 3.76(1H, m), 3.87 1H, m), 4.03(1H, dd, J=2.8, 3.1Hz), 4.27(1H, m), 6.52(1H, d, J=8.2Hz), 6.55(1H, d, J=8.5Hz), 7.24(1H, dd, J=8.2, 8.5Hz), 7.29(2H, br s), 7.61(1H, s), 8.62(1H, br s), 8.92(1H, br s). |
| 2-81 | 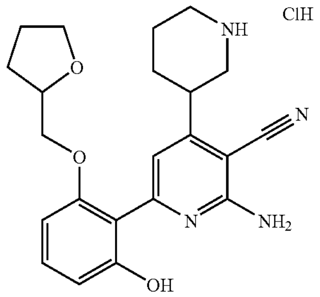 | 430.94 | 395 | A | A | (500MHz, DMSO-d6): 1.61(1H, m), 1.71 1H, m), 1.76–1.86(3H, m), 1.87–2.03 3H, m), 2.78(1H, m), 3.13(1H, m), 3.25–3.35(3H, m), 3.75–3.80(2H, m, 3.88 (1H, m), 4.03(1H, m), 4.27(1H, m), 7.51 (1H, d, J=8.2 Hz), 7.56(1H, d, J=8.2 Hz), 7.24(1H, t, J=8.2Hz), 7.53(1H, br s), 7.58(1H, s), 8.93(1H, m), 9.53(1H, m). |
| 2-82 | 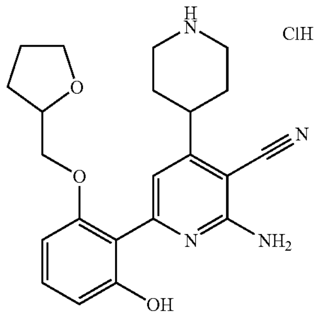 | 430.94 | 395 | A | A | (300MHz, DMSO-d6): 1.59(1H, m), 1.76–1.97(7H, m), 3.07–3.10(3H, m), 3.37–3.41(2H, m), 3.70(2H, dd, J=6.8, 14.7 Hz), 3.92(1H, dd, J=6.8, 7.2Hz), 4.01(1H, dd, J=6.8, 7.2Hz), 4.22(1H, m), 6.54(1H, d, J=8.3Hz), 6.58(1H, d, J=8.3Hz), 7.20(1H, br s), 7.22(1H, t, J=8.3Hz), 7.34(1H, s), 8.74(1H, br s), 8.92(1H, br s). |
| 2-83 | 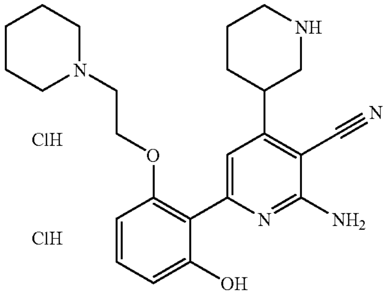 | 494.47 | 422 | B | B | (500MHz, DMSO-d6): 1.26–1.38(1H, m), 1.65–1.93(10H, m), 2.84–3.39(8H, m), 4.36–4.43(3H, m), 6.61(2H, d, J=8.2Hz), 7.05(1H, s), 7.22–7.26(3H, m), 8.78–8.85(1H, m), 9.38(1H, br d, J=10.1Hz), 10.56(1H, br s). |

TABLE 2-continued

| Ex. No | Structure | Mol weight | Mass | in vi-tro | A549 | NMR |
|---|---|---|---|---|---|---|
| 2-84 | 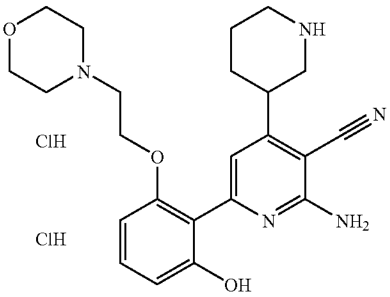 | 496.44 | 424 | A | B | (500MHz, DMSO-d6): 1.71–1.93(5H, m), 2.95–3.47(12H, m), 3.75(1H, br s), 4.36–4.44(2H, br s), 6.61(2H, d, J=8.2 Hz), 7.01(1H, s), 7.16(2H, br s), 7.23 1H, t, J=8.4 H), 8.76–8.85(1H, m), 9.29(1H, br d, J=10.4Hz), 11.34(1H, br s). |
| 2-85 | 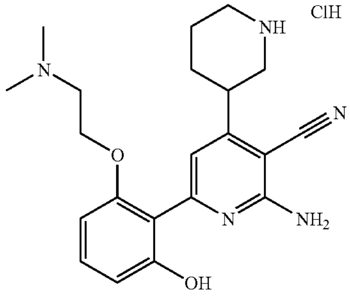 | 417.94 | 382 | B | B | (500MHz, DMSO-d6): 1.68–1.83(2H, m), 1.92(2H, m), 2.73(6H, d, J=4.4 Hz), 2.97(1H, m), 3.17–3.19(3H, m), 3.22–3.39(3H, m), 4.36(2H, br), 6.61 1H, d, J=8.5Hz), 6.63(1H, d, J=8.2 Hz), 7.09(1H, s), 7.21(1H, br s), 7.25 1H, dd, J=8.2, 8.5Hz), 8.80(1H, br), 9.37(1H, br s), 10.6(1H, br s). |
| 2-86 | 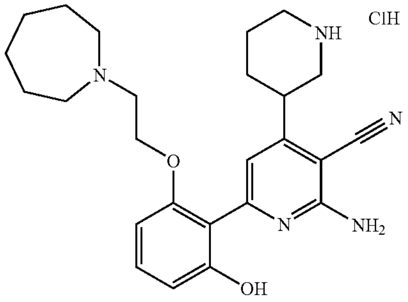 | 472.04 | 436 | C | B | (500MHz, DMSO-d6): 1.53–1.54(2H, m), 1.62–1.64(2H, m), 1.67–1.84(6H, m), 1.91–1.92(2H, m), 2.97(1H, m), 3.05–3.10(2H, m), 3.17–3.25(2H, m), 3.29–3.45(6H, m), 4.39(2H, br), 6.60 (1H, d, J=8.2 Hz), 6.61(1H, d, J=8.2 Hz), 7.05(1H, s), 7.18(1H, br s), 7.24 1H, t, J=8.2Hz), 8.77(1H, br s), 9.30 1H, br s), 10.6(1H, br s). |
| 2-87 | 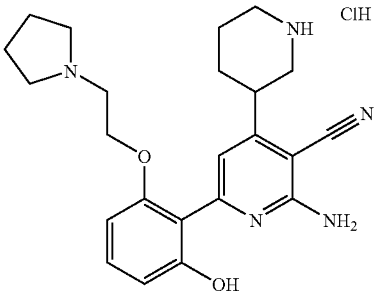 | 443.98 | 408 | C | B | (500MHz, DMSO-d6): 1.72–1.85(5H, m), 1.90–1.93(3H, m), 2.91–3.17(3H, m), 3.21–3.39(4H, m), 3.43–3.44(2H, m), 3.50–3.51(2H, m), 4.36(2H, br), 6.62(1H, d, J=8.5Hz), 6.65(1H, d, J=8.2Hz), 7.15(1H, s), 7.26(1H, dd, J=8.2, 8.5Hz), 7.53(1H, br s), 9.00(1H, br s), 9.64(1H, br s), 11.2(1H, br s). |

Example 3-1

(1) With the use of the starting compound 1G, 2B and other materials, 2-amino-6-[2-(cyclopropylmethoxy)-6-hydroxyphenyl]-4-(3-piperidinyl)nicotinonitrile hydrochloride was prepared in a similar manner as described in Example 2-3.

(2) To a stirred solution of 2-amino-6-[2-(cyclopropylmethoxy)-6-hydroxyphenyl]-4-(3-piperidinyl)nicotinonitrile hydrochloride (200.0 mg, 0.50 mmol) in MeOH were added formaldehyde (0.5 mL) and sodium cyanoborohydride (40.8 mg, 0.65 mmol) and stirred for 2 hrs at room temperature. The reaction was quenched by an addition of water, extracted with ethyl acetate, dried over $MgSO_4$, filtered and evaporated. The residue was triturated with hexane and dried. The crude product was purified by preparative silica gel TLC (5% MeOH in dichloromethane) to give 2-amino-6-[2-(cyclopropylmethoxy)-6-hydroxyphenyl]-4-(1-methyl-3-piperidinyl)nicotinonitrile as a yellow solid. (28.5 mg, yield 15%)

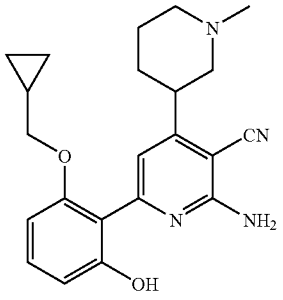

Molecular weight: 378.48

Mass spectrometry: 379 $(M+H)^+$

In vitro activity grade: A

Cellular activity grade: (A549)A $^1$H-NMR (300 MHz, CDCl3): 0.37–0.42 (2H, m), 0.67–0.73 (2H, m), 0.82–0.88 (1H, m), 1.27–1.35 (1H, m), 1.76–2.09 (4H, m), 2.31 (3H, s), 2.91–3.00 (2H, m), 3.14–3.23 (1H, m), 3.86 (2H, pent, J=8.8 Hz), 5.15 (2H, br s), 6.39 (1H, d, J=8.3 Hz), 6.62 (1H, d, J=8.3 Hz), 7.20 (1H, t, J=8.3 Hz), 7.95 (1H, s).

Example 3-2

To a stirred solution of 2-amino-6-[2-(cyclopropylmethoxy)-6-hydroxyphenyl]-4-(3-piperidinyl)nicotinonitrile hydrochloride (200.0 mg, 0.50 mmol),which was obtained in the step (1) of example 3-1, in MeOH was added benzaldehyde (0.25 mL, 2.49 mmol)) followed by sodium cyanoborohydride (40.8 mg, 0.65 mmol), and the stirring was continued for 2 hrs at room temperature. The reaction was quenched by an addition of water, extracted with ethyl acetate, dried over $MgSO_4$, filtered and evaporated. The residue was triturated with hexane and dried. The crude product was purified by preparative silica gel TLC (5% MeOH in dichloromethane) to give 2-amino-4-(1-benzyl-3-piperidinyl)-6-[2-(cyclopropylmethoxy)-6-hydroxy-phenyl] nicotinonitrile as a yellow solid. (35.7 mg, yield 16%)

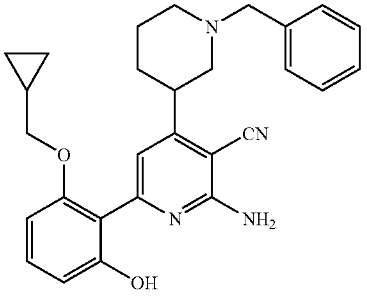

Molecular weight: 454.58

Mass spectrometry: 455 $(M+H)^+$

In vitro activity grade: C

Cellular activity grade: (A549)C $^1$H-NMR (300 MHz, CDCl3): 0.35–0.37 (2H, m), 0.62–0.64 (2H, m), 0.83–1.29 (2H, m), 1.75–2.21 (5H, m), 2.93–3.24 (3H, m), 3.50–3.61 (2H, m), 3.78–3.88 (2H, m), 5.12 (2H, br s), 6.39 (1H, d, J=8.3 Hz), 6.60 (1H, d, J=8.3 Hz), 7.16–7.32 (6H, m), 7.93 (1H, s), 13.33 (1H, br s).

Examples 3-3 to 3-8

According to the similar synthetic procedure of Examples 3-1 to 3-2, compounds shown in Table 3 were prepared.

TABLE 3

| Ex. No | Structure | Mol weight | Mass | in vitro | A549 | NMR |
|---|---|---|---|---|---|---|
| 3-03 | 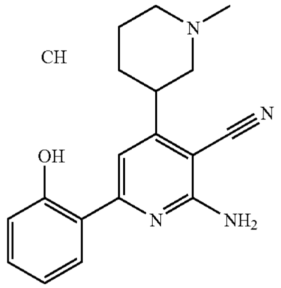 | 344.85 | 309 | A | A | (300MHz, DMSO-d6): 1.70–1.96 4H, m), 2.73(3H, d, J=1.8Hz), 2.93–2.98(1H, m), 3.35–3.49 4H, m), 6.90–6.95(2H, m), 7.33–7.46(3H, m), 8.02(1H, dd, J=8.5, 1.3Hz), 10.62(1H, br s). |
| 3-04 | 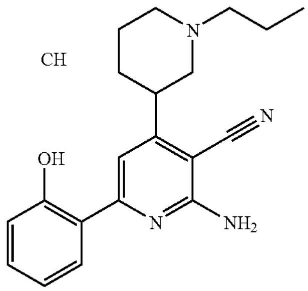 | 372.90 | 337 | A | B | (300MHz, DMSO-d6): 0.92(3H, t, J=7.4Hz), 1.71–1.76(3H, m), 1.81–1.98(3H, m), 2.92–3.04 3H, m), 6.90–6.95(2H, m), 7.34–7.38(2H, m), 7.45(1H, br s), 8.01(1H, d, J=7.4Hz), 9.80(1H, br s). |

TABLE 3-continued
| Ex. No | Structure | Mol weight | Mass | in vitro | A549 | NMR |
|---|---|---|---|---|---|---|
| 3-05 | 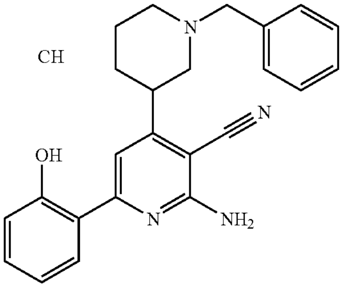 | 420.95 | 385 | A | A | (300MHz, DMSO-d6): 1.81–1.96 4H, m), 2.72–2.73(1H, m), 3.31–3.50(4H, m), 4.26–4.35(2H, m), 6.89–6.95(2H, m), 7.34–7.51(6H, m), 7.59–7.62(2H, m), 8.00–8.02(1H, m), 10.57(1H ,br s). |
| 3-06 | 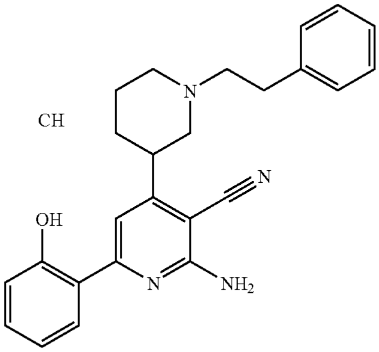 | 434.97 | 399 | B | B | (300MHz, DMSO-d6): 1.78–2.01 5H, m), 3.04–3.15(4H, m), 3.30–3.67(2H, m), 6.90–6.95(2H, m), 7.24–7.49(11H, m), 8.03 1H, d, J=7.5Hz), 10.58(1H, br s). |
| 3-07 | 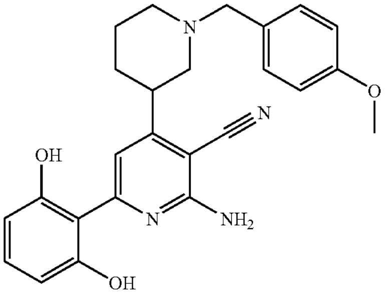 | 430.51 | 431 | A | B | (500MHz, DMSO-d6): 1.39(1H, dd, J=3.5, 11.7Hz), 1.59(1H, m), 1.73(1H, d, J=12.9Hz), 1.88(1H, d, J=11.7Hz), 1.95 1H, t, J=10.4Hz), 2.02(1H, t, J=11.0Hz), 2.84(1H, d, J=11.0 Hz), 2.89(1H, d, J=10.4Hz), 2.97(1H, t, J=11.0Hz), 3.45 2H, m), 3.72(3H, s), 6.36(2H, d, J=8.2Hz), 6.86(2H, d, J=8.5 Hz), 7.06(1H, t, J=8.2Hz), 7.16 2H, br), 7.21(1H, d, J=8.5Hz), 7.78(1H, s), 11.91(2H, s). |
| 3-08 | 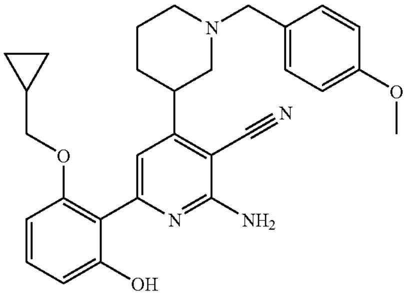 | 484.60 | 485 | C | C | (300MHz, CDCl3): 0.33–0.38 2H, m), 0.60–0.66(2H, m), 1.24–2.21(8H, m), 2.94–3.25(2H, m), 3.52(2H, br s), 3.79–3.84 5H, m), 5.16(2H, br s), 6.39(1H, d, J=8.3Hz), 6.60(1H, d, J=8.3 Hz), 6.84(2H, d, J=8.7Hz), 7.16–7.26(3H, m) , 7.93(1H, s). |

Example 4-1

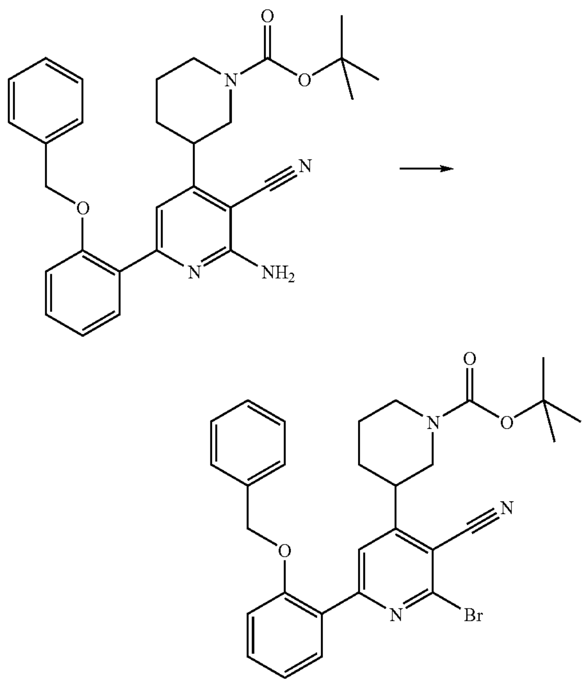

(1) A mixture of copper (II) bromide (1.106 g, 4.953 mmol) and tert-butyl nitrite (0.736 mL, 6.191 mmol) in acetonitrile (30 mL) was stirred at 65° C. for 15 min. A solution of tert-butyl 3-{2-amino-6-[2-(benzyloxy)phenyl]-3-cyano-4-pyridinyl}-1-piperidinecarboxylate (2.000 g, 4.127 mmol), which was obtained in the step (1) of Example 1-1, in acetonitrile (20 mL) was added dropwise to the mixture. The mixture was stirred at 65° C. for 2 hrs. After cooled to room temperature, the reaction mixture was diluted with ethyl acetate. The separated organic phase was washed with an aqueous 1N HCl solution and brine, dried over $Na_2SO_4$, filtered, and concentrated. The residue was recrystallized from diethyl ether to give tert-butyl 3-{2-bromo-6-[2-(benzyloxy)phenyl]-3-cyano-4-pyridinyl}-1-piperidinecarboxylate as a white solid (1.010 g, yield; 45%).

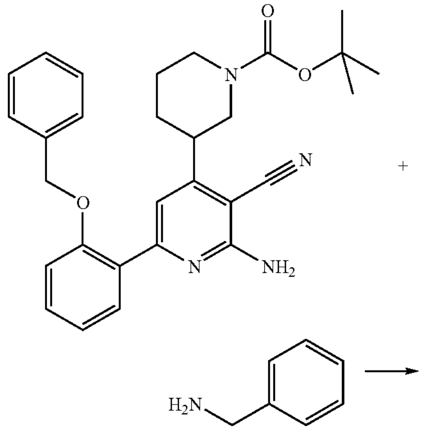

-continued

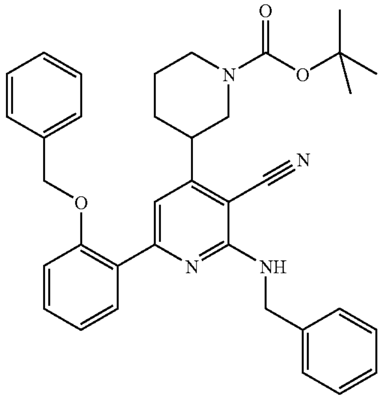

(2) To a stirred solution of tert-butyl 3-{6-[2-(benzyloxy)phenyl]-2-bromo-3-cyano-4-pyridinyl}-1-piperidinecarboxylate (0.300 g, 0.547 mmol) in DMSO were added triethylamine (0.229 mL, 1.341 mmol) and benzylamine (0.147 g, 1.367 mmol). The mixture was stirred at 70° C. for 12 hrs. After cooled to room temperature, the reaction mixture was quenched with water and extracted with ethyl acetate. The separated organic phase was washed with brine, dried over $Na_2SO_4$, filtrated, and concentrated. The residue was purified by silica gel column chromatography (hexane/ethyl acetate=4/1-2/1) to give tert-butyl 3-{6-[2-(benzyloxy)phenyl]-2-benzylamino-3-cyano-4-pyridinyl}-1-piperidinecarboxylate as a yellow amorphous. (0.290 g, yield; 92%)

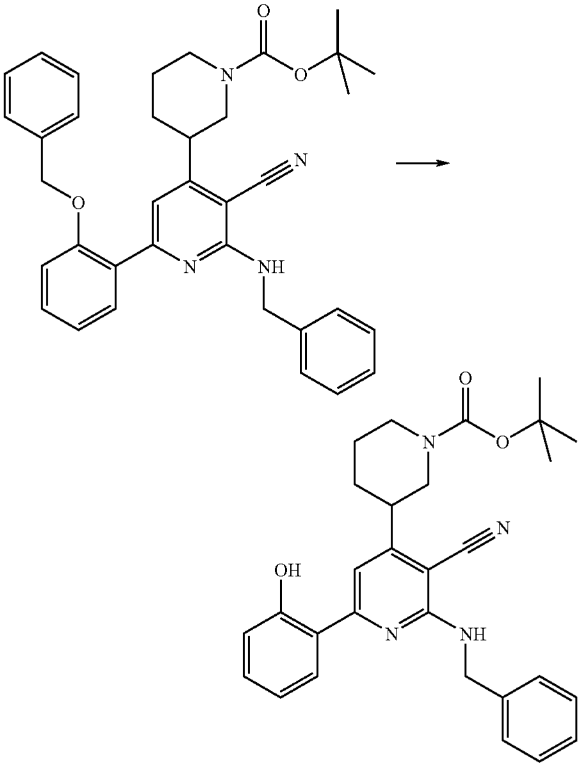

(3) Then benzyl moiety was removed in a same manner as described in step (2) of Example 1-1. The residue was suspended in ethanol and filtrated to give tert-butyl 3-[2-

(benzylamino)-3-cyano-6-(2-hydroxyphenyl)-4-pyridinyl]-1-piperidinecarboxylate as a white solid. (0.150 g, yield; 61%)

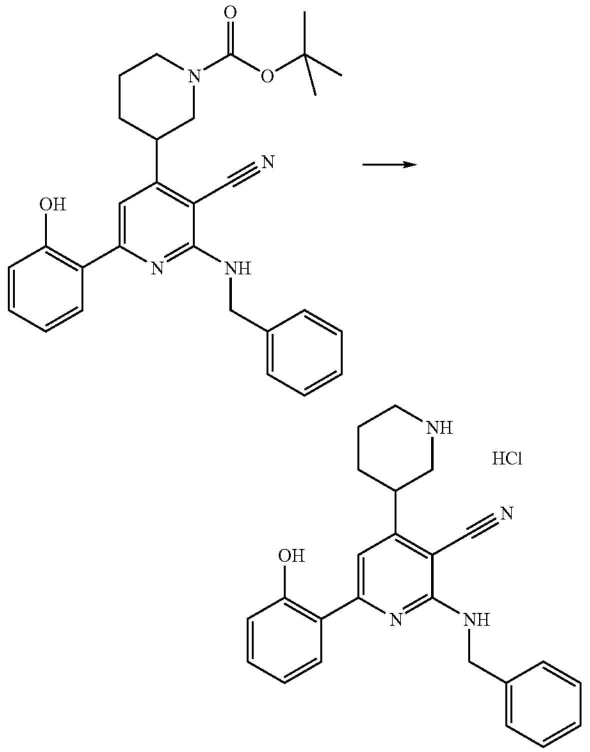

(4) tert-butyl 3-[2-(benzylamino)-3-cyano-6-(2-hydroxyphenyl)-4-pyridinyl]-1-piperidinecarboxylate (0.145 g, 0.299 mmol) was treated under acidic conditions in a similar manner as described in step (3) in Example 1-1. The resulting solid was collected by filtration, and dried under reduced pressure to give 2-(benzylamino)-6-(2-hydroxyphenyl)-4-(3-piperidinyl)nicotinonitrile hydrochloride. (0.075 g, yield; 60%)

Molecular weight: 420.95

Mass spectrometry: 385 $(M+H)^+$

In vitro activity grade: A

Cellular activity grade: (A549)-B/Jurkat-B $^1$H-NMR (300 MHz, DMSO-d6): 1.80–1.92 (4H, m), 2.90–2.93 (1H, m), 3.31–3.40 (4H, m), 4.59 (2H, d, J=5.6 Hz), 6.84–6.92 (2H, m), 7.19–7.31 (5H, m), 7.47 (1H, s), 8.00 (1H, d, J=6.8 Hz), 8.11–8.15 (1H, m), 8.91 (1H, br s), 9.52 (1H, br s), 12.59 (1H, br s), 12.90 (1H, br s).

Example 4-2

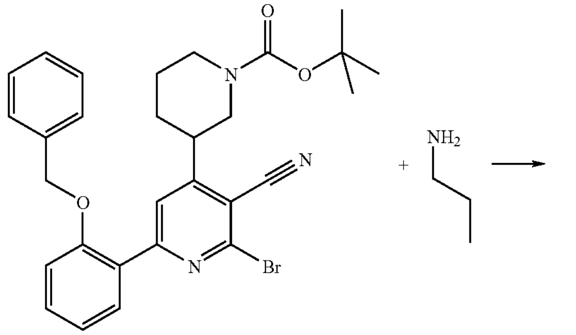

-continued

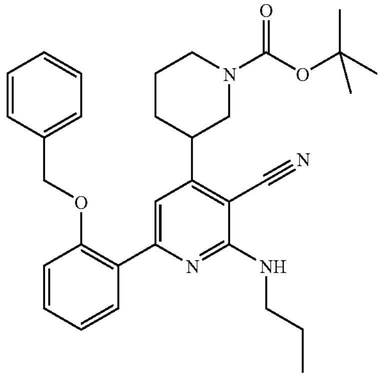

To a stirred solution of tert-butyl 3-{6-[2-(benzyloxy)phenyl]-2-bromo-3-cyano-4-pyridinyl}-1-piperidinecarboxylate (0.100 g, 0.182 mmol), which was obtained in the steps (1) of Example 4-1, in DMSO (2 mL) were added propylamine (0.108 g, 1.823 mmol) and triethylamine (0.038 mL, 0.273 mmol). The mixture was stirred at 40° C. for 12 hrs. The reaction was quenched with water and the resulting reaction mixture was extracted with ethyl acetate. The organic phase was dried over $Na_2SO_4$, filtered, and concentrated. The concentrates was purified by silica gel column (hexane/ethyl acetate=4/1) to give tert-butyl 3-{6-[2-(benzyloxy)phenyl]-3-cyano-2-propylamino-4-pyridinyl}-1-piperidinecarboxylate as a colorless oil. (0.104 g, yield; quant.)

Then benzyl moiety was removed in a same manner as described in the step (2) in Example 1-1. The residue was washed with diethyl ether to give the desired product as a white solid. (0.112 g, yield; quant.)

Then tert-butyl 3-[3-cyano-6-(2-hydroxyphenyl)-2-(propylamino)-4-pyridinyl]-1-piperidinecarboxylate (0.110 g, 0.252 mmol) was treated under acidic conditions in a same manner as described in the step (3) in Example 1-1. The resulting solid was collected with filtration, and dried under reduced pressure to give 6-(2-hydroxyphenyl)-4-(3-piperidinyl)-2-(propylamino)nicotinonitrile hydrochloride. (0.062 g, yield; 66%)

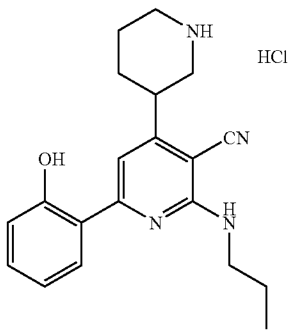

Molecular weight: 372.90

Mass spectrometry: 337 $(M+H)^+$

In vitro activity grade: C

Cellular activity grade: (A549)-C $^1$H-NMR (300 MHz, DMSO-d6): 0.92 (3H, t, J=7.4 Hz), 1.62 (2H, m), 1.80–1.95 (4H, m), 2.89–2.93 (1H, m), 3.33–3.46 (6H, m), 6.91–6.97 (2H, m), 7.34–7.40 (1H, m), 7.48 (1H, s), 7.57 (1H, br s), 8.08–8.17 (1H, m), 8.97–9.07 (1H, m), 9.67–9.71 (1H, m).

Example 4-3

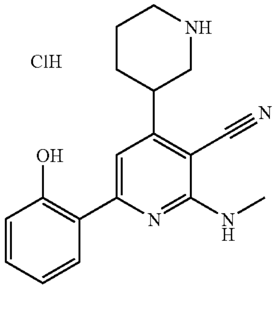

In a similar manner as that of Example 4-2, 6-(2-hydroxyphenyl)-2-(methylamino)-4-(3-piperidinyl)nicotinonitrile hydrochloride was prepared.

Molecular weight: 344.85

Mass spectrometry: 309 $(M+H)^+$

In vitro activity grade: C

Cellular activity grade: (A549)-C $^1$H-NMR (300 MHz, DMSO-d6): 1.83–1.96 (4H, m), 3.31 (4H, s), 3.30–3.56 (4H, m), 6.90–6.96 (2H, m), 7.34–7.37 (1H, m), 7.39 (1H, s), 7.55 (1H, br s), 8.10 (1H, d, J=7.9 Hz), 8.87–8.90 (1H, m), 9.52–9.54 (1H, m), 13.80 (1H, br s).

Example 4-4

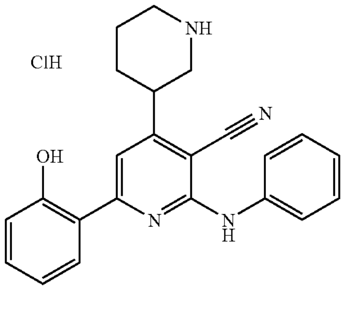

In a similar manner as that of Example 4-2, 2-anilino-6-(2-hydroxyphenyl)-4-(3-piperidinyl)nicotinonitrile hydrocloride was prepared.

Molecular weight: 406.92

Mass spectrometry: 371 $(M+H)^+$

In vitro activity grade: D

Cellular activity grade: (A549)-B $^1$H-NMR (300 MHz, DMSO-d6): 1.87–2.00 (4H, m), 2.91–2.95 (1H, m), 3.34 (1H m), 6.79 (1H, d, J=8.3 Hz), 6.91 (1H, t, J=7.2 Hz), 7.18–7.44 (1H, brs), 7.66 (1H, s), 8.06 (1H, d, J=6.8 Hz), 8.84 (1H, m), 9.43 (2H, m), 12.42 (1H, br s).

Example 4-5

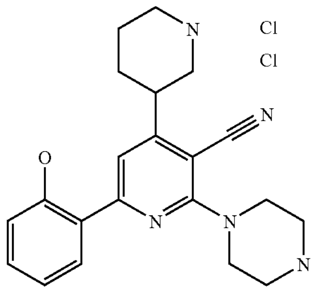

In a similar manner as that of Example 4-2, 6-(2-hydroxyphenyl)-2-(1-piperazinyl)-4-(3-piperidinyl)nicotinonitrile dihydrochloride was prepared.

Molecular weight: 436.39

Mass spectrometry: 364 $(M+H)^+$

In vitro activity grade: D$^1$H-NMR (500 MHz, DMSO-d6): 1.81–1.83 (2H, m), 1.90–1.95 (2H, m), 2.93–2.95 (1H, m), 3.76–3.78 (4H, m), 6.98 (1H, t, J=7.3 Hz), 7.37–7.40 (1H. m), 7.84 (1H, s), 8.03–8.05 (1H, m), 8.78–8.81 (1H, m), 9.14 (1H, br s), 9.24–9.27 (1H, m), 12.10 (1H, s).

Example 5-1

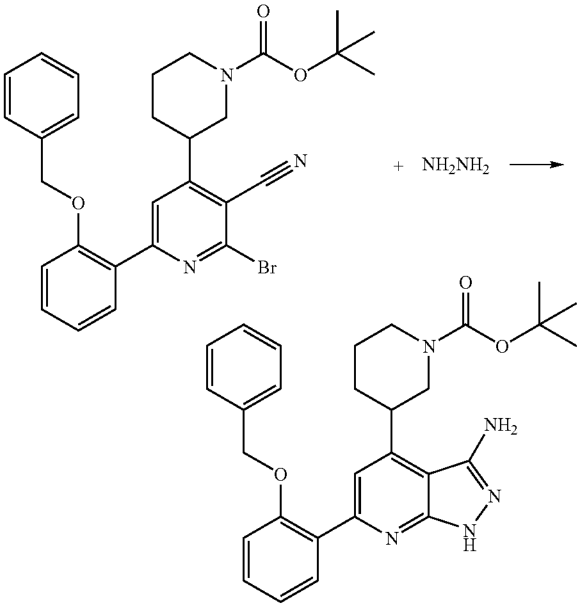

(1) A mixture of tert-butyl 3-{6-[2-(benzyloxy)phenyl]-2-bromo-3-cyano-4-pyridinyl}-1-piperidinecarboxylate (0.300 g, 0.547 mmol), which was obtained in the step (1) of Example 4-1, hydrazine monohydrate (3 mL) and 1,4-dioxane (1 mL) was stirred at 100° C. for 1.5 hrs. The reaction was quenched with water and extracted with ethyl acetate. The organic phase was washed with brine and dried over $Na_2SO_4$, filtered, and concentrated. The residue was recrystallized from ethanol to give tert-butyl {3-[3-amino- 6-(2-benzyloxy-phenyl)-1H-pyrazolo[3,4-b]pyridin-4-yl]-1-piperidinecarboxylate as a yellow solid. (0.210 g, yield; 72%)

(2) Then the benzyl moiety was removed in a same manner as described in the step (2) of Example 1-1. The residue was purified by silica gel column (hexane/ethyl acetate=2/1-1/1) to give tert-butyl 3-[3-amino-6-(2-hydroxyphenyl)-1H-pyrazolo[3,4-b]pyridin-4-yl]-1-piperidinecarboxylate as an orange solid. (0.080 g, yield; 49%)

To a stirred solution tert-butyl 3-[3-amino-6-(2-hydroxyphenyl)-1H-pyrazolo[3,4-b]pyridin-4-yl]-1-piperidinecarboxylate (0.075 g, 0.183 mmol) in 1,4-dioxane (3 mL) was added 4N HCl in 1,4-dioxane (3 mL). The mixture was stirred at room temperature for 12 hrs. The resulting solid was collected with filtration to give 2-[3-amino-4-(3-piperidinyl)-1H-pyrazolo[3,4-b]pyridin-6-yl]phenol hydrochloride. (0.062 g, yield; 98%)

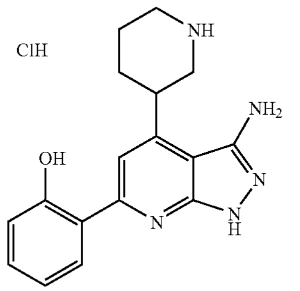

Molecular weight: 345.83

Mass spectrometry: 310 $(M+H)^+$

In vitro activity grade: C

Cellular activity grade: A549-B $^1$H-NMR (300 MHz, DMSO-d6): 1.97–2.27 (4H, m), 2.95–3.11 (1H, m), 3.12–3.23 (1H, m), 3.30–3.39 (3H, m), 6.94–6.99 (2H, m), 7.32–7.38 (1H, m), 7.73 (1H, s), 8.12 (1H, d, J=7.2 Hz).

Example 5-2

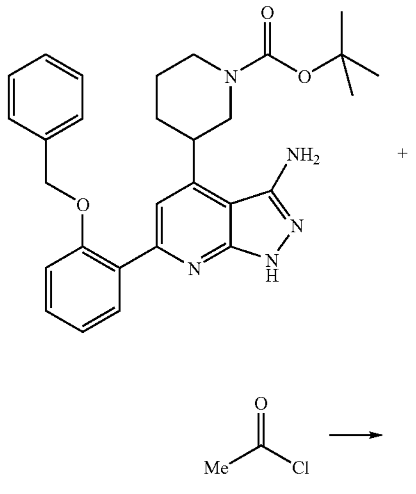

-continued

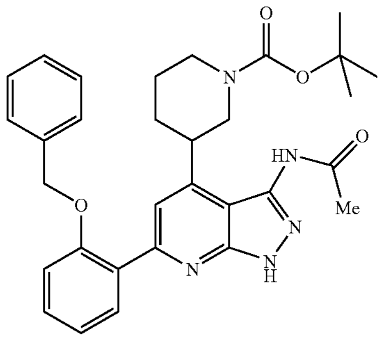

To a cooled (0° C.), stirred solution of tert-butyl 3-{3-amino-6-[2-(benzyl-oxy)phenyl]-1H-pyrazolo[3,4-b]pyridin-4-yl}-1-piperidinecarboxylate (0.200 g, 0.400 mmol) obtained in the step (1) of Example 5-1 in THF (3 mL) were added pyridine (1 mL) and acetyl chloride (0.035 g, 0.440 mmol). The mixture was stirred at 0° C. for 1 hr. The reaction was quenched with water and extracted with ethyl acetate. The organic phase was washed with saturated brine, dried over $Na_2SO_4$, filtered, and concentrated. The residue was recrystallized from diisopropyl ether to give a white solid. (0.180 g, yield; 83%)

Then the benzyl moiety was removed in a same manner as described in the step (2) of Example 1-1. The residue was suspended in ethanol and filtrated to give the desired product as a white solid. (0.120 g, yield; 82%)

tert-Butyl 3-[3-(acetylamino)-6-(2-hydroxyphenyl)-1H-pyrazolo[3,4-b]pyridin-4-yl]-1-piperidinecarboxylate (0.115 g, 0.260 mmol) was treated under acidic conditions in a same manner as described in the step (3) of Example 1-1 to give N-[6-(2-hydroxyphenyl)-4-(3-piperidinyl)-1H-pyrazolo[3,4-b]pyridin-3-yl]acetamide hydrochloride. (0.097 g, yield; 96%)

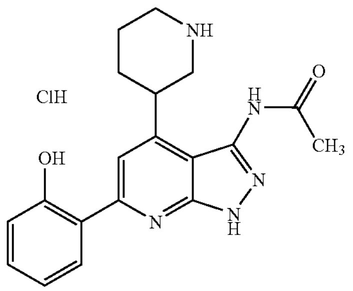

Molecular weight: 387.87

Mass spectrometry: 352 $(M+H)^+$

In vitro activity grade: D

Cellar activity grade: A549-C $^1$H-NMR (500 MHz, DMSO-d6): 1.80–1.91 (4H, m), 1.95 (3H, s), 2.82–2.92 (1H, m), 3.34–3.44 (4H, m), 6.92–6.95 (2H, m), 7.36–7.39 (1H, m), 7.66 (1H, s), 8.12 (1H, d, J=8.2 Hz), 8.83–8.85 (1H, m), 9.48–9.49 (1H, m), 9.56 (1H, s) 10.21 (1H, s), 13.59 (1H, br s).

Example 6-1

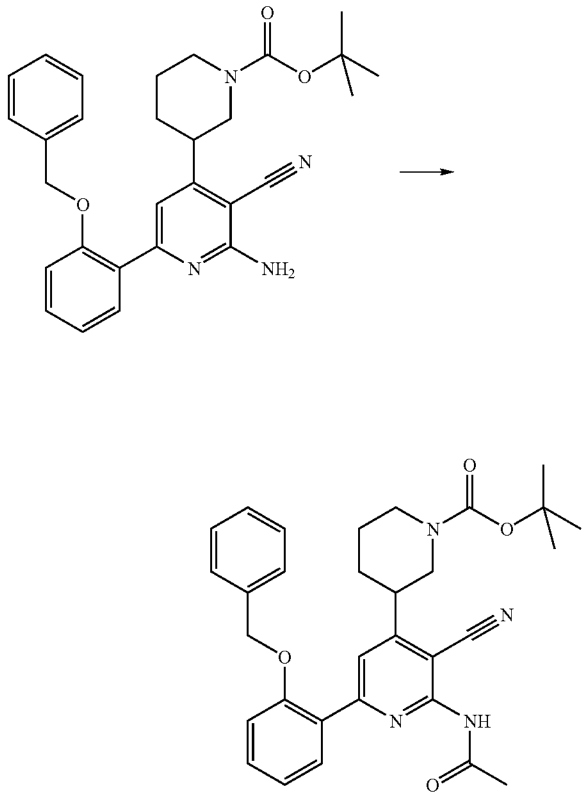

To a cooled (0° C.), stirred solution of tert-butyl 3-{2-amino-6-[2-(benzyl-oxy)phenyl]-3-cyano-4-pyridinyl}-1-piperidinecarboxylate, which was obtained in the step (1) of Example 1-1, (0.500 g, 1.032 mmol) in pyridine (10 mL) was added acetyl chloride (0.477 mL, 6.70 mmol). The mixture was stirred at 0° C. to room temperature for 3 hrs, and the stirring was continued at room temperature for 5 hrs. The reaction mixture was quenched with water, and extracted with ethyl acetate. The organic phase was dried over $Na_2SO_4$, filtered, and concentrated. The residue was purified by column chromatography on silica gel (hexane/ethyl acetate=9/1-4/1-2/1) to give a mixture of the desired product, tert-butyl 3-{2-(acetylamino)-6-[2-(benzyloxy)phenyl]-3-cyano-4-pyridinyl}-1-piperidinecarboxylate, and the corresponding diacylated compound. The mixture obtained was dissolved in THF (5 mL), treated with an aqueous 1N $NH_3$ solution (1 mL), and stirred at room temperature for 1 hr. The reaction mixture was extracted with ethyl acetate. The organic phase was washed with brine, dried over $Na_2SO_4$, filtered and concentrated to give tert-butyl 3-{2-(acetylamino)-6-[2-(benzyloxy)phenyl]-3-cyano-4-pyridinyl}-1-piperidinecarboxylate as a white amorphous. (0.432 g, yield; 80%)

Then the benzyl moiety was removed in a same manner as described in the step (2) of Example 1-1. The residue was recrystallized from ethanol to give the desired product as a yellow solid. (0.110 g, yield; 31%)

tert-Butyl 3-[2-(acetylamino)-3-cyano-6-(2-hydroxyphenyl)-4-pyridinyl]-1-piperidinecarboxylate (0.100 g, 0.229 mmol) was treated under acidic conditions in a similar manner as described in the step (3) of Example 1-1. The resulting precipitate was collected by filtration, washed with 1,4-dioxane, and dried under reduced pressure to give N-[3-cyano-6-(2-hydroxyphenyl)-4-(3-piperidinyl)-2-pyridinyl]acetamide hydrochloride. (0.101 g, yield; quant.)

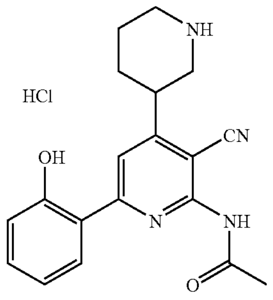

Molecular weight: 372.86

Mass spectrometry: 337 $(M+H)^+$

In vitro activity grade: A

Cellular activity grade: (A549)-B $^1$H-NMR '(500 MHz, DMSO-d6): 1.86–1.97 (4H, m), 2.19 (3H, s), 2.91–2.94 (1H, m), 3.33–3.47 (4H, m), 6.96–6.99 (2H, m), 7.38–7.41 (1H, m), 8.11–8.13 (2H, m), 8.94–8.96 (1H, m), 9.62–9.64 (1H, m), 10.97 (1H, s).

Example 6-2

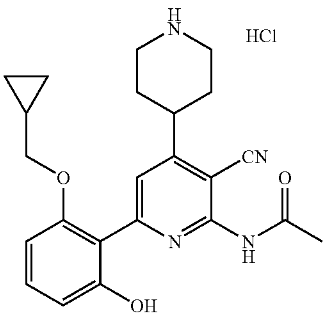

With the use of the starting compound 1G and the 4-formyl piperidine-1 carboxylic acid tert-butyl ester and other materials, N-[3-cyano-6-[2-(cyclopropylmethoxy)-6-hydroxyphenyl]-4-(4-piperidinyl)-2-pyridinyl]acetamide hydrochloride was prepared in the similar manner as that of Example 6-1.

Molecular weight: 442.95

Mass spectrometry: 407 $(M+H)^+$

In vitro activity grade: A

Cellular activity grade: (A549)-A $^1$H-NMR (500 MHz, DMSO-d6): 0.28–0.31 (2H, m), 0.55–0.58 (2H, m), 1.32 (1H, m), 1.98–2.01 (2H, m), 2.16 (3H, s), 3.09–3.13 (2H, m), 3.24–3.28 (1H, m), 3.40–3.42 (2H, m), 3.87 (2H, d, J=6.9 Hz), 6.57 (2H, dd, J=8.5, 2.8 Hz), 7.24 (1H, t, J=8.5 Hz), 7.92 (1H, s), 9.06–9.15 (2H, m), 10.93 (1H, s).

Example 7-1

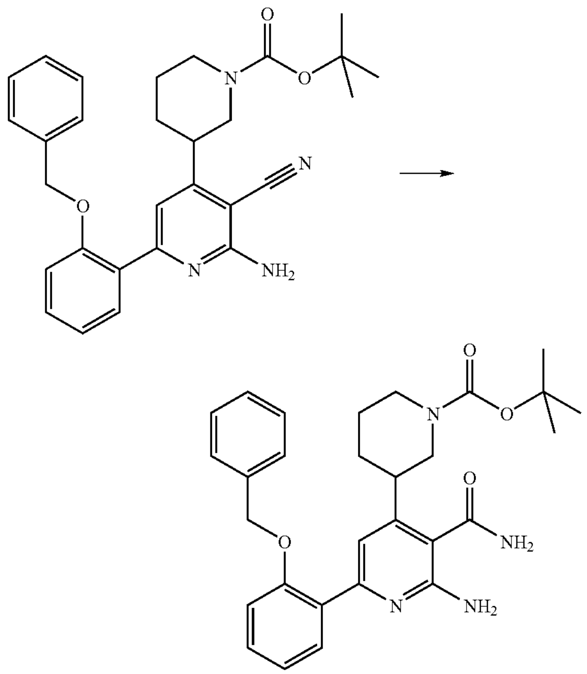

(1) To a stirred suspension of tert-butyl 3-{2-amino-6-[2-(benzyloxy)phenyl]-3-cyano-4-pyridinyl}-1-piperidinecarboxylate (0.300 g, 0.619 mmol), which was obtained in the step (1) of Example 1-1, in ethanol (10 mL) was added a solution of potassium hydroxide (0.695 g, 12.381 mmol) in ethanol (20 mL). The reaction mixture was stirred at 70° C. for 60 hrs. After cooled to room temperature, the reaction mixture was poured into water and the resulting solid was filtrated and dried under reduced pressure to give tert-butyl 3-{2-amino-6-[2-(benzyloxy)phenyl]-3-carbamoyl-4-pyridinyl}-1-piperidinecarboxylat as a white amorphous. (0.226 g, yield; 73%)

(2) Then benzyl moiety was removed in a same manner as described in the step (2) of Example 1-1. The residue was suspended in ethanol and filtrated to give tert-butyl 3-[2-amino-3-(carbamoyl)-6-(2-hydroxyphenyl)-4-pyridinyl]-1-piperidinecarboxylate as a white solid. (0.045 g, yield; 46%)

(3) tert-butyl 3-[2-amino-3-(carbamoyl)-6-(2-hydroxyphenyl)-4-pyridinyl]-1-piperidinecarboxylate (0.040 g, 0.097 mmol) was treated under acidic conditions in a similar manner as described in the step (3) of Example 1-1 to give 2-amino-6-(2-hydroxyphenyl)-4-(3-piperidinyl)nicotinamide hydrochloride as a yellow solid. (0.008 g, yield; 24%)

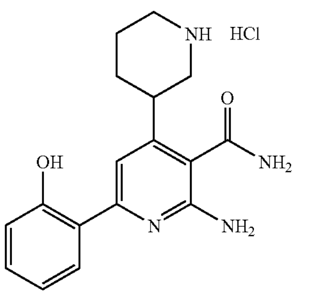

Molecular weight: 348.84

Mass spectrometry: 313 $(M+H)^+$

In vitro activity grade: A

Cellular activity grade: (A549)-B $^1H$-NMR (300 MHz, DMSO-d6): 1.68–1.92 (4H, m), 2.90–2.93 (1H, m), 3.17–3.34 (4H, m), 6.89–6.97 (2H, m), 7.29–7.34 (2H, m), 7.80–7.86 (2H, m), 8.09 (1H, brs), 8.80–8.82 (1H, m), 9.34–9.37 (1H, m).

Example 7-2

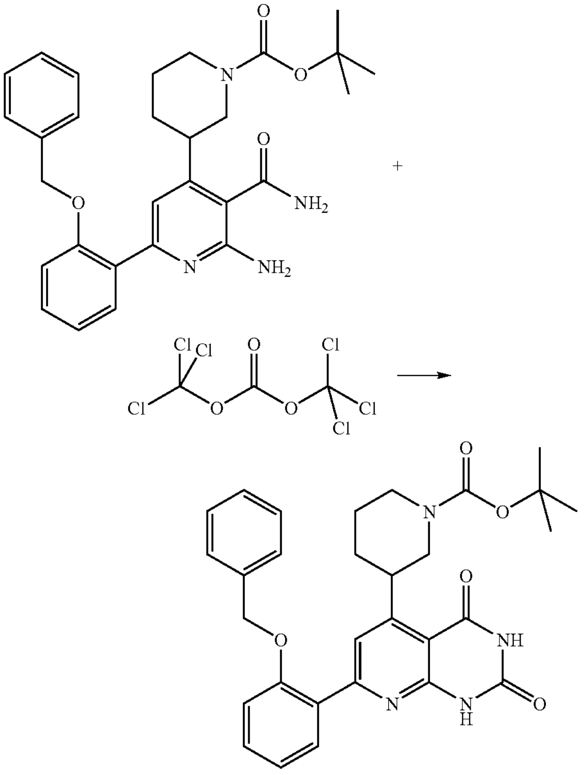

To a cooled (0° C.), stirred solution of tert-butyl 3-{2-amino-6-[2-(benzyl-oxy)phenyl]-3-carbamoyl-4-pyridinyl}-1-piperidinecarboxylate (0.400 g, 0.800 mmol), which was obtained in the step (1) of Example 7-1, in THF (10 mL) were added triethylamine (0.50 mL, 3.58 mmol) followed by triphosgene (0.354 g, 1.19 mmol). The reaction mixture was stirred at room temperature for 12 hrs. The reaction was quenched with water and extracted with ethyl acetate. The organic phase was washed with brine, dried over $Na_2SO_4$, filtered, and concentrated. The residue was purified by silica gel column chromatography (hexane/ethyl acetate=2/1–1/1) and recrystallized from ethanol to give tert-butyl 3-{7-[2-(benzyloxy)phenyl]-2,4-dioxo-1,2,3,4-tetrahydropyrido[2,3-d]pyrimidin-5-yl}-1-piperidinecarboxylate as a white solid. (0.406 g, yield; 97%)

Then the benzyl moiety was removed in a same manner as described in the step (2) of Example 1-1. The residue was washed with ethanol to give tert-butyl 3-[7-(2-hydroxyphenyl)-2,4-dioxo-1,2,3,4-tetrahydropyrido[2,3-d]pyrimidin-5-yl]-1-piperidinecarboxylate as a white solid. (0.036 g, yield; 29%)

tert-butyl 3-[7-(2-hydroxyphenyl)-2,4-dioxo-1,2,3,4-tetrahydropyrido[2,3-d]pyrimidin-5-yl]-1-piperidinecarboxylate (0.036 g, 0.80 mmol) in dioxane (3 mL) was treated under acidic conditions in a similar manner as described in the step (3) of Example 1-1 to give 7-(2-hydroxyphenyl)-5-(3-piperidinyl)pyrido[2,3-d]pyrimidine-2,4(1H,3H)-dione hydrochloride as a yellow solid. (0.016 g, yield; 52%)

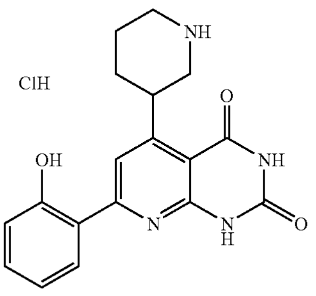

Molecular weight: 374.83

Mass spectrometry: 339 $(M+H)^+$

In activity grade: A

Cellular activity grade: (A549)-C $^1$H-NMR (500 MHz, DMSO-d6): 1.78–1.83 (2H, m), 1.94–1.95 (2H, m), 2.90–2.92 (1H, m), 4.68–4.69 (1H, m), 6.97–6.99 (2H, m), 7.39–7.42 (1H, m), 7.85 (1H, s), 8.16 (1H, dd, J=8.4, 1.4 Hz), 8.75 (1H, br s), 9.43 (1H, m), 11.45 (1H, d, J=1.4 Hz), 12.05 (1H, d, J=1.4 Hz), 12.44 (1H, br s).

Example 7-3

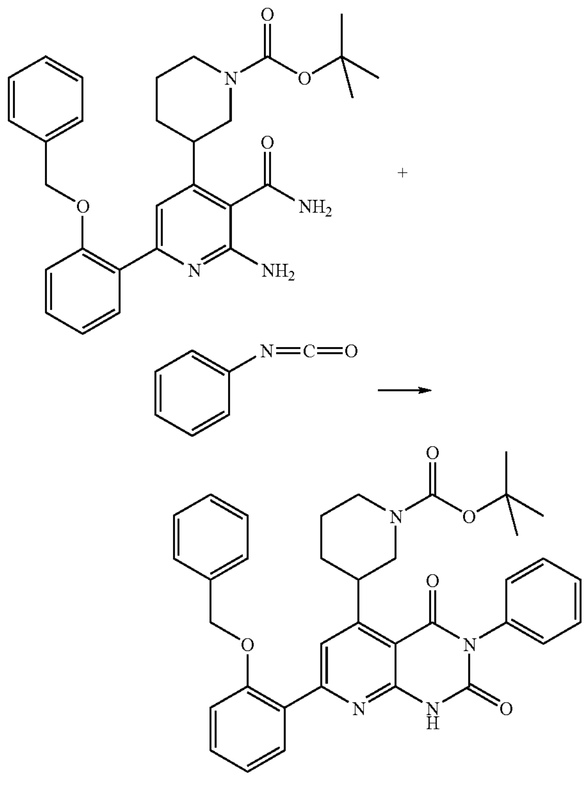

To a stirred solution of tert-butyl 3-{2-amino-6-[2-(benzyloxy)phenyl]-3-carbamoyl-4-pyridinyl}-1-piperidinecarboxylate (0.100 g, 0.199 mmol), which was obtained in the step (1) of Example 7-1, in phenyl ether (1 mL) was added phenyl isocyanate (0.047 g, 0.398 mmol). The mixture was stirred at 140° C. for 12 hrs. After cooled to room temperature, the resulting solid (urea) was removed by filtration. The filtrate was concentrated under reduced pressure. The residue was purified by silica gel column chromatography to give tert-butyl 3-[7-(2-benzyloxy phenyl)-2,4-dioxo-3-phenyl-1,2,3,4-tetrahydropyrido[2,3-d]pyrimidin-5-yl]-1-piperidinecarboxylate as a white amorphous. (0.090 g, yield; 78%)

Then benzyl moiety was removed in a same manner as described in the step (2) of Example 1-1. The residue was washed with ethanol to give the desired product as a white solid. (0.060 g, yield; 83%)

tert-butyl 3-[7-(2-hydroxyphenyl)-2,4-dioxo-3-phenyl-1,2,3,4-tetrahydropyrido[2,3-d]pyrimidin-5-yl]-1-piperidinecarboxylate (0.050 g, 0.100 mmol) was treated under acidic conditions in a similar manner as described in the step (3) of Example 1-1 to give 7-(2-hydroxyphenyl)-3-phenyl-5-(3-piperidinyl)pyrido[2,3-d]pyrimidine-2,4(1H,3H)-dione hydrochloride as a yellow solid. (0.016 mg, yield; 37%)

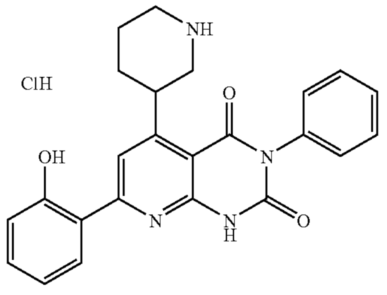

Molecular weight: 450.93

Mass spectrometry: 415 $(M+H)^+$

In vitro activity grade: B

Cellular activity grade: (A549)-C $^1$H-NMR (300 MHz, DMSO-d6): 1.71–1.96 (4H, m), 2.71–2.91 (1H, m), 3.27–3.53 (3H, m), 4.56 (1H, m), 6.98–7.03 (2H, m), 7.34–7.53 (6H, m), 7.89 (1H, s), 8.18–8.21 (1H, m), 8.69–8.70 (1H, m), 9.24–9.25 (1H, m), 12.47 (1H, s).

Example 8-1

(1) A solution of 1-{2-[(4-methoxybenzyl)oxy]phenyl}ethanone (14.2 g, 55.4 mmol) (starting compound 1D), benzyl 3-formyl-1-piperidinecarboxylate (13.7 g, 55.4 mmol) (starting compound 2C), tert-butyl cyanoacetate (7.8 g, 55.4 mmol), and ammonium acetate (9.8 g, 166.1 mmol) in 1,2-dimethoxyethane (60 mL) was stirred under reflux for 3.5 hrs. After cooled to room temperature, the mixture was partitioned between ethyl acetate and water. The separated organic phase was washed with water and brine, dried over $MgSO_4$, filtered, and concentrated under reduced pressure. The residue was purified by column chromatography on silica gel (ethyl acetate:hexane, 1:2) to give tert-butyl 2-amino-4-{1-[(benzyloxy)carbonyl]-3-piperidinyl}-6-{2-[(4-methoxybenzyl)oxy]phenyl}nicotinate as a pale yellow oil (4.89 g, yield; 14%).

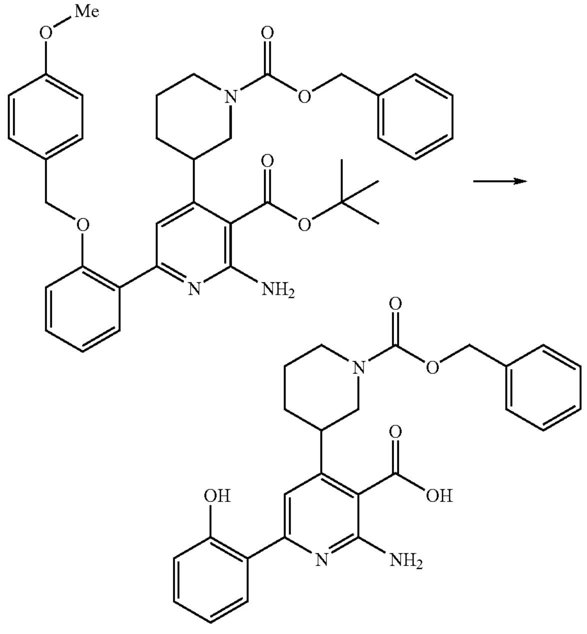

(2) To a solution of tert-butyl 2-amino-4-{1-[(benzyloxy)carbonyl]-3-piperidinyl}-6-{2-[(4-methoxybenzyl)oxy]phenyl}nicotinate (0.95 g, 1.67 mmol) in $CH_2Cl_2$ (10 mL) was added trifluoroacetic acid (10 mL), and the stirring was continued at room temperature overnight. The mixture was concentrated under reduced pressure. The residue was diluted with toluene, then concentrated under reduced pressure to remove excess of trifluoroacetic acid by azeotropic distillation to give 2-amino-4-{1-[(benzyloxy)carbonyl]-3-piperidinyl}-6-(2-hydroxyphenyl)nicotinic acid (1.1 g, yield; quant.).

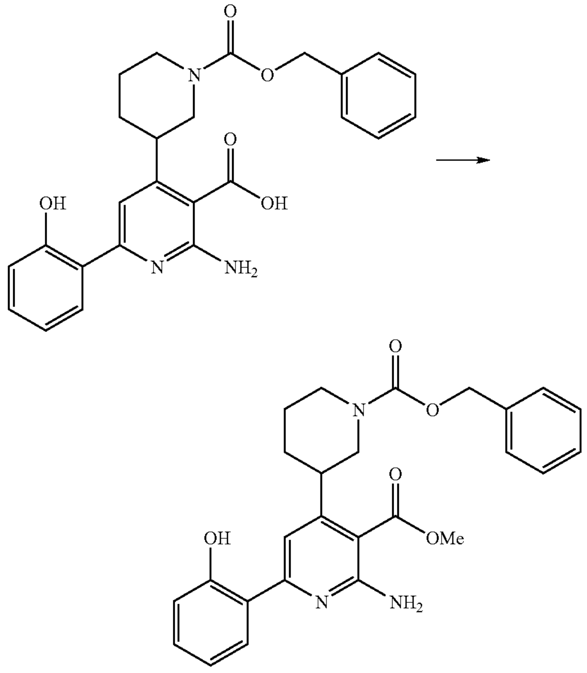

(3) To a solution of 2-amino-4-{1-[(benzyloxy)carbonyl]-3-piperidinyl}-6-(2-hydroxyphenyl)nicotinic acid (1.1 g, 2.5 mmol) in THF (10 mL) and MeOH (5 mL) was added dropwise trimethylsilyldiazomatane (4.0 mL) at room temperature. The reaction mixture was stirred at room temperature for 1.5 hrs, and the reaction was quenched by acetic acid. The mixture was partitioned between ethyl acetate and water. The separated organic phase was washed with brine, dried over $MgSO_4$, filtered, and concentrated under reduced pressure. The residue was purified by column chromatography on silica gel (hexane:ethyl acetate, 3:1) followed by recrystallization from a mixture of $CH_2Cl_2$ and hexane to give methyl 2-amino-4-{1-[(benzyloxy)carbonyl]-3-piperidinyl}-6-(2-hydroxyphenyl)nicotinate as a yellow solid (0.39 g, yield; 34%).

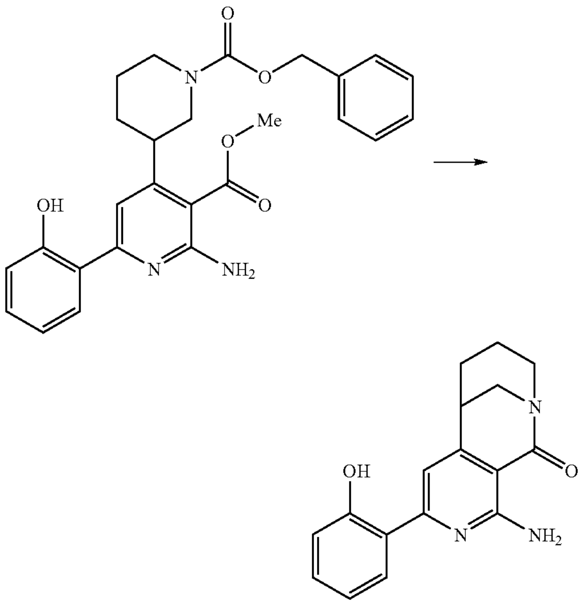

(4) To a solution of methyl 2-amino-4-{1-[(benzyloxy)carbonyl]-3-piperidinyl}-6-(2-hydroxyphenyl)nicotinate (60 mg, 0.130 mmol) in methanol (2.0 mL) and THF (1.0 mL) was added 10% Pd—C (200 mg). The mixture was stirred at room temperature under a hydrogen atmosphere (1 atm) for 6.5 hrs. The mixture was filtrated on Celite®, and washed with MeOH and THF successively. The filtrate was concentrated under reduced pressure. The residue was purified by preparative TLC (hexane:ethyl acetate, 2:1) to give 6-amino-4-(2-hydroxy-phenyl)-5,9-diaza-tricyclo[7.3.1.$0^{2,7}$]trideca-2(7),3,5-trien-8-one as a yellow solid (16 mg, yield; 40%).

Molecular weight: 295.34

Mass spectrometry: 296 $(M+H)^+$

In vitro activity grade: B

Cellular activity grade: (A549)-B $^1$H-NMR (300 MHz, CDCl3-d): 1.42 (1H, d, J=14.3 Hz), 1.84 (1H, m), 1.92 (1H, d, J=13.6 Hz), 2.17 (1H, m), 2.85 (1H, s), 3.16 (1H, td, J=3.0, 12.7 Hz), 3.35 (1H, dd, J=1.9, 12.2 Hz), 3.63 (1H, d, J=13.2 Hz), 3.92 (1H, dd, J=4.5, 12.8 Hz), 6.88 (1H, td, J=1.1, 8.3 Hz), 6.99 (1H, dd, J=1.1, 8.3 Hz), 7.04 (1H, s), 7.32 (1H, td, J=1.1, 8.3 Hz), 7.75 (1H, dd, J=1.5, 8.0 Hz).

Example 8-2

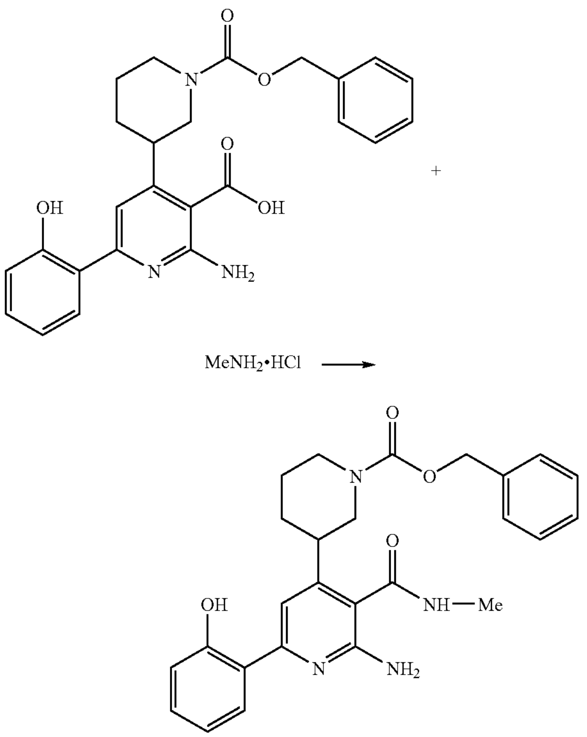

To a solution of 2-amino-4-{1-[(benzyloxy)carbonyl]-3-piperidinyl}-6-(2-hydroxy-phenyl)nicotinic acid (750 mg, 1.676 mmol), which was obtained in the step (2) of Example 8-1, methylamine hydrochloride (230 mg, 3.352 mmol), triethylamine (340 mg, 3.35 mmol), and 1-hydroxybenzotriazole (360 mg, 2.68 mmol), was added 1-ethyl-3-(3-dimethylaminopropyl)carbodiimide hydrochloride (390 mg, 2.0 mmol) at 0° C. under an argon atmosphere. The mixture was stirred at room temperature overnight. The reaction mixture was extracted with ethyl acetate, washed with water and brine, dried over $MgSO_4$, filtered, and concentrated under reduced pressure. The residue was purified by column chromatography on silica gel (Hexane:ethyl acetate, 2:1) to give benzyl 3-{2-amino-6-(2-hydroxyphenyl)-3-(N-methylcarbamoyl)-4-pyridinyl}-1-piperidinecarboxylate as a pale yellow solid (3 37 mg, yield; 44%).

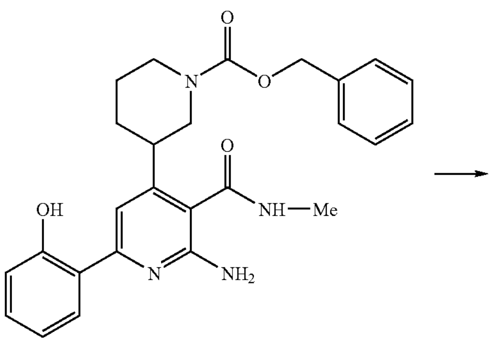

-continued

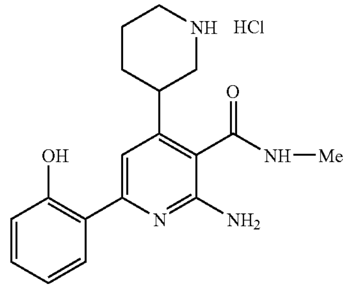

To a solution of benzyl 3-{2-amino-6-(2-hydroxyphenyl)-3-(N-methylcarbamoyl)-4-pyridinyl}-1-piperidinecarboxylate (130 mg, 0.274 mmol) in MeOH (2 mL) and THF (2 mL) was added Pd—C (180 mg). The mixture was stiffed at room temperature under a hydrogen atmosphere overnight. The reaction mixture was filtered on Celite®, washed with THF, and then concentrated under reduced pressure. The residue was diluted with ethyl acetate, and added 4N HCl in 1,4-dioxane. The resulting yellow precipitates were washed with acetonitrile. The collected solid was dried under reduced pressure to give 2-amino-6-(2-hydroxyphenyl)-N-methyl-4-(3-piperidinyl)nicotinamide hydrochloride(10 mg, yield; 81%).

Molecular weight: 362.86

Mass spectrometry: 327 $(M+H)^+$

In vitro activity grade: B

Cellular activity grade: (A549)-B $^1$H-NMR (500 MHz, DMSO-d6): 1.69–1.77 (2H, m), 1.82–1.86 (2H, m), 2.80 (3H, d, J=4.4 Hz), 2.88 (1H, m), 3.03 (1H, m), 3.19–3.29 (3H, m), 6.89–6.93 (3H, m), 7.29–7.32 (2H, m), 7.85 (1H, br), 8.50 (1H, br), 8.85 (1H, br), 9.16 (1H, br).

Example 8-3

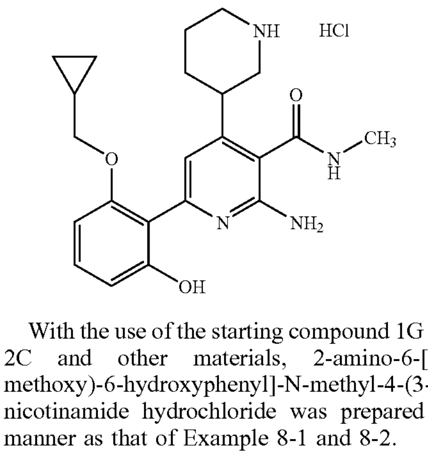

With the use of the starting compound 1G (instead of 1D), 2C and other materials, 2-amino-6-[2-(cyclopropylmethoxy)-6-hydroxyphenyl]-N-methyl-4-(3-piperidinyl)-nicotinamide hydrochloride was prepared in the similar manner as that of Example 8-1 and 8-2.

Molecular weight: 432.95

Mass spectrometry: 397 $(M+H)^+$

In vitro activity grade: A

Cellular activity grade: (A549)-A $^1$H-NMR (300 MHz, DMSO-d6): 0.29–0.34 (2H, m), 0.49–0.55 (2H, m), 1.21 (1H, m), 1.74–1.89 (5H, m), 2.84 (3H, d, J=4.5 Hz), 3.10–3.11 (2H, m), 3.25–3.28 (2H, m), 3.78–3.90 (2H, m), 6.59 (1H, d, J=8.3 Hz), 6.65 (1H, d, J=8.3 Hz), 7.20 (1H, s), 7.26 (1H, t, J=8.3 Hz), 7.56 (1H, br s), 8.76 (1H, br s), 9.08 (1H, br s), 13.8 (1H, br s).

Example 9-1

(1) A mixture of the starting compound 1A (3.500 g, 15.47 mmol), starting compound 2B (3.299 g, 15.47 mmol), tert-butyl cyanoacetate (2.184 g, 15.47 mmol), ammonium acetate (3.577 g, 46.40 mmol) and 1,2-dimethoxyethane (17 mL) was heated at reflux for 3.5 hrs. After cooled to room temperature, the mixture was concentrated under reduced pressure, and the residue was partitioned between ethyl acetate and water. The separated organic phase was washed with brine, dried over $Na_2SO_4$, filtered, and concentrated under reduced pressure. The residue was purified by flash chromatography on silica gel (hexane: ethyl acetate, 4:1) to give tert-butyl 2-amino-6-[2-(benzyloxy)phenyl]-4-[1-(tert-butoxycarbonyl)-3-piperidinyl]nicotinate. (1.892 g, yield; 22%)

(2) Then benzyl moiety was removed in a similar manner as described in the step (2) of Example 1-1. The resulting solid was suspended in ethanol, collected by filtration, washed with ethanol, and dried under reduced pressure to give tert-butyl 2-amino-4-[1-(tert-butoxycarbonyl)-3-piperidinyl]-6-(2-hydroxyphenyl)nicotinate (0.322 g, yield; 38%)

(3) tert-Butyl 2-amino-4-[1-(tert-butoxycarbonyl)-3-piperidinyl]-6-(2-hydroxy-phenyl)nicotinate (0.050 g, 0.106 mmol)) was treated under acidic conditions in a similar manner as described in the step (3) of Example 1-1. to give tert-butyl 2-amino-6-(2-hydroxyphenyl)-4-(3-piperidinyl) nicotinate hydrochloride (0.034 g, yield; 79%).

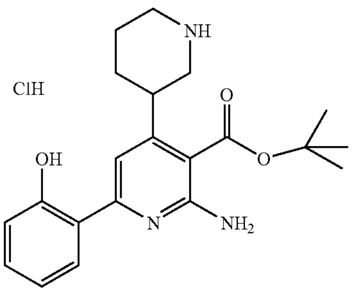

Molecular weight: 405.92

Mass spectrometry: 370 $(M+H)^+$

In vitro activity grade: A

Cellular activity grade: (A549)-B $^1$H-NMR (500 MHz, DMSO-d6): 1.60 (9H, s), 1.76–1.95 (4H, m), 2.90–2.97 (1H, m), 3.20–3.46 (4H, m), 6.89–6.94 (2H, m), 7.31–7.36 (1H, m), 7.38 (1H, s), 8.02 (1H, dd, J=1.3, 8.2 Hz), 9.09 (1H, br), 9.29 (1H, br), 13.78 (1H, br).

Example 9-2

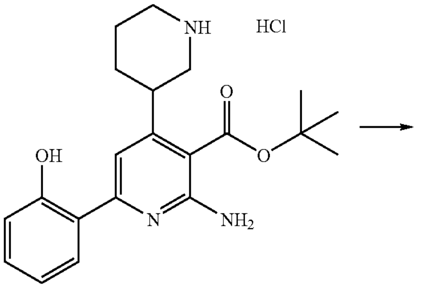

-continued

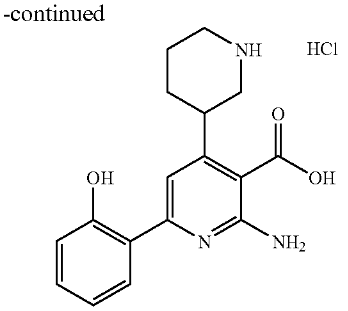

To a solution of tert-butyl 2-amino-6-(2-hydroxyphenyl)-4-(3-piperidinyl)nicotinate hydrochloride (0.023 g, 0.057 mmol), which was obtained in Example 9-1, in methylene chloride (1.0 mL) was added trifluoroacetic acid (TFA) (1.0 mL). After being stirred for 6 hrs, the mixture was concentrated under reduced pressure. The residue was dissolved in 1,4-dioxane (3.0 mL), and then treated with a HCl solution of 1,4-dioxane (4N, 0.2 mL). The resulting precipitates were collected by filtration under an argon atmosphere, washed with 1,4-dioxane and acetonitrile, and dried under reduced pressure to give 2-amino-6-(2-hydroxyphenyl)-4-(3-piperidinyl)-nicotinic acid hydrochloride (0.020 g, yield; quant.).

Molecular weight: 349.82

Mass spectrometry: 314 $(M+H)^+$

In vitro activity grade: A

Cellular activity grade: (A549)-B $^1$H-NMR (500 MHz, DMSO-d6): 1.75–1.93 (4H, m), 2.92 (1H, br m), 2.92–3.39 (3H, m), 3.63–3.67 (1H, br m), 6.91–6.96 (2H, m), 7.32–7.36 (1H, m), 7.37 (1H, s), 7.95 (1H, d, J=7.9 Hz), 8.84 (1H, br), 9.41 (1H, br), 13.80 (1H, br).

Example 9-3

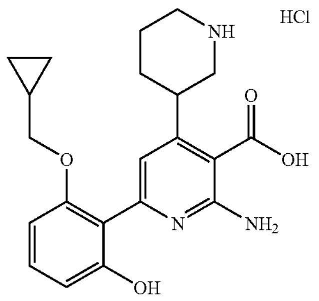

With the use of 1-(2-benzyloxy-6-cyclopropylmethoxy-phenyl)-ethanone prepared in the similar manner as that of the starting compound 1G, the starting compound 2B and other materials, 2-amino-6-[2-(cyclopropylmethoxy)-6-hydroxyphenyl]-4-(3-piperidinyl)nicotinic acid hydrochloride was prepared in a similar manner as described in Example 9-2.

Molecular weight: 419.91

Mass spectrometry: 384 $(M+H)^+$

In vitro activity grade: A

Cellular activity grade: (A549)-C $^1$H-NMR (500 MHz, DMSO-d6): 0.31–0.32 (2H, m), 0.51–0.53 (2H, m), 1.20 (1H, m), 1.70–1.74 (2H, m), 1.89–1.91 (2H, m), 2.89 (1H, m), 3.18 (1H, m), 3.26–3.28 (3H, m), 3.83 (2H, dd, J=6.9, 7.3 Hz), 6.58 (1H, d, J=8.2

Hz), 6.65 (1H, d, J=8.5 Hz), 7.28 (1H, dd, J=8.2, 8.5 Hz), 7.30 (1H, s), 7.81 (1H, br s), 8.92 (1H, s), 9.37 (1H, br s).

Example 10-1

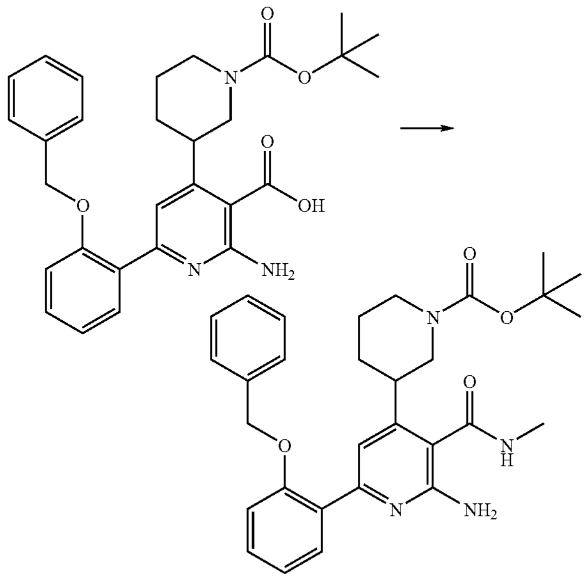

(1) To a solution of 2-amino-6-[2-(benzyloxy)phenyl]-4-[1-(tert-butoxycarbonyl)-3-piperidinyl]nicotinic acid (0.500 g, 0.993 mmol) which was derived from the product in the step (1) of Example 9-1, methylamine hydrochloride (0.134 g, 1.896 mmol), triethylamine (0.277 mL, 1.986 mmol), and 1-hydroxybenzotriazole (0.215 g, 1.589 mmol) in dichloromathane (10.0 mL), at 0° C. under an argon atmosphere was added 1-ethyl-3-(3-dimethylaminopropyl)carbodiimide hydrochloride (0.228 g, 1.191 mmol). The mixture was stirred at room temperature overnight. The reaction mixture was concentrated under reduced pressure, then extracted with ethyl acetate and water. The separated organic phase was washed with brine, dried over $MgSO_4$, filtered, then concentrated under reduced pressure. The resulting residue was purified by column chromatography on Silica-gel (dichloromathane/methanol=19/1) to give tert-butyl 3-{2-amino-6-[2-(benzyloxy)phenyl]-3-[(methylamino)carbonyl]-4-pyridinyl}-1-piperidinecarboxylate as a yellow oil (0.11 g, 21%).

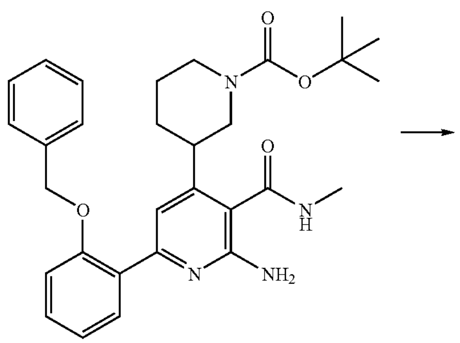

-continued

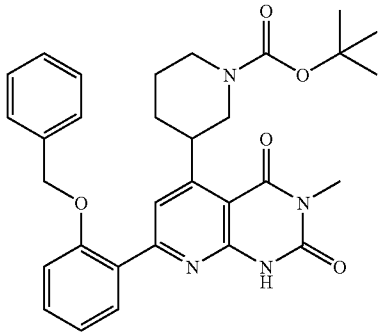

(2) To a cooled (−20° C.) solution of tert-butyl 3-{2-amino-6-[2-(benzyloxy)phenyl]-3-[(methylamino)carbonyl]-4-pyridinyl}-1-piperidinecarboxylate (0.120 g, 0.232 mmol) and triethylamine (0.213 g, 2.090 mmol) in tetrahydrofuran (10 mL) was added triphosgene (0.069 g, 0.232 mmol) under an argon atmosphere. The stirring was continued at 0° C. to room temperature overnight. The reaction mixture was extracted with ethyl acetate and water. The separated organic phase was washed with brine, dried over $MgSO_4$, filtered, and concentrated under reduced pressure. The resulting residue was purified by preparative TLC (hexane/ethyl acetate=2/1) to give tert-butyl 3-{7-[2-(benzyloxy)phenyl]-3-methyl-2,4-dioxo-1,2,3,4-tetrahydro-pyrido[2,3-d]pyrimidin-5-yl}-1-piperidinecarboxylate as a pale yellow solid (0.0655 g, 52%).

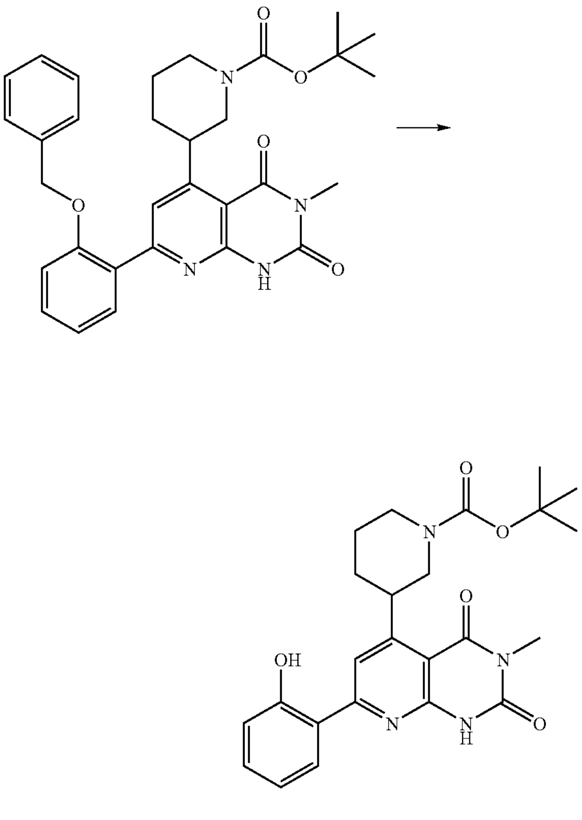

(3) tert-butyl 3-{7-[2-(benzyloxy)phenyl]-3-methyl-2,4-dioxo-1,2,3,4-tetrahydro-pyrido[2,3-d]pyrimidin-5-yl}-1- piperidinecarboxylate (0.065 g, 0.120 mmol) was treated in a similar manner as that of the step (2) of Example 1-1. The residue was purified by preparative TLC (hexane/ethyl acetate=1/1) to give tert-butyl 3-[7-(2-hydroxyphenyl)-3-methyl-2,4-dioxo-1,2,3,4-tetrahydropyrido[2,3-d]pyrimidin-5-yl]-1-piperidinecarboxylate (0.010 g, 18%), which is then treated as described in the step (3) of Example 1-1 to obtain 7-(2-hydroxy-phenyl)-3-methyl-5-piperidin-3-yl-1H-pyrido[2,3-d]pyrimidine-2,4-dione hydrochloride.

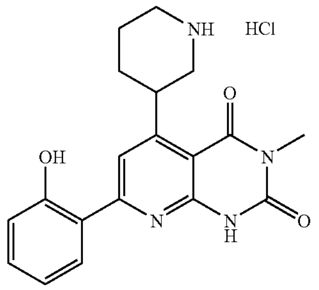

Molecular weight: 388.86

Mass spectrometry: 353 $(M+H)^+$

In vitro activity grade: A

Cellular activity grade: A549-B $^1$H-NMR (500 MHz, DMSO-d6): 1.81–1.85 (2H, m), 1.96–1.98 (2H, m), 2.91 (1H, m), 3.26 (3H, s), 3.31–3.40 (3H, m), 4.70 (1H, m), 6.97–7.00 (2H, m), 7.39 (1H, m), 7.86 (1H, s), 8.16 (1H, m), 8.73 (1H, br), 9.17 (1H, br), 12.37 (1H, s).

Example 10-2

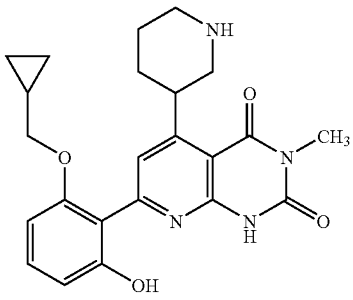

With the use of 1-(2-benzyloxy-6-cyclopropylmethoxy-phenyl)-ethanone prepared in the similar manner as that of the starting compound 1G, the starting compound 2B and other materials, 7-(2-Cyclopropylmethoxy-6-hydroxy-phenyl)-3-methyl-5-piperidin-3-yl-1H-pyrido[2,3-d]pyrimidine-2,4-dione was prepared in a similar manner as that of Example 10-1.

Molecular weight: 458.95

In vitro activity grade: A $^1$H-NMR (500 MHz, DMSO-d6): 0.31–0.34 (2H, m), 0.56–0.60 (2H, m), 1.27 (1H, m), 1.67 (1H, m), 1.79 (1H, m), 1.91–2.01 (2H, m), 2.87 (1H, m), 3.06 (1H, m), 3.27 (3H, s), 3.30 (1H, m), 3.39 (1H, m), 3.83 (1H, dd, J=7.3, 9.8 Hz), 3.91 (2H, dd, J=6.9, 9.8 Hz), 4.65 (1H, m), 6.58 (2H, d, J=8.5 Hz), 7.25 (1H, dd, J=8.2, 8.5 Hz), 7.91 (1H, s), 8.83 (1H, br s), 9.32 (1H, br s), 12.2 (1H, br s).

Example 11-1

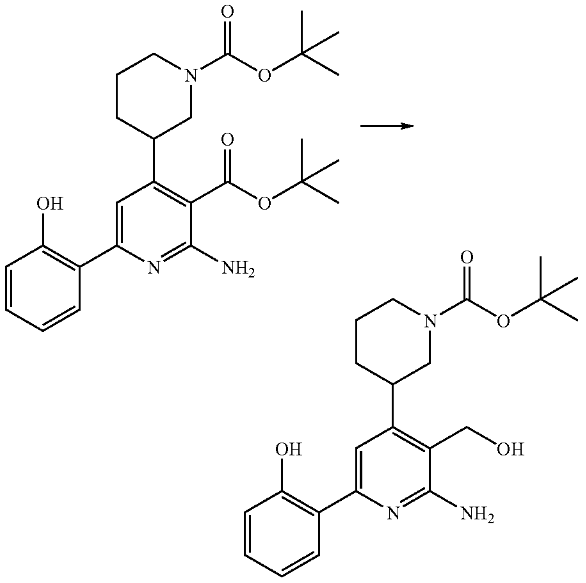

(1) To a cold (0° C.) solution of tert-butyl 2-amino-4-[1-(tert-butoxycarbonyl)-3-piperidinyl]-6-(2-hydroxyphenyl) nicotinate, obtained in the step (2) of Example 9-1, (0.200 g, 0.426 mmol) in THF (3.0 mL) under an argon atmosphere was added $LiBH_4$ (0.019 g, 0.85 mmol). After stirred at room temperature overnight, the mixture was quenched with water, and then extracted with ethyl acetate and 0.5N HCl. The separated organic phase was washed with water and brine, dried over $Na_2SO_4$, filtered and concentrated under reduced pressure. The residue was purified by column chromatography on silica gel (hexane:ethyl acetate, 1:1) to give tert-butyl 3-[2-amino-3-(hydroxymethyl)-6-(2-hydroxyphenyl)-4-pyridinyl]-1-piperidine-carboxylate. (0.161 g, yield; 95%)

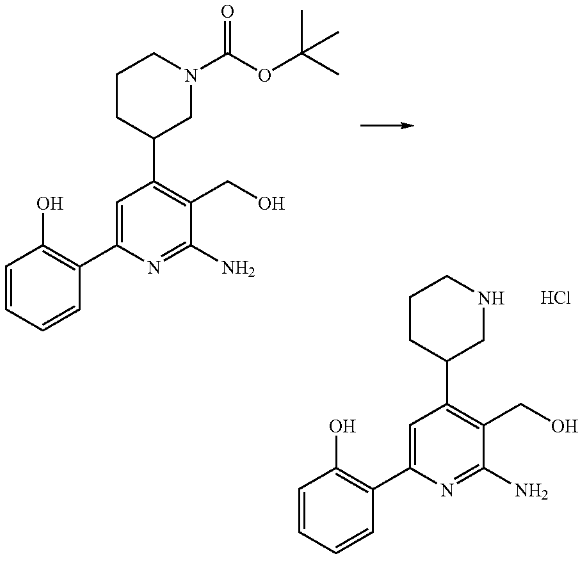

tert-Butyl 3-[2-amino-3-(hydroxymethyl)-6-(2-hydroxyphenyl)-4-pyridinyl]-1-piperidinecarboxylate (0.160 g, 0.401 mmol) in 1,4-dioxane (3.0 mL) was treated under acidic conditions in a similar manner as described in the step (3) of Example 1-1 to give 2-[6-amino-5-(hydroxymethyl)-4-(3-piperidinyl)-2-pyridinyl]phenol hydro-chloride. (0.132 g, yield; 98%)

Molecular weight: 335.84

Mass spectrometry: 300 $(M+H)^+$

In vitro activity grade: A

Cellular activity grade: (A549)-A $^1$H-NMR (500 MHz, DMSO-d6): 1.75–1.98 (4H, m), 2.90 (1H, br), 3.14–3.33 (3H, m), 3.56–3.60 (1H, br), 4.58 (2H, dd, J=13.0, 20.2 Hz), 6.96 (1H, t, J=7.6 Hz), 7.06 (1H, d, J=7.9 Hz), 7.19 (1H, s), 7.37 (1H, br t, J=7.3 Hz), 7.65 (1H, br d, J=7.6 Hz), 9.03 (1H, br), 9.32 (1H, br), 13.59 (1H, br).

Example 11-2

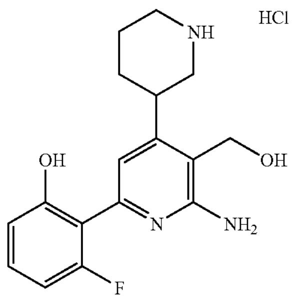

With the use of starting compound 1I and 2B, and other materials, 2-[6-amino-5-(hydroxymethyl)-4-(3-piperidinyl)-2-pyridinyl]-3-fluorophenol hydrochloridewas prepared in a similar manner as that of Example 11-1.

Molecular weight: 353.83

Mass spectrometry: 318 $(M+H)^+$

In vitro activity grade: A

Cellular activity grade: (A549)-A $^1$H-NMR (500 MHz, DMSO-d6): 1.03 (3H, t, J=7.6 Hz), 1.83 (4H, m), 3.00 (2H, m), 3.31 (2H, m), 3.71 (1H, m), 4.56 (2H, dd, J=13.1, 19.4), 5.16 (1H, br), 6.79 (2H, m), 7.12 (1H, s), 7.32 (1H, m), 8.52 (1H, d, J=9.8 Hz), 8.86 (1H, d, J=9.8 Hz), 14.0 (1H, br).

Example 11-3

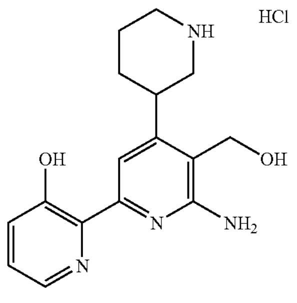

With the use of the starting compound 1F, the starting compound 2B, and other materials, 6'-amino-5'-(hydroxymethyl)-4'-(3-piperidinyl)-2,2'-bipyridin-3-ol hydro-chloride was prepared in a similar manner as that of Example 11-1.

Molecular weight: 336.82

Mass spectrometry: 301 $(M+H)^+$

In vitro activity grade: A

Cellular activity grade: (A549)-A $^1$H-NMR (500 MHz, DMSO-d6): 1.81–1.95 (3H, m), 2.46–2.64 (1H, m), 3.00–3.06 (2H, m), 3.28–3.39 (2H, m), 3.54–3.60 (1H, m), 4.56 (1H, d, J=13.0 Hz). 4.59 (1H, d, J=13.0 Hz), 7.41–7.50 (2H, m), 7.81 (1H, s), 8.24 (1H, d, J=3.8 Hz), 8.92 (1H, br), 9.07 (1H, br).

Example 11-4

(1) With the use of the starting compound 1D instead of 1A and 2H instead of 2B, di(tert-butyl) 2'-amino-6'-{2-[(4-methoxybenzyl)oxy]phenyl}-5,6-dihydro-3,4'-bipyridine-1,3'(2H)-dicarboxylate was prepared in a similar method as that of step (1) of Example 9-1.

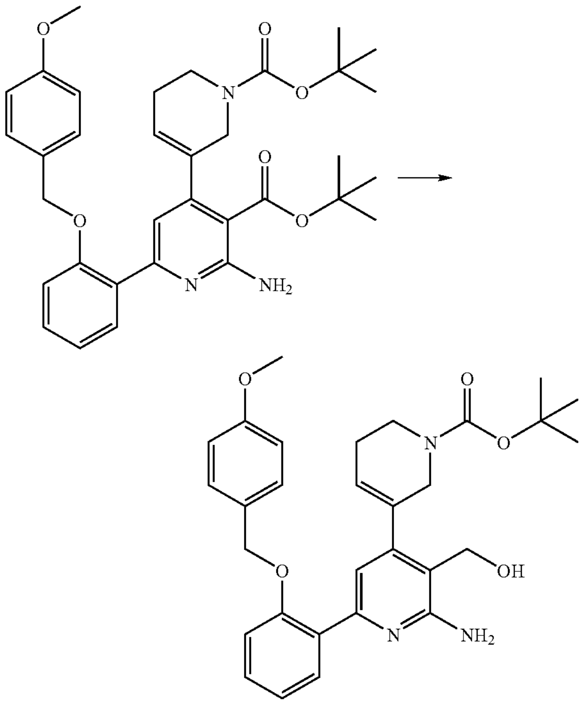

(2) To a cooled (0° C.) solution of di(tert-butyl) 2'-amino-6'-{2-[(4-methoxy-benzyl)oxy]phenyl}-5,6-dihydro-3,4'-bipyridine-1,3'(2H)-dicarboxylate (50.0 mg, 0.09 mmol) in THF (4.5 mL) was added sodium bis(2-methoxyethoxy) aluminum hydride (0.10 mL) dropwise, then stirred for 1 hr at 0° C. The reaction was quenched by an addition of saturated $NH_4Cl$ solution, filtered, and washed with ethyl acetate. The combined organic phase was washed with brine, dried over $MgSO_4$, filtered and evaporated. The crude product was purified by preparative silica gel TLC (15% acetone in chloroform) to give tert-butyl 2'-amino-3'-(hydroxymethyl)-6'-{2-[(4-methoxybenzyl)oxy]phenyl}-5,6-dihydro-3,4'-bipyridine-1(2H)-carboxylate as a white foam (25 mg, yield 57%).

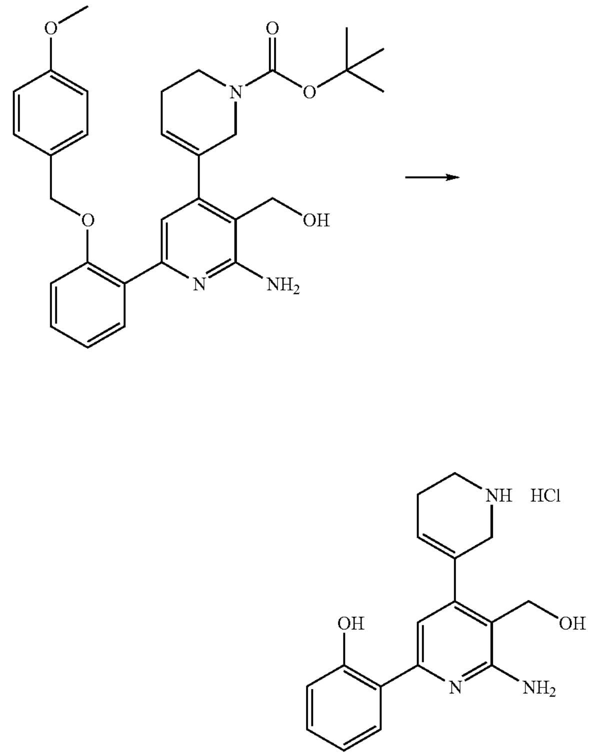

(3) tert-butyl 2'-amino-3'-(hydroxymethyl)-6'-{2-[(4-methoxybenzyl)oxy]phenyl}-5,6-dihydro-3,4'-bipyridine-1(2H)-carboxylate (25.0 mg, 0.05 mmol) was treated with 2N HCl in dioxane (4.0 mL) overnight at room temperature. The resulting solid was collected by filtration, washed with ether and dried under reduced pressure to give 2-[6'-amino-5'-(hydroxymethyl)-1,2,5,6-tetrahydro-3,4'-bipyridin-2'-yl]phenol hydrochloride. (14 mg, yield 87%)

Molecular weight: 333.82

Mass spectrometry: 298 $(M+H)^+$

In vitro activity grade: A

Cellular activity grade: (A549)-A $^1$H-NMR (300 MHz, D2O):2.51 (2H, br s), 3.35 (2H, br s), 3.83 (2H, s), 4.58 (2H, s), 6.04 (1H, br s), 6.93–7.01 (3H, m), 7.34–7.47 (2H, m).

Example 12-1

(1) A mixture of 1-[2,6-bis(benzyloxy)phenyl]ethanone (8.00 g, 24.067 mmol) (starting compound 1E), tert-butyl 3-formyl-1-piperidinecarboxylate (5.133 g, 24.067 mmol) (starting compound 2B), tert-butylcyanoacetate (3.398 g, 24.067 mmol), and ammonium acetate (5.432 g, 72.202 mmol) in 1,2-dimethoxyethane (24 mL) was stirred at 100° C. in a sealed tube overnight. After cooled to room temperature, the reaction mixture was partitioned between ethyl acetate and water. The separated organic phase was washed with brine, dried over $MgSO_4$, filtered and concentrated under reduced pressure. The residue was diluted with 30 mL of dichloromethane, and $MnO_2$ was added to the mixture, and then the mixture was stirred at room temperature for 5 hrs. The mixture was filtered on Celite®, and concentrated under reduced pressure. The resulting residue (liquid) was purified by column chromatography on silica gel (hexane/ethyl acetate=2/1) to give tert-butyl 2-amino-6-[2,6-bis(benzyloxy)phenyl]-4-[1-(tert-butoxycarbonyl)-3-piperidinyl] nicotinate as a pale yellow oil. (2.5 g, yield; 16%)

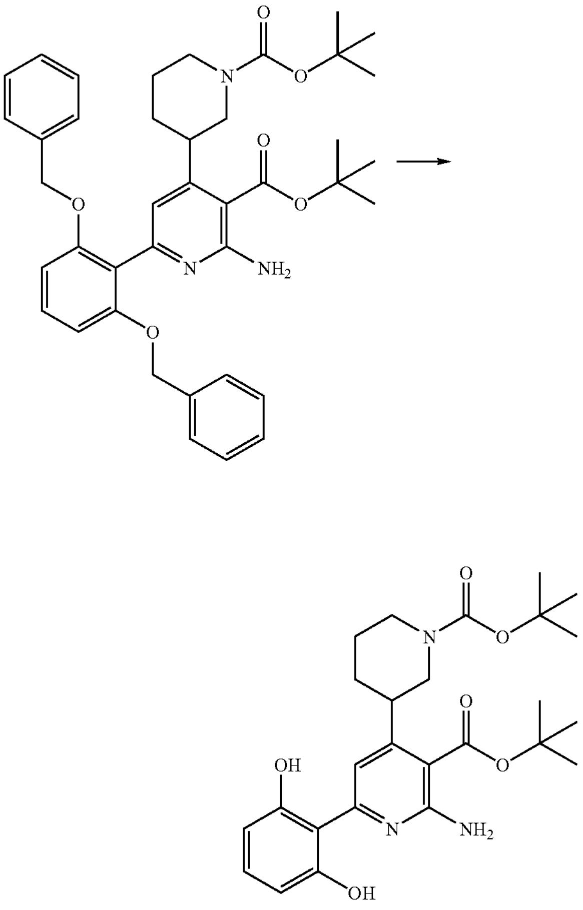

(2) A suspension of tert-butyl 2-amino-6-[2,6-bis(benzyloxy)phenyl]-4-[1-(tert-butoxycarbonyl)-3-piperidinyl] nicotinate (1.00 g, 1.052 mmol) and 10% Paradium-carbon (0.500 g) in 20 mL of ethyl acetate was stirred at room temperature under a hydrogen atmosphere (1 atm) overnight. After paradium carbon was removed by filtration on Celite®, the filtrate was concentrated under reduced pressure to give tert-butyl 2-amino-4-[1-(tert-butoxycarbonyl)-3-piperidinyl]-6-(2,6-dihydroxyphenyl)-nicotinate as a brown oil. (0.710 g, yield; 97%)

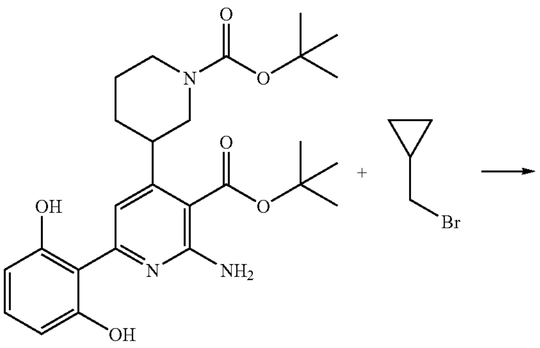

-continued

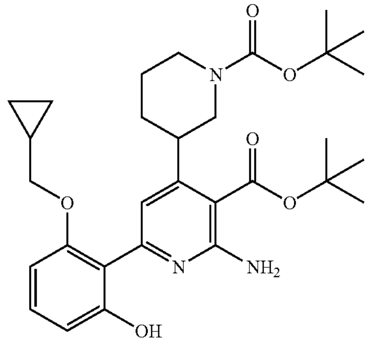

(3) To a solution of tert-butyl 2-amino-4-[1-(tert-butoxycarbonyl)-3-piperidinyl]-6-(2,6-dihydroxyphenyl)nicotinate (1.280 g, 2.636 mmol) and $K_2CO_3$ (3.643 g, 26.36 mmol) in DMF (100 mL) was added (bromomethyl)cycropropane (0.268 mL, 2.768 mmol). The stirring was continued at 50° C. for 20 hrs. After the solvent was removed by evaporation, the residue was extracted with ethyl acetate and water. The separated organic phase was washed with brine, dried over $MgSO_4$, filtered, then concentrated under reduced pressure. The resulting residue was purified by column chromatography on Silica-gel(hexane/ethyl acetate=3/1) to give tert-butyl 2-amino-4-[1-(tert-butoxycarbonyl)-3-piperidinyl]-6-[2-(cyclopropylmethoxy)-6-hydroxyphenyl]nicotinate as a brown solid (0.820 g, yield; 58%).

tert-butyl 2-amino-4-[1-(tert-butoxycarbonyl)-3-piperidinyl]-6-[2-(cyclopropyl-methoxy)-6-hydroxyphenyl]nicotinate was treated in a similar manner as that of the step (1) of Example 11-1 and then in a similar manner as that of the step (3) of Example 1-1 to obtain 2-[6-amino-5-(hydroxymethyl)-4-(3-piperidinyl)-2-pyridinyl]-3-(cyclopropylmethoxy)phenol hydrochloride.

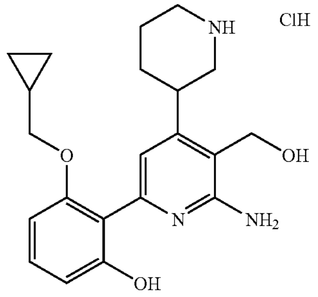

Molecular weight: 405.93

Mass spectrometry: 370 $(M+H)^+$

In vitro activity grade: A

Cellular activity grade: (A549)-A $^1$H-NMR (300 MHz, DMSO-d6): 0.26–0.29 (2H, m), 0.47–0.52 (2H, m), 1.13 (1H, m), 1.75–1.83 (5H, m), 2.90–2.93 (2H, m), 3.04–3.17 (2H, m), 3.81–3.86 (2H, m), 4.60 (2H, s), 6.55 (1H, d, J=8.3 Hz), 6.60 (1H, d, J=8.3 Hz), 7.06 (1H, s), 7.27 (1H, t, J=8.3 Hz), 7.59 (1H, br), 8.96 (1H, br), 9.25 (1H, br), 13.58 (1H, br).

Examples 12-2 to 12-7

According to the similar synthetic procedure of Example 12-1, compounds shown in Table 4 were prepared.

TABLE 4

| Ex. No | Structure | Mol weight | Mass | in vitro | A549 | NMR |
|---|---|---|---|---|---|---|
| 12-02 | 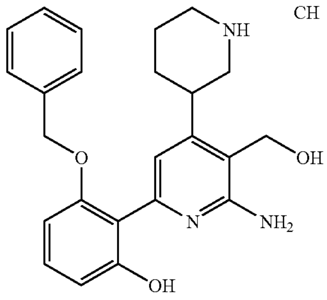 | 441.96 | 406 | A | B | (500MHz, DMSO-d6): 1.56–1.88 (4H, m), 2.84–3.20(3H, m), 4.54 (1H, d, J=13.2Hz), 4.57(1H, d, J=13.2Hz), 5.08(2H, s), 6.70 (1H, d, J=8.2Hz), 6.76(1H, d, J = 8.5Hz), 7.05(1H, s), 7.29–7.41(6H, m), 7.60(1H, br), 8.95 (1H, br), 9.25(1H, br), 10.42(1H, br), 13.67(1H, br). |
| 12-03 | 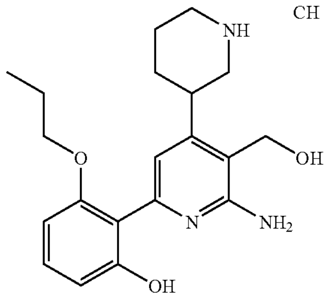 | 393.92 | 358 | A | A | (500MHz, DMSO-d6): 0.87(3H, t, J=7.2Hz), 1.64(2H, q, J=6.9 Hz), 1.88–1.90(3H, m), 2.07 (1H, m), 2.88(1H, m), 3.05(1H, m), 3.22–3.24(2H, m), 3.56(1H, m), 3.92(2H, t, J=6.6Hz), 4.59 (2H, d, J=3.1Hz), 4.96(1H, br), 6.62(1H, d, J=8.2Hz), 6.66(1H, d, J=8.2Hz), 7.00(1H, s), 7.29 (1H, t, J=8.2Hz), 7.58(1H, br), 8.92(1H, br), 9.21(1H, br), 13.57 (1H, br). |

TABLE 4-continued
| Ex. No | Structure | Mol weight | Mass | in vitro | A549 | NMR |
|---|---|---|---|---|---|---|
| 12-04 | 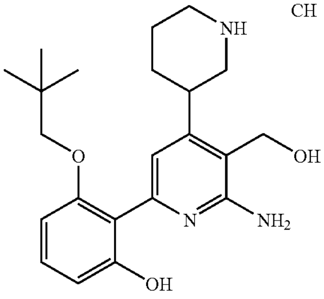 CH | 421.97 | 386 | A | A | (500MHz, DMSO-d6): 0.83(9H, s), 0.82–1.05(4H, m), 1.75–1.93(4H, m), 2.87(1H, br), 3.02–3.07(4H, m), 4.61(2H, dd, J=13.2, 18.6Hz), 4.99(1H, br), 6.60 (1H, d, J=8.5Hz), 6.67(1H, d, J = 8.2Hz), 6.79–6.89(1H, m), 6.98(1H, s), 7.07(1H, br), 7.27–7.29(1H, br), 7.62(1H, br), 13.72 (1H, br). |
| 12-05 | 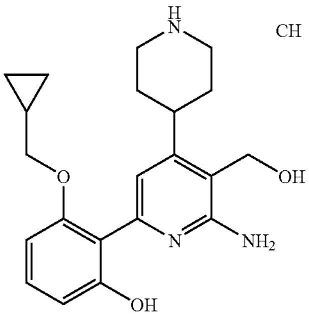 CH | 405.93 | 370 | A | A | (500MHz, DMSO-d6): 0.29–0.32 (2H, m), 0.46–0.50(2H, m), 1.19 (1H, m), 1.89–2.05(2H, m), 3.01–3.07(2H, m), 3.34–3.48(3H, m), 3.84(2H, d, J=6.9Hz), 4.61 (2H, s), 6.59(1H, d, J=8.5Hz), 6.69(1H, d, J=8.2Hz), 6.80(1H, s), 7.27(1H, dd, J=8.2, 8.5Hz), 7.75(1H, br s), 9.14–9.25(2H, m), 13.6(1H, br). |
| 12-06 | 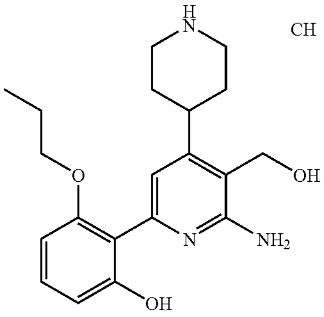 CH | 393.92 | 358 | A | A | (500MHz, DMSO-d6): 0.85(3H, t, J=7.3Hz), 1.63–1.67(2H, m), 1.82–1.85(2H, m), 1.90–1.95 (2H, m), 3.03–3.08(2H, m), 3.34–3.45(4H, m), 3.92(2H, t, J=6.6 Hz), 4.60(2H, s), 6.62(1H, d, J=8.2Hz), 6.68(1H, d, J=8.2Hz), 6.75(1H, s), 7.28(1H, t, J=8.2 Hz), 7.63(1H, br), 8.98(2H, br). |
| 12-07 | 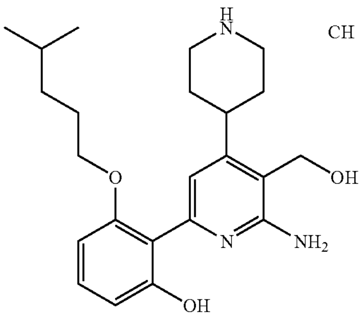 CH | 436.00 | 400 | A | A | (500MHz, DMSO-d6): 0.79–0.82 (7H, m), 1.12–1.16(2H, m), 1.42–1.49(1H, m), 1.60–1.66(2H, m), 1.82–1.84(2H, m), 1.93–1.98(2H, m), 3.93–3.95(2H, m), 4.60(2H, s), 6.61(1H, d, J=8.2 Hz), 6.68(1H, d, J=8.2Hz), 6.74 (1H, s), 7.28(1H, t, J=8.2Hz), 7.68(2H, s), 9.07(2H, s), 10.38 (1H, brs). |

Example 13-1

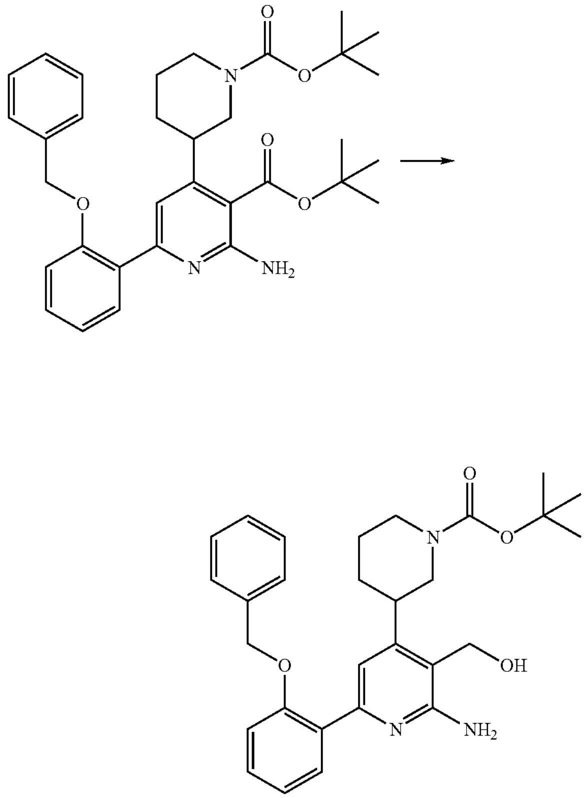

(1) To a cold (0° C.) solution of tert-butyl 2-amino-6-[2-(benzyloxy)phenyl]-4-[1-(tert-butoxycarbonyl)-3-piperidinyl]nicotinate, which was obtained in the step (1) of Example 9-1, (2.590 g, 4.627 mmol) in THF (25 mL) was added $LiBH_4$ (0.202 g, 9.255 mmol). The mixture was stirred at room temperature for 5 hrs, and then quenched with water. The mixture was extracted with ethyl acetate and water. The separated organic phase was washed with water and brine, dried over $Na_2SO_4$, filtered and concentrated under reduced pressure. The residue was purified by column chromatography on silica gel (hexane: ethyl acetate, 2:3) to give tert-butyl 3-[2-amino-6-[2-(benzyloxy)phenyl]-3-(hydroxymethyl)-4-pyridinyl]-1-piperidine-carboxylate. (0.904 g, yield; 40%)

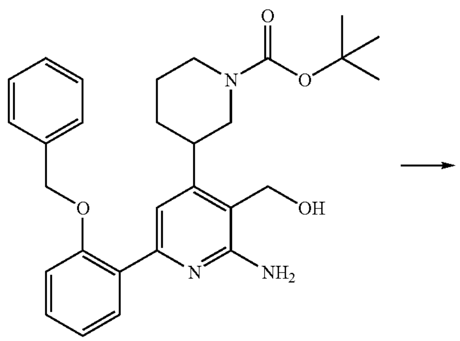

-continued

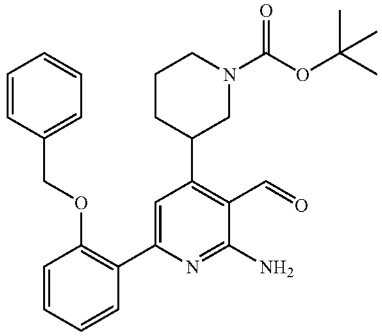

(2) To a solution of tert-butyl 3-[2-amino-6-[2-(benzyloxy)phenyl]-3-(hydroxy-methyl)-4-pyridinyl]-1-piperidinecarboxylate (0.900 g, 1.838 mmol) in methylene chloride (20 mL) was added manganese (IV) oxide (3.20 g, 36.8 mmol). After stirred at room temperature for 40 min, the mixture was filtered to remove the manganese salt. The filtrate was concentrated under reduced pressure. The resulting solid was purified by recrystallization from a mixture of ethyl acetate and hexane to give tert-butyl 3-[2-amino-6-[2-(benzyloxy)phenyl]-3-formyl-4-pyridinyl]-1-piperidine-carboxylate. (0.651 g, yield; 73%)

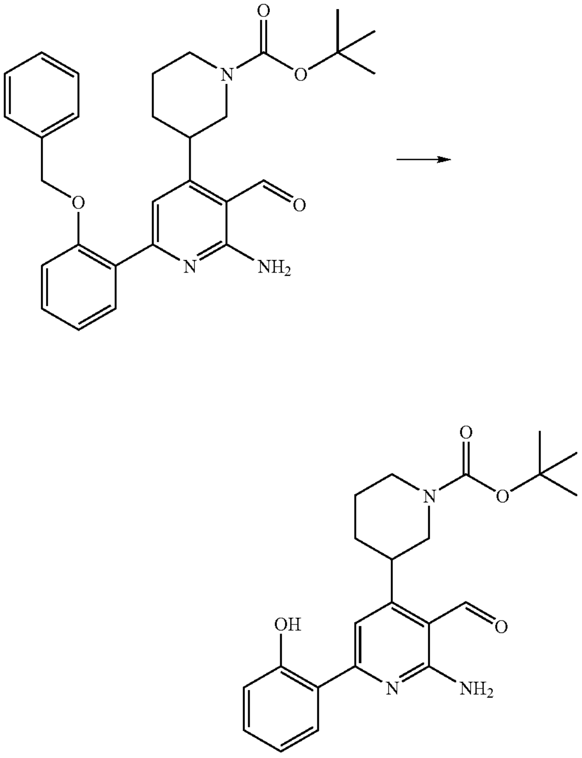

(3) Then the benzyl moiety was removed in a similar manner as described in the step (2) of Example 1-1. The residue was purified by column chromatography on silica gel (hexane: ethyl acetate, 2:1) to give tert-butyl 3-[2-amino-3-formyl-6-(2-hydroxy-phenyl)-4-pyridinyl]-1-piperidinecarboxylate. (0.536 g, yield; quant.)

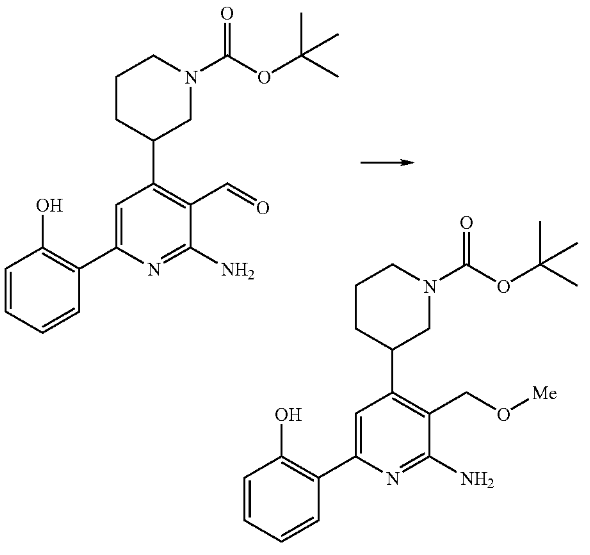

(4) To a solution of tert-butyl 3-[2-amino-3-formyl-6-(2-hydroxyphenyl)-4-pyridinyl]-1-piperidinecarboxylate (0.100 g, 0.252 mmol) in 1,4-dioxane (2.0 mL) under an argon atmosphere was added a HCl solution of 1,4-dioxane (4N, 2.0 mL), and the stirring was continued at room temperature for 1 hr. The mixture was diluted with $Et_2O$, and the supernatant was decanted. The precipitates were washed twice with $Et_2O$, and dried under reduced pressure to give a pale yellow solid, which was then dissolved in methanol (2.0 mL). The mixture was allowed to cool with ice-water bath. Then sodium cyanoborohydride (0.047 g, 0.76 mmol) was added to the mixture under an argon atmosphere. The mixture was allowed to warm to room temperature, and the stirring was continued overnight. The resulting mixture was concentrated under reduced pressure. The residue was dissolved in a mixture of methylene chloride (2.0 mL) and THF (2.0 mL). To the mixture was added triethyl-amine (0.140 mL, 1.006 mmol) followed by di-tert-butyl dicarbonate (0.110 g, 0.503 mmol), and the stirring was continued for 2 hrs. The resulting mixture was partitioned between ethyl acetate and water. The separated organic phase was washed with brine, dried over $Na_2SO_4$, filtered, and concentrated under reduced pressure. The residue was purified by column chromatography on silica gel (hexane:ethyl acetate, 2:1) to give tert-Butyl 3-[2-amino-6-(2-hydroxyphenyl)-3-(meth-oxy-methyl)-4-pyridinyl]-1-piperidinecarboxylate. (0.033 g, yield; 47%)

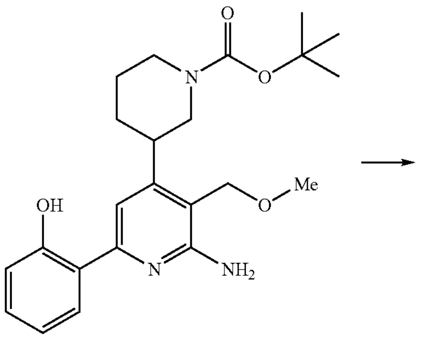

-continued

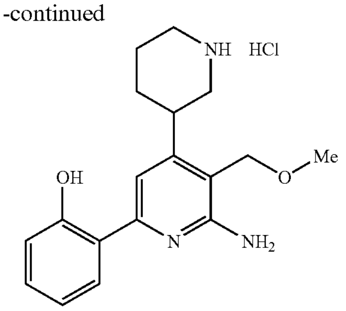

(4) tert-Butyl 3-[2-amino-6-(2-hydroxyphenyl)-3-(methoxymethyl)-4-pyridinyl]-1-piperidinecarboxylate (0.025 g, 0.060 mmol) was treated under acidic conditions in a similar manner as described in the step (3) of Example 1-1 to give 2-[6-amino-5-(methoxymethyl)-4-(3-piperidinyl)-2-pyridinyl]phenol hydrochloride.

Molecular weight: 349.86

Mass spectrometry: 314 $(M+H)^+$

In vitro activity grade: A

Cellular activity grade: (A549)-A $^1$H-NMR (500 MHz, DMSO-d6): 1.40–1.74 (4H, m), 2.80–2.92 (2H, m), 4.03–4.13 (2H, m), 4.42 (1H, d, J=11.5 Hz), 4.50 (1H, d, J=11.5 Hz), 6.22–6.32 (2H, m), 6.81–6.85 (2H, m), 7.17 (1H, s), 7.21 (1H, br t, J=7.3 Hz), 7.93 (1H, br d, J=7.6 Hz), 14.30 (1H, br).

Example 14-1

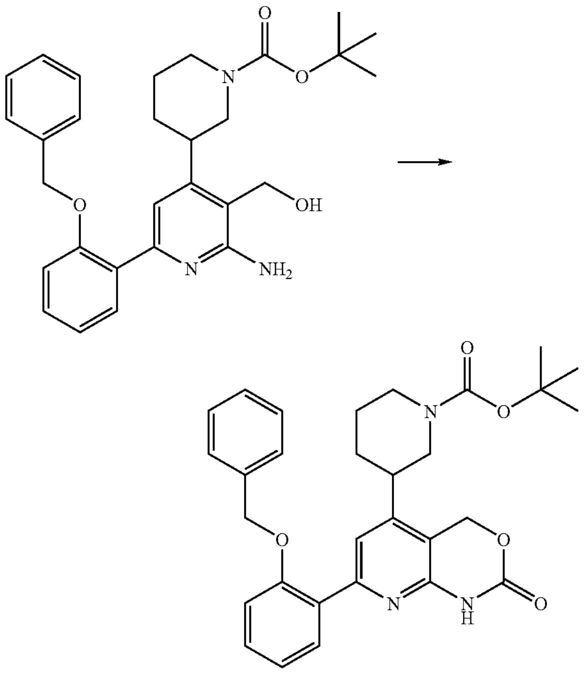

To a cold (0° C.) solution of tert-butyl 3-[2-amino-6-[2-(benzyloxy)phenyl]-3-(hydroxymethyl)-4-pyridinyl]-1-piperidinecarboxylate (0.104 g, 0.212 mmol) obtained in the step (1) of Example 13-1 in THF (2.0 mL) including triethylamine (0.089 mL, 0.64 mmol) was added triphosgene (0.044 g, 0.15 mmol). After stirred for 30 min, the mixture was allowed to warm to room temperature, and the stirring was continued for further 1 hr. The resulting mixture was quenched with water and extracted with ethyl acetate. The separated organic phase was washed with brine, dried over $Na_2SO_4$, filtered and concentrated under reduced pressure. The residue was purified by column chromatography on silica gel (hexane:ethyl acetate, 5:3) to give tert-butyl 3-{7-[2-benzyloxy]phenyl]-2-oxo-1,4-dihydro-2H-pyrido[2,3-d][1,3]-oxazin-5-yl}-1-piperazinecarboxylate. (0.058 g, yield; 53%)

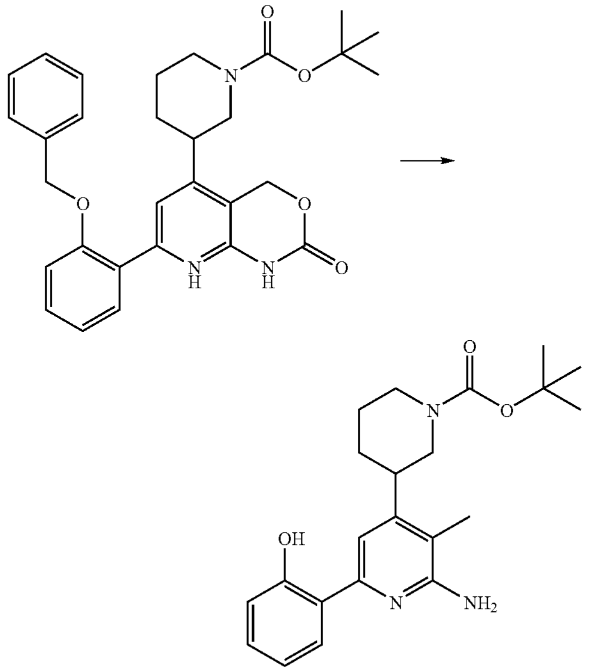

A solution of tert-butyl 3-{7-[2-benzyloxy]phenyl]-2-oxo-1,4-dihydro-2H-pyrido-[2,3-d][1,3]oxazin-5-yl}-1-piperazinecarboxylate (0.050 g, 0.097 mmol) in ethyl acetate (3.0 mL) was hydrogenated at 1 atm in the presence of palladium on charcoal (10%, 0.10 g) overnight. The resulting mixture was filtered on Celite® and washed with ethyl acetate and THF. The combined filtrate was concentrated under reduced pressure, and the residue was purified by column chromatography on silica gel (hexane:ethyl acetate, 2:1) to give tert-Butyl 3-[2-amino-6-(2-hydroxyphenyl)-3-methyl-4-pyridinyl]-1-piperidinecarboxylate. (0.027 g, yield; 73%)

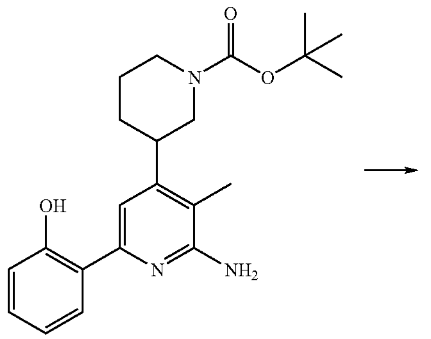

-continued

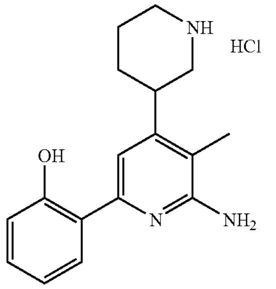

tert-Butyl 3-[2-amino-6-(2-hydroxyphenyl)-3-methyl-4-pyridinyl]-1-piperidine-carboxylate (0.025 g, 0.065 mmol) was treated under acidic conditions in a similar manner as described in the step (3) of Example 1-1 to give 2-[6-amino-5-methyl-4-(3-piperidinyl)-2-pyridinyl]phenol hydrochloride. (0.017 g, yield; 82%)

Molecular weight: 319.84

Mass spectrometry: 284 $(M+H)^+$

In vitro activity grade: A

Cellular activity grade: (A549)-A/Jurkat-B $^1$H-NMR '(500 MHz, DMSO-d6): 1.08–1.75 (4H, m), 2.10 (3H, s), 2.55–2.98 (3H, m), 4.12 (1H, br), 6.19 (2H, br d, J=15.1 Hz), 6.79–6.83 (2H, m), 7.12 (1H, s), 7.18 (1H, br t, J=7.9 Hz), 7.88 (1H, br).

Example 15-1

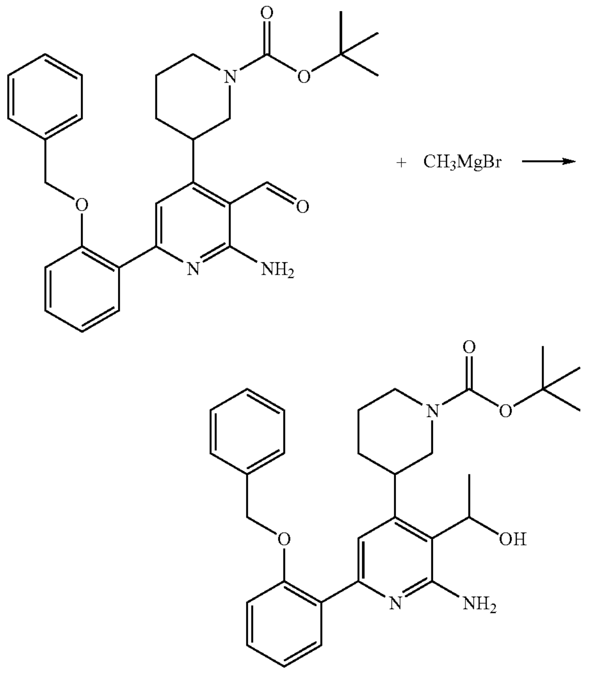

(1) To a cold (−20° C.) solution of tert-butyl 3-{2-amino-6-[2-(benzyloxy)phenyl]-3-formyl-4-pyridinyl}-1-piperidinecarboxylate (400 mg, 0.82 mmol), which was obtained in the step (2) of Example 13-1, in THF (2.0 mL) was added dropwise a solution methyl magnesium bromide in THF (7.38 mL, 7.38 mol). The mixture was stirred at −20° C. for 2 hrs , quenched with saturated aqueous $NH_4Cl$ solution, and extracted with ethyl acetate. The separated organic phase was washed with water and brine, dried over $Na_2SO_4$, filtered and concentrated under reduced pressure. The residue was purified by silica gel column chromatography (hexane/ethyl acetate, 3:2) to give tert-butyl 3-[2-amino-6-[2-(benzyloxy)phenyl]-3-(1-hydroxyethyl)-4-pyridinyl]-1-piperidinecarboxylate as a yellow oil. (356 mg, yield; 86%)

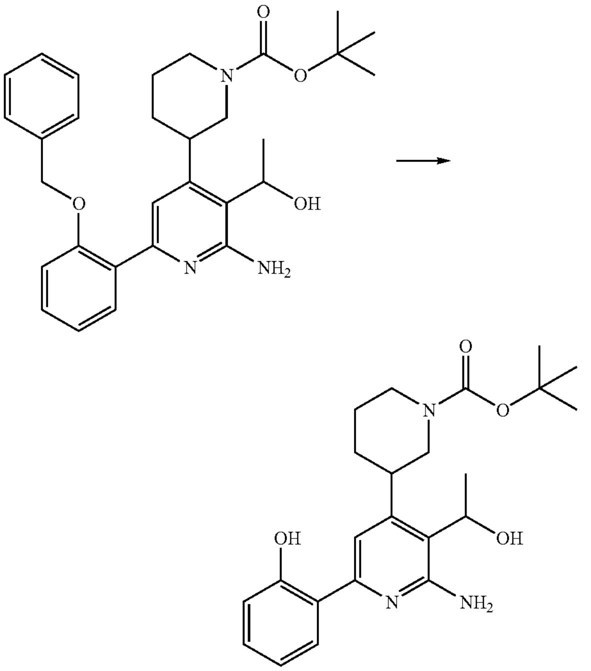

(2) Then benzyl moiety was removed in a similar manner as described in the step (2) of Example 1-1 to give tert-Butyl 3-[2-amino-3-(1-hydroxyethyl)-6-(2-hydroxy-phenyl)-4-pyridinyl]-1-piperidinecarboxylate as a pale yellow oil. (147 mg, yield; 96%)

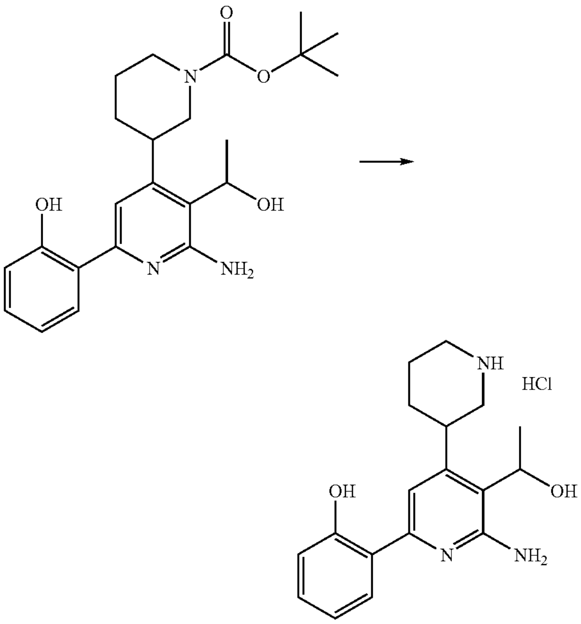

(3) tert-Butyl 3-[2-amino-3-(1-hydroxyethyl)-6-(2-hydroxyphenyl)-4-pyridinyl]-1-piperidinecarboxylate (30 mg, 0.07 mmol) was treated under acidic conditions in a similar manner as described in the step (3) of Example 1-1 to give 2-[6-amino-5-(1-hydroxyethyl)-4-(3-piperidinyl)-2-pyridinyl]phenol hydrochloride as a yellow solid. (20 mg, yield; 78%)

Molecular weight: 349.86

Mass spectrometry: 296 $(M+H)^+$

In vitro activity grade: A

Cellular activity grade: (A549)-B $^1$H-NMR (500 MHz, DMSO-d6): 1.83–1.92 (7H, m), 2.90–2.91 (1H, m), 3.13–3.15 (1H, m), 3.57 (3H, s), 5.29–5.39 (1H, m), 6.89–6.99 (1H, m), 7.05-7.10 (1H, m), 7.17 (1H, d, J=3.16 Hz), 7.27–7.40 (2H, m), 7.62 (1H, d, J=5.0Hz), 7.68–7.87 (2H, m), 13.50 (1H, br s).

Example 15-2

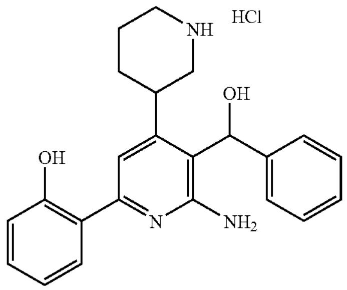

In a similar manner as that of Example 15-1,2-[6-amino-5-[hydroxy(phenyl)methyl]-4-(3-piperidinyl)-2-pyridinyl]phenol hydrochloride was prepared.

Molecular weight: 411.94

Mass spectrometry: 376 $(M+H)^+$

In vitro activity grade: A

Cellular activity grade: (A549)-B $^1$H-NMR (500 MHz, DMSO-d6): 1.67–1.74 (2H, m), 1.89–1.99 (2H, m), 2.88–2.93 (1H, m), 3.14–3.24 (4H, m), 6.32 (1H, s), 6.91 (1H, d, J=2.2 Hz), 6.92–7.01 (2H, m), 7.24–7.32 (3H, m), 7.34–7.40 (6H, m), 7.42–7.44 (1H, m), 7.75 (1H, d, J=7.9 Hz). Example 15-3

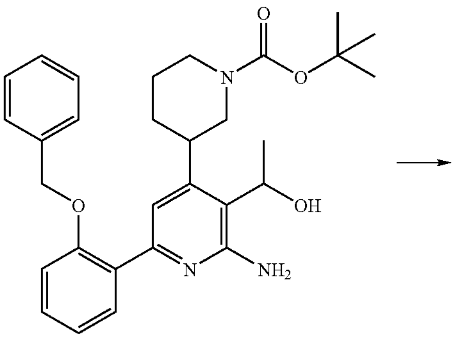

-continued

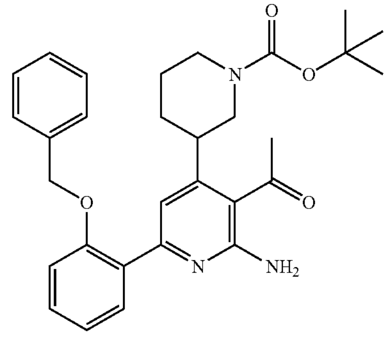

To a stirred solution of tert-butyl 3-[2-amino-6-[2-(benzyloxy)phenyl]-3-(1-hydroxyethyl)-4-pyridinyl]-1-piperidinecarboxylate (0.100 g, 0.199 mmol) obtained in the step (1) of Example 15-1 in dichrolomethane (1 mL) was added $MnO_2$ (0.350 g, 3.971 mmol). The mixture was stirred at room temperature for 2 hrs. The mixture was filtered on Celite® and concentrated under reduced pressure to give tert-butyl 3-{3-acetyl-2-amino-6-[2-(benzyloxy)phenyl]-4-pyridinyl}-1-piperidine carboxylate.

tert-butyl 3-{3-acetyl-2-amino-6-[2-(benzyloxy)phenyl]-4-pyridinyl}-1-piperidin carboxylate (0.090 g, 0.169 mmol) was then treated in a similar manner as that of the step (2) of Example 1-1. The residue was recrystallized from ethyl alcohol to give tert-butyl 3-[3-acetyl-2-amino-6-(2-hydroxyphenyl)-4-pyridinyl]-1-piperidine-carboxylate as a pale yellow solid. (0.019 g, yield 27%)

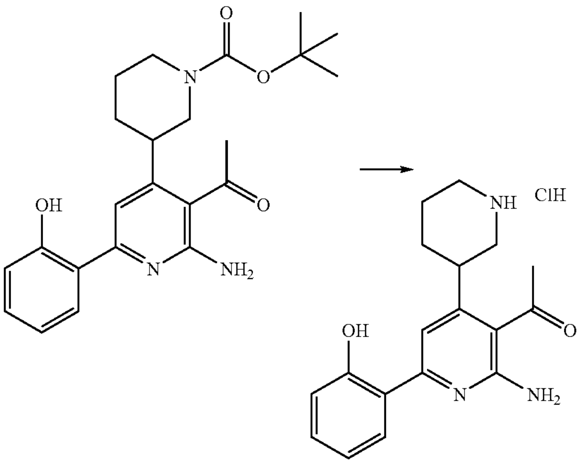

Then tert-butyl 3-[3-acetyl-2-amino-6-(2-hydroxyphenyl)-4-pyridinyl]-1-piperidine-carboxylate (0.020 g, 0.044 mmol) was treated in a similar manner as that of the step (3) of Example 1-1. The resulting precipitate was collected by filtration, washed with acetonitril, and dried under reduced pressure to give 1-[2-amino-6-(2-hydroxy-phenyl)-4-(3-piperidinyl)-3-pyridinyl]ethanone hydrochloride. (0.014 g, yield 89%)

Molecular weight: 347.85

Mass spectrometry: 312 $(M+H)^+$

In vitro activity grade: A

Cellular activity grade: (A549)-A $^1H$-NMR (500 MHz, DMSO): 1.17–1.87 (4H, m), 2.92–2.98 (1H, m), 2.56 (3H, s), 3.00–3.29 (4H, m), 6.98–6.91 (4H, m), 7.30 (1H, dd, J=7.3, 7.9 Hz), 7.37 (1H, s), 8.73 (1H, d, J=7.6 Hz), 13.73 (1H, br s).

Example 16-1

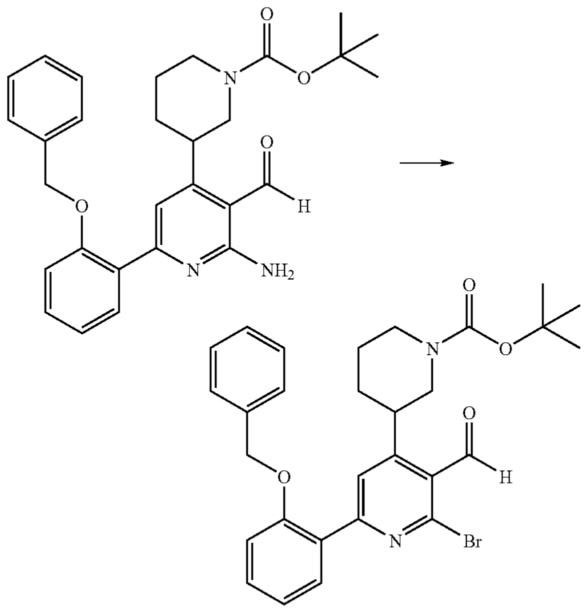

To a solution of copper (II) bromide (0.82 g, 3.692 mmol) in acetonitrile (10 mL) was added tert-butyl nitrate (0.550 mL, 4.614 mmol). The mixture was stirred at 65° C. for 15 min. A solution of tert-butyl 3-{2-amino-6-[2-(benzyloxy) phenyl]-3-formyl-4-pyridinyl}-1-piperidinecarboxylate (1.50 g, 3.076 mmol), which was obtained in the step (2) of Example 13-1, in acetonitrile (10 mL) was added to the mixture, and stirred at 65° C. for 3 hrs. After cooled to room temperature, the reaction mixture was diluted with water and extracted with ethyl acetate. The organic phase was dried over sodium sulfate, filtered and concentrated under reduced pressure. The resulting residue was purified by silica gel column chromatography (hexane/ethyl acetate=4/1-2/1-1/1) to give tert-butyl 3-{6-[2-(benzyl-oxy)phenyl]-2-bromo-3-formyl-4-pyridinyl}-1-piperidinecarboxylate as a white solid (0.260 g, yield; 15%).

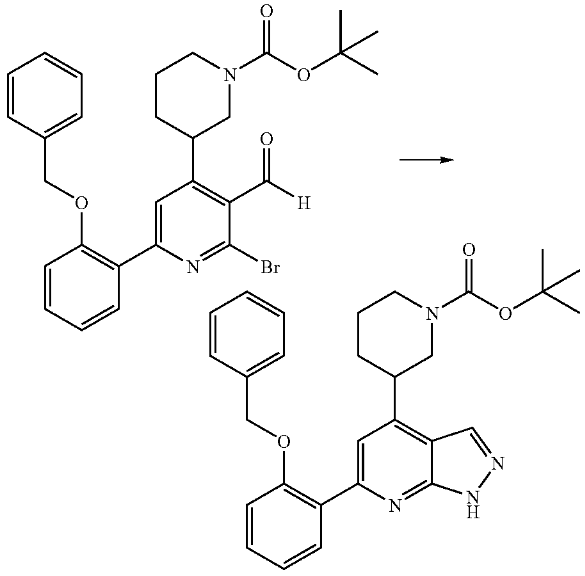

To a stirred solution of tert-butyl 3-{6-[2-(benzyloxy) phenyl]-2-bromo-3-formyl-4-pyridinyl}-1-piperidinecarboxylate (0.150 g, 0.272 mmol) in 1,4-dioxane (1 mL) was added hydrazine monohydrate (0.5 mL). The reaction mixture was stirred at 90° C. for 15 hrs. After cooled to room temperature, the reaction was quenched with water and extracted with ethyl acetate. The organic phase was dried over sodium sulfate, filtered and concentrated under reduced pressure. The residue was recrystallized from diethyl ether to give tert-butyl 3-{6-[2-(benzyloxy)phenyl]-1H-pyrazolo [3,4-b]pyridin-4-yl}-1-piperidinecarboxylate as a white solid (0.030 g, 23%). Then tert-butyl 3-{6-[2-(benzyloxy) phenyl]-1H-pyrazolo[3,4-b]pyridin-4-yl}-1-piperidine-carboxylate was treated in a similar manner as that of the step (2) of Example 1-1 and then the step (3) of Example 1-1 to obtain 2-(4-Piperidin-3-yl-1H-pyrazolo[3,4-b]pyridin-6-yl)-phenol hydrochloride.

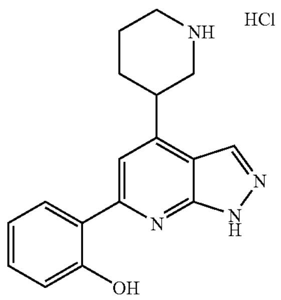

Molecular weight: 330.82

Mass spectrometry: 295 $(M+H)^+$

In vitro activity grade: B

Cellular activity grade: (A549)-B $^1$H-NMR (500 MHz, DMSO-d6): 1.91–2.05 (4H, m), 6.97–7.00 (2H, m), 7.35–7.87 (1H, m), 7.87 (1H, s), 8.16 (1H, d, J=7.3 Hz), 8.42 (1H, s), 8.96 (1H, br s), 9.26 (1H, br s).

Example 17-1

(1) A mixture of the starting compound 1G (10.00 g, 30.638 mmol), 2B (13.069 g, 61.275 mmol), tert-butylcyanoacetate (8.650 g, 61.275 mmol), and ammonium acetate (6.902 g, 91.913 mmol) in dioxane (10 mL) was stirred at 90° C. overnight. After cooled to room temperature, the reaction mixture was diluted with ethyl acetate (100 mL). To the mixture was added chloranil (1.507 g, 6.128 mmol), and stirred at room temperature. After 1.5 hrs, ascorbic acid (1.079 g, 6.128 mmol) was added to the mixture. After stirred for 1.5 hrs, the mixture was partitioned between ethyl acetate and water. The organic phase was washed with brine, dried over $MgSO_4$, filtered, and then concentrated under reduced pressure. The resulting residue was purified by column chromatography on Silica-gel (hexane/ethyl acetate=2/1) to give tert-butyl 2-amino-4-[1-(tert-butoxycarbonyl)-3-piperidinyl]-6-{2-(cyclopropyl-methoxy)-6-[(4-methoxybenzyl)oxy]phenyl}nicotinate as a pale brown form (4.9 g, 24%)

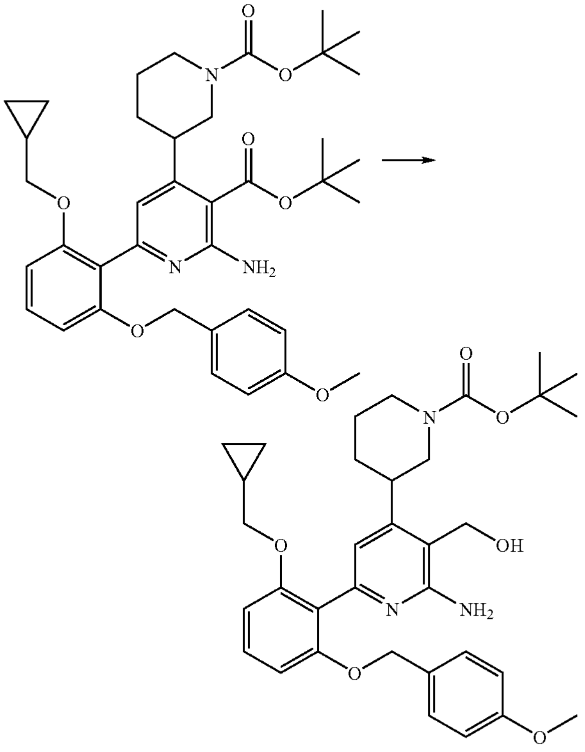

(2) To a cooled solution of tert-butyl 2-amino-4-[1-(tert-butoxycarbonyl)-3-piperidinyl]-6-{2-(cyclopropyl-methoxy)-6-[(4-methoxybenzyl)oxy]phenyl}nicotinate (4.9 g, 7.426 mmol) in tetrahydrofuran (60 mL) was added dropwise Vitride® (10 mL) under an argon atmosphere. The stirring was continued at 0° C. for 1 hr. After quenched by saturated aqueous $NH_4Cl$ solution, saturated aqueous potassium sodium tartrate was added to the mixture, then the mixture was stirred vigorously. The mixture was extracted with ethyl acetate, washed with water and brine, dried over $MgSO_4$, filtered, and concentrated under reduced pressure to give tert-butyl 3-[2-amino-6-{2-(cyclopropylmethoxy)-6-[(4-methoxybenzyl)oxy]phenyl}-3-(hydroxy-methyl)-4-pyridinyl]-1-piperidinecarboxylate, which was used for the next step without further purification (4.38 g, yield; quant.).

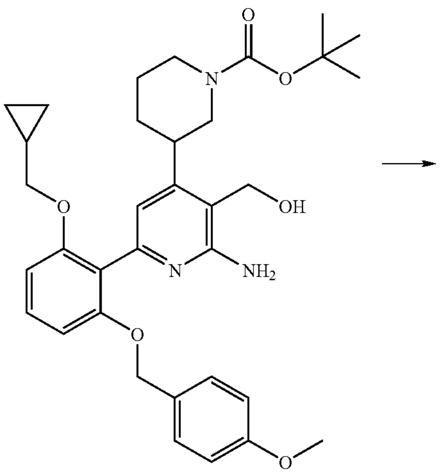

-continued

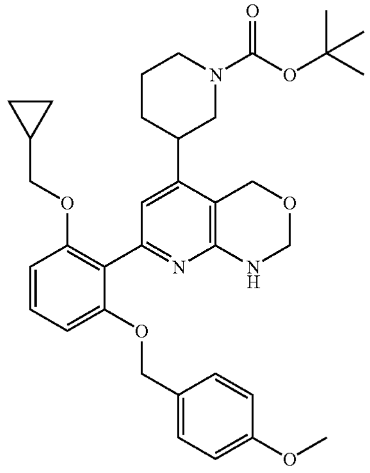

(3) To a stirred solution of tert-butyl 3-[2-amino-6-{2-(cyclopropylmethoxy)-6-[(4-methoxybenzyl)oxy]phenyl}-3-(hydroxymethyl)-4-pyridinyl]-1-piperidine-carboxylate (0.501 g, 0.850 mmol) in 1,4-dioxane was added 37% formaldehyde solution (5.000 mL) and 1N HCl (5.000 mL). The mixture was stirred at room temperature for 2 hrs. The reaction mixture was extracted with ethyl acetate and water. The separated organic phase was washed with brine, dried over $Na_2SO_4$, filtered and concentrated under reduced pressure. The resulting residue was purified by column chromatography on silica gel (ethyl acetate/hexane=3/2) to give 1,1-dimethylethyl(tert-butyl)-3-{7-[2-[(cyclopropylmethyl)oxy]-6-({[4-(methyloxy)-phenyl]methyl}oxy)phenyl]-1,4-dihydro-2H-pyrido[2,3-d][1,3]oxazin-5-yl}-1-piperidinecarboxylate as a colorless foam (0.319 g, yield; 62%).

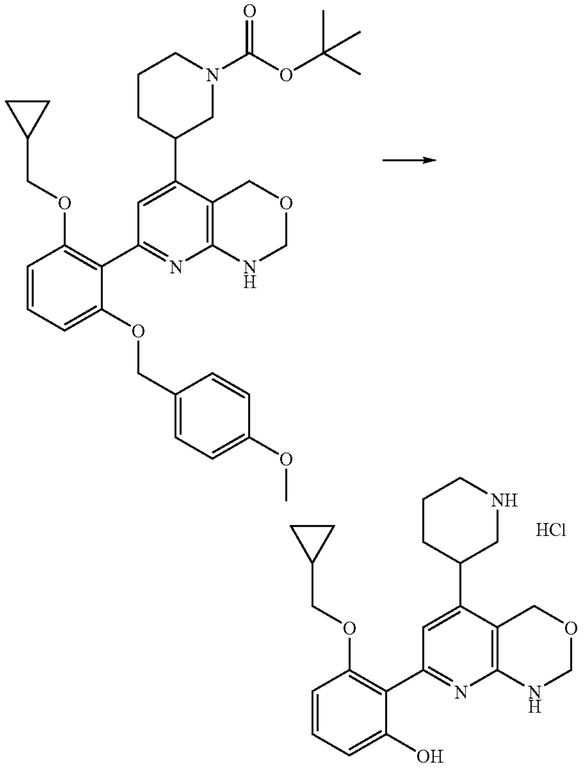

(4) To a stirred solution of 1,1-dimethylethyl(tert-butyl)-3-{7-[2-[(cyclo-propylmethyl)oxy]-6-({[4-(methyloxy)phenyl]methyl}oxy)phenyl]-1,4-dihydro-2H-pyrido[2,3-d][1,3]oxazin-5-yl}-1-piperidinecarboxylate (0.050 g, 0.083 mmol) in 1,4-Dioxane was added 4N HCl in 1,4-dioxane (2.000 mL). The mixture was stirred at room temperature for 6 hrs. The reaction mixture was concentrated under reduced pressure. The resulting residue was washed with acetonitrile to give 3-(cyclo-propylmethoxy)-2-[5-(3-piperidinyl)-1,4-dihydro-2H-pyrido[2,3-d][1,3]oxazin-7-yl-]-phenol hydrochloride as a colorless solid (0.033 g, yield; 95%).

Molecular weight: 417.94

Mass spectrometry: 382 $(M+H)^+$

In vitro activity grade: A

Cellular activity grade: (A549)-A $^1$H-NMR (500 MHz, DMSO-d6): 0.30 (2H, br s), 0.51 (2H, br s), 1.17 (1H, m) 1.84 (4H, m), 2.86 (1H, m), 4.91 (2H, br), 5.01 (2H, br), 6.58 (1H, d, J=7.9 Hz), 6.64 (1H, br), 7.16 (1H, br), 7.26 (1H, t, J=7.9 Hz), 8.30 (1H, br), 9.14 (1H, br), 9.29 (1H, br), 13.95 (1H, br).

Example 18-1

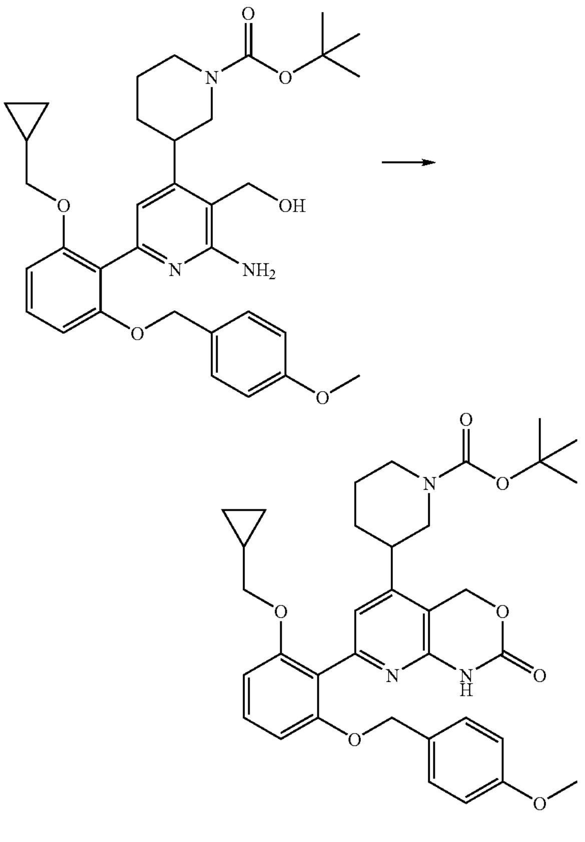

To a cooled (0° C.) solution of tert-butyl 3-[2-amino-6-{2-(cyclopropylmethoxy)-6-[(4-methoxybenzyl)oxy]phenyl}-3-(hydroxymethyl)-4-pyridinyl]-1-piperidine-carboxylate (5.0 g, 8.478 mmol), which was obtained in the step (2) of Example 17-1, and diisopropylethyl amine (4.12 mL, 25.435 mmol) in tetrahydrofuran (200 mL) under argon atmosphere was added dropwise to a solution of triphosgene (1.258 g, 4.239 mmol) in tetrahydrofuran (100 mL) . The mixture was allowed to warm to room temperature, and the stirring was continued for 3 hrs. After quenched by water, the mixture was extracted with ethyl acetate. The separated organic phase was washed with brine, dried over $MgSO_4$, filtered, and concentrated under reduced pressure. The resulting residue was purified by column chromatography on Silica-gel (hexane/ethyl acetate=1/1) to give tert-butyl 3-(7-{2-(cyclopropylmethoxy)-6-[(4-methoxybenzyl)oxy]phenyl}-2-oxo-1,4-dihydro-2H-pyrido[2,3-d][1,3]oxazin-5-yl)-1-piperidinecarboxylate as a white form (3.2 g, yield; 61%).

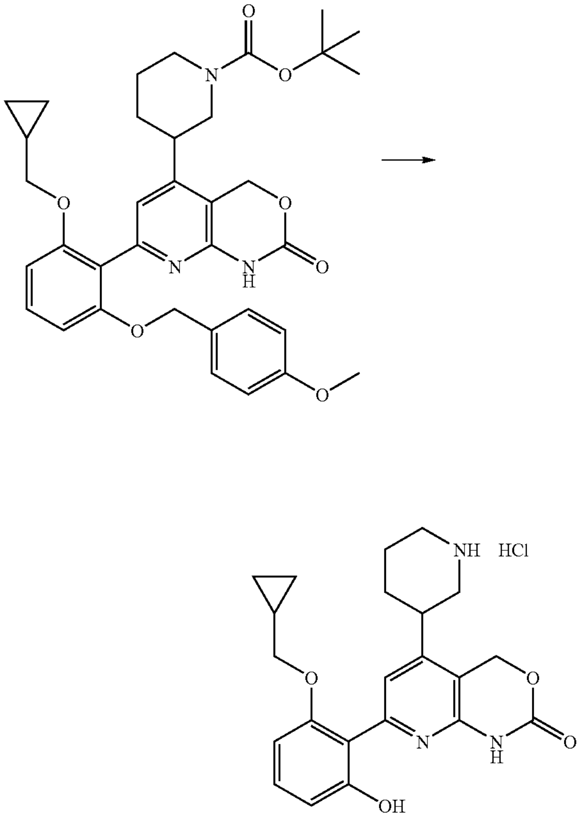

To a solution of tert-butyl 3-(7-{2-(cyclopropylmethoxy)-6-[(4-methoxybenzyl)-oxy]phenyl}-2-oxo-1,4-dihydro-2H-pyrido[2,3-d][1,3]oxazin-5-yl)-1-piperidine-carboxylate (2.0 g, 3.248 mmol) in dioxane (15 mL) was added 4N HCl in dioxane (30 mL) at room temperature. The stirring was continued for 3 hrs. After the solvent was removed by evaporation, the resulting solid was triturated with acetonitril, collected by filtration, and washed with acetonitrile. The solid was dried under reduced pressure to give 7-[2-(cyclopropylmethoxy)-6-hydroxyphenyl]-5-(3-piperidinyl)-1,4-dihydro-2H-pyrido[2,3-d][1,3]oxazin-2-one hydrochloride as a white solid (0.865 g, yield; 62%).

Molecular weight: 431.92

Mass spectrometry: 396 $(M+H)^+$

In vitro activity grade: A

Cellular activity grade: (A549)-A $^1$H-NMR (500 MHz, DMSO-d6): 0.26–0.37 (2H, m), 0.51–0.63 (2H, m), 1.20–1.31 (1H, m), 1.72–1.95 (4H, m), 2.80–2.96 (2H, m), 3.17–3.37 (3H, m), 3.79–3.88 (2H, m), 5.48 (1H, d, J=14.2 Hz), 5.53 (1H, d, J=14.2 Hz), 6.54 (2H, d, J=8.2 Hz), 7.17 (1H, t, J=8.2 Hz), 7.77 (1H, s), 9.05 (1H, br), 9.27 (1H, br), 10.96 (1H, s).

Example 18-2

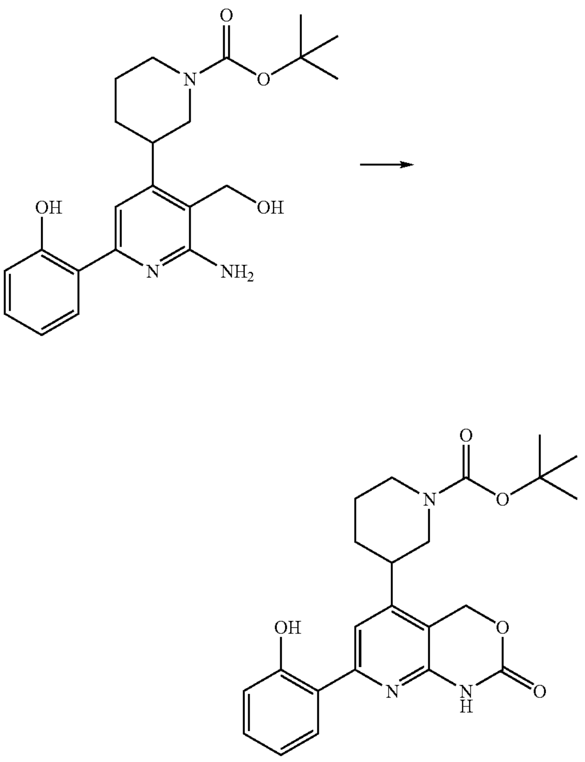

To a cold (0° C.) solution of tert-butyl 3-[2-amino-3-(hydroxymethyl)-6-(2-hydroxyphenyl)-4-pyridinyl]-1-piperidinecarboxylate (0.297 g, 0.74 mmol), which was obtained in the step (1) of Example 11-1 in THF (3.00 mL) including triethylamine (0.226 g, 2.23 mmol) was added triphosgene (0.221 g, 0.74 mmol). After 30 min, the mixture was allowed to warm to room temperature and the stirring was continued for 1 hr. The reaction was quenched with an aqueous $NaHCO_3$ solution, and extracted with ethyl acetate. The organic phase was washed with aqueous $NH_4Cl$ solution, water, and brine successively. The organic phase was dried over $Na_2SO_4$, filtered and concentrated under reduced pressure. The resulting residue was purified by silica gel column chromatography (hexane/ethyl acetate, 3:2) to give tert-butyl 3-[7-(2-hydroxyphenyl)-2-oxo-1,4-dihydro-2H-pyrido[2,3-d][1,3]oxazin-5-yl]-1-piperidinecarboxylate as a pale yellow solid. (46.2 mg, yield; 14.6%)

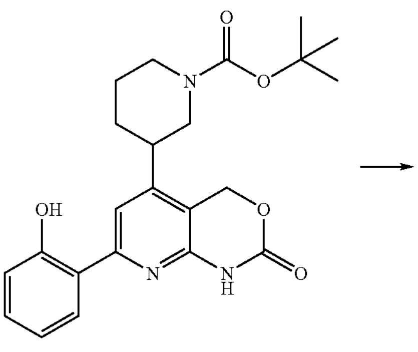

-continued

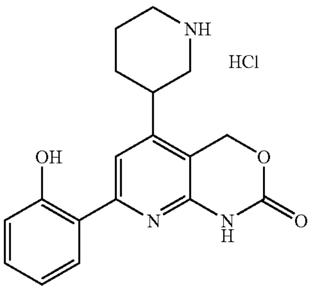

To a solution of tert-butyl 3-[7-(2-hydroxyphenyl)-2-oxo-1,4-dihydro-2H-pyrido-[2,3-d][1,3]oxazin-5-yl]-1-piperidinecarboxylate (45 mg, 0.11 mmol) in 1,4-dioxane (1.0 mL) was added 4N HCl in 1,4-dioxane (2.0 mL). The mixture was stirred for 1 hr at room temperature. The resulting solid was collected by filtration, washed with 1,4-dioxane, and dried under reduced pressure to give 7-(2-hydroxyphenyl)-5-(3-piperidinyl)-1,4-dihydro-2H-pyrido[2,3-d][1,3]oxazin-2-one hydrochloride as a white solid. (22.8 mg, yield; 60%)

Molecular weight: 361.83

Mass spectrometry: 326 $(M+H)^+$

In vitro activity grade: A

Cellular activity grade: (A549)-A /Jurkat-B $^{1}$H-NMR (500 MHz, DNSO-d6): 1.80–1.96 (5H, m), 2.86–2.93 (1H, m), 3.13–3.26 (3H, m), 5.46–5.55 (2H, m), 6.91–6.94 (2H, m), 7.30–7.33 (1H, m), 7.77 (11H, s), 8.03–8.04 (1H, m), 11.15 (1H, s), 12.46 (1H, br s).

Example 18-3

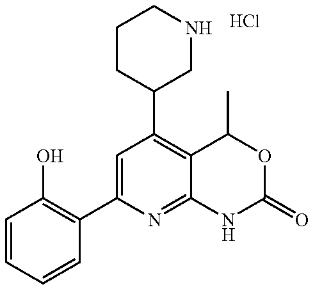

With the use of tert-butyl 3-[2-amino-3-(1-hydroxyethyl)-6-(2-hydroxyphenyl)4-pyridinyl]-1-piperidinecarboxylate, which was obtained in the step (2) of Example 15-1, 7-(2-Hydroxy-phenyl)-4-methyl-5-piperidin-3-yl-1,4-dihydro-benzo[d][1,3]-oxazin-2-one hydrochloride was prepared in a similar manner as that of Example 18-2.

Molecular weight: 375.86

Mass spectrometry: 340 $(M+H)^+$

In vitro activity grade: B

Cellular activity grade: (A549)-B $^{1}$H-NMR (500 MHz, DMSO-d6): 1.52–1.53 (3H, m), 1.80–2.04 (5H, m), 2.91–2.95 (1H, m), 3.13–3.21 (3H, m), 5.83–5.85 (1H, m), 6.92–6.95 (3H, m), 7.32 (1H, dd, J=7.9, 7.3 Hz), 8.04 (1H, d, J=7.6 Hz), 11.2 (1H, s), 12.44 (1H, br s).

Example 18-4/18-5

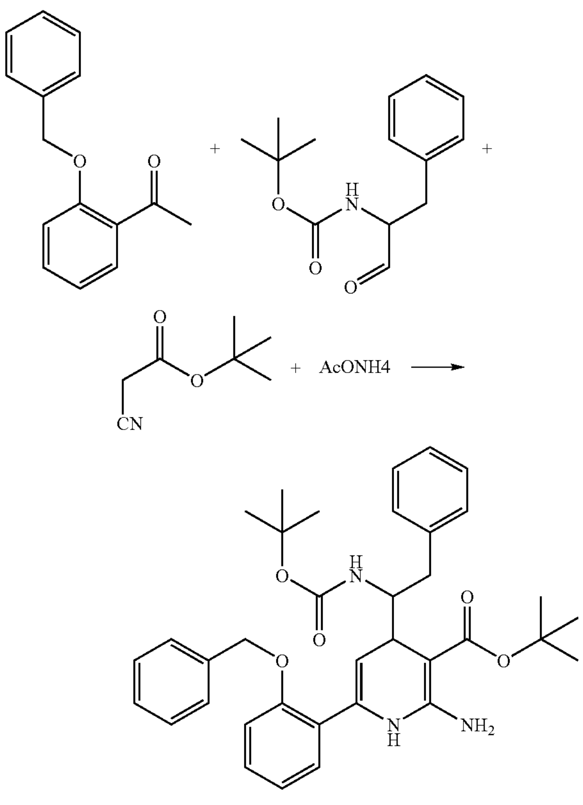

A mixture of the starting compound 1A (3.000 g, 13.258 mmol), N-tert-butoxy-carbonyl-phenylalaninal (3.305 g, 13.258 mmol), tert-butyl cyanoacetate (1.872 g, 13.258 mmol), ammonium acetate (3.066 g, 39.774 mmol) and 1,2-dimethoxyethane (5.0 mL) was heated at reflux for 6 hrs. After cooled to room temperature, the mixture was extracted with ethyl acetate and saturated $NaHCO_3$ solution. The separated organic phase was washed with water and brine successively, dried over $Na_2SO_4$, filtered and concentrated under reduced pressure. The residue was triturated with diisopropyl ether to give tert-butyl 2-amino-6-[2-(benzyloxy)phenyl]4-{1-[(tert-butoxycarbonyl)amino]-2-phenylethyl}-1,4-dihydro-3-pyridinecarboxylate as a yellow solid (1.281 g, yield; 16%).

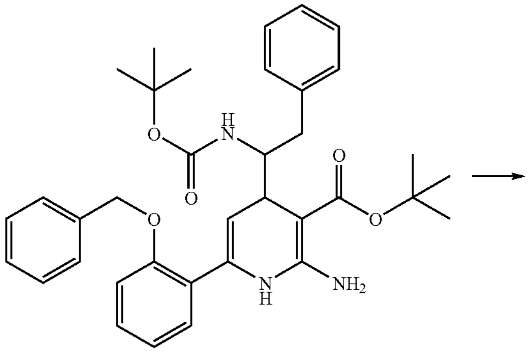

-continued

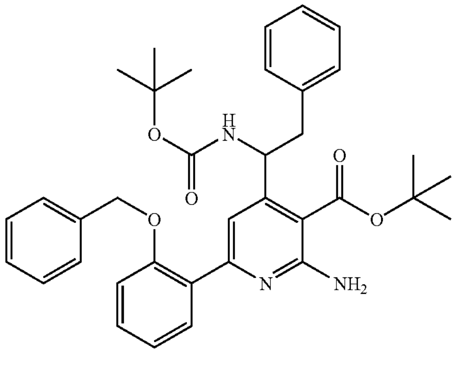

To a solution of tert-butyl 2-amino-6-[2-(benzyloxy)phenyl]-4-{1-[(tert-butoxy-carbonyl)amino]-2-phenylethyl}-1,4-dihydro-3-pyridinecarboxylate (1.200 g, 2.007 mmol) in methylene chloride (20.0 mL) at room temperature was added chloranil (0.543 g, 2.208 mmol), and the stirring was continued for 1 hr. The mixture was filtered and the filtrate was concentrated under reduced pressure. The residue was extracted with ethyl acetate and 10% aqueous $NaHCO_3$ solution. The separated organic phase was washed with water and brine successively, dried over $Na_2SO_4$, filtered and concentrated under reduced pressure. The crude product was crystallized from ethanol to give tert-butyl 2-amino-6-[2-(benzyloxy)phenyl]-4-{1-[(tert-butoxy-carbonyl)amino]-2-phenylethyl}nicotinate as a pale yellow solid (0.972 g, yield; 84%).

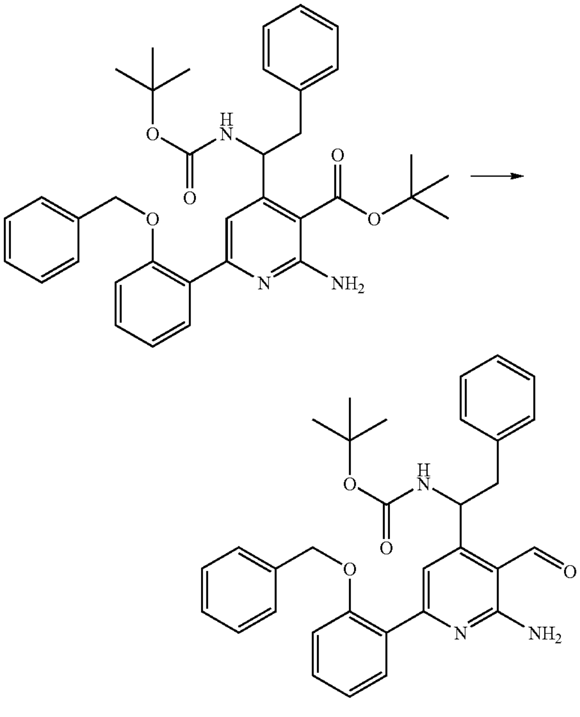

To a cold (0° C.) solution of tert-butyl 2-amino-6-[2-(benzyloxy)phenyl]-4-{1-[(tert-butoxycarbonyl)amino]-2-phenylethyl}nicotinate (0.100 g, 0.198 mmol) in THF (1.50 mL) was added dropwise Vitride® (0.500 mL), and the stirring was continued for 2 hrs. The mixture was quenched at 0° C. with saturated aqueous $NH_4Cl$ solution, and extracted with ethyl acetate. The separated organic phase was washed with water and brine successively, dried over $Na_2SO_4$, filtered and concentrated under reduced pressure. The crude product was purified by column chromatography on silica gel (hexane:ethyl acetate, 1:1) to give tert-butyl-1-{2-amino-6-[2-(benzyloxy)phenyl]-3-formyl-4-pyridinyl}-2-phenylethylcarbamate as a colorless oil (0.044 g, yield; 51%).

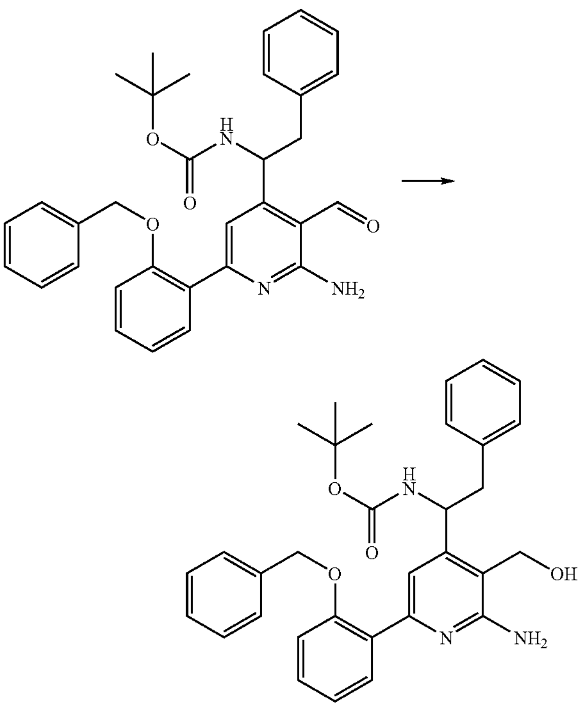

To a solution of tert-butyl 1-{2-amino-6-[2-(benzyloxy)phenyl]-3-formyl-4-pyridinyl}-2-phenylethylcarbamate (0.040 g, 0.092 mmol) in ethanol (1.0 mL) was added $NaBH_4$ (0.010 g, 0.26 mmol), and the stirring was continued for 3 hrs. The mixture was extracted with ethyl acetate and saturated aqueous ammonium chloride solution. The separated organic phase was washed with water and brine successively, dried over $Na_2SO_4$, filtered and concentrated under reduced pressure. The crude product was crystallized from ethanol to give tert-butyl 1-[2-amino-6-[2-(benzyloxy)phenyl]-3-(hydroxymethyl)-4-pyridinyl]-2-phenylethylcarbamate as a pale yellow solid (0.023 g, yield; 57%).

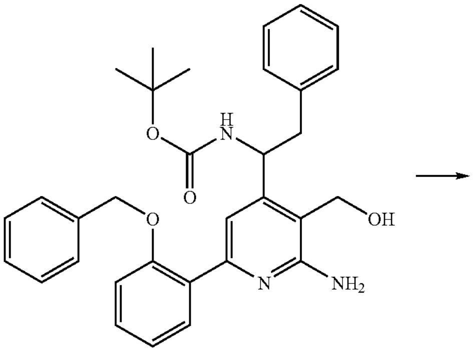

-continued

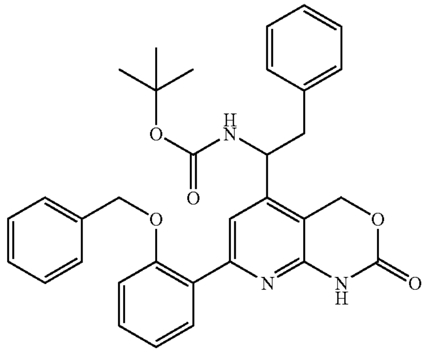

To a cold (0° C.) solution of tert-butyl 1-[2-amino-6-[2-(benzyloxy)phenyl]-3-(hydroxymethyl)-4-pyridinyl]-2-phenylethylcarbamate (0.210 g, 0.400 mmol) in THF (3.0 mL) including triethylamine (0.167 mL, 1.199 mmol) was added dropwise a solution of triphosgene (0.059 g, 0.200 mmol) in THF (1.0 mL). After stirred at 0° C. for 45 min, the mixture was allowed to warm to room temperature, and the stirring was continued for 30 min. The reaction mixture was cooled at 0° C., and then quenched with saturated aqueous $NaHCO_3$ solution. The resulting mixture was extracted with ethyl acetate and water. The separated organic phase was washed with brine, dried over $Na_2SO_4$, filtered and concentrated under reduced pressure. The crude product was purified by column chromatography on silica gel (hexane:ethyl acetate, 2:1) to give tert-butyl 1-{7-[2-(benzyloxy)phenyl]-2-oxo-1,4-dihydro-2H-pyrido[2,3-d][1,3]oxazin-5-yl}-2-phenylethylcarbamate as a colorless oil (0.170 g, yield; 77%).

Then in a similar manner as that of the step (2) of Example 1-1 and the step (3) of Example 1-1, tert-butyl 1-{7-[2-(benzyloxy)phenyl]-2-oxo-1,4-dihydro-2H-pyrido-[2,3-d][1,3]oxazin-5-yl}-2-phenylethylcarbamate was treated to give 5-(1-Amino-2-phenyl-ethyl)-7-(2-hydroxy-phenyl)-1,4-dihydro-pyrido[2,3-d][1,3]oxazin-2-one hydrochloride.

Example 18-4/18-5

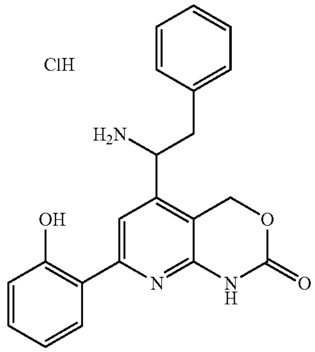

Molecular weight: 397.86
Mass spectrometry: 362 $(M+H)^+$
In vitro activity grade: A
Cellular activity grade: (A549)-B
$^1H$-NMR (500 MHz, DMSO-d6): 3.11 (1H, dd, J=10.1, 12.9 Hz), 3.44 (1H, dd, J=5.0, 12.9 Hz), 4.25 (1H, d, J=14.5 Hz), 4.71–4.74 (1H, m), 5.35 (1H, d, J=14.5 Hz), 6.93–6.99 (2H, m), 7.08 (2H, dd, J=1.9, 7.3 Hz), 7.23–7.28 (3H, m), 7.33–7.36 (1H, m), 8.13 (1H, dd, J=1.3, 7.9 Hz), 8.37 (1H, s), 8.98 (3H, br), 11.18 (1H, s), 12.32 (1H, br).

Example 18-6

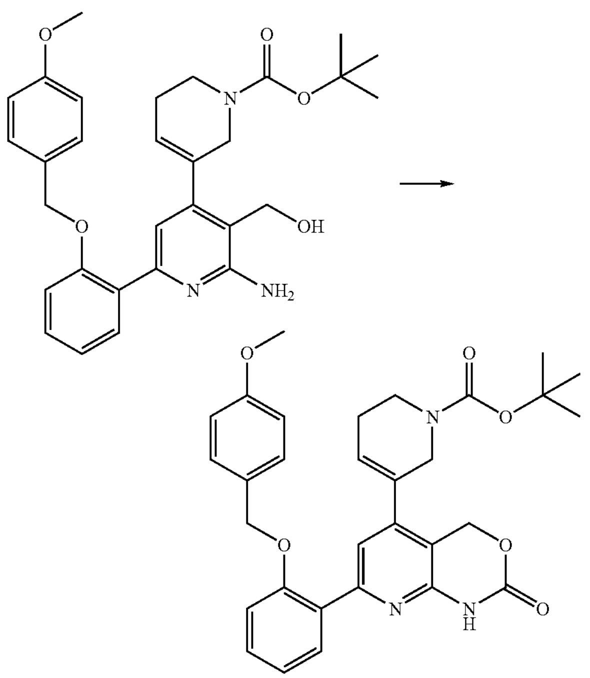

To a cooled (0° C.) solution of tert-butyl 2'-amino-3'-(hydroxymethyl)-6'-{2-[(4-methoxybenzyl)oxy]phenyl}-5,6-dihydro-3,4'-bipyridine-1(2H)-carboxylate (25.0 mg, 0.05 mmol), which was obtained in the step (2) of Example 11-4, and triethylamine (0.02 mL, 0.14 mmol) in THF (3.0 mL) was added a solution of triphosgene (5.7 mg, 0.02 mmol) in THF (3.0 mL), and the stirring was continued for 30 min. The reaction mixture was allowed to warm to room temperature. The reaction was cooled to 0° C. and then quenched by an addition of saturated aqueous $NaHCO_3$ solution, extracted with ethyl acetate. The separated organic phase was washed with brine, dried over $MgSO_4$, filtered and evaporated. The crude product was purified by preparative silica gel TLC (10% acetone in chloroform) to give tert-butyl 5-(7-{2-[(4-methoxybenzyl)oxy]phenyl}-2-oxo-1,4-dihydro-2H-pyrido[2,3-d][1,3]oxazin-5-yl)-3,6-dihydro-1(2H)-pyridinecarboxylate as a white solid. (21.7 mg, yield 83%)

Then the tert-butyl and methoxy benzyl were removed in a similar manner as that of the steo(2) of Example 1-1.

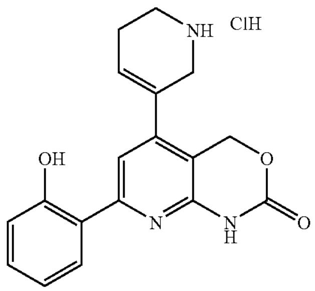

Molecular weight: 359.82
Mass spectrometry: 324 $(M+H)^+$
In vitro activity grade: A
Cellular activity grade: (A549)-A

$^1$H-NMR (500 MHz, MeOH-d4): 2.63–2.65 (2H, m), 3.44–3.49 (2H, m), 4.02 (2H, br d, J=1.9 Hz), 5.45 (2H, s), 6.04 (1H, s), 6.88–6.95 (2H, m), 7.29–7.32 (1H, m), 7.63 (1H, s), 7.90 (1H, dd, J=1.3, 7.9 Hz).

Examples 18-7 to 18-16

According to the similar synthetic procedure of Examples 18-1 to 18-6, compounds shown in Table 5 were prepared.

TABLE 5

| Ex. No | Structure | Mol weight | Mass | in vitro | A549 | NMR |
|---|---|---|---|---|---|---|
| 18-07 | 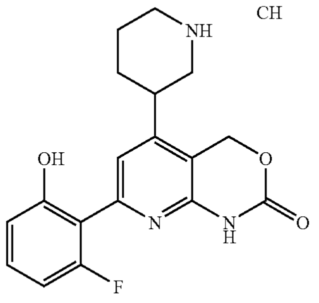 | 379.82 | no peak | A | A | (500 MHZ, DMSO-d6): 1.82(4H, m), 3.02(3H, m), 3.29(2H, d, J=21.5Hz), 5.50(2H, dd, J=23.9, 39.6Hz), 6.73(1H, d, J=23.9 Hz), 6.78(1H, m), 7.28(1H, dd, J=13.6, 24.8Hz), 7.34(1H, s), 8.58(1H, m), 8.97(1H, m), 10.95 (1H, s). |
| 18-08 | 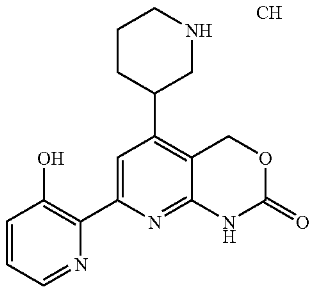 | 362.82 | 327 | A | A | (500MHz, DMSO-d6): 1.88–1.94 (4H, m), 3.26 –3.33(2H, m), 3.57–3.59(1H, m), 3.63–3.74(2H, m), 5.51(1H, d, J=14.2Hz), 5.58(1H, d, J=14.2Hz), 7.39–7.40(2H, m) 8.14(1H, s), 8.22 (1H, t, J=2.8Hz), 11.25(1H, s). |
| 18-09 | 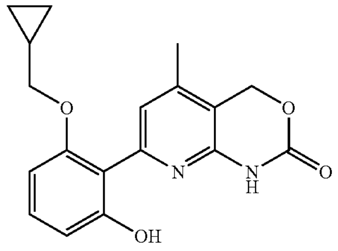 | 326.36 | 327 | C | A | (500MHz, CDCl3): 0.34–0.44 (2H, m), 0.61–0.72(2H, m), 1.24–1.35(1H, m), 2.33(3H, s), 3.89 (2H, d, J=6.9Hz), 5.39(2H, s), 6.45(1H, dd, J=1.0, 8.5Hz), 6.65(1H, dd, J=1.0, 8.5Hz), 7.18(1H, t, J=8.5Hz), 7.54(1H, br s), 8.10(1H, s), 12.48(1H, br s). |
| 18-10 | 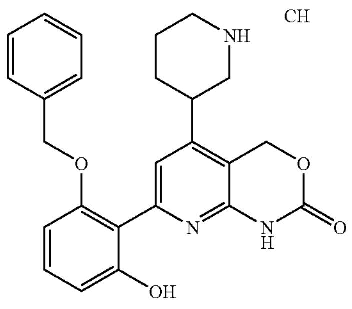 | 467.96 | 432 | A | A | (500MHz, DMSO-d6): 1.25–1.32 (1H, m), 1.53–1.83(3H, m), 2.58–2.80(2H, m), 3.01–3.07(1H, m), 3.13–3.18(1H, m), 3.27–3.30(1H, m), 5.07(2H, dd, J=11.0, 18.2Hz), 5.44(2H, dd, J=14.2, 24.0Hz), 6.58(1H, d, J=8.2Hz), 6.72(1H, d, J=8.2Hz), 7.22(1H, t, J=8.2Hz), 7.34–7.46(6H, m), 8.77(1H, br), 9.04 (1H, br), 10.92(1H, s). |

TABLE 5-continued
| Ex. No | Structure | Mol weight | Mass | in vitro | A549 | NMR |
| --- | --- | --- | --- | --- | --- | --- |
| 18-11 | 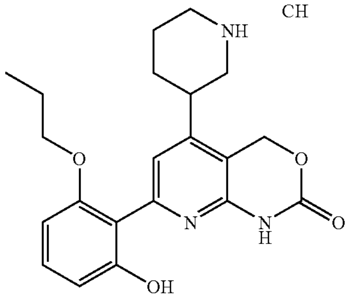 | 419.91 | 384 | A | A | (300MHz, DMSO-d6): 0.90(3H, t, J=7.2Hz), 1.72(2H, m), 1.84–1.88(2H, m), 2.85–2.92(2H, m), 3.18–3.34(4H, m), 3.90–3.95 (2H, m), 5.48(2H, d, J=5.6Hz), 6.55(2H, dd, J=8.3, 8.5Hz), 7.17(1H, t, J=8.3Hz), 7.54(1H, s), 8.88(1H, br), 9.13(1H, br), 10.89(1H, s). |
| 18-12 | 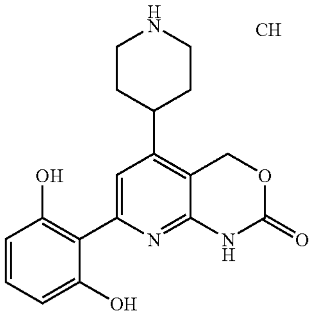 | 377.83 | 342 | B | C | (500MHz, DMSO-d6): 1.70–1.73 (2H, m), 1.78–1.89(2H, m), 2.87–2.90(2H, m), 3.00–3.05(2H, m), 4.05(1H, m), 5.49(2H, s), 6.39(1H, d, J=8.2Hz), 6.42 (1H, d, J=8.2Hz), 7.04(1H, m), 7.92(1H, m), 8.55(1H, br), 8.77 (1H, br), 10.95(1H, s), 10.99(1H, s). |
| 18-13 | 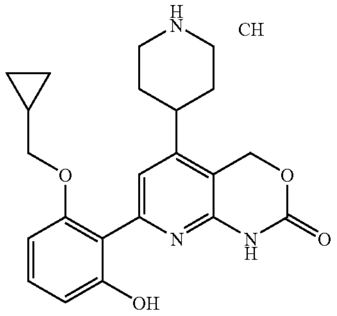 | 431.92 | 396 | A | A | (500MHz, DMSO-d6): 0.28–0.30 (2H, m), 0.55–0.58(2H, m), 1.31 (1H, m), 1.88(4H, m), 3.01–3.04 (3H, m), 3.35–3.38(2H, m), 3.84 (2H, d, J=6.9Hz), 5.50(2H, s), 6.53(2H, d, J=8.2Hz), 7.17(1H, t, J=8.2Hz), 7.74(1H, s), 8.92 (1H, br), 9.00(1H, br), 10.95(1H, s). |
| 18-14 | 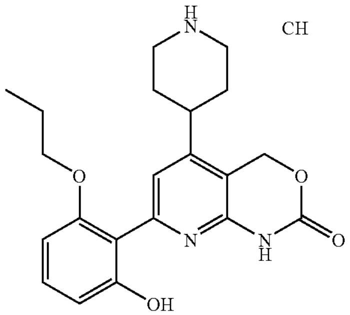 | 419.91 | 384 | A | A | (500MHz, DMSO-d6): 0.90(3H, t, J=7.5Hz), 1.75(2H, m), 1.85 (4H, m), 3.02(3H, m), 3.36(2H, m) 3.95(2H, t, J=7.6Hz), 5.49 (2H, s), 6.53(1H, d, J=7.9Hz), 6.57(1H, d, J=8.2Hz), 7.18(1H, t, J=8.2Hz), 7.50(1H, s), 8.88 (1H, br), 8.99(1H, br), 10.90(1H, s). |

TABLE 5-continued

| Ex. No | Structure | Mol weight | Mass | in vitro | A549 | NMR |
|---|---|---|---|---|---|---|
| 18-15 | 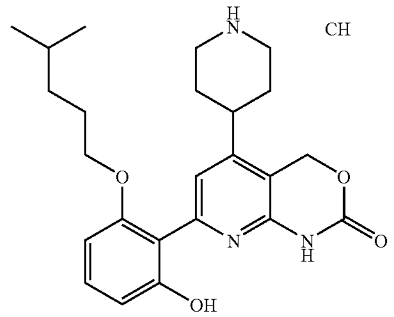 | 461.99 | 426 | A | A | (500MHz, DMSO-d6): 0.81(6H, d, J=6.6Hz), 1.14–1.19(2H, m), 1.47–1.51(1H, m), 1.67–1.71(2H, m), 1.83–1.90(4H, m), 2.96–3.06(3H, m), 3.31–3.33 (2H, m), 3.95–3.97(2H, m), 5.49 (2H, s), 6.53–6.58(2H, m), 7.17 (1H, t, J=8.3Hz), 7.42(1H, s), 9.05–9.11(1H, m), 10.88(1H, s). |
| 18-16 | 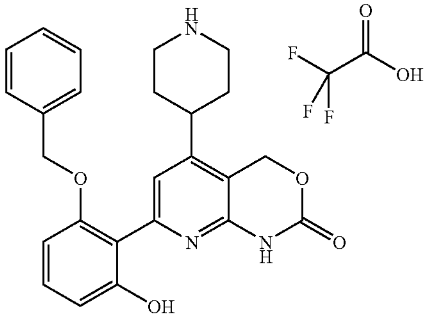 | 545.52 | | A | B | (500MHz, DMSO-d6): 1.56–1.64 (4H, m), 2.95(4H, br s), 5.09(2H, s), 5.45(2H, s), 6.55–6.59(1H, m), 6.70(1H, d, J=8.3Hz), 7.20 (1H, t, J=8.1Hz), 7.33–7.38 (6H, m), 8.26(1H, br s), 8.57 (1H, br s), 10.85(1H, br s), 11.11 (1H, br s). |

Example 19-1

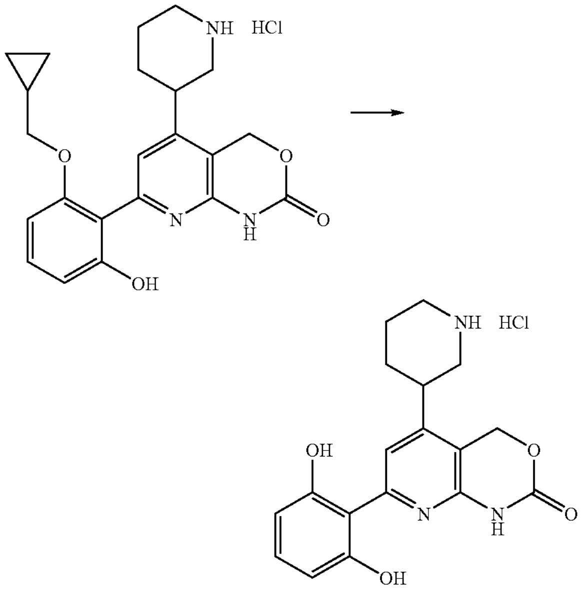

A mixture of 7-[2-(cyclopropylmethoxy)-6-hydroxyphenyl]-5-(3-piperidinyl)-1,4-dihydro-2H-pyrido[2,3-d][1,3]oxazin-2-one hydrochloride (0.070 g, 0.160 mmol), which was obtained in Example 18-1, and 2.5N HCl in 1,4-dioxane (4 mL) was stirred at 80° C. overnight. After cooled to room temperature, the mixture was concentrated under reduced pressure. The resulting residue was diluted with dichloromethane (3 mL), and triethylamine (0.064 g, 0.497 mmol) was added. To the cooled (0° C.) mixture was added di-tert-butyl dicarbonate (0.047 g, 0.218 mmol) under an argon atmosphere. The stirring was continued at room temperature overnight. After quenched by water, the mixture was extracted with ethyl acetate and water. The separated organic phase was washed with brine, dried over $MgSO_4$, filtered, and concentrated under reduced pressure. The residue was purified by preparative TLC (hexane/ethyl acetate=1/1) to give tert-butyl 3-[7-(2,6-di-hydroxyphenyl)-2-oxo-1,4-dihydro-2H-pyrido[2,3-d][1,3]oxazin-5-yl]-1-piperidine-carboxylate (0.019 g, 19%). To a solution of tert-butyl 3-[7-(2,6-dihydroxyphenyl)-2-oxo-1,4-dihydro-2H-pyrido[2,3-d][1,3]oxazin-5-yl]-1-piperidinecarboxylate in dioxane (1 mL) was added 4N HCl in dioxane (1 mL) at room temperature. The stirring was continued for 3 hrs. After the solvent was removed by evaporation, the resulting residue was washed with acetonitril, and dried under reduced pressure to give 7-(2,6-dihydroxyphenyl)-5-(3-piperidinyl)-1,4-dihydro-2H-pyrido[2,3-d][1,3]-oxazin-2-one hydrochloride as a brown solid (0.007 g, 46%).

Molecular weight: 377.83

Mass spectrometry: 342 $(M+H)^+$

In vitro activity grade:

Cellular activity grade: (A549)-

$^1$H-NMR (500 MHz, DMSO-d6): 1.73–1.89 (4H, m), 2.89–2.94 (2H, m), 3.19 (1H, m), 3.25–3.32 (2H, m), 5.46 (1H, d, J=14.2 Hz), 5.51 (1H, d, J=14.2 Hz), 6.41 (2H, d, J=8.2 Hz), 7.03 (1H, t, J=8.2 Hz), 7.88 (1H, s), 8.90 (1H, br), 9.14 (1H, br), 11.01 (1H, s).

Example 20-1

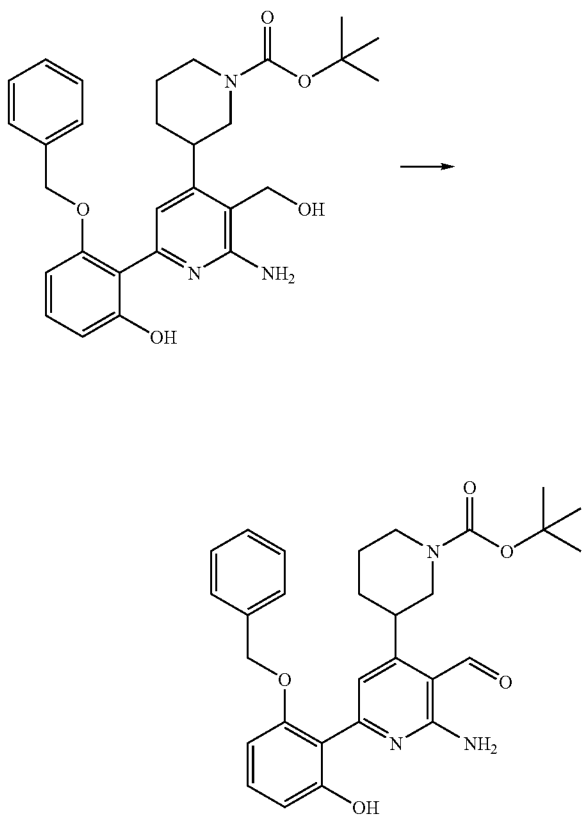

To a stirred solution of tert-butyl 3-[2-amino-6-[2-(benzyloxy)-6-hydroxyphenyl]-3-(hydroxymethyl)-4-pyridinyl]-1-piperidinecarboxylate (0.100 g, 0.198 mmol), which was obtained in the similar procedure as that of Example 13-1, in dichrolomethane (3 mL) was added $MnO_2$ (0.340 g, 3.956 mmol). The mixture was stirred at room temperature for 2 hrs. The mixture was filtered on Celite® and concentrated under reduced pressure. The residue was recrystallized from ethyl alcohol to give tert-butyl 3-{2-amino-6-[2-(benzyloxy)-6-hydroxyphenyl]-3-formyl-4-pyridinyl}-1-piperidine-carboxylate as a yellow solid. (0.092 g, yield 93%)

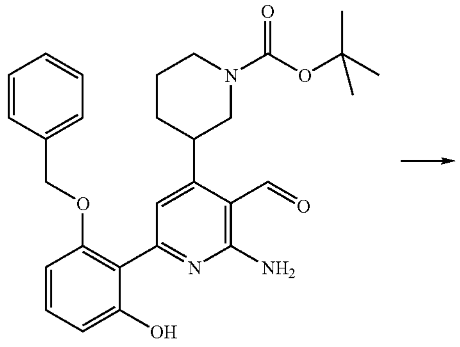

-continued

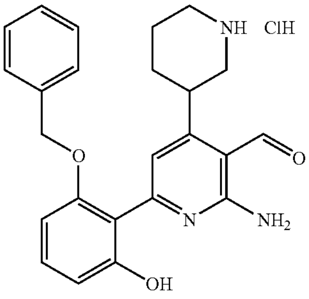

To a stirred solution of tert-butyl 3-{2-amino-6-[2-(benzyloxy)-6-hydroxyphenyl]-3-formyl-4-pyridinyl}-1-piperidinecarboxylate (0.090 g, 0.183 mmol) in 1,4-dioxane (2 mL) was added 4N HCl in dioxane (2 mL). The mixture was stirred at room temperature for 2 hrs. The resulting precipitate was collected by filtration, washed with acetonitril, and dried under reduced pressure to give 2-amino-6-[2-(benzyloxy)-6-hydroxyphenyl]-4-(3-piperidinyl)nicotinaldehyde hydrochloride. (0.103 g, yield quant.)

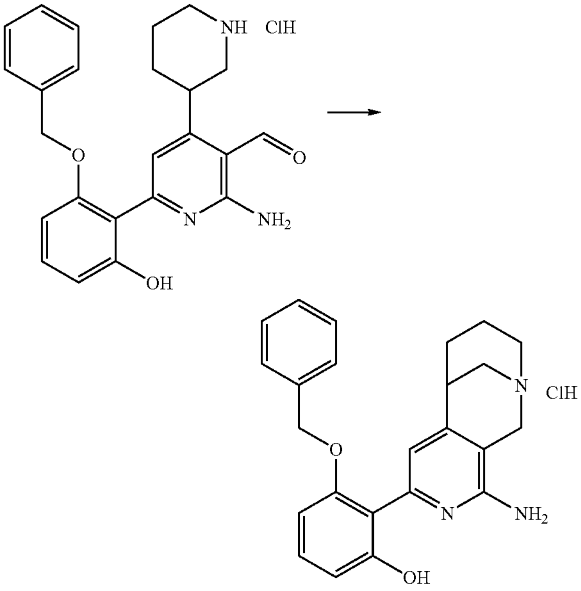

To a cold (0° C.) solution of 2-amino-6-[2-(benzyloxy)-6-hydroxyphenyl]-4-(3-piperidinyl)nicotinaldehyde hydrochloride (0.100 g, 0.227 mmol) in methanol was added $NaBH_3CN$ (0.040 mL, 0.682 mmol) under an argon atmosphere. The mixture was stirred at room temperature for 12 hrs and concentrated under reduced pressure. The residue was extracted with ethyl acetate and water. The separated organic phase was washed with saturated aqueous $NaHCO_3$ solution and brine, dried over $Na_2SO_4$, filtered and concentrated under reduced pressure. The resulting residue was purified by column chromatography on silica gel (hexane/ethyl acetate=2/1) to give 2-(6-amino-5,9-diazatricyclo[7.3.1.02,7]trideca-2,4,6-trien-4-yl)-3-(benzyloxy)phenol as a white solid.

To a stirred solution of 2-(6-amino-5,9-diazatricyclo[7.3.1.02,7]trideca-2,4,6-trien-4-yl)-3-(benzyloxy)phenol in 1,4-dioxane (2 mL) was added 4N HCl in dioxane (2 mL). The mixture was stirred at room temperature for 2 hrs. The resulted precipitate was collected by filtration, washed with acetonitril, and dried under reduced pressure to give 2-(6-amino-5,9-diazatricyclo[7.3.1.02,7]trideca-2,4,6-trien-4-yl)-3-(benzyl-oxy)phenol hydrochloride.(0.018 g, yield 19%)

Molecular weight: 423.95

Mass spectrometry: 388 $(M+H)^+$

In vitro activity grade: B

Cellular activity grade: (A549)-C $^1$H-NMR (500 MHz, DMSO-d6): 1.10–1.23 (2H, m), 1.41 (1H, d, J=12.3 Hz), 1.71–1.80 (1H, m), 2.79 (1H, d, J=12.9 Hz), 2.89–2.91 (2H, m), 2.97 (1H, d, J=12.9 Hz), 3.44 (2H, d, J=18.3 Hz), 3.81 (1H, d, J=18.0 Hz), 5.09–5.17 (2H, m), 6.01 (1H, s), 6.64 (1H, d, J=8.5 Hz), 7.13 (1H, t, J=8.2 Hz), 7.33–7.41 (4H, m), 7.49 (2H, d, J=1.6 Hz).

Example 20-2

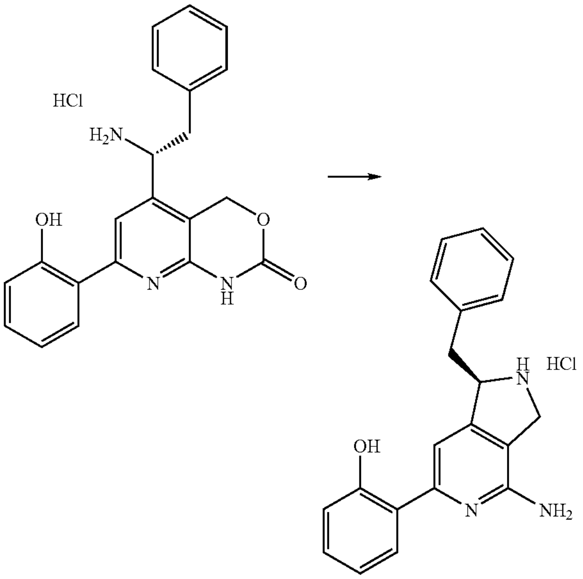

A mixture of 5-[(1R)-1-amino-2-phenylethyl]-7-(2-hydroxyphenyl)-1,4-dihydro-2H-pyrido[2,3-d][1,3]oxazin-2-one hydrochloride (0.014 g, 0.035 mmol), which was obtained in Example 18-4, in acetonitrile (3.0 mL) was heated at reflux for 2 hrs. The resulting mixture was concentrated under reduced pressure. The residue was dissolved in 1,4-dioxane (1.0 mL), treated with 4N HCl solution in 1,4-dioxane (0.5 mL), and concentrated under reduced pressure. The residue was triturated with acetonitrile, and dried under reduced pressure to give 2-[(1R)-4-amino-1-benzyl-2,3-dihydro-1H-pyrrolo[3,4-c]pyridin-6-yl]phenol hydrochloride as a white solid (0.010 g, yield; 80%).

Molecular weight: 353.85

Mass spectrometry: 318 $(M+H)^+$

In vitro activity grade: A

Cellular activity grade: (A549)-B $^1$H-NMR (500 MHz, DMSO-d6): 3.30 (1H, dd, J=9.1, 14.1 Hz), 3.54 (1H, dd, J=5.0, 14.1 Hz), 4.26–4.42 (2H, br m), 5.20 (1H, br), 6.91 (1H, t, J=7.9 Hz), 6.97 (1H, d, J=8.2 Hz), 7.29–7.39 (2H, m), 7.41 (1H, t, J=7.9 Hz), 7.62 (1H, d, J=7.3 Hz), 10.14 (1H, br), 10.31 (1H, br), 13.90 (1H, br).

Example 20-3

In a similar manner as described in Examples 20-1 and 20-2, 2-[(1S)-4-amino-1-benzyl-2,3-dihydro-1H-pyrrolo[3,4-c]pyridin-6-yl]phenol hydrochloride was prepared.

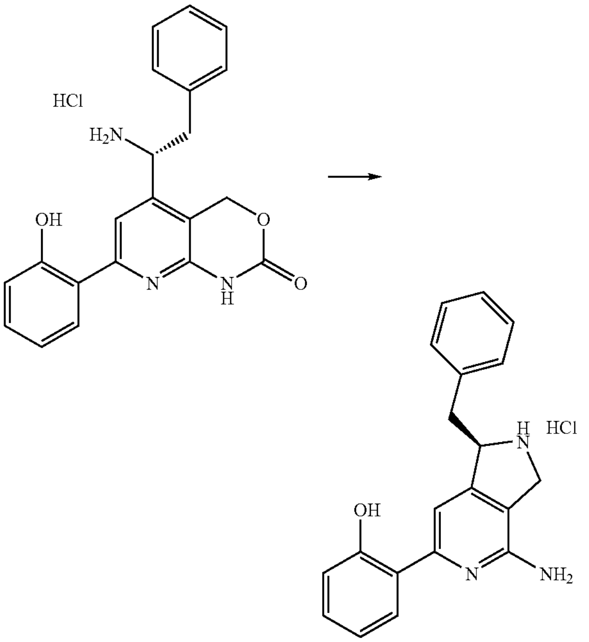

Molecular weight: 353.85

Mass spectrometry: 318 $(M+H)^+$

In vitro activity grade: A

Cellular activity grade: (A549)-B $^1$H-NMR (500 MHz, DMSO-d6): 3.30 (1H, dd, J=9.1, 14.1 Hz), 3.54 (1H, dd, J=5.0, 14.1 Hz), 4.26–4.42 (2H, br m), 5.20 (1H, br), 6.91 (1H, t, J=7.9 Hz), 6.97 (1H, d, J=8.2 Hz), 7.29–7.39 (2H, m), 7.41 (1H, t, J=7.9 Hz), 7.62 (1H, d, J=7.3 Hz), 10.14 (1H, br), 10.31 (1H, br), 13.90 (1H, br).

Example 21-1

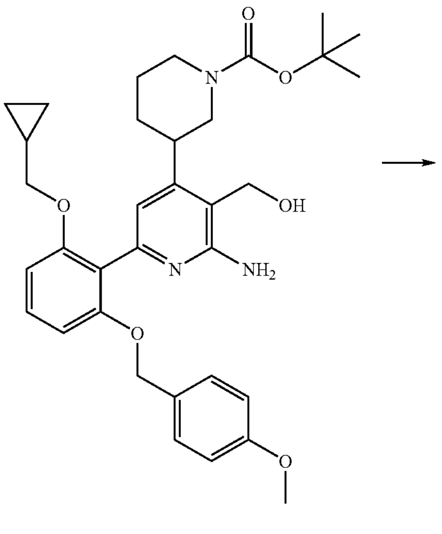

-continued

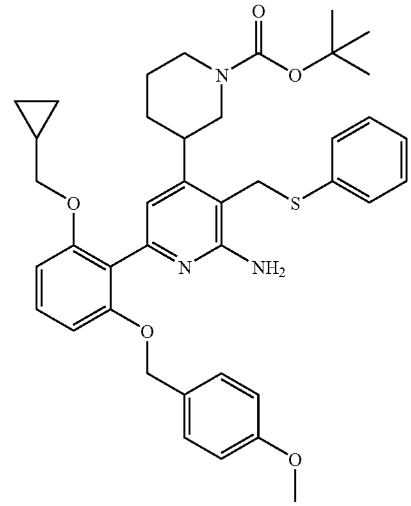

(1) To a stirred solution of tert-butyl 3-[2-amino-6-{2-(cyclopropylmethoxy)-6-[(4-methoxybenzyl)oxy]phenyl}-3-(hydroxymethyl)-4-pyridinyl]-1-piperidinecarboxylate (0.050 g, 0.085 mmol), which was obtained in the step (2) of Example 17-1, and phenyl disulfide (0.055 g, 0.254 mmol) in tetrahydrofuran (3 mL) was added tributyl phosphine (0.060 mL, 0.254 mmol). The mixture was stirred at room temperature for 24 hrs. The mixture was extracted with ethyl acetate and water. The separated organic phase was washed with brine, dried over $Na_2SO_4$, filtered, and concentrated under reduced pressure. The resulting residue (liquid) was purified by column chromatography on silica gel (hexane/ethyl acetate=3/1-1/1) to give tert-butyl 3-{2-amino-6-{2-(cyclopropylmethoxy)-6-[(4-methoxybenzyl)oxy]phenyl}-3-[(phenyl-sulfanyl)methyl]-4-pyridinyl}-1-piperidinecarboxylate (0.021 g, yield; 37%) as a form.

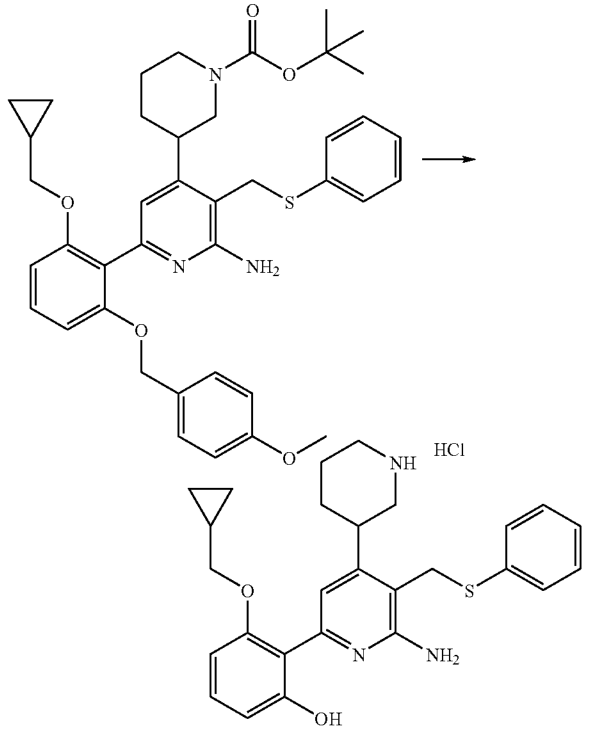

(2) To a stirred solution of tert-butyl 3-{2-amino-6-{2-(cyclopropylmethoxy)-6-[(4-methoxybenzyl)oxy]phenyl-{-3-[(phenylsulfanyl)methyl]-4-pyridinyl}-1-piperidinecarboxylate in 1,4-dioxane (2 mL) was added 4 N HCl in dioxane (2 mL). The mixture was stirred at room temperature overnight, and diluted with ethyl acetate. The resulting precipitate was collected by filtration, washed with ethanol, and dried under reduced pressure to give 2-[6-amino-5-[(phenylsulfanyl)methyl]-4-(3-piperidinyl)-2-pyridinyl]-3-(cyclopropylmethoxy)phenol hydrochloride.

Molecular weight: 498.09

Mass spectrometry: 462 $(M+H)^+$

In vitro activity grade: A

Cellular activity grade: (A549)-B $^1$H-NMR (500 MHz, DMSO-d6): 0.30 (2H, br s), 0.51 (2H, br s), 1.67 (2H, m), 1.80 (1H, br), 4.26 (1H, d, J=12.6 Hz), 4.37 (1H, br), 6.59 (2H, br), 7.36 (2H, t, J=7.6 Hz), 7.46 (2H, d, J=7.6 Hz), 7.72 (1H, br), 8.61-8.98 (2H, br), 10.36 (1H, br), 13.58 (1H, br).

Example 21-2

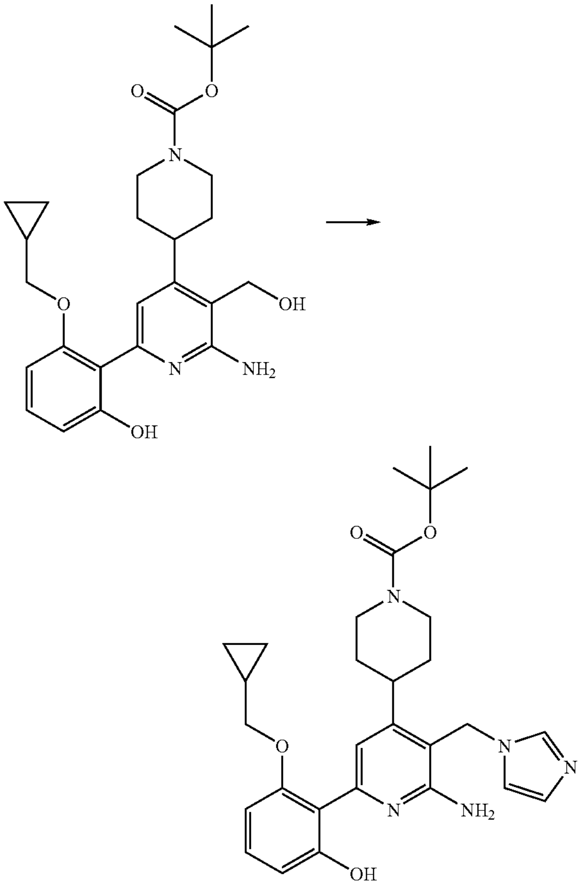

(1) With the use of the starting compound 1G, tert-butyl 4-formyl-piperidine-1-carboxylic acid prepared in a similar manner as that of the starting compound 2B, and other materials, tert-butyl 4-[2-amino-6-[2-(cyclopropylmethoxy)-6-hydroxy-phenyl]-3-(hydroxymethyl)-4-pyridinyl]-1-piperidinecarboxylate was prepared in a similar manner as that of the step (1) of Example 11-1.

(2) To a stirred solution of tert-butyl 4-[2-amino-6-[2-(cyclopropylmethoxy)-6-hydroxyphenyl]-3-(hydroxymethyl)-4-pyridinyl]-1-piperidinecarboxylate (0.250 g, 0.528 mmol) in acetonitrile (10 mL) was added 1,1'-carbonyldiimidazole (0.170 g, 1.056 mmol) at room temperature. After stirred for 2 hrs, the reaction mixture was extracted with ethyl acetate and water. The separated organic phase was washed with brine, dried over $Na_2SO_4$, filtered, and concentrated under reduced pressure. The resulting solid was collected by filtration, washed with hexane, and dried under reduced pressure to give tert-butyl 4-[2-amino-6-[2-(cyclopropylmethoxy)-6-hydroxyphenyl]-3-( 1H-imidazol-1-ylmethyl)-4-pyridinyl]-1-piperidinecarboxylate. (0.242 g, yield 88%)

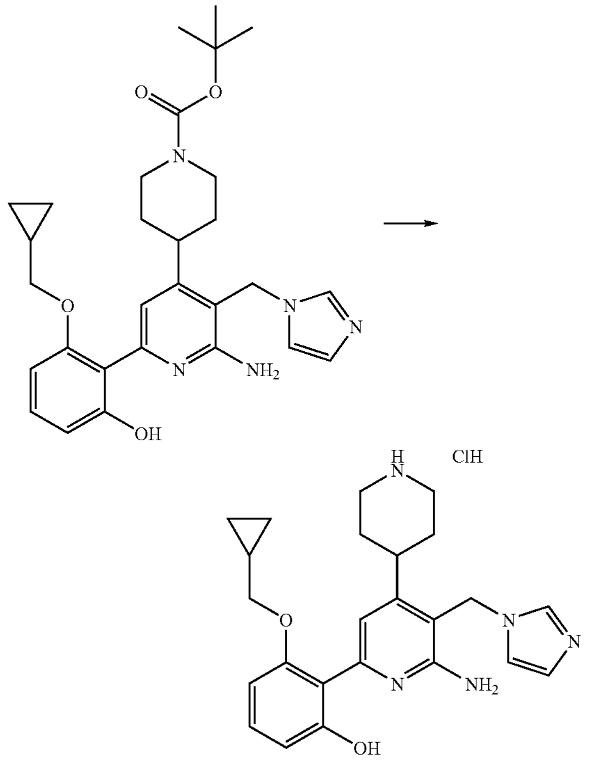

(3) To a stirred solution of tert-butyl 4-[2-amino-6-[2-(cyclopropylmethoxy)-6-hydroxyphenyl]-3-(1H-imidazol-1-ylmethyl)-4-pyridinyl]-1-piperidinecarboxylate (0.260 g, 0.500 mmol) in 1,4-dioxane (10 mL) was added 4N HCl in dioxane (10 mL). The mixture was stirred at room temperature for 2 hrs. The resulting precipitate was collected by filtration, washed with acetonitrile, and dried under reduced pressure to give 2-[6-amino-5-(1H-imidazol-1-ylmethyl)-4-(4-piperidinyl)-2-pyridinyl]-3-(cyclopropylmethoxy)phenol hydrochloride. (0.248 g, yield; quant.)

Molecular weight: 455.99

Mass spectrometry: 420 $(M+H)^+$

In vitro activity grade: A

Cellular activity grade: (A549)-A $^1$H-NMR (500 MHz, DMSO-d6): 0.32 (2H, d, J=4.7 Hz), 0.52 (2H, d, J=4.7 Hz), 1.27 (1H, br s), 1.71 (2H, d, J=13.6 Hz), 1.91–1.98 (2H, m), 3.00–3.31 (2H, m), 3.32–3.35 (3H, m), 3.86 (2H, d, J=6.9 Hz), 5.62(2H, s), 6.58 (1H, d, J=8.5 Hz), 6.64 (1H, d, J=6.9 Hz), 7.26 (1H, dd, J=8.5, 7.9 Hz), 7.66 (1H, s), 7.71 (1H, s), 9.31 (1H, s).

Example 21-3

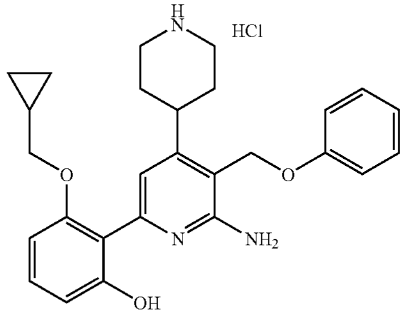

With the use of diphenyl carbonate instead of 1,1'-carbonyldiimidazole, 2-[6-amino-5-(phenoxymethyl)-4-(4-piperidinyl)-2-pyridinyl]-3-(cyclopropylmethoxy)phenol hydrochloride was prepared in a similar manner as that of Example 21-2.

Molecular weight: 482.03

Mass spectrometry: 446 $(M+H)^+$

In vitro activity grade: A

Cellular activity grade: (A549)-A $^1$H-NMR (500 MHz, DMSO-d6): 0.31 (2H, d, J=4.7 Hz), 0.50 (2H, d, J=6.9 Hz), 1.16–1.19 (1H, m), 1.84 (2H, d, J=13.2 Hz), 1.91–1.99 (2H, m), 2.96 (2H, m), 3.57 (1H, s), 3.76 (2H, d, J=6.6 Hz), 5.20 (2H, s), 6.61 (1H, d, J=8.2 Hz), 6.66 (1H, d, J=6.0 Hz), 6.75 (1, d, J=8.5 Hz), 7.20 (1H, t, J=7.3 Hz), 7.08 (2H, d, J=7.9 Hz), 7.15 (1H, t, J=7.9 Hz), 7.36 (2H, t, J=7.9 Hz).

Example 21-4

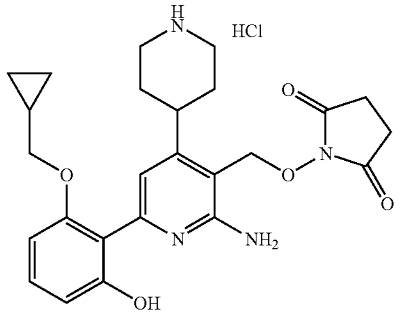

With the use of N,N'-disuccinimidyl carbonate instead of 1,1'-carbonyldiimidazole, 1-{[2-amino-6-[2-(cyclopropylmethoxy)-6-hydroxyphenyl]-4-(4-piperidinyl)-3-pyridinyl] methoxy}-2,5-pyrrolidinedione hydrochloride was prepared in a similar manner as that of Example 21-2.

Molecular weight: 503.00

Mass spectrometry: 467 $(M+H)^+$

In vitro activity grade: A

Cellular activity grade: (A549)-A $^1$H-NMR (500 MHz, DMSO-d6): 0.19 (2H, d, J=5.0 Hz), 0.52 (2H, d, J=7.3 Hz), 1.21 (1H, br s), 1.91–1.96 (4H, m), 2.71 (4H, s), 3.03 (2H, d, J=8.2 Hz), 3.85 (2H, d, J=6.9 Hz), 5.18 (2H, s), 6.59 (1H, d, J=8.5 Hz), 6.64 (1H, d, J=7.6 Hz), 7.05 (1H, br s), 7.27 (1H, t, J=7.9 Hz), 7.60 (1H, br s), 8.82 (1H, br s), 8.92 (1H, d, J=9.1 Hz).

Example 22-1

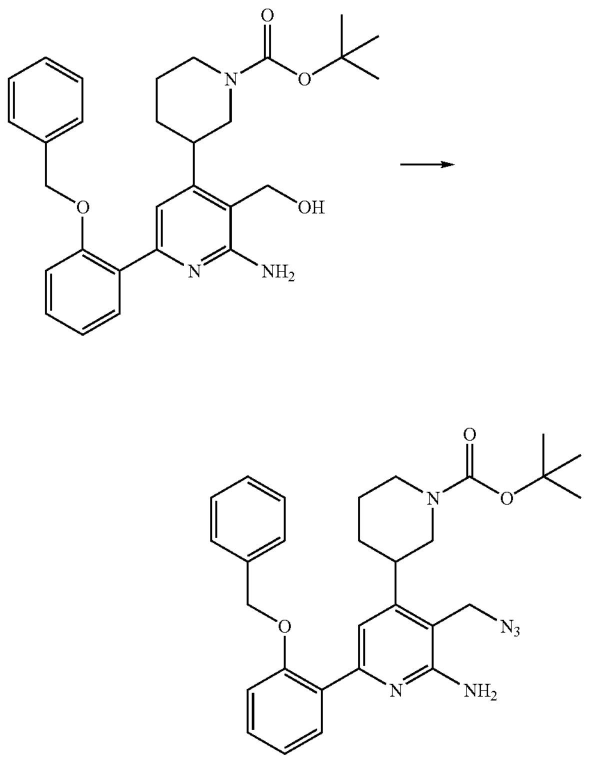

(1) To a cold (0° C.) solution of tert-butyl 3-[2-amino-6-[2-(benzyloxy)phenyl]-3-(hydroxymethyl)-4-pyridinyl]-1-piperidinecarboxylate (0.050 g, 0.102 mmol), obtained in the step (1) of Example 13-1, in toluene (1.0 mL) was added diphenyl-phosphoryl azide (0.024 mL, 0.112 mmol) followed by 1,8-diazabicyclo-[5.4.0.]undec-7-ene (0.017 mL, 0.112 mmol). After 30 min, the mixture was allowed to warm to room temperature, and the stirring was continued for 2 hrs. The mixture was concentrated under reduced pressure, and the residue was partitioned between ethyl acetate and water. The separated organic phase was washed with brine, dried over $Na_2SO_4$, filtered and concentrated under reduced pressure. The residue was purified by column chromatography on silica gel (hexane:ethyl acetate, 2:1) to give tert-butyl 3-{2-amino-3-(azidomethyl)-6-[2-(benzyloxy)phenyl]-4-pyridinyl}-1-piperidinecarboxylate. (0.038 g, yield; 72%)

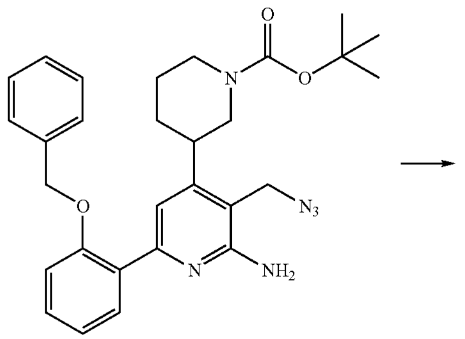

-continued

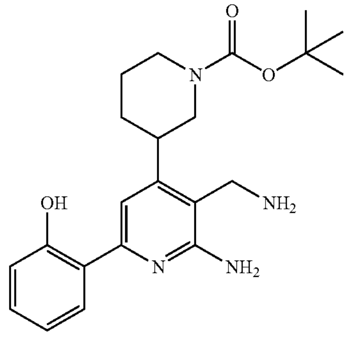

(2) A solution of tert-butyl 3-{2-amino-3-(azidomethyl)-6-[2-(benzyloxy)phenyl]-4-pyridinyl}-1-piperidinecarboxylate (0.030 g, 0.058 mmol) in ethyl acetate (1.0 mL) was hydrogenated at 1 atm in the presence of palladium on charcoal (10%, 0.015 g) overnight. The resulting mixture was filtered and washed with ethyl acetate. The combined filtrate was concentrated under reduced pressure to give tert-butyl 3-[2-amino-3-(aminomethyl)-6-(2-hydroxyphenyl)-4-pyridinyl]-1-piperidinecarboxylate, which was used for the next step without further purification.

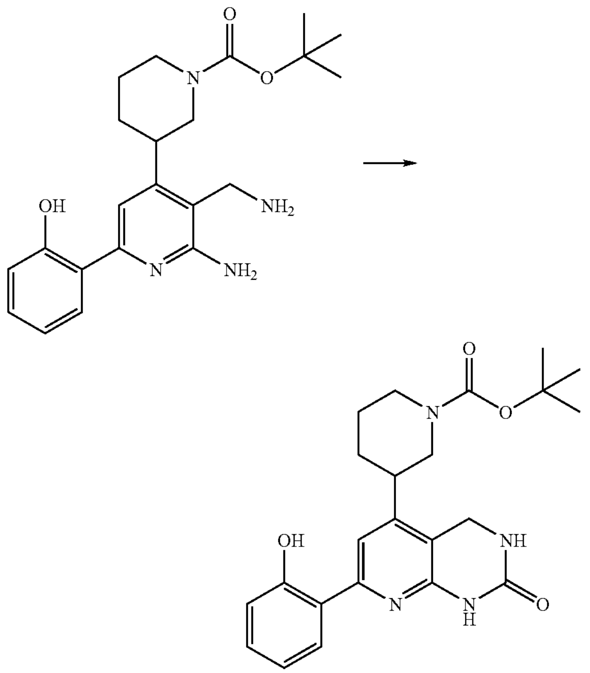

(3) To a cold (0° C.) solution of tert-butyl 3-[2-amino-3-(aminomethyl)-6-(2-hydroxyphenyl)-4-pyridinyl]-1-piperidinecarboxylate (0.020 g, 0.050 mmol) in THF (2.0 mL) under an argon atmosphere was added 1,1'-carbonyldiimidazole (0.009 g, 0.055 mmol). After stirred for 15 min, the mixture was quenched with saturated sodium bicarbonate solution. The resulting mixture was partitioned between ethyl acetate and saturated ammonium chloride solution. The separated organic phase was washed with water and brine, dried over $Na_2SO_4$, filtered and concentrated under reduced pressure. The residue was dissolved in ethyl acetate (2.0 mL). The mixture was heated at 60° C. for 1 hr and allowed to cool to room temperature. The resulting precipitates were collected by filtration, washed with ethyl acetate and dried under reduced pressure to give tert-Butyl 3-[7-(2-hydroxyphenyl)-2-oxo-1,2,3,4-tetrahydropyrido[2,3-d]pyrimidin-5-yl]-1-piperidinecarboxylate. (0.007 g, yield; 33%)

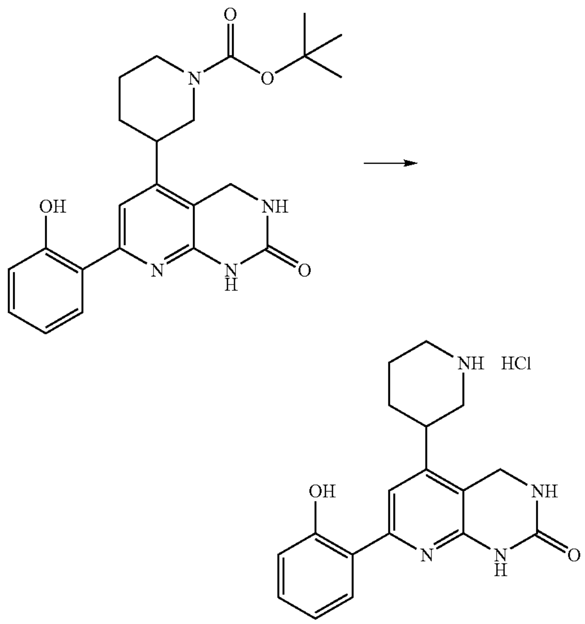

(4) tert-Butyl 3-[7-(2-hydroxyphenyl)-2-oxo-1,2,3,4-tetrahydropyrido[2,3-d]-pyrimidin-5-yl]-1-piperidinecarboxylate (0.006 g, 0.014 mmol) was treated under acidic conditions in a similar manner as described in the step (3) of Example 1-1 to give 7-(2-hydroxyphenyl)-5-(3-piperidinyl)-3,4-dihydropyrido[2,3-d]pyrimidin-2(1H)-one hydrochloride. (0.005 g, yield; 98%)

Molecular weight: 360.85

Mass spectrometry: 325 $(M+H)^+$

In vitro activity grade: A

Cellular activity grade: B $^1$H-NMR (500 MHz, DMSO-d6): 1.76–1.93 (4H, m), 2.88–3.37 (5H, m), 4.47 (2H, dd, J=15.4, 24.3 Hz), 6.87–6.92 (2H, m), 7.26–7.30 (2H, m), 7.63 (1H, s), 8.00 (1H, d, J=8.2 Hz), (1H, br), 9.01 (1H, br), 10.08 (1H, s), 12.78 (1H, br).

Example 22-2

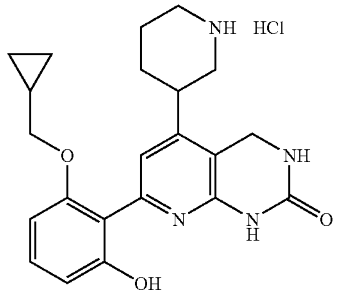

With the use of the starting compound 1G, 2B and other materials, 7-[2-(cyclo-propylmethoxy)-6-hydroxyphenyl]-5-(3-piperidinyl)-3,4-dihydro-1H-pyrido[2,3-d]-pyrimidin-2-one hydrochloride was prepared in a similar manner as that of Example 22-1.

Molecular weight: 430.94

Mass spectrometry: 395 $(M+H)^+$

In vitro activity grade: A

Cellular activity grade: (A549)-A $^1$H-NMR (500 MHz, DMSO-d6): 0.34 (2H, m), 0.57 (2H, m), 1.27 (1H, m), 1.73–1.87 (4H, m), 2.82–2.90 (2H, m), 3.14 (1H, m), 3.29–3.33 (2H, m), 3.80–3.88 (2H, m), 4.49 (2H, s), 6.52 (2H, d, J=8.2 Hz), 7.16 (1H, t, J=8.2 Hz), 7.75 (1H, s), 9.11 (1H, br), 9.26 (1H, br), 9.92 (1H, s).

Example 22-3

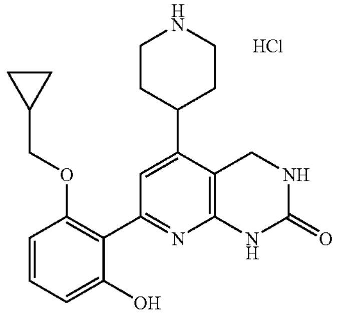

With the use of the starting compound 1G and tert-butyl 4-formyl-piperidine-1-carboxylic acid and other materials, 7-[2-(cyclopropylmethoxy)-6-hydroxyphenyl]-5-(4-piperidinyl)-3,4-dihydro-1H-pyrido[2,3-d]pyrimidin-2-one hydrochloride was prepared in a similar manner as that of Example 22-1.

Molecular weight: 430.94

Mass spectrometry: 395 $(M+H)^+$

In vitro activity grade: A

Cellular activity grade: (A549)-A $^1$H-NMR (500 MHz, DMSO-d6): 0.32 (2H, d, J=4.5 Hz), 0.57 (2H, d, J=1.7 Hz), 1.33–1.38 (1H, m), 1.80–1.91 (4H, m), 2.96–3.05 (3H, m), 3.34–3.39 (3H, m), 4.47 (2H, s), 6.51 (2H, dd, J=3.8, 8.3 Hz), 7.15 (1H, t, J=7.9 Hz), 7.24 (1H, s), 7.74 (1H,s), 9.86 (1H, s).

Example 22-4

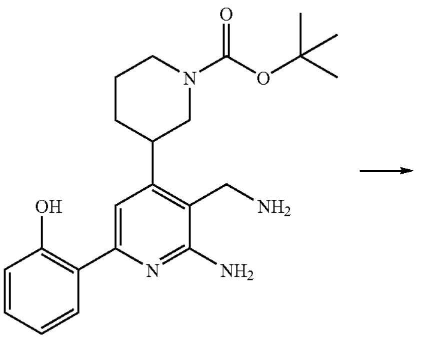

-continued

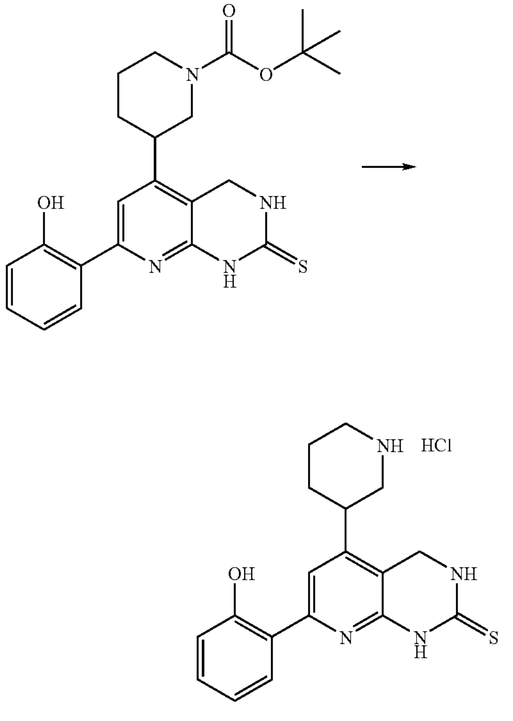

With the use of tert-butyl 3-[2-amino-3-(aminomethyl)-6-(2-hydroxyphenyl)-4-pyridinyl]-1-piperidinecarboxylate obtained in the step (2) of Example 22-1, 7-(2-hydroxyphenyl)-5-(3-piperidinyl)-3,4-dihydro-1H-pyrido[2,3-d]pyrimidine-2-thione hydrochloride was prepared in a similar manner as that of Example 22-1 or 22-2.

Molecular weight: 447.00

Mass spectrometry: 411 $(M+H)^+$

In vitro activity grade:

Cellular activity grade: (A549)-

$^1$H-NMR (500 mHz, DMSO-d6): 0.33–0.36 (2H, m), 0.57–0.59 (2H, m), 1.28 (1H, m), 1.72–1.81 (2H, m), 1.89–1.90 (2H, m), 2.82–2.89 (2H, m), 3.00 (1H, m), 3.27–3.34 (2H, m), 3.82–3.85 (2H, m), 4.54–4.56 (2H, m), 6.52 (2H, d, J=8.2 Hz), 7.16 (1H, t, J=8.2 Hz), 7.83 (1H, s), 8.73 (1H, br), 9.08 (2H, br), 11.13 (1H, s),

Example 22-5

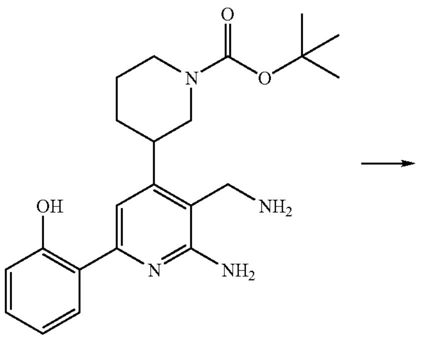

-continued

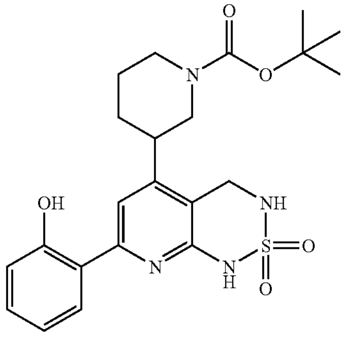

A mixture of tert-butyl 3-[2-amino-3-(aminomethyl)-6-(2-hydroxyphenyl)-4-pyridinyl]-1-piperidinecarboxylate (0.060 g, 0.151 mmol), which was obtained in the step (2) of Example 22-1, sulfamine (0.022 g, 0.226 mmol) and pyridine (2.0 mL) was stirred at reflux overnight. After cooled to room temperature, the mixture was partitioned between ethyl acetate and water. The separated organic phase was washed with 0.5N HCl solution, water and brine successively, dried over $Na_2SO_4$, filtered and concentrated under reduced pressure. The crude product was purified by column chromatography on silica gel (hexane:ethyl acetate, 1:1) to give tert-butyl 3-[7-(2-hydroxyphenyl)-2,2-dioxido-3,4-dihydro-1H-pyrido[2,3-c][1,2,6]thiadiazin-5-yl]-1-piperidinecarboxylate as a pale yellow foam (0.059 g, yield; 85%).

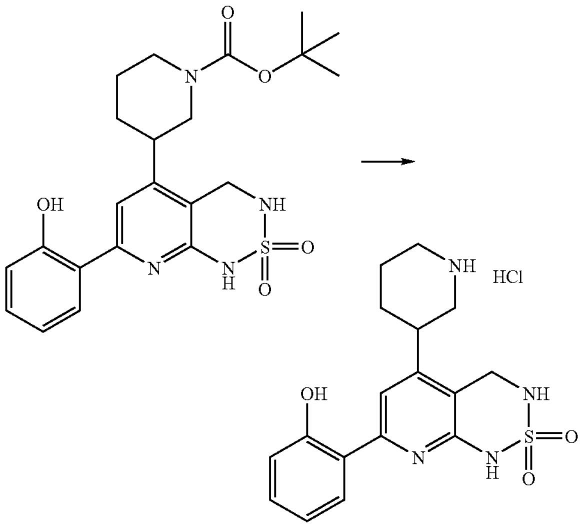

Then the tert-butyl carbamate was treated in a similar manner as that of the step (3) of Example 1-1 to give 2-[2,2-dioxido-5-(3-piperidinyl)-3,4-dihydro-1H-pyrido-[2,3-c][1,2,6]thiadiazin-7-yl]phenol hydrochloride.

Molecular weight: 396.90

Mass spectrometry: 361 $(M+H)^+$

In vitro activity grade: A

Cellular activity grade: (A549)-B $^1$H-NMR' (500 MHz, DMSO-d6): 1.82–1.91 (4H, m), 2.86–2.93 (1H, m), 3.18–3.36 (4H, m), 4.52 (2H, s), 6.90–6.93 (2H, m), 7.30 (1H, dt, J=1.6, 8.5 Hz), 7.65 (1H, br s), 8.00 (1H, d, J=7.6 Hz), 8.97 (1H, br), 9.32 (1H, br).

Example 23-1

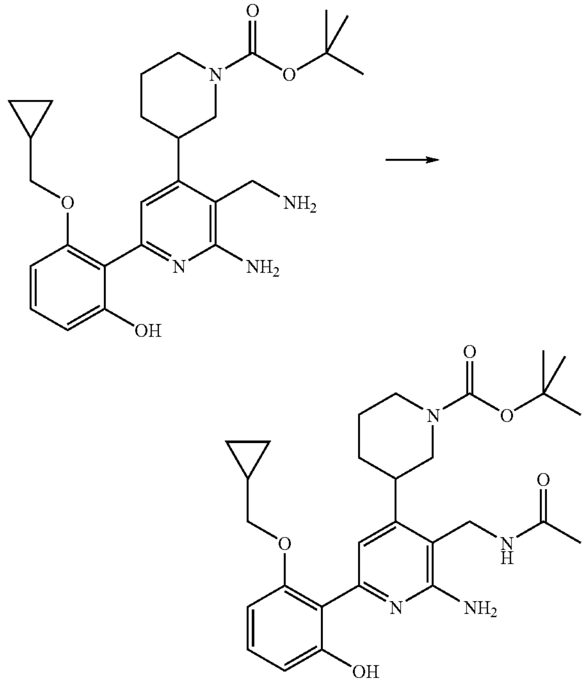

-continued

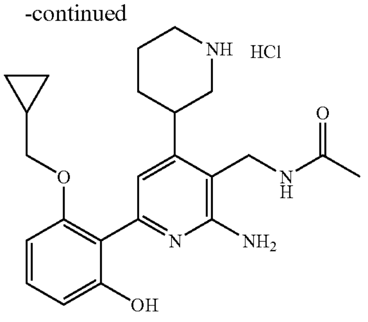

(1) With the use of the starting compounds 1G, 2B,and similar processes as those of the step (1) and (2) of Example 22-1, tert-butyl 3-{2-amino-3-(aminomethyl)-6-[2-(cyclopropylmethoxy)-6-hydroxyphenyl]-4-pyridinyl}-1-piperidinecarboxylate was prepared.

(2) To a cold (0° C.) solution of tert-butyl 3-{2-amino-3-(aminomethyl)-6-[2-(cyclopropylmethoxy)-6-hydroxyphenyl]-4-pyridinyl}-1-piperidinecarboxylate (1.9 g, 4.055 mmol) and triethylamine (1.13 mL, 8.109 mmol) in tetrahydrofuran (40.0 mL) was added acetic anhydride (0.457 mL, 4.865 mmol). The mixture was stirred at 0° C. for 4 hrs. After quenched by water, the mixture was extracted with ethyl acetate and water. The separated organic phase was washed with brine, dried over $MgSO_4$, filtered and concentrated under reduced pressure. The resulting residue (yellow solid) was purified by recrystallization from ethyl acetate/diisopropyl ether to give tert-butyl 3-{3-(acetylamino-methyl)-2-amino-6-[2-(cyclopropylmethoxy)-6-hydroxyphenyl]-4-pyridinyl}-1-piperidinecarboxylate (1.13 g, yield; 55%).

(3) The tert-butyl carbamate was treated in a similar manner as that of the step (3) of Example 1-1 to give N-{[2-amino-6-[2-(cyclopropylmethoxy)-6-hydroxyphenyl]-4-(3-piperidinyl)-3-pyridinyl]methyl}acetamide hydrochoride.

Molecular weight: 446.98

Mass spectrometry: 411 $(M+H)^+$

In vitro activity grade: A

Cellular activity grade: (A549)-A $^1$H-NMR (500 MHz, DMSO-d6): 0.28–0.30 (2H, m), 0.47–0.50 (2H, m), 1.13 (1H, m), 1.85–1.90 (4H, m), 1.93 (3H, s), 2.88 (1H, m), 3.06 (1H, m), 3.23 (1H, m), 3.33 (1H, m), 3.73 (1H, m), 3.80 (2H, m), 4.32–4.39 (2H, dd, J=5.6, 15.5 Hz), 6.58 (1H, d, J=8.5 Hz), 6.65 (1H, d, J=8.2 Hz), 7.09 (1H, s), 7.27 (1H, t, J=8.2 Hz), 7.80 (1H, br), 8.98 (2H, br), 9.29 (1H, br), 13.63 (1H, br).

Example 23-2

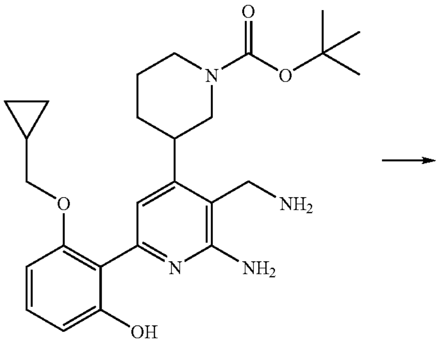

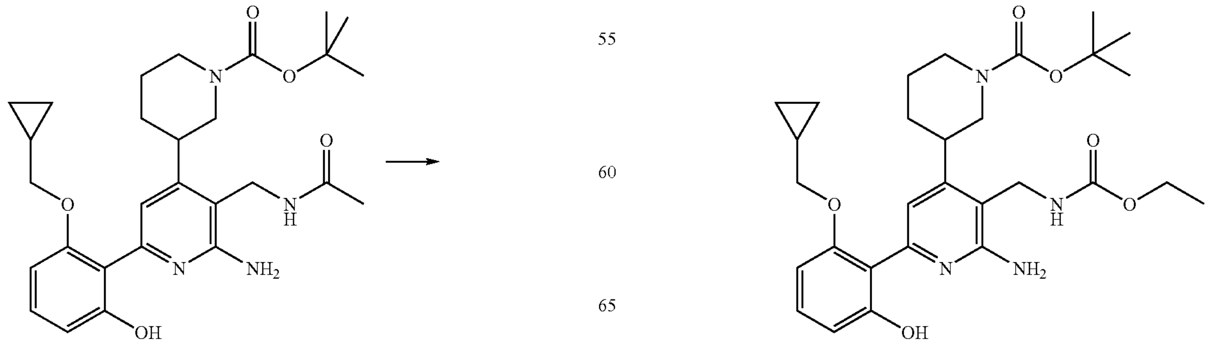

(1) To a cold (0° C.) solution of tert-butyl 3-{2-amino-3-(aminomethyl)-6-[2-(cyclopropylmethoxy)-6-hydroxyphenyl]-4-pyridinyl}-1-piperidinecarboxylate (0.300 g, 0.640 mmol), which was obtained in the step (1) of Example 23-1, and triethylamine (0.067 mL, 0.704 mmol) in tetrahydrofuran (30 mL) was added ethyl chloroformate (0.134 mL, 0.960 mmol) under an argon atmosphere. The mixture was allowed to warm to room temperature, and the stirring was continued for 4 hrs. After quenched by water, the mixture was extracted with ethyl acetate. The separated organic phase was washed with brine, dried over $MgSO_4$, filtered, then concentrated under reduced pressure. The resulting residue was purified by column chromatography on Silicagel (hexane/ethyl acetate=1/1) to give tert-butyl 3-(2-amino-6-[2-(cyclopropylmethoxy)-6-hydroxyphenyl]-3-{[(ethoxycarbonyl)amino]methyl}-4-pyridinyl)-1-piperidinecarboxylate as a pale yellow form (0.246 g, yield; 71%).

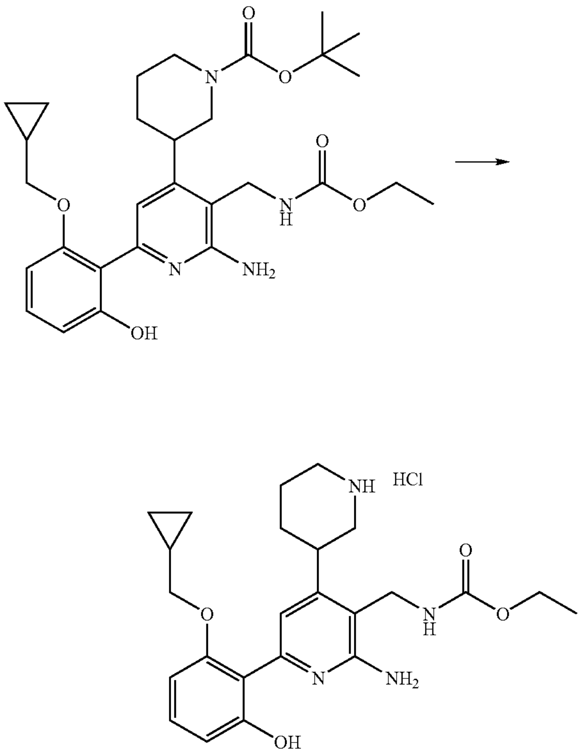

(2) Then the tert-butyl carbamate was treated in a similar manner as that of the step (3) of Example 1-1 to give ethyl[2-amino-6-[2-(cyclopropylmethoxy)-6-hydroxy-phenyl]-4-(3-piperidinyl)-3-pyridinyl]methylcarbamate hydrochloride.

Molecular weight: 477.01

Mass spectrometry: 441 $(M+H)^+$

In vitro activity grade: A

Cellular activity grade: (A549)-A $^1$H-NMR (500 MHz, DMSO-d6): 0.28–0.30 (2H, m), 0.48–0.51 (2H, m), 1.17 (3H, t, J=7.1 Hz), 1.22 (1H, m), 1.82–1.89 (5H, m), 2.88 (1H, m), 3.03 (1H, m), 3.25 (1H, m), 3.69 (1H, m), 3.84 (2H, m), 4.03 (2H, q, J=6.9 Hz), 4.28 (2H, dd, J=5.4, 15.1 Hz), 6.59 (1H, d, J=8.2 Hz), 6.65 (1H, d, J=8.2 Hz), 7.11 (1H, s), 7.27 (1H, t, J=8.2 Hz), 7.64 (1H, s), 7.86 (1H, s), 8.80 (1H, s), 9.27 (1H, s).

Example 23-3

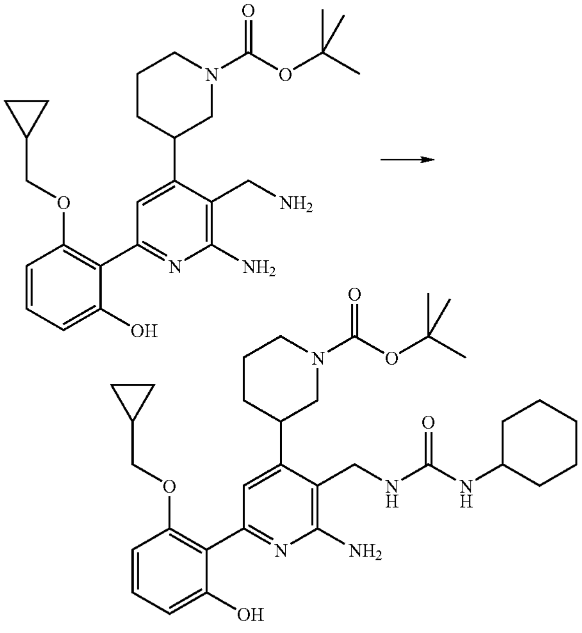

(1) To a solution of tert-butyl 3-{2-amino-3-aminomethyl}-6-[2-(cyclopropyl-methoxy)-6-hydroxyphenyl]-4-pyridinyl}-1-piperidinecarboxylate (0.150 g, 0.320 mmol), which was obtained in the step (1) of Example 23-1, in tetrahydrofuran (10.0 mL) was added cyclohexyl isocyanate (0.044 g, 0.352 mmol). The mixture was stirred at room temperature for 1.5 hrs and concentrated under reduced pressure. The resulting residue was purified by preparative TLC (ethyl acetate) to give tert-butyl 3-[2-amino-3[(3-cyclohexyl-ureido)-methyl]-6-[2-(cyclopropylmethoxy)-6-hydroxy-phenyl]-4-pyridinyl}-1-piperidinecarboxylate as a yellow form (0.113 g, yield; 60%).

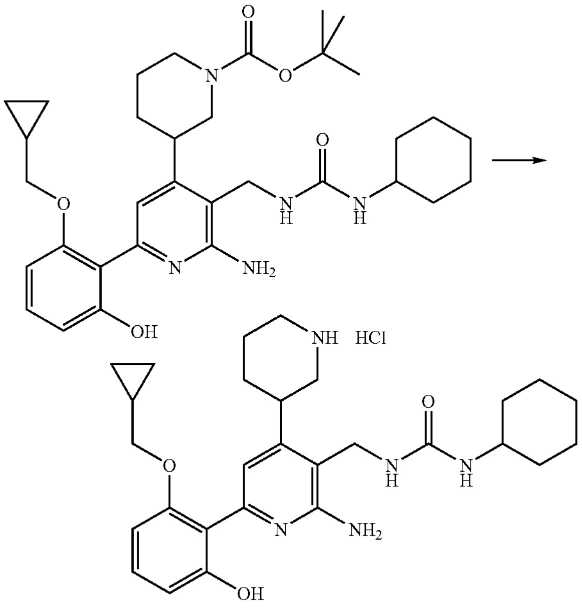

(2) Then the tert-butyl carbamate was treated in a similar mariner as that of the step (3) of Example 1-1 to give N-{[2-amino-6-[2-(cyclopropylmethoxy)-6-hydroxy-phenyl]-4-(3-piperidinyl)-3-pyridinyl]methyl}-N'-cyclohexylurea hydrochloride.

Molecular weight: 530.12

Mass spectrometry: 494 $(M+H)^+$

In vitro activity grade: A

Cellular activity grade: (A549)-A $^1$H-NMR (500 MHz, DMSO-d6): 0.27–0.28 (2H, m), 0.47–0.49 (2H, m), 1.10–1.14 (4H, m), 1.22–1.27 (3H, m), 1.51 (1H, m), 1.62–1.65 (2H, m), 1.73–1.74 (3H, m), 1.83–1.89 (5H, m), 2.88 (1H, m), 3.01 (1H, m), 3.72 (1H, m), 3.78–3.85 (2H, m), 4.29–4.32 (2H, m), 6.59 (1H, d, J=8.5 Hz), 6.66 (1H, d, J=8.2 Hz), 7.05 (1H, s), 7.27 (1H, t, J=8.2 Hz), 8.98 (1H, s), 9.25 (1H, s), 10.3 (1H, s), 13.5 (1H, s).

Examples 23-4 to 23-15

According to the similar synthetic procedure of Examples 23-1 to 23-3, compounds shown in Table 6 were prepared.

TABLE 6

| Ex. No | Structure | Mol weight | Mass | in vitro | A549 | NMR |
|---|---|---|---|---|---|---|
| 23-04 | 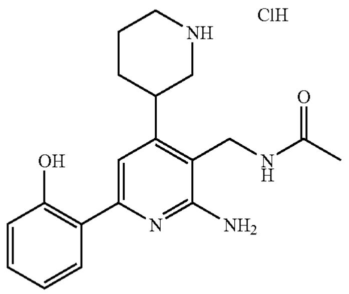 | 376.89 | 341 | A | A | (500MHz, DMSO-d6): 1.80–1.95(4H, m), 2.90 –2.95(1H, m), 3.13–3.34(2H, m), 4.26(1H, dd, J=5.8, 15.2Hz), 4.34 (1H, dd, J=5.8, 15.2Hz), 6.95(1H, t, J=7.3Hz), 6.98(1H, d, J=8.2Hz), 7.22 (1H, s), 7.35(1H, t, J=8.2Hz), 7.67(1H, br s), 8.81(1H, br), 8.93(1H, br), 9.26 (1H, br), 13.66(1H, br). |
| 23-05 | 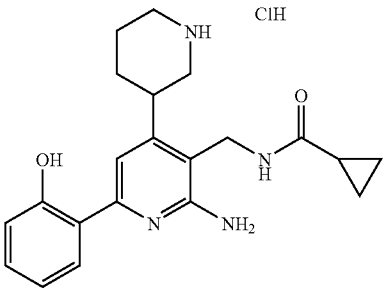 | 402.93 | 367 | A | A | (500MHz, DMSO-d6): 0.78(4H, m), 1.68 (1H, m), 1.88(4H, m), 1.99(1H, m), 3.05 (2H, dd, J=11.4, 23.9Hz), 3.38(2H, m), 3.49(1H, m), 4.34(2H, ddd, J=6.0, 13.5, 44.4Hz), 6.94(1H, t, J=7.6Hz), 7.00(1H, d, J=8.2Hz), 7.23(1h, S), 7.35(1H, t, J=8.2Hz), 7.70(1H, br), 8.90(1H, br), 9.02(1H, br), 9.21(1H, br), 13.7(1H, br). |
| 23-06 | 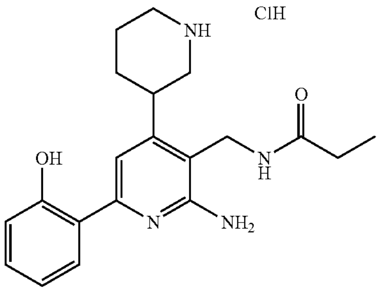 | 390.92 | 355 | B | B | (500MHz, DMSO-d6): 1.03(3H, t, J=7.6Hz), 1.85(2H, d, J=13.3Hz), 1.99 (1H, m), 2.18(2H, q, J=7.6Hz), 3.05 (2H, dd, J=11.4, 23.9Hz), 3.38(2H, m), 3.49(1H, m), 4.33(2H, d, J=6.0 Hz), 6.97(2H, t, J=7.9Hz), 7.07(1H, m), 7.37(1H, t, J=7.9Hz), 7.56(1H, br s), 7.88(1H, br), 8.75(1H, br), 8.96(1H, m), 13.6(1H, br). |
| 23-07 | 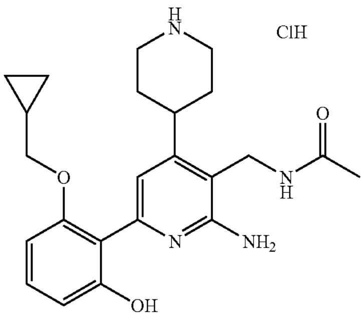 | 446.98 | 411 | A | A | (500MHz, DMSO-d6): 0.28–0.31(2H, m), 0.47–0.50(2H, m), 1.18(1H, m), 1.85–1.91(3H, m), 1.92(3H, s), 1.94–2.00(2H, m), 3.04–3.09(2H, m), 3.49–3.57(2H, m), 3.83(2H, d, J=6.9Hz), 4.35(2H, d, J=5.7Hz), 6.60(1H, d, J=8.5Hz), 6.68(1H, d, J=8.2Hz), 6.83 (1H, m), 7.27(1H, dd, J=8.2, 8.5Hz), 7.84(1H, br s), 8.96(3H, m), 10.4(1H, br s), 13.6(1H, br s). |

TABLE 6-continued

| Ex. No | Structure | Mol weight | Mass | in vitro | A549 | NMR |
|---|---|---|---|---|---|---|
| 23-08 | 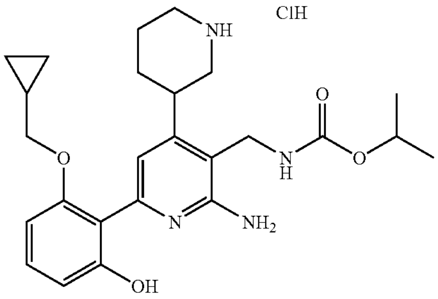 | 491.04 | 455 | A | A | (300MHz, DMSO-d6): 0.23–0.35(2H, m), 0.41–0.57(2H, m), 1.19(6H, d, J=6.4Hz), 1.06–1.28(1H, m), 1.70–1.98 (4H, m), 2.76–3.15(2H, m), 3.15–3.60 (2H, m), 3.60–3.75(1H, m), 3.75–3.90 (2H, m), 4.15–4.45(2H, m), 4.70–4.90 (1H, m), 6.59(1H, d, J=8.3Hz), 6.66 (1H, d, J=8.3Hz), 7.11(1H, br s), 7.27 (1H, t, J=8.3Hz), 7.61(1H, br), 7.80 (1H, br s), 8.65–8.95(1H, m), 9.15–9.40(1H, m), 10.38(1H, br), 13.64(1H, br). |
| 23-09 | 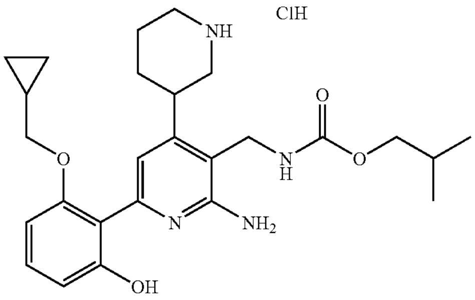 | 505.06 | 469 | A | A | (300MHz, DMSO-d6): 0.22–0.35(2H, m), 0.41–0.56(2H, m), 0.88(6H, d, J=6.8Hz), 1.02–1.25(1H, m), 1.70–2.00 (5H, m), 2.75–3.15(2H, m), 3.15–3.65 (2H, m), 3.65–3.97(5H, m), 4.15–4.44 (2H, m), 6.59(1H, d, J=8.3Hz), 6.67 (1H, d, J=8.3Hz), 7.10(1H, br s), 7.27 (1H, t, J=8.3Hz), 7.69(1H, br), 7.92 (1H, br s), 8.94(1H, br), 9.41(1H, br), 10.41(1H, br), 13.68(1H, br). |
| 23-10 | 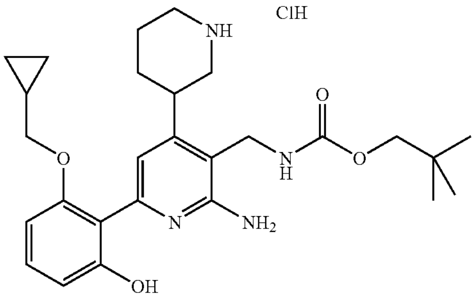 | 519.09 | 483 | A | A | (300MHz, DMSO-d6): 0.24–0.35(2H, m), 0.40–0.57(2H, m), 0.89(9H, s), 1.06–1.25(1H, m), 1.70–2.00(4H, m), 2.75–3.15(2H, m), 3.15–3.50(2H, m), 3.72(2H, s), 3.67–3.90(3H, m), 4.24 (1H, dd, J=5.7, 15.5Hz), 4.37(1H, dd, J = 5.7, 15.5Hz), 6.58(1H, d, J=8.3Hz), 6.67(1H, d, J=8.3Hz), 7.11(1H, br s), 7.26(1H, t, J=8.3Hz), 7.67(1H, br), 7.91(1H, br s), 8.95(1H, br), 9.39(1H, br), 10.39(1H, br), 13.68(1H, br). |
| 23-11 | 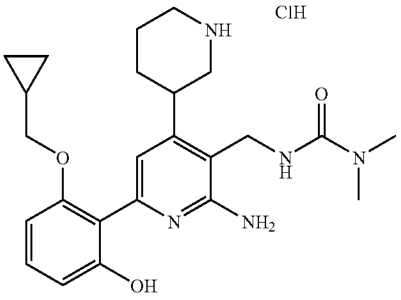 | 476.02 | 440 | A | A | (500MHz, DMSO-d6): 0.28–0.29(2H, m), 0.47–0.49(2H, m), 1.13(1H, m), 1.85–1.90(5H, m), 2.86(6H, s), 3.01 (1H, m), 3.25–3.27(2H, m), 3.78–3.84 (2H, m), 3.96(1H, m), 4.31(2H, d, J=5.0Hz), 6.59(1H, d, J=7.9Hz), 6.64 (1H, d, J=7.0Hz), 7.04(1H, s), 7.27 (1H, t, J=7.5Hz), 8.00(1H, s), 9.09(2H, s), 10.35(1H, s). |
| 23-12 | 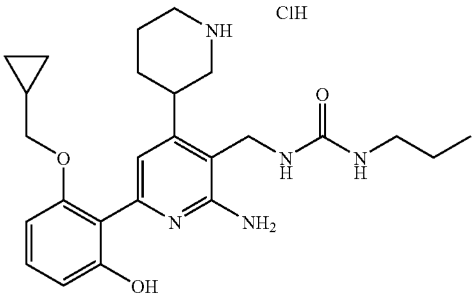 | 490.05 | 454 | A | A | (500MHz, DMSO-d6): 0.28–0.29(2H, m), 0.47–0.49(2H, m), 0.82(3H, t, J=7.4Hz), 1.13(1H, m), 1.37–1.42(2H, m), 1.84–1.89(4H, m), 2.90(1H, m), 3.00–3.01(3H, m), 3.02–3.05(2H, m), 3.78–3.85(3H, m), 4.30–4.36(2H, m), 6.58(1H, d, J=8.5Hz), 6.67(1H, d, J=8.2Hz), 7.04(1H, s), 7.18(1H, s), 7.26 (1H, t, J=8.2Hz), 8.06(2H, s), 9.05(1H, s), 9.39(1H, s), 10.39(1H, s), 13.60(1H, s). |

TABLE 6-continued

| Ex. No | Structure | Mol weight | Mass | in vitro | A549 | NMR |
|---|---|---|---|---|---|---|
| 23-13 | 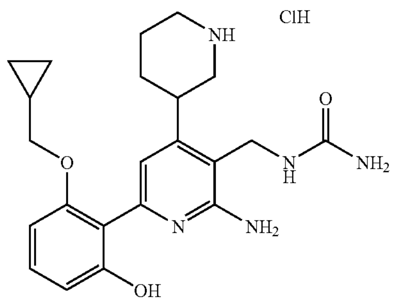 | 447.97 | 412 | A | A | (500MHz, DMSO-d6): 0.28–0.29(2H, q), 0.47–0.49(2H, q), 1.14(1H, br s), 1.85–1.89(4H, m), 2.88(1H, m), 3.02 (1H, m), 3.25–3.33(2H, m), 3.71(1H, m), 3.78–3.86(2H, m), 4.28–4.34(2H, m), 5.95(1H, br), 6.58(1H, d, J=8.2 Hz), 6.67(1H, d, J=8.2Hz), 7.04(1H, s), 7.26(1H, t, J=8.2Hz), 8.09(2H, br), 9.04(1H, br), 9.40(1H, br), 10.40(1H, br), 13.35(1H, s). |
| 23-14 | 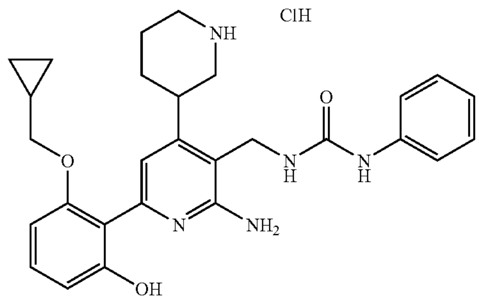 | 524.07 | 488 | A | A | (500MHz, DMSO-d6): 0.27–0.28(2H, m), 0.47–0.48(2H, m), 1.12(1H, m), 1.88–1.90(4H, m), 2.89–3.09(2H, m), 3.35–3.38(3H, m), 3.70–3.85(2H, m), 4.38–4.45(2H, m), 6.58(1H, d, J=8.8Hz), 6.66(1H, d, J=8.2Hz), 6.91–7.00(1H, m), 7.10(1H, s), 7.25(3H, t, J=7.6Hz), 7.40(2H, d, J=7.6Hz), 7.82(1H, s), 8.85(1H, s), 9.28(2H, s), 10.37(1H, s). |
| 23-15 | 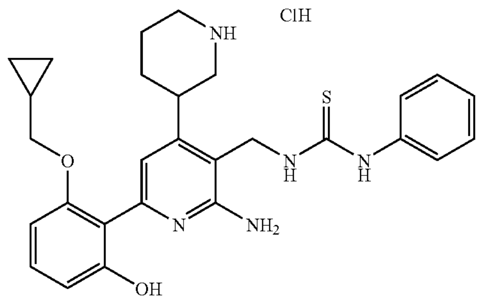 | 540.13 | 504 | A | A | (500MHz, DMSO-d6): 0.29–0.31(2H, m), 0.48–0.50(2H, m), 1.14(1H, m), 1.81–1.92(4H, m), 2.89(1H, m), 3.08 (1H, m), 3.59–3.60(2H, m), 3.61(1H, m), 3.82(2H, dd, J=6.2, 10.1Hz), 4.85 (2H, dd, J=5.4, 15.6Hz), 6.59(1H, d, J = 8.5Hz), 6.65(1H, d, J=8.2Hz), 7.12 (1H, t, J=7.5Hz), 7.14(1H, s), 7.27(1H, t, J=8.5Hz), 7.32(2H, t, J=7.6Hz), 7.49(2H, d, J=7.8Hz), 7.70(1H, br), 8.71(2H, br), 9.25(1H, br), 10.23(1H, br). |

Example 24-1

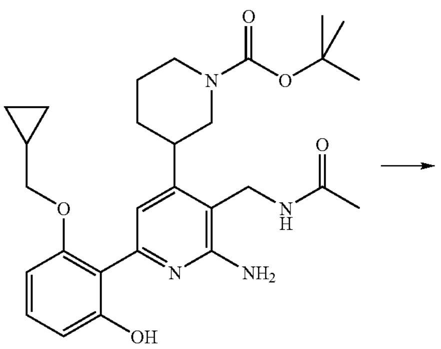

-continued

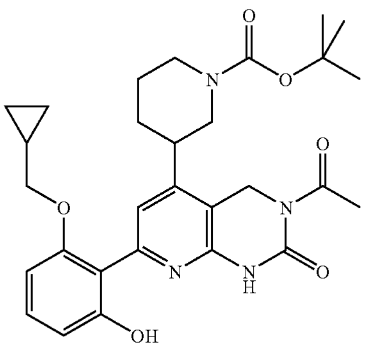

To a cold (0° C.) solution of tert-butyl 3-{3-[(acetylamino)methyl]-2-amino-6-[2-(cyclopropylmethoxy)-6-hydroxyphenyl]-4-pyridinyl}-1-piperidinecarboxylate (1.134 g, 2.220 mmol), which was obtained in the step (1) of Example 23-1, and triethylamine (1.871 mL, 13.320 mmol) in tetrahydrofuran (150 mL) was added dropwise a solution of triphosgene (0.652 g, 2.220 mmol) in tetrahydrofuran (150 mL) under an argon atmosphere. After stirred overnight, the reaction mixture was quenched by water. The mixture was extracted with ethyl acetate. The separated organic phase was washed with brine, dried over $MgSO_4$, filtered and concentrated under reduced pressure. The resulting residue (yellow solid) was purified by column chromatography on silica gel (hexane/ethyl acetate=1/1) to give tert-butyl 3-{3-acetyl-7-[2-(cyclopropylmethoxy)-6-hydroxyphenyl]-2-oxo-1,2,3,4-tetrahydropyrido-[2,3-d]pyrimidin-5-yl}-1-piperidinecarboxylate as a white form (0.569 g, yield; 48%).

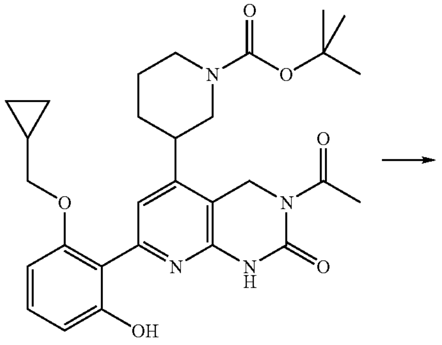

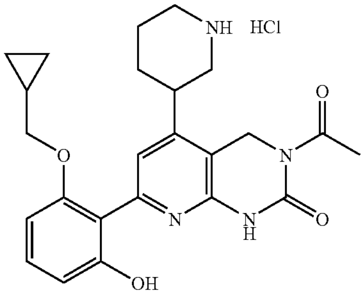

Then the tert-butyl carbamate was treated in a similar manner as that of the step (3) of Example 1-1 to give 3-acetyl-7-[2-(cyclopropylmethoxy)-6-hydroxyphenyl]-5-(3-piperidinyl)-3,4-dihydropyrido[2,3-d]pyrimidin-2(1H)-one hydrochloride.

Molecular weight: 472.98

Mass spectrometry: 437 $(M+H)^+$

In vitro activity grade: A

Cellular activity grade: (A549)-A $^1$H-NMR (500 MHz, DMSO-d6): 0.31–0.34 (2H, m), 0.56–0.59 (2H, m), 1.26 (1H, m), 1.74–1.79 (2H, m), 1.81–1.93 (2H, m), 2.47 (H, s), 2.85–2.98 (2H, m), 3.21–3.34 (3H, m), 3.81–3.86 (2H, m), 4.93 (2H, s), 6.52 (2H, d, J=8.2 Hz), 7.16 (1H, t, J=8.2 Hz), 7.78 (1H, s), 8.79 (1H, br), 9.30 (1H, br), 10.95 (1H, s).

Example 24-2

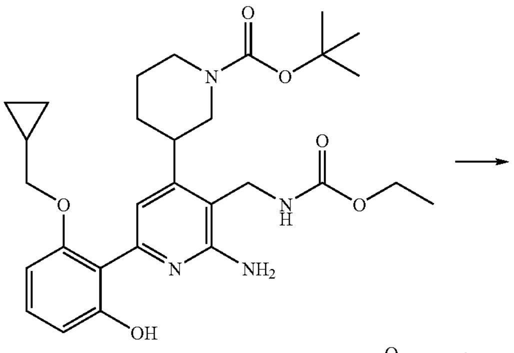

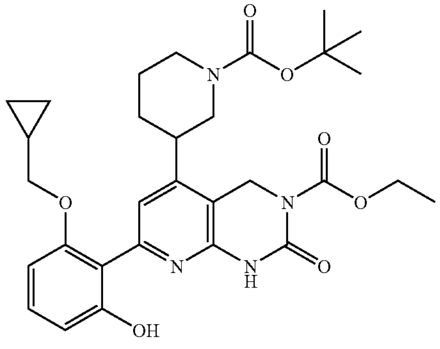

To a cooled (0° C.) solution of tert-butyl 3-(2-amino-6-[2-(cyclopropylmethoxy)-6-hydroxyphenyl]-3-{[(ethoxycarbonyl)amino]methyl}-4-pyridinyl)-1-piperidine-carboxylate (0.145 g, 0.268 mmol), which was obtained in the step (1) of Example 23-2, and triethylamine (0.226 mL, 1.609 mmol) in tetrahydrofuran(30 mL) was added triphosgene (0.079 g, 0.268 mmol) in tetrahydrofuran (10 mL) under an argon atmosphere. The mixture was allowed to warm to room temperature, and the stirring was continued for 3 hrs. After quenched by water, the mixture was extracted with ethyl acetate. The separated organic phase was washed with water and brine successively, dried over $MgSO_4$, filtered, and concentrated under reduced pressure. The resulting residue was purified by preparative TLC (hexane/ethyl acetate=1/1) to give ethyl 5-[1-(tert-butoxycarbonyl)-3-piperidinyl]-7-[2-(cyclopropylmethoxy)-6-hydroxyphenyl]-2-oxo-1,4-dihydropyrido[2,3-d]pyrimidine-3(2H)-carboxylate as a white solid (0.904 g, yield; 60%).

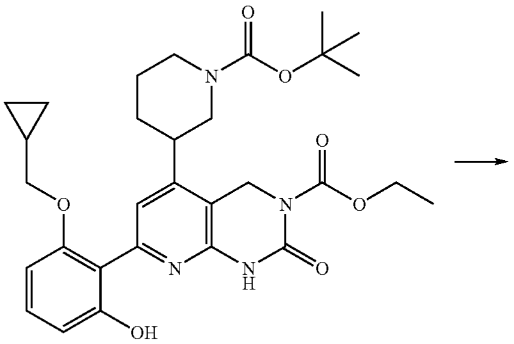

-continued

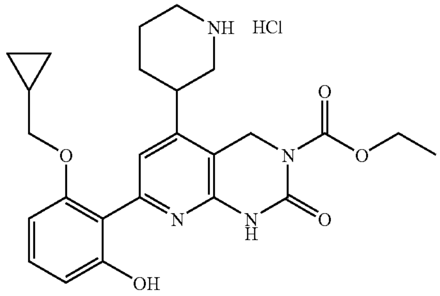

Then the tert-butyl ester was treated in a similar manner as that of the step (3) of Example 1-1 to give ethyl 7-[2-(cyclopropylmethoxy)-6-hydroxyphenyl]-2-oxo-5-(3-piperidinyl)-1,4-dihydropyrido[2,3-d]pyrimidine-3(2H)-carboxylate hydrochloride.

Molecular weight: 503.00

Mass spectrometry: 467 $(M+H)^+$

In vitro activity grade: A

Cellular activity grade: (A549)-A $^1$H-NMR(500 MHz, DMSO-d6): 0.31–0.34 (2H, m), 0.55–0.59 (2H, m), 1.26–1.28 (1H, br s), 1.27 (3H, t, J=7.3 Hz), 1.74–1.85 (3H, m), 2.8–2.95 (2H, m), 3.22–3.25 (1H, m), 3.30–3.32 (2H, m), 3.79–3.87 (1H, m), 4.22–4.25 (2H, m), 4.91 (2H, s), 6.52 (2H, d, J=8.2 Hz), 7.16 (1H, t, J=8.2 Hz), 7.78 (1H, s), 8.91 (1H, br s), 9.29 (1H, br), 10.86 (1H, s).

Example 24-3

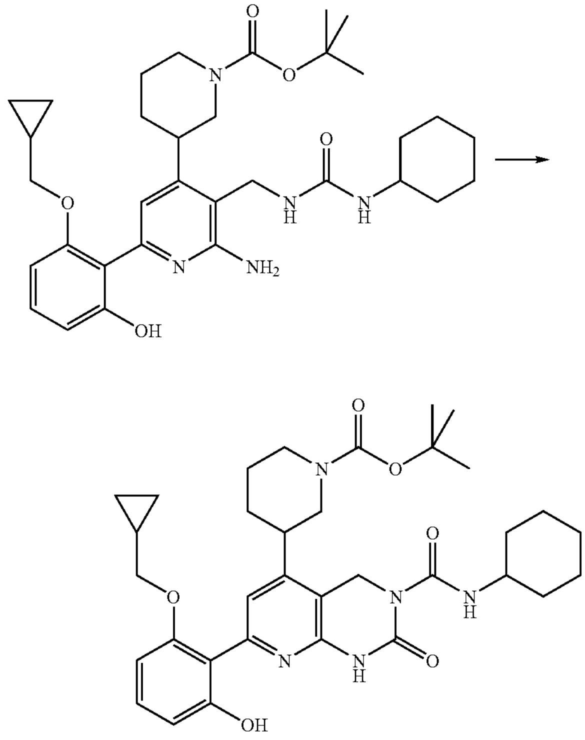

To a cooled (0° C.) solution of tert-butyl 3-{2-amino-3-({[(cyclohexylamino)-carbonyl]amino}methyl)-6-[2-(cyclopropylmethoxy)-6-hydroxyphenyl]-4-pyridinyl}-1-piperidinecarboxylate (0.039 g, 0.065 mmol), which was obtained in the step (1) of Example 23-3, and triethylamine (15.0 mL, 0.389 mmol) in tetrahydrofuran (10.0 mL) was added dropwise a solution of triphosgene (0.019 g, 0.065 mmol) in tetrahydrofuran (5.0 mL) under an argon atmosphere. The mixture was stirred at 0° C. for 2 hrs. After quenched by water, the mixture was extracted with ethyl acetate. The separated organic phase was washed with brine, dried over $MgSO_4$, filtered and concentrated under reduced pressure. The resulting residue (white solid) was triturated with diisopropyl ether, collected by filtration, washed with diisopropyl ether, and dried under reduced pressure to give tert-butyl 3-{3-[(cyclo-hexylamino)carbonyl]-7-[2-(cyclopropylmethoxy)-6-hydroxyphenyl]-2-oxo-1,2,3,4-tetrahydropyrido[2,3-d]pyrimidin-5-yl}-1-piperidinecarboxylate (0.021 g, yield; 52%).

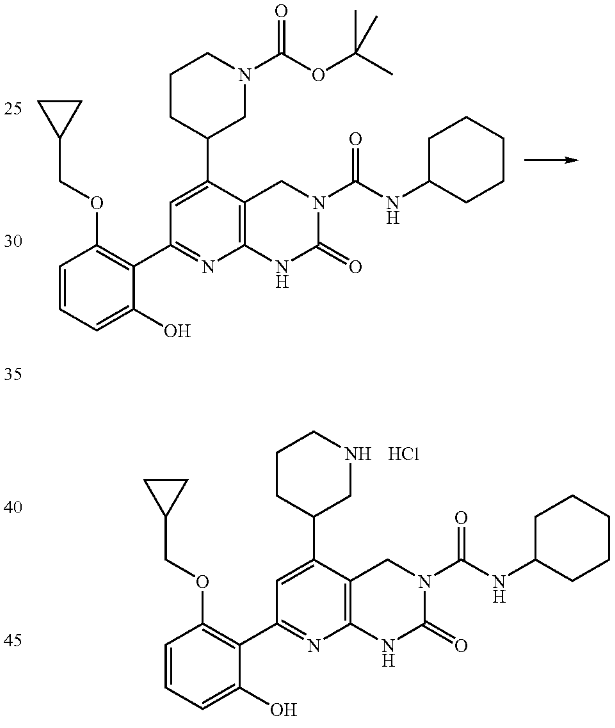

Then the tert-butyl carbamate was treated in a similar manner as that of the step (3) of Example 1-1 to give N-cyclohexyl-7-[2-(cyclopropylmethoxy)-6-hydroxyphenyl]-2-oxo-5-(3-piperidinyl)-1,4-dihydropyrido[2,3-d]pyrimidine-3(2H)-carboxamide hydrochloride.

Molecular weight: 556.11

Mass spectrometry: 520 $(M+H)^+$

In vitro activity grade: A

Cellular activity grade: (A549)-A $^1$H-NMR'(500 MHz, DMSO-d6): 0.32–0.34 (2H, m), 0.55–0.59 (2H, m), 1.24–1.35 (8H, m), 1.64 (1H, m), 1.75–1.78 (2H, m), 1.82–1.84 (4H, m), 1.91–1.93 (2H, m), 2.86 (1H, m), 2.96 (1H, m), 3.16 (1H, m), 3.62 (1H, m), 3.63–3.88 (2H, dd, J=6.9, 9.8 Hz), 4.98 (2H, s), 6.52 (2H, d, J=8.2 Hz), 7.16 (1H, t, J=8.5 Hz), 7.77 (1H, s), 9.00 (1H, s), 10.82 (1H, s), 11.73 (1H, s).

Example 24-4

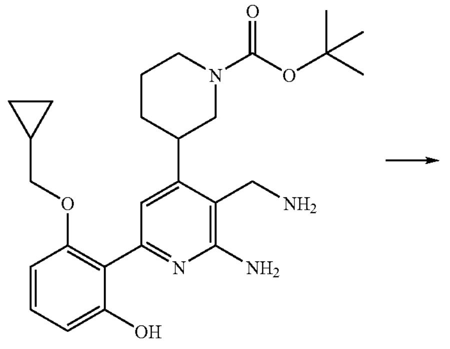

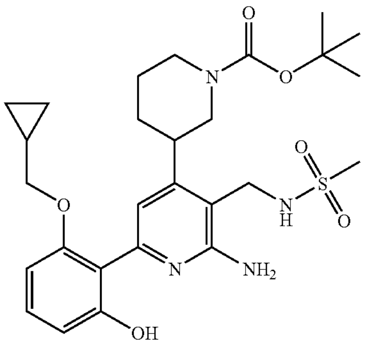

To a cold (0° C.) solution of tert-butyl 3-{2-amino-3-(aminomethyl)-6-[2-(cyclo-propylmethoxy)-6-hydroxyphenyl]-4-pyridinyl}-1-piperidinecarboxylate (0.150 g, 0.320 mmol), which was obtained in the step (1) of Example 23-1, and triethylamine (0.067 mL, 0.480 mmol) in tetrahydrofuran (9 mL) was added methanesulfonyl chloride (0.027 mL, 0.352 mmol) under an argon atmosphere. The stirring was continued at 0° C. for 1 hr. After quenched by water, the mixture was extracted with ethyl acetate. The separated organic phase was washed with brine, dried over $MgSO_4$, filtered, and concentrated under reduced pressure. The resulting yellow residue was purified by recrystallization from diisopropyl ether/dichloromethane to give tert-butyl 3-(2-amino-6-[2-(cyclopropylmethoxy)-6-hydroxyphenyl]-3-{[(methylsulfonyl)amino]methyl}-4-pyridinyl)-1-piperidinecarboxylate as a yellow solid (0.097 g, yield; 56%).

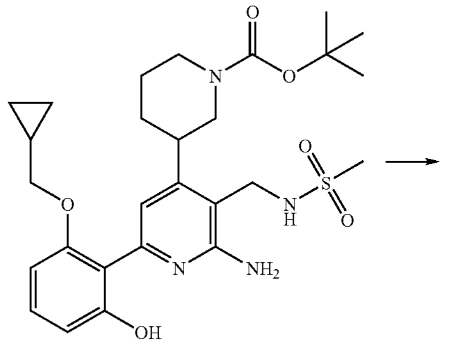

-continued

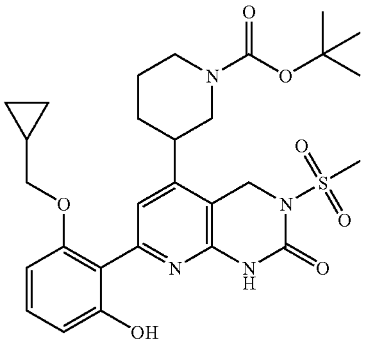

To a cooled (0° C.) solution of tert-butyl 3-(2-amino-6-[2-(cyclopropylmethoxy)-6-hydroxyphenyl]-3-{[(methylsulfonyl)amino]methyl}-4-pyridinyl)-1-piperidine-1-piperidine-carboxylate (0.050 g, 0.091 mmol) and triethylamine (0.077 mL, 0.549 mmol) in tetrahydrofuran (15 mL) was added to a solution of triphosgene (0.027 g, 0.091 mmol) in tetrahydrofuran(5 mL) under an argon atmosphere. The mixture was allowed to warm to room temperature, and the stirring was continued for 3 hrs under an argon atmosphere. After quenched by water, the mixture was extracted with ethy acetate. The separated organic phase was washed with brine, dried over $MgSO_4$, filtered, and concentrated under reduced pressure. The resulting yellow solid was triturated with diisopropyl ether and collected by filtration to give tert-butyl 3-[7-[2-(cyclopropylmethoxy)-6-hydroxyphenyl]-3-(methylsulfonyl)-2-oxo-1,2,3,4-tetra-hydropyrido[2,3-d]pyrimidin-5-yl]-1-piperidinecarboxylate as a yellow solid (0.028 g, yield; 55%).

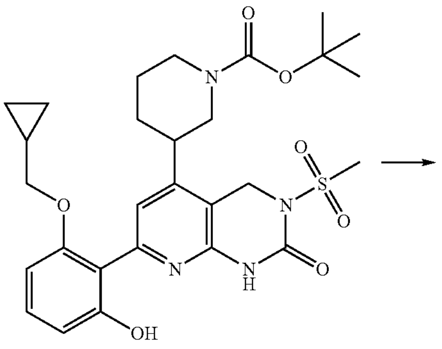

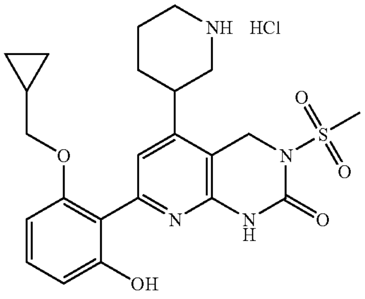

Then the tert-butyl carbamate was treated in a similar manner as that of the step (3) of Example 1-1 to give 7-[2-(cyclopropylmethoxy)-6-hydroxyphenyl]-3-(methylsulfonyl)-5-(3-piperidinyl)-3,4-dihydropyrido[2,3-d]pyrimidin-2(1H)-one hydro-chloride.
Molecular weight: 509.03
Mass spectrometry: 473 $(M+H)^+$
In vitro activity grade: A
Cellular activity grade: (A549)-A $^1$H-NMR'(500 MHz, DMSO-d6): 0.30–0.33 (2H, m), 0.54–0.58 (2H, m), 1.26 (1H, m), 1.73–1.78 (2H, m), 1.88–1.93 (2H, m), 2.88 (1H, m), 2.99(1H, m), 3.13 (1H, m), 3.30–3.35 (2H, m), 3.50 (3H, s), 3.83 (2H, dd, J=6.9, 7.2 Hz), 4.97 (2H, s), 6.53 (2H, d, J=8.2 Hz), 7.17 (1H, t, J=8.5 Hz), 7.75 (H,s), 8.67 (1H, s), 9.11 (1H,s), 11.02 (1H, s).

Examples 24-5 to 24-10

According to the similar synthetic procedure of Examples 24-1 to 24-4, compounds shown in Table 7 were prepared.

TABLE 7

| Ex. No | Structure | Mol weight | Mass | in vitro | A549 | NMR |
|---|---|---|---|---|---|---|
| 24-05 | 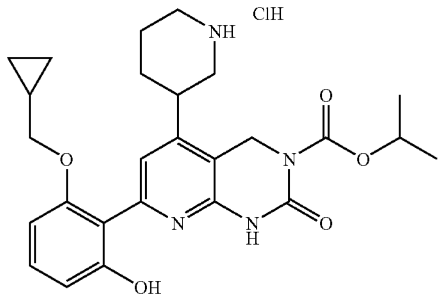 | 517.03 | 481 | A | A | (300MHz, DMSO-d6): 0.25–0.38(2H, m), 0.50–0.64(2H, m), 1.29(6H, d, J=6.0Hz), 1.20–1.32(1H, m), 1.60–2.00 (4H, m), 2.75–3.05(2H, m), 3.15–3.40 (3H, m), 3.75–3.92(2H, m), 4.89(2H, s), 4.90–5.04(1H, m), 6.53(2H, d, J=8.3 Hz), 7.17(1H, t, J=8.3Hz), 7.78(1H, s), 8.92(1H, br), 9.25(1H, br), 10.82(1H, s). |
| 24-06 | 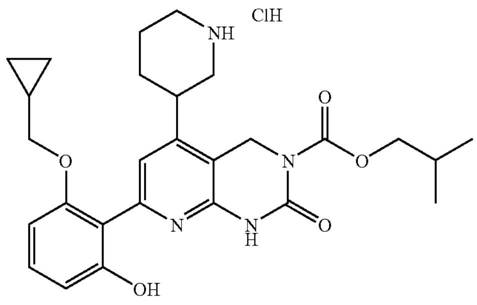 | 531.06 | 495 | A | A | (300MHz, DMSO-d6): 0.25–0.38(2H, m), 0.51–0.64(2H, m), 0.95(6H, d, J=6.4Hz), 1.17–1.35(1H, m), 1.63–2.05 (5H, m), 2.75–3.10(2H, m), 3.10–3.45 (3H, m), 3.75–3.92(2H, m), 3.99(2H, d, J=8.3Hz), 4.89(1H, d, J=15.8Hz), 4.95(1H, d, J=15.8Hz), 6.53(2H, d, J=8.3Hz), 7.17(1H, t, J=8.3Hz), 7.78 (1H, br), 8.65–9.20(1H, m), 9.20–9.75 (1H, m), 10.84(1H, s). |
| 24-07 | 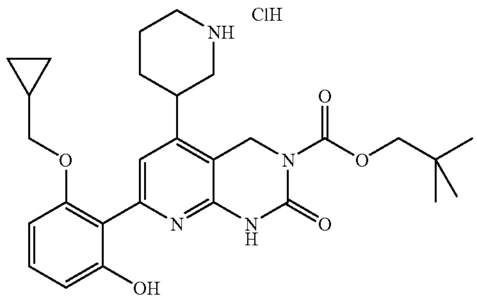 | 545.08 | 509 | A | A | (300MHz, DMSO-d6): 0.25–0.37(2H, m), 0.52–0.63(2H, m), 0.97(9H, s), 1.17–1.35(1H, m), 1.60–2.00(4H, m), 2.75–3.10(2H, m), 3.10–3.40(2H, m), 3.76–3.92(3H, m), 3.90(2H, s), 4.89 (1H, d, J=15.8Hz), 4.96(1H, d, J=15.8 Hz), 6.53(2H, d, J=8.3Hz), 7.17(1H, t, J=8.3Hz), 7.77(1H, s), 8.65–9.05(1H, m), 9.25–9.60(1H, m), 10.83(1H, s). |
| 24-08 | 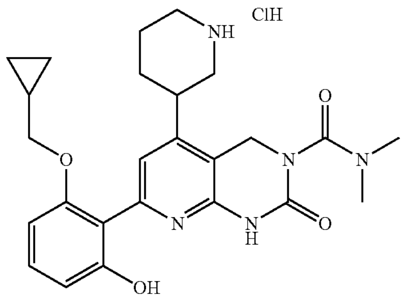 | 502.02 | 466 | A | A | (500MHz, DMSO-d6): 0.33–0.35(2H, m), 0.56–0.58(2H, m), 1.26(1H, m), 1.76–1.80(2H, m), 1.90–1.92(2H, m), 2.84–2.91(10H, m), 3.14(1H, m), 3.83–3.85(2H, m), 4.64–4.70(2H, m), 6.51–6.54(2H, m), 7.16(1H, t, J=8.2Hz), 7.80(1H, s), 8.47(1H, s), 8.97(1H, s), 10.68(1H s). |

TABLE 7-continued

| Ex. No | Structure | Mol weight | Mass | in vitro | A549 | NMR |
|---|---|---|---|---|---|---|
| 24-09 | 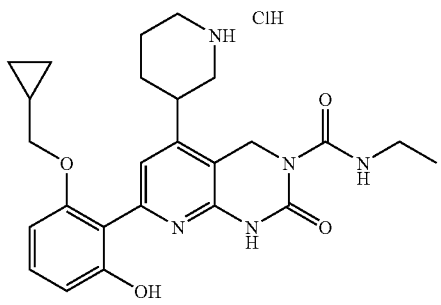 | 502.02 | 466 | | | (500MHz, DMSO-d6): 0.32–0.33(2H, m), 0.56–0.58(2H, m), 1.10(3H, t, J=7.3Hz), 1.27(1H, m), 1.72–1.91(4H, m), 2.85–2.95(2H, m), 3.16(1H, m), 3.22–3.27(2H, m), 3.31–3.33(2H, m), 3.82–3.86(2H, m), 4.99(2H, s), 6.52 (2H, d, J=8.2Hz), 7.17(1H, t, J=8.2 Hz), 7.78(1H, s), 8.96(1H, br), 9.17(1H, br), 10.84(1H, s). |
| 24-10 | 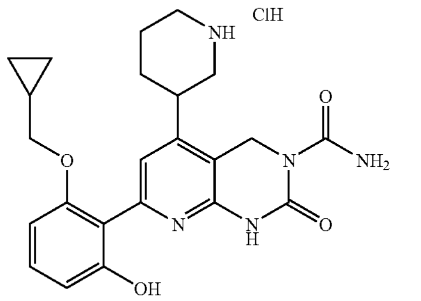 | 473.96 | 438 | A | A | (300MHz, DMSO-d6): 0.32–0.33(2H, m), 0.56–0.58(2H, m), 1.26(1H, m), 1.73–1.95(3H, m), 2.85–2.97(3H, m), 3.19–3.34(4H, m), 3.78–3.86(2H, m), 4.98(2H, a), 6.53(2H, d, J=7.9Hz), 7.16(1H, t, J=8.3Hz), 7.46(1H, br), 7.78(1H, s), 8.33(1H, br), 8.67(1H, br), 9.12(1H, br), 10.80(1H, s). |

Example 25-1

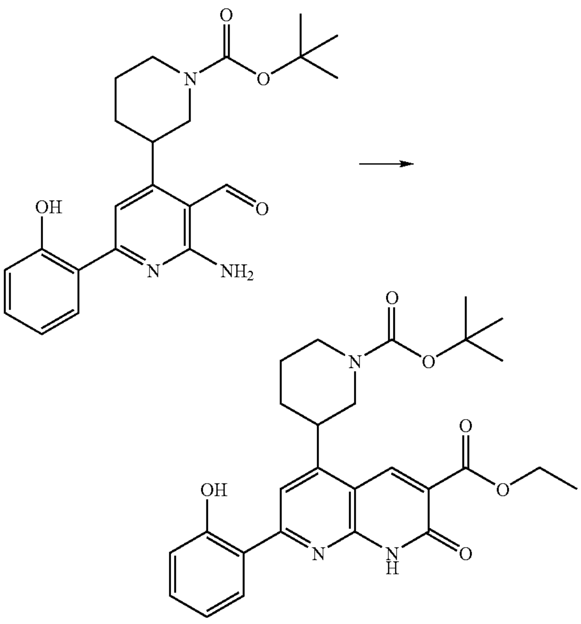

To a suspension of tert-butyl 3-[2-amino-3-formyl-6-(2-hydroxyphenyl)-4-pyridinyl]-1-piperidinecarboxylate (0.86 g, 2.16 mmol) in ethanol (25 mL) were added diethyl malonate (6.93 g, 43.27 mmol) and piperidine (2.14 mL, 21.64 mmol) and, and the mixture was heated at reflux overnight. The mixture was allowed to cool to room temperature, and then diluted with ethanol. The resulting precipitate was collected by filtration, washed with ethanol and dried under reduced pressure to give ethyl 5-[1-(tert-butoxycarbonyl)-3-piperidinyl]-7-(2-hydroxyphenyl)-2-oxo-1,2-dihydro-1,8-naphthyridine-3-carboxylate as a yellow solid (0.752 g, yield; 71%).

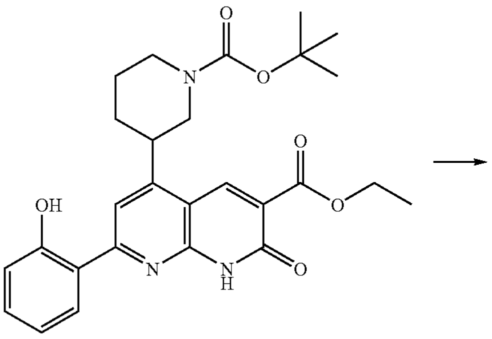

-continued

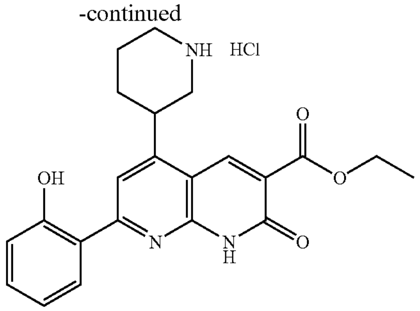

Then the tert-butyl carbamate was treated in a similar manner as that of the step (3) of Example 1-1 to give ethyl 7-(2-hydroxyphenyl)-2-oxo-5-(3-piperidinyl)-1,2-dihydro-1,8-naphthyridine-3-carboxylate hydrochloride.

Molecular weight: 429.91

Mass spectrometry: 394 $(M+H)^+$

In vitro activity grade: A

Cellular activity grade: (A549)-B $^1$H-NMR (500 MHz, DMSO-d6): 1.34 (3H, t, J=7.1 Hz), 1.89–2.07 (4H, m,), 2.92–3.00 (1H, m), 3.40–3.44 (1H, m, 3.77 (1H, br), 4.32 (2H, q, J=7.1 Hz), 6.97–7.01 (2H, m), 7.41 (1H, t, J=7.25 Hz), 8.01 (1H, d, J=7.25 Hz), 8.62 (1H, s), 8.83 (1H, br), 9.18 (1H, br), 12.69 (1H, s), 12.96 (1H, br s).

Example 25-2

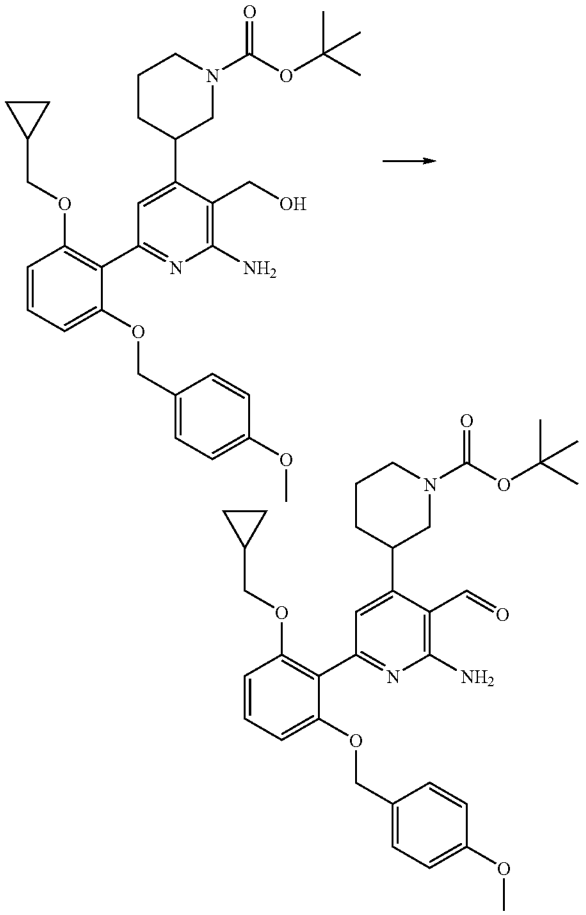

(1) To a stirred solution of tert-butyl 3-[2-amino-6-{2-(cyclopropylmethoxy)-6-[(4-methoxybenzyl)oxy]phenyl}-3-(hydroxymethyl)-4-pyridinyl]-1-piperidinecarboxylate (1.100 g, 1.863 mmol), which was obtained in the step (2) of Example 17-1, in dichloromethane (50 mL) was added manganese dioxide (3.240 g, 37.261 mmol). The mixture was stirred at room temperature for 3 hrs and filtered on Celite®. The filtrate was concentrated under reduced pressure to give tert-butyl 3-(2-amino-6-{2-(cyclopropylmethoxy)-6-[(4-methoxybenzyl)oxy]phenyl}-3-formyl-4-pyridinyl)-1-piperidinecarboxylate (0.978 g, yield; 89%).

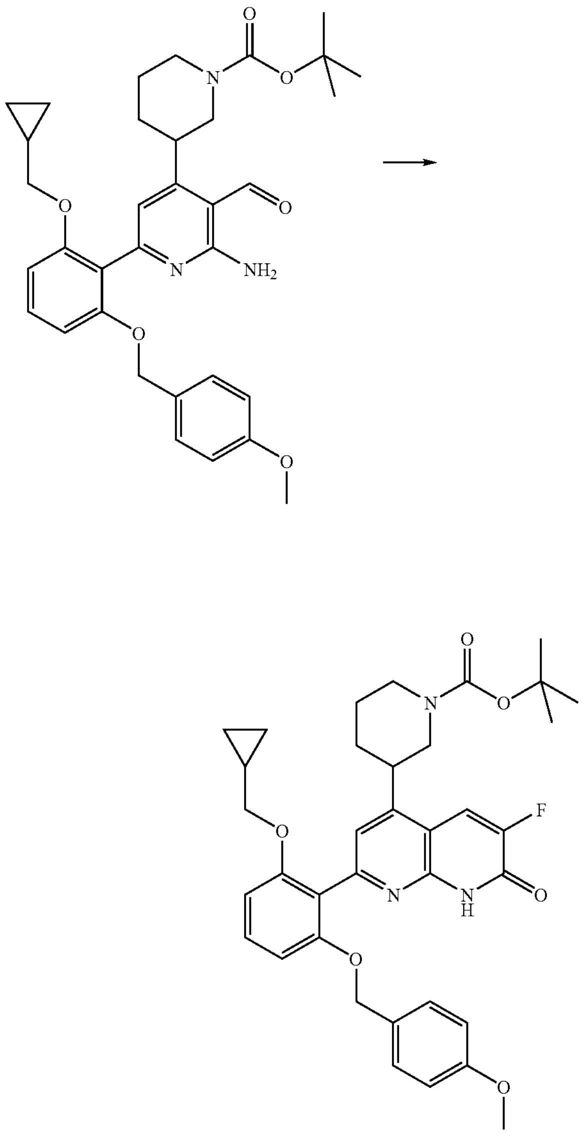

(2) To a stirred solution of tert-butyl 3-(2-amino-6-55 2-(cyclopropylmethoxy)-6-[(4-methoxybenzyl)oxy]phenyl}-3-formyl-4-pyridinyl)-1-piperidinecarboxylate (0.500 g, 0.851 mmol), triethyl-2-fluoro-2-phosphonoacetate (0.350 mL, 1.701 mmol) and anhydrous lithium chloride (0.072 g, 1.701 mmol) in acetonitrile (20 mL) was added 1,8-diazabicyclo[5,4,0]undec-7-ene (0.250 mL, 1.701 mmol). The mixture was stirred at room temperature for 30 min and concentrated under reduced pressure. The residue was extracted with ethyl acetate and water. The separated organic phase was washed with brine, dried over $Na_2SO_4$, filtered, and concentrated under reduced pressure. The resulting residue (liquid) was purified by column chromatography on silica gel (hexane/ethyl acetate=2/1-1/1) to give tert-butyl 3-(2-{2-(cyclo-propylmethoxy)-6-[(4-methoxy-benzyl)oxy]phenyl}-6-fluoro-7-oxo-7,8-dihydro-1,8-naphthyridin-4-yl)-1-piperidinecarboxylate as a form (0.261 g, 49%).

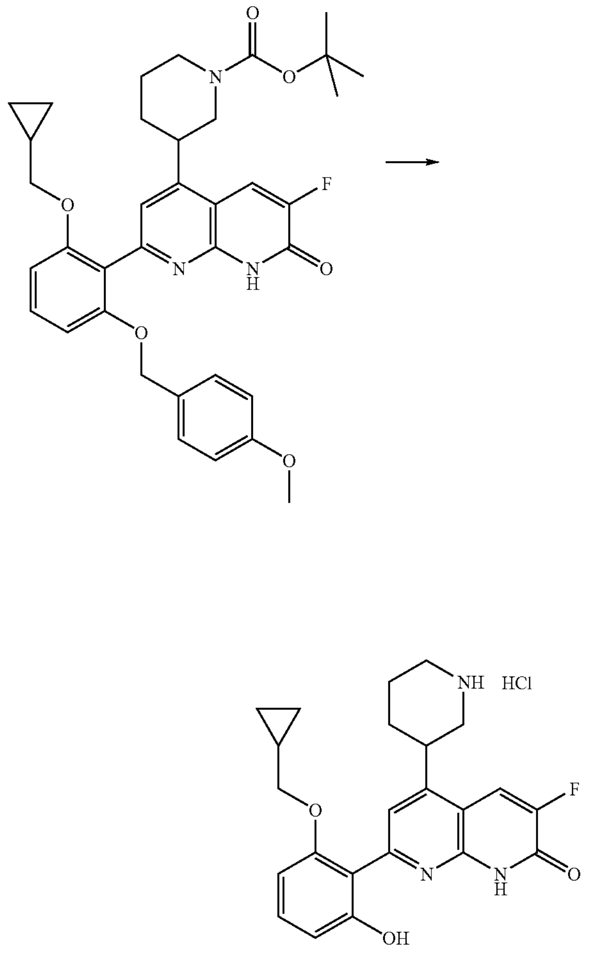

Then the tert-butyl carbamate was treated in a similar manner as that of the step (2) of Example 21-1 to give 7-[2-(cyclopropylmethoxy)-6-hydroxyphenyl]-3-fluoro-5-(3-piperidinyl)-1,8-naphthyridin-2(1H)-one hydrochloride.

Molecular weight: 445.93

Mass spectrometry: 410 $(M+H)^+$

In vitro activity grade: A

Cellular activity grade: (A549)-A $^1H$-NMR (500 MHz, DMSO-d6): 0.32 (2H, m), 0.55 (2H, m), 1.25 (1H, m), 1.94 (4H, m), 2.95 (2H, m), 3.65 (1H, br), 6.58 (2H, d, J=8.2 Hz), 7.23 (1H, t, J=8.2 Hz), 7.97 (1H, s), 8.15 (1H, d, J=11.4 Hz), 8.64 (1H, br), 9.01 (1H, br), 11.66 (1H, br), 13.02 (1H, d, J=5.4 Hz).

Example 25-3

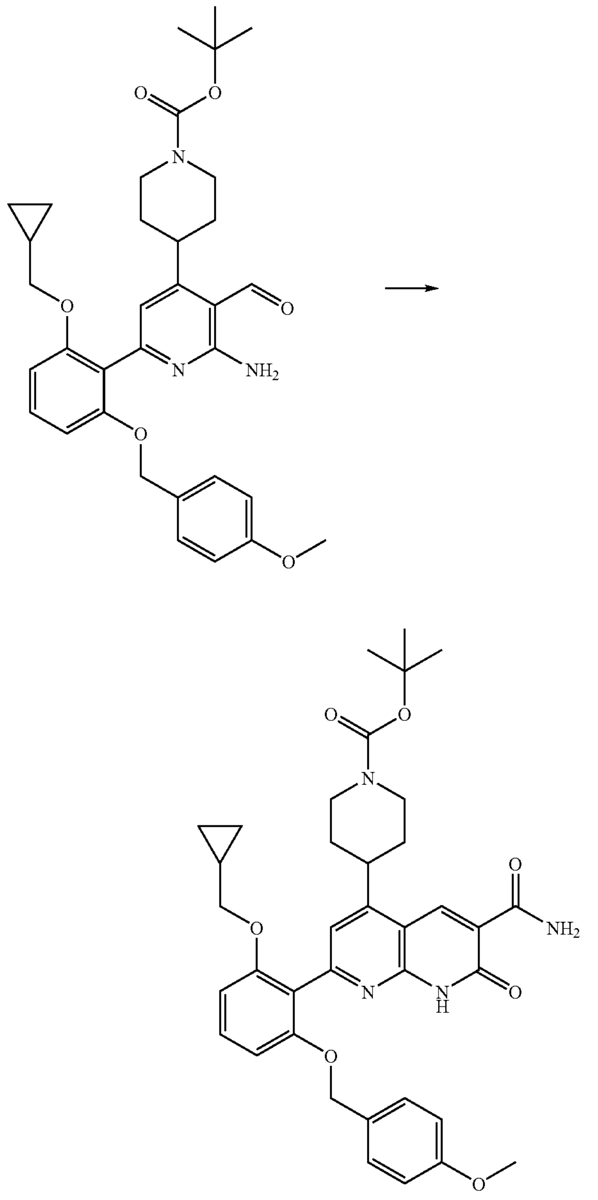

(1) With the use of the starting compound 1G and tert-butyl 4-formyl piperidine-1-carboxylic acid, tert-butyl 4-(2-amino-6-{2-(cyclopropylmethoxy)-6-[(4-methoxy-benzyl) oxy]phenyl}-3-formyl-4-pyridinyl)-1-piperidinecarboxylate was prepared in a similar manner as that of the step (1) of Example 25-2. To a solution of tert-butyl 4-(2-amino-6-{2-(cyclopropylmethoxy)-6-[(4-methoxybenzyl)oxy]phenyl}-3-formyl-4-pyridinyl)-1-piperidinecarboxylate (0.400 g, 0.681 mmol) in ethyl alcohol (5.0 mL) was added ethyl malonate monoamine (1.780 g, 13.612 mmol) and piperidine (0.580 g, 6.806 mmol). The mixture was refluxed 12 hrs. The reaction mixture was extracted with ethyl acetate and water. The separated organic phase was washed with $NaHCO_3$ and brine, dried over $Na_2SO_4$, filtered, and concentrated under reduced pressure. The resulting residue (liquid) was purified by column chromatography on silica gel (hexane/ethyl acetate=1/1 and ethylacetate 100%) to give tert-butyl 4-(6-(aminocarbonyl)-2-{2-(cyclopropylmethoxy)-6-[(4-methoxybenzyl)oxy]phenyl}-7-oxo-7,8-dihydro-1,8-naphthyridin-4-yl)-1-piperidinecarboxylate as a yellow form. (0.455 g, yield; quant.)

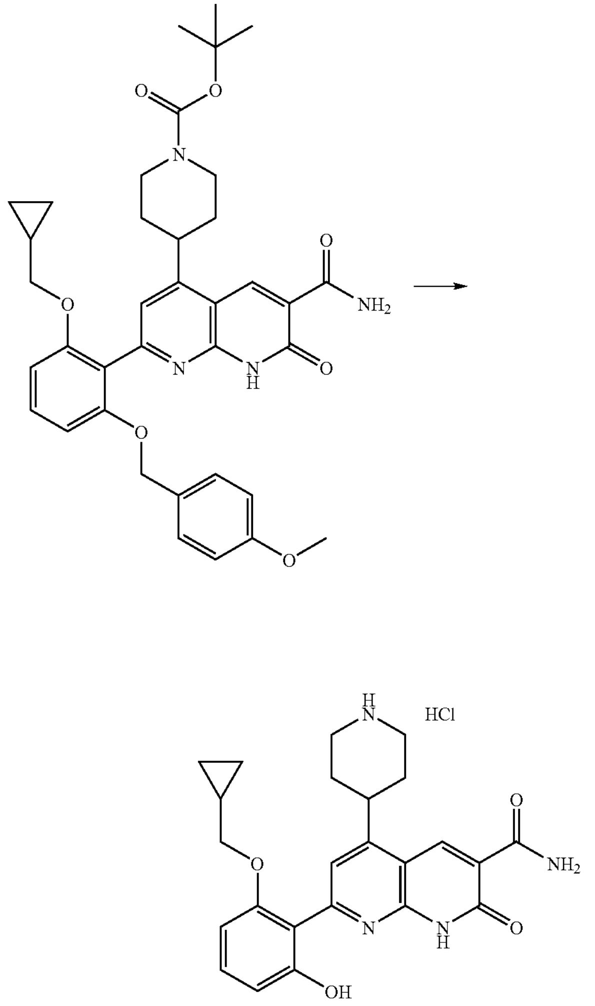

(2) Then the tert-butyl carbamate was treated in a similar manner as that of the step (2) of Example 21-1 to give 7-[2-(cyclopropylmethoxy)-6-hydroxyphenyl]-2-oxo-5-(4-piperidinyl)-1,2-dihydro-1,8-naphthyridine-3-carboxamide hydrochloride.

Molecular weight: 470.96

Mass spectrometry: 435 $(M+H)^+$

In vitro activity grade: A

Cellular activity grade: (A549)-B $^1$H-NMR(500 MHz, DMSO-d6): 0.32 (2H, d, J=4.7 Hz), 0.57 (2H, d, J=7.9 Hz), 1.32–1.35 (1H, m), 1.91–2.01 (5H, m), 3.23–3.26 (3H, m), 3.70–3.80 (2H, m), 3.90 (2H, d, J=6.9 Hz), 6.59 (2H, dd, J=1.7, 8.3 Hz), 7.26 (1H, t, J=8.2 Hz), 7.87 (1H, d, J=3.5 Hz), 8.01 (1H, s), 8.70 (1H, d, J=12.3 Hz), 8.87 (1H, d, J=10.7 Hz), 8.99 (1H, d, J=3.4 Hz), 9.06 (1H, s), 13.05 (1H, s).

Example 25-4

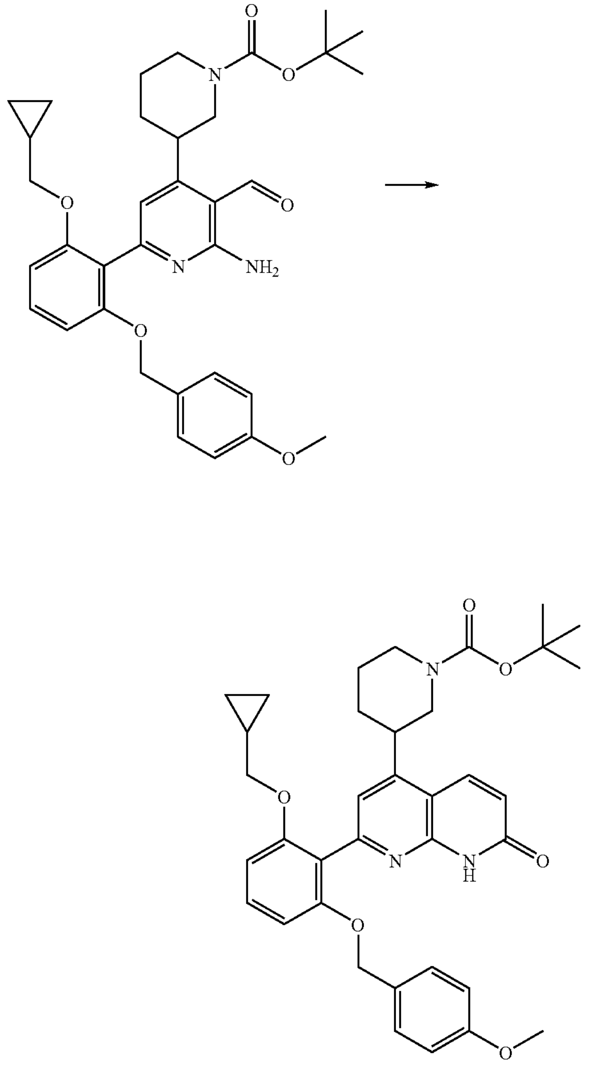

(1) To a solution of ethyl(diphenoxyphosphoryl)acetate (1.090 g, 3.403 mmol) in THF (15 mL) were added 1,8-diazabicyclo[5,4,0]undec-7-ene (0.520 g, 3.403 mmol) and NaI (0.510 g, 3.403 mmol) followed by a solution of tert-butyl 3-(2-amino-6-{2-(cyclopropylmethoxy)-6-[(4-methoxybenzyl)oxy]-phenyl}-3-formyl-4-pyridinyl)-1-piperidinecarboxylate (1.000 g, 1.701 mmol), obtained in the step (1) of Example 25-2, in THF (5 mL). The mixture was stirred at 0° C. for 1.5 hrs and quenched with saturated aqueous $NaHCO_3$ solution. The mixture was extracted with ethyl acetate, and the extract was washed with brine, dried over $Na_2SO_4$, filtered, and concentrated under reduced pressure. The residue was purified by column chromatography on silica gel (hexane/ethyl acetate=3:2 to 1:2) to give tert-butyl 3-(2-{2-(cyclo-propylmethoxy)-6-[(4-methoxybenzyl)oxy]phenyl}-7-oxo-7,8-dihydro-1,8-naphthyridin-4-yl)-1-piperidinecarboxylate as an amorphous solid (0.276 g, 27%).

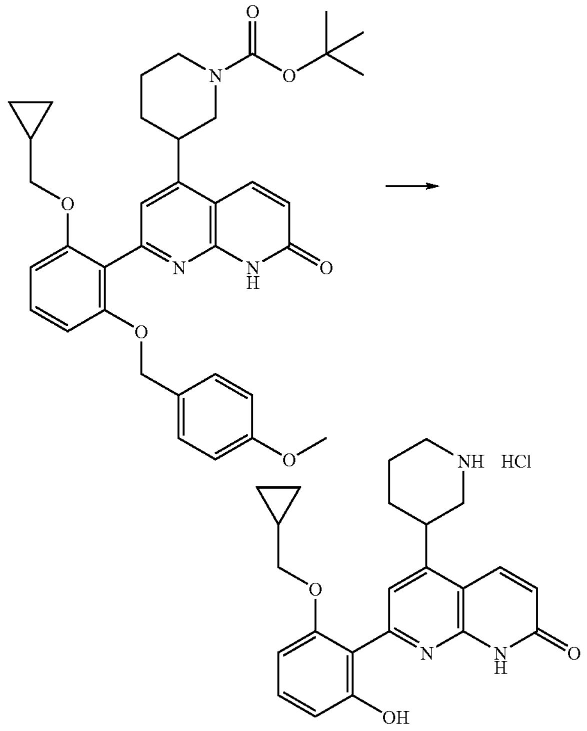

(2) To a stirred solution of tert-butyl 3-(2-{2-(cyclopropylmethoxy)-6-[(4-methoxybenzyl)oxy]phenyl}-7-oxo-7,8-dihydro-1,8-naphthyridin-4-yl)-1-piperidine-carboxylate (0.260 g, 0.425 mmol) in 1,4-dioxane (2 mL) was added 4 N HCl in dioxane (2 mL). The mixture was stirred at room temperature overnight, and diluted with ethyl acetate. The resulting precipitate was collected by filtration, washed with ethanol, and dried under reduced pressure to give 7-[2-(cyclopropylmethoxy)-6-hydroxyphenyl]-5-(3-piperidinyl)-1,8-naphthyridin-2(1H)-one hydrochloride as a yellow solid (0.146 g, 80%).

Molecular weight: 427.93

Mass spectrometry: 392 $(M+H)^+$

In vitro activity grade: A

Cellular activity grade: (A549)-A $^1$H-NMR (500 MHz, DMSO-d6): 0.34 (2H, m), 0.58 (2H, m), 1.28 (1H, m), 1.91 (4H, m), 2.89 (1H, br d, J=6.6 Hz), 3.00 (1H, dd, J=10.4, 12.3 Hz), 3.37 (2H, dd, J=12.3, 12.6 Hz), 6.57 (2H, d, J=8.2 Hz), 6.67 (1H, d, J=9.8 Hz), 7.23 (1H, t, J=8.2 Hz), 7.99 (1H, s), 8.21 (1H, d, J=9.8 Hz), 9.02 (1H, br), 9.14 (1H, br), 12.45 (1H, br s).

Examples 25-5 to 25-8

According to the similar synthetic procedure of Examples 25-1 to 25-4, compounds shown in Table 8 were prepared.

TABLE 8

| Ex. No | Structure | Mol weight | Mass | in vitro | A549 | NMR |
|---|---|---|---|---|---|---|
| 25-05 | 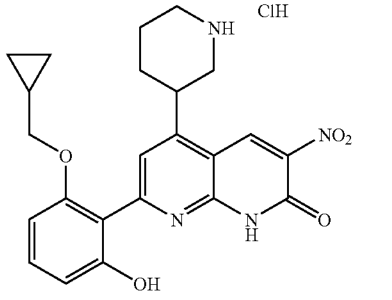 | 472.93 | 437 | A | B | (500MHz, DMSO-d6): 0.33(2H, dd, J=4.7, 9.1Hz), 0.56(2H, m), 1.25(1H, m), 1.94(4H, m), 2.90(1H, br), 3.00(1H, t, J = 12.3Hz), 3.40(2H, br d, J=12.3Hz), 6.59(2H, d, J=8.2Hz), 7.27(1H, t, J=8.2Hz), 8.03(1H, s), 9.02(1H, s), 11.57 (1H, s), 13.32(1H, br). |
| 25-06 | 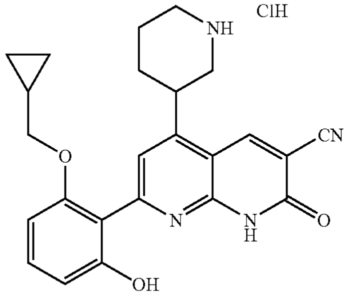 | 452.94 | 417 | A | A | (500MHz, DMSO-d6): 0.32(2H, dd, J=4.7, 9.1Hz), 0.57(2H, m), 1.25(1H, m), 1.93(4H, m), 2.89(1H, br d, J=7.3Hz), 2.97(1H, dd, J=11.4, 11.7Hz), 3.39 (2H, t, J=14.5Hz), 6.59(2H, d, J=8.5 Hz), 7.26(1H, t, J=8.5Hz), 8.00(1H, s), 8.81(1H, br), 9.01(1H, s), 9.26(1H, br), 11.66(1H, s), 13.13(1H, s). |

TABLE 8-continued

| Ex. No | Structure | Mol weight | Mass | in vitro | A549 | NMR |
|---|---|---|---|---|---|---|
| 25-07 | 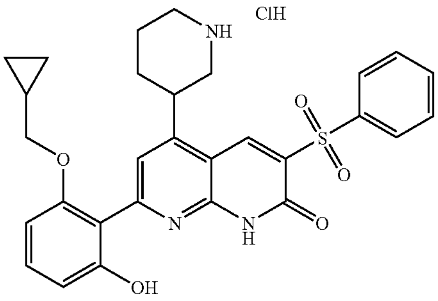 | 568.10 | 532 | A | A | (500MHz, DMSO-d6): 0.32(2H, m), 0.57 (2H, m), 1.25(1H, m), 1.95(4H, m), 2.93 (1H, br d, J=11.0Hz), 3.06(1H, dd, J=11.0, 12.0Hz), 6.58(2H, dd, J=2.5, 8.2 Hz), 7.25(1H, t, J=8.2Hz), 7.64(2H, t, J=7.6Hz), 7.74(1H, t, J=7.6Hz), 8.04 (3H, m), 8.85(1H, br), 9.01(1H, s), 9.35 (1H, br), 11.47(1H, br), 12.93(1H, s). |
| 25-08 | 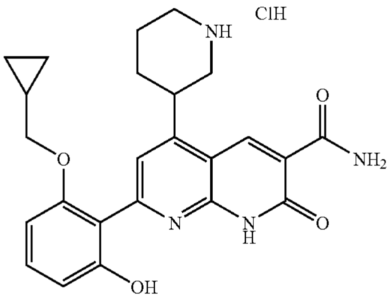 | 470.96 | 435 | A | A | (500MHz, DMSO-d6): 0.33(2H, m), 0.58 (2H, m), 1.28(1H, m), 1.90(4H, m), 2.91 (1H, d, J=11.3Hz), 3.06(1H, dd, J=11.3, 12.3Hz), 6.59(2H, d, J=8.2Hz), 7.26(1H, t, J=8.2Hz), 7.90(1H, d, J=3.5Hz), 8.06(1H, s), 8.81(1H, br), 9.00 (1H, d, J=3.5Hz), 9.02(1H, s), 9.31 (1H, br), 11.80(1H, br), 13.07(1H, s). |

Example 26-1

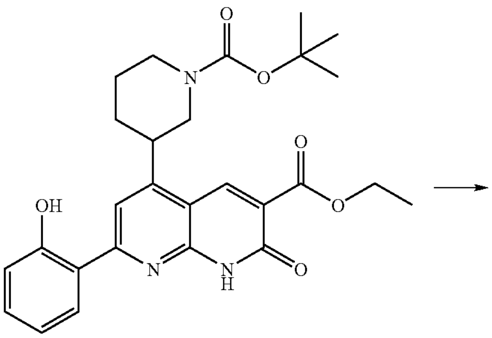

(1) To a cold (0° C.) suspension of ethyl 5-[1-(tert-butoxycarbonyl)-3-piperidinyl]-7-(2-hydroxyphenyl)-2-oxo-1,2-dihydro-1,8-naphthyridine-3-carboxylate (0.050 g, 0.101 mmol) in THF (2.0 mL) under an argon atmosphere was added $LiBH_4$ (0.004 g, 0.20 mmol). The mixture was allowed to warm to room temperature, and the stirring was continued for 3 hrs. The resulting mixture was quenched with water, and partitioned between ethyl acetate and a saturated ammonium chloride solution. The separated organic phase was washed with water and brine, dried over $Na_2SO_4$, filtered and concentrated under reduced pressure. The residue was purified by column chromatography on silica gel (hexane:ethyl acetate, 3:2) to give Ethyl 5-[1-(tert-butoxycarbonyl)-3-piperidinyl]-7-(2-hydroxyphenyl)-2-oxo-1,2,3,4-tetrahydro-1,8-naphthyridine-3-carboxylate. (0.027 g, yield; 54%)

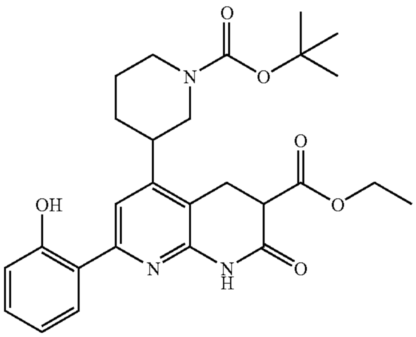

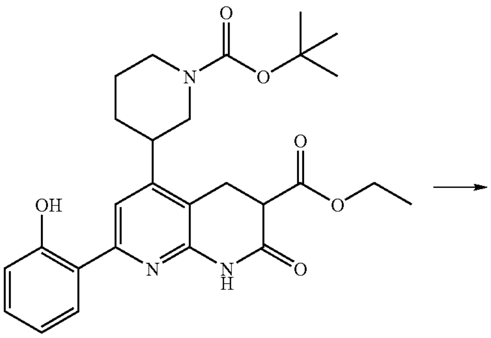

-continued

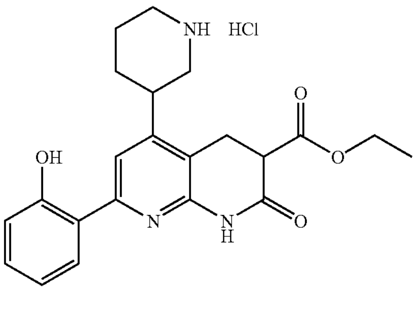

(2) Ethyl 5-[1-(tert-butoxycarbonyl)-3-piperidinyl]-7-(2-hydroxyphenyl)-2-oxo-1,2,3,4-tetrahydro-1,8-naphthyridine-3-carboxylate (0.024 g, 0.048 mmol) was treated under acidic conditions in a similar manner as described in Example 1-1 to give ethyl 7-(2-hydroxyphenyl)-2-oxo-5-(3-piperidinyl)-1,2,3,4-tetrahydro-1,8-naphthyridine-3-carboxylate. (0.019 g, yield; 91%)

Molecular weight: 431.92

Mass spectrometry: 396 $(M+H)^+$

In vitro activity grade: A

Cellular activity grade: (A549)-A $^1$H-NMR'(500 MHz, DMSO-d6): 1.16–1.21 (3H, m), 1.83–1.95 (4H, m), 2.87–2.94 (1H, m), 3.18–3.37 (6H, m), 4.12–4.17 (2H, m), 6.90–6.93 (2H, m), 7.29 (1H, t, J=7.88 Hz), 7.73 (1H, s), 8.03 (1H, d, J=7.88 Hz), 8.81–8.90 (1H, m), 9.23–9.30 (1H, m), 11.33 (1H, s).

-continued

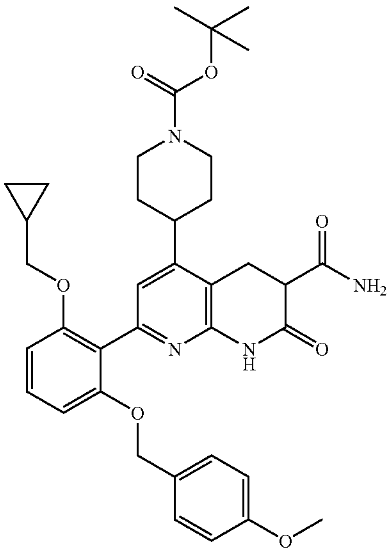

To a cold (0° C.) solution of 4-(6-(aminocarbonyl)-2-{2-(cyclopropylmethoxy)-6-[(4-methoxybenzyl)oxy]phenyl}-7-oxo-7,8-dihydro-1,8-naphthyridin-4-yl)-1-piperidine-carboxylate (0.200 g, 0.305 mmol), which was obtained in the step (1) of Example 25-3, in methyl alcohol (5.0 mL) under an argon atmosphere was added $NaBH_4$ (0.010 g, 0.367 mmol). The mixture was allowed to warm to room temperature, and the stirring was continued for 12 hrs. The reaction mixture was quenched with water, and extracted with ethyl acetate. The separated organic phase was washed with brine, dried over $Na_2SO_4$, filtered, and concentrated under reduced pressure to give tert-butyl 4-(6-(aminocarbonyl)-2-{2-(cyclopropylmethoxy)-6-[(4-methoxybenzyl)-oxy]phenyl}-7-oxo-5,6,7,8-tetrahydro-1,8-naphthyridin-4-yl)-1-piperidinecarboxy-late. (0.133 g, yield; 67%)

Example 26-2

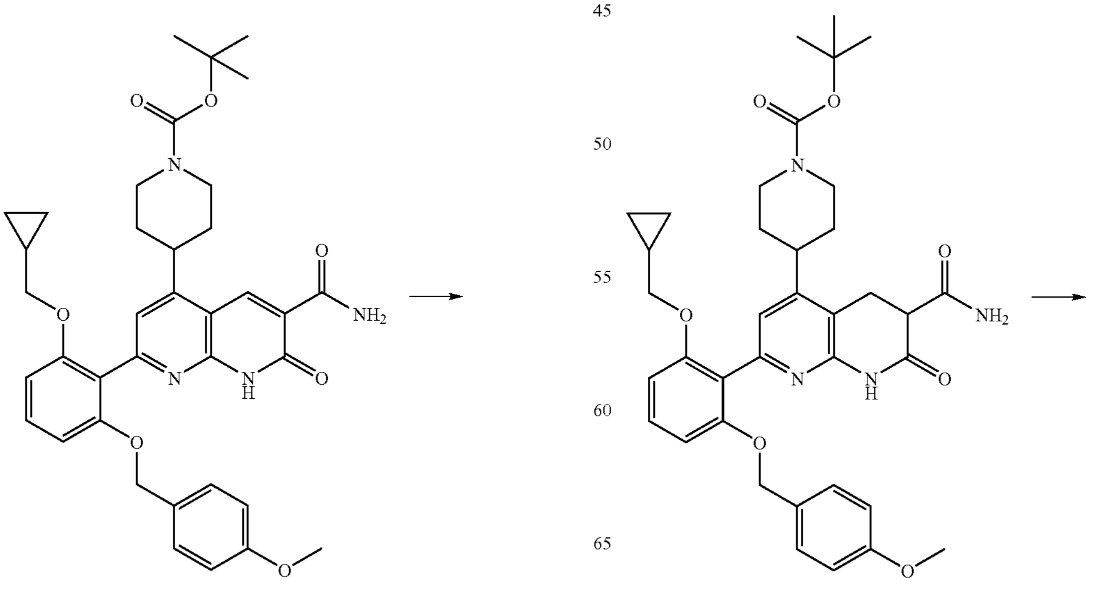

-continued

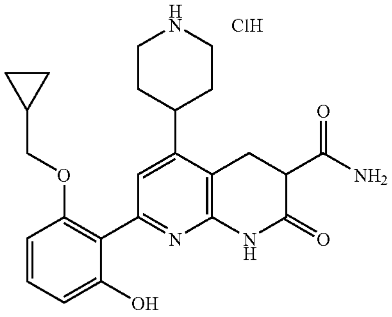

To a stirred solution of tert-butyl 4-(6-(aminocarbonyl)-2-{2-(cyclopropylmethoxy)-6-[(4-methoxybenzyl)oxy]phenyl}-7-oxo-5,6,7,8-tetrahydro-1,8-naphthyridin-4-yl)-1 piperidinecarboxylate (0.120 g, 0.187 mmol) in 1,4-dioxane (3 mL) was added 4N HCl in dioxane (1 mL). The mixture was stirred at room temperature for 2 hrs. The resulted precipitate was collected by filtration, washed with acetonitrile, and dried under reduced pressure to give 7-[2-(cyclopropylmethoxy)-6-hydroxyphenyl]-2-oxo-5-(4-piperidinyl)-1,2,3,4-tetrahydro-1,8-naphthyridine-3-carboxamide hydrochloride. (0.080 g, yield 90%)

Molecular weight: 472.98

Mass spectrometry: 437 $(M+H)^+$

In vitro activity grade: A

Cellular activity grade: (A549)-A $^1$H-NMR (500 MHz, DMSO-d6): 0.33 (2H, d, J=4.4 Hz), 0.60 (2H, d, J=6.3 Hz), 1.33–1.39 (1H, m), 1.77–1.91 (5H, m), 3.06–3.10 (2H, m), 3.20 (3H, d, J=8.2 Hz), 3.86 (2H, dd, J=2.2, 7.1 Hz), 6.53 (2H, dd, J=8.2, 7.0 Hz), 7.16 (1H, t, J=8.2 Hz), 7.20 (1H, s), 7.56 (1H, s), 7.84 (1H, s), 11.02 (1H, s).

Examples 26-3 to 26-6

According to the similar synthetic procedure of Examples 26-1 to 26-2, compounds shown in Table 9 were prepared.

TABLE 9

| Ex. No | Structure | Mol weight | Mass | in vitro | A549 | NMR |
|---|---|---|---|---|---|---|
| 26-03 | 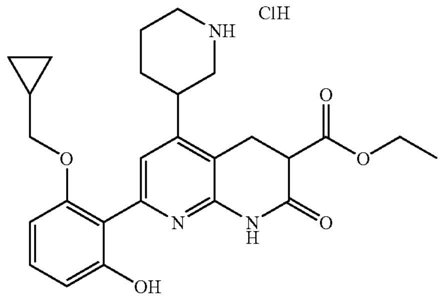 | 502.02 | 466 | A | A | (300MHz, DMSO-d6): 0.31–0.36(2H, m), 0.56–0.60(2H, m), 1.17(3H, t, J=7.2Hz), 1.26(1H, m), 1.82–1.90(4H, m), 2.84–2.89(2H, m), 3.23–3.39(6H, m), 3.80–3.89(2H, m), 4.16(2H, q, J=7.2Hz), 6.52(2H, d, J=8.3Hz), 7.16 (1H, t, J=8.3Hz), 7.85(1H, s), 9.17(1H, br), 9.39(1H, br), 11.17(1H, s). |
| 26-04 | 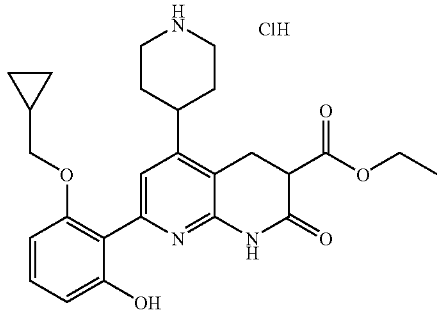 | 502.02 | 466 | A | A | (500MHz, DMSO-d6): 0.30–0.33(2H, m), 0.56–0.59(2H, m), 1.17(3H, t, J=7.2Hz), 1.36(1H, m), 1.86–1.92(4H, m), 3.06–3.09(2H, m), 3.18–3.23(2H, m), 3.30–3.38(3H, m), 3.80(1H, m), 3.85–3.87(2H, d, J=7.0Hz), 4.12(2H, q, J=7.2Hz), 6.51(1H, d, J=8.2Hz), 6.53(1H, d, J=8.2Hz), 7.16(1H, t, J=8.2Hz), 7.83(1H, s), 8.96(1H, br), 9.03 (1H, br), 11.16(1H, s). |
| 26-05 | 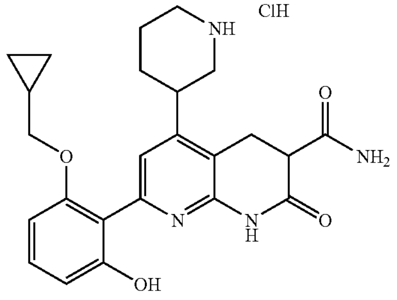 | 472.98 | 437 | A | A | (500MHz, DMSO-d6): 0.36(2H, m), 0.60 (2H, m), 1.30(1H, m), 1.73–1.94(4H, m), 2.94(2H, m), 6.52, 6.53(2H, d x 2, J = 8.2Hz), 7.16(1H, t, J=8.2Hz), 7.22, 7.23(1H, br x 2), 7.54, 7.59(1H, br s x 2), 7.85, 7.87(1H, s x 2), 8.86 1H, br), 9.15(1H, br), 11.04, 11.04(1H, s x 2). |

TABLE 9-continued

| Ex. No | Structure | Mol weight | Mass | in vitro | A549 | NMR |
|---|---|---|---|---|---|---|
| 26-06 | 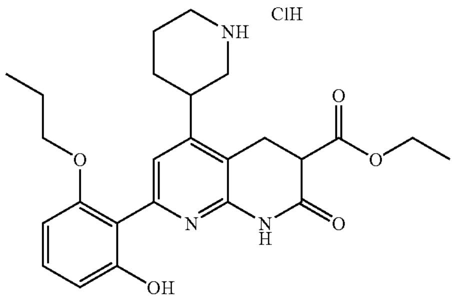 | 490.00 | 454 | A | A | (500MHz, DMSO-d6): 0.93(3H, t, J=7.3Hz), 1.17(3H, td, J=3.5, 7.2Hz), 1.74–1.79(3H, m), 1.85–1.91(3H, m), 2.87–2.89(2H, m), 3.34–3.40(3H, m), 3.80–3.85(1H, m), 3.93–3.97(2H, m), 4.14(2H, q, J=7.2Hz), 6.52(1H, d, J=8.2Hz), 6.57(1H, d, J=8.5Hz), 7.17 (1H, t, J=8.2Hz), 7.65(1J, s), 8.86(1H, br), 9.15(1H, br), 11.13(1H, s). |

Example 27-1

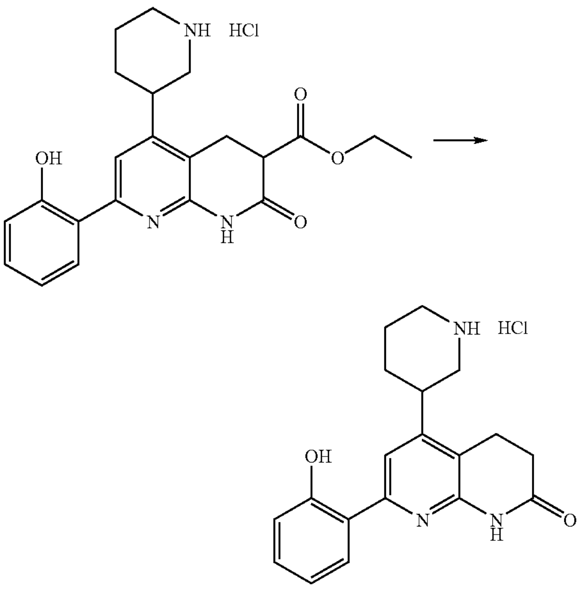

A solution of ethyl 7-(2-hydroxyphenyl)-2-oxo-5-(3-piperidinyl)-1,2,3,4-tetrahydro-1,8-naphthyridine-3-carboxylate hydrochloride (0.012 g, 0.023 mmol), which was obtained in the step(2) of Example 26-1, in 2.5N HCl (3.0 mL) was heated at reflux for 4 hrs. After being cooled to room temperature, the mixture was concentrated under reduced pressure. The residue was washed with acetonitrilee and dried under reduced pressure to give 7-(2-hydroxyphenyl)-5-(3-piperidinyl)-3,4-dihydro-1,8-naphthyridin-2(1H)-one hydrochloride. (0.007 g, yield; 70%)

Molecular weight: 359.86

Mass spectrometry: 324 $(M+H)^+$

In vitro activity grade: A

Cellular activity grade: (A549)-A $^1$H-NMR (500 MHz, DMSO-d6): 1.83–1.94 (4H, m), 2.57–2.64 (2H, m), 2.89–3.01 (3H, m), 3.19–3.37 (4H, m), 6.88–6.93 (2H, m), 7.28 (1H, t, J=8.2 Hz), 7.69 (1H, s), 8.01 (1H, d, J=7.9 Hz), 8.90 (1H, br), 9.16 (1H, br), 10.99 (1H, s).

Examples 27-2 to 27-5

In similar manners as described in Example 27-1 above, compounds in Examples 27-2 to 27-5 were synthesized.

According to the similar synthetic procedure of Example 27-1, compounds shown in Table 10 were prepared.

TABLE 10

| Ex. No | Structure | Mol weight | Mass | in vitro | A549 | NMR |
|---|---|---|---|---|---|---|
| 27-02 | 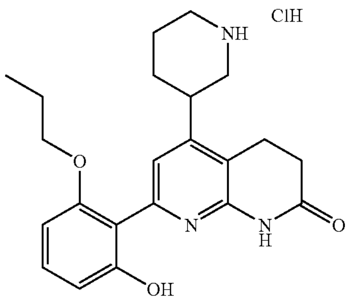 | 417.94 | 382 | A | A | (500MHz, DMSO-d6): 0.94(3H, t, J=7.5Hz), 1.72–1.80(2H, m), 1.87–1.89(4H, m), 2.59–2.61(2H, m), 2.88–2.91(2H, m), 2.99–3.02(2H, m), 3.26–3.33(2H, m), 3.43(1H, m), 3.95 (2H, m), 6.54(1H, d, J=8.2Hz), 6.58 (1H, d, J=7.9Hz), 7.18(1H, t, J=7.4 Hz) 7.64(1H, s), 9.26(1H, br), 10.84 (1H, s). |

TABLE 10-continued

| Ex. No | Structure | Mol weight | Mass | in vitro | A549 | NMR |
|---|---|---|---|---|---|---|
| 27-03 | 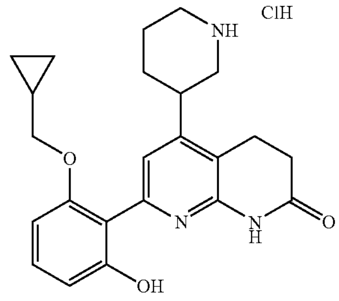 ClH | 429.95 | 394 | A | A | (300MHz, DMSO-d6): 0.32–0.37(2H, m), 0.56–0.62(2H, m), 1.29 (1H, m), 1.75–1.83(4H, m), 2.57–2.61(2H, m), 2.88(1H, m), 2.96–3.01 (2H, m), 3.33–3.36(4H, m), 3.82 3.87(2H, m), 6.52(2H, d, J=7.9Hz), 17.15(1H, t, J=7.9Hz), 7.83(1H, s), 9.07(1H, br), 10.81(1H, s). |
| 27-04 | 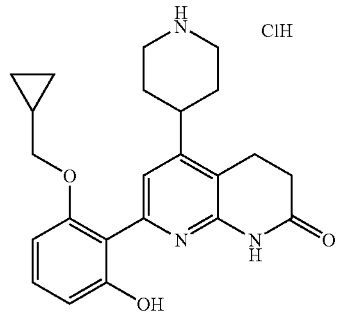 ClH | 429.95 | 394 | A | A | (500MHz, DMSO-d6): 0.31–0.34(2H, m), 0.57–0.60(2H, m), 1.33(1H, m), 1.81–1.85(2H, m), 1.90–1.93(2H, m), 2.57(2H, t, J=7.2Hz), 2.99(2H t, J=7.2Hz), 3.06–3.08(2H, m), 3.18 (1H, m), 3.38–3.40(2H, m), 3.85(2H, d, J=6.9Hz), 6.52(2H, d, J=7.9Hz), 7.15(1H, t, J=8.2Hz), 7.80(1H, s) 18.52(1H, br), 8.77(1H, br), 10.80(1H, s). |
| 27-05 | 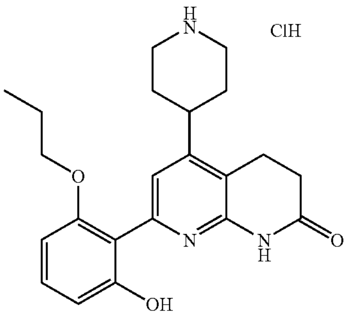 ClH | 417.94 | 382 | A | A | (500MHz, DMSO-d6): 0.93(3H, t, J=7.3Hz), 1:80–1.84(2H, m), 2.57–2.59(2H, m), 2.99–3.08(4H, m), 3.12 (1H, m), 3.36–3.39(2H, m), 3.97(2H, t, J=7.7Hz), 6.52(1H, d, J=8.2Hz), 6.57(1H, d, J=8.5Hz), 7.18(1H, t, J=8.2Hz), 7.59(1H, s), 9.03(2H, br), 10.80(1H, s). |

Example 28-01

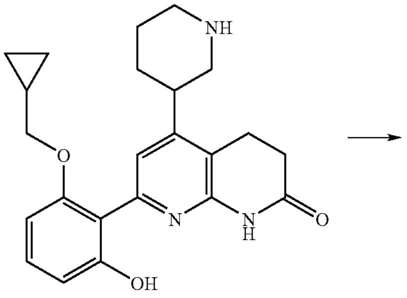

-continued

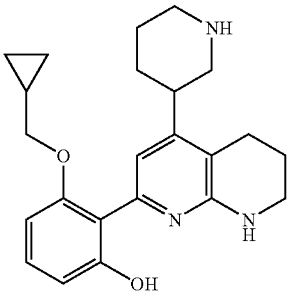

To a stirred solution of 7-[2-(cyclopropylmethoxy)-6-hydroxyphenyl]-5-(3-piperidinyl)-3,4-dihydro-1,8-naphthyridin-2(1H)-one (0.029 g, 0.074 mmol), which was obtained in the Example 27-3, in THF (1.5 mL) was added dropwise Vitride® (70% toluene solution, 0.500 mL). The mixture was stirred at 65° C. for 1 hr. After cooled to room temperature, the mixture was quenched with saturated aqueous potassium sodium tartrate solution. The mixture was extracted with ethyl acetate and water. The separated organic phase was washed with brine, dried over $Na_2SO_4$, filtered, and concentrated under reduced pressure. The resulting residue was purified by preparative TLC (chloroform/methanol=4/1) to give 3-(cyclopropylmethoxy)-2-[4-(3-piperidinyl)-5,6,7,8-tetrahydro-1,8-naphthyridin-2-yl]phenol.

(0.003 g, yield; 11%)

Molecular weight: 379.51

Mass spectrometry: 380 $(M+H)^+$

In vitro activity grade: A

Cellular activity grade: (A549)-A $^1$H-NMR (500 MHz, CDC13): 0.42 (2H, m), 0.68 (2H, m), 1.35 (1H, m), 1.91 (1H, d, J=12.0 Hz), 1.98 (2H, m), 2.63 (1H, dt, J=2.8, 12. Hz), 2.77 (3H, m), 2.86 (1H, m), 3.11 (2H, dd, J=2.3, 10.5 Hz), 3.40 (2H, dt, J=2.8, 5.4 Hz), 3.83 (2H, d, J=6.9 Hz), 4.75 (1H, br s), 6.38 (1H, dd, J=1.3, 8.2 Hz), 6.59 (1H, dd, J=1.3, 8.2 Hz), 7.09 (1H, t, J=8.2 Hz), 7.78 (1H, s), 14.69 (1H, br).

Example 29-01

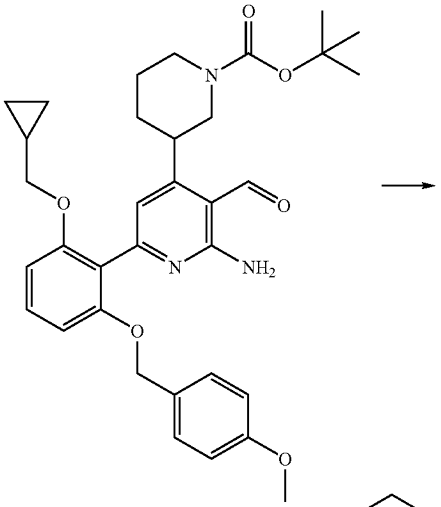

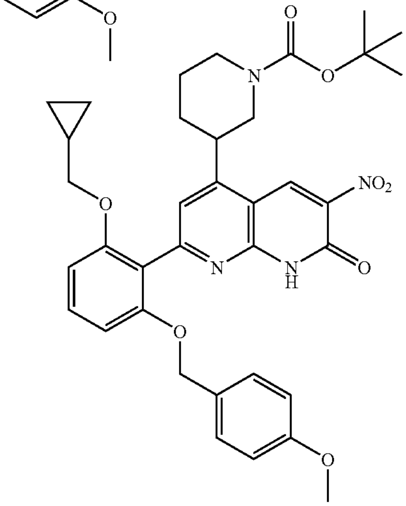

(1) To a stirred solution of tert-butyl 3-(2-amino-6-{2-(cyclopropylmethoxy)-6-[(4-methoxybenzyl)oxy]phenyl}-3-formyl-4-pyridinyl)-1-piperidinecarboxylate (0.100 g, 0.170 mmol), which was obtained in the step (1) of Example 25-2, and ethyl nitroacetate (0.060 mL, 0.510 mmol) in ethanol (5 mL) was added piperidine (0.050 mL, 0.510 mmol). The mixture was stirred at 75° C. for 18 hrs, and concentrated under reduced pressure. The residue was extracted with ethyl acetate and water. The separated organic phase was washed with brine, dried over $Na_2SO_4$, filtered, and concentrated under reduced pressure. The resulting residue (liquid) was purified by column chromatography on silica gel (hexane/ethyl acetate=3/1-3/2) to give tert-butyl 3-(2-{2-(cyclopropylmethoxy)-6-[(4-methoxybenzyl)oxy] phenyl}-6-nitro-7-oxo-7,8-dihydro-1,8-naphthyridin-4-yl)-1-piperidinecarboxylate (0.105 g, yield; 94%).

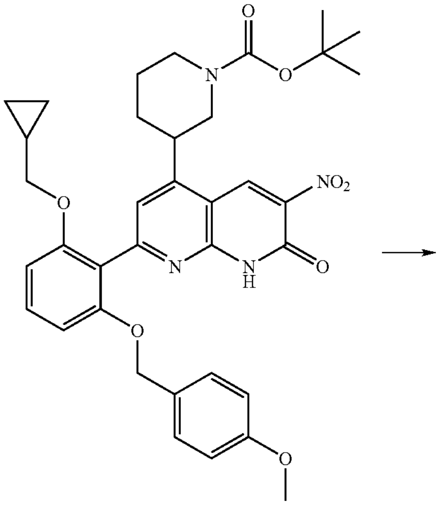

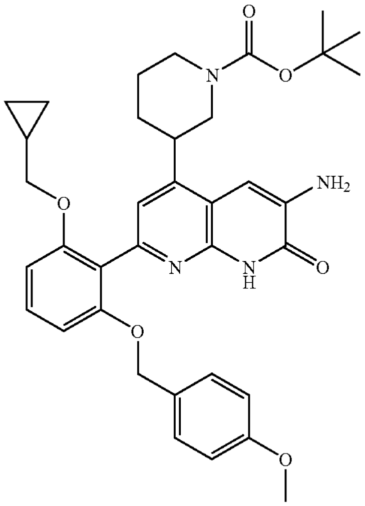

(2) To a stirred mixture of tert-butyl 3-(2-{2-(cyclopropylmethoxy)-6-[(4-methoxy-benzyl)oxy]phenyl}-6-nitro-7-oxo-7,8-dihydro-1,8-naphthyridin-4-yl)-1-piperidine-carboxylate (0.085 g, 0.129 mmol), iron powder (0.300 g), ethanol (4.5 mL) and water (0.5 mL) was added ammonium chloride (0.100 g). The mixture was stirred at 85° C. for 30 min. After cooled to room temperature, the mixture was filtered through Celite®. The filtrate was concentrated under reduced pressure. The residue was extracted with ethyl acetate and water. The separated organic phase was washed with brine, dried over $Na_2SO_4$, filtered, and concentrated under reduced pressure to give tert-butyl 3-(6-amino-2-{2-(cyclopropylmethoxy)-6-[(4-methoxybenzyl)oxy]-phenyl}-7-oxo-7,8-dihydro-1,8-naphthyridin-4-yl)-1-piperidinecarboxylate (0.068 g, yield; 84%).

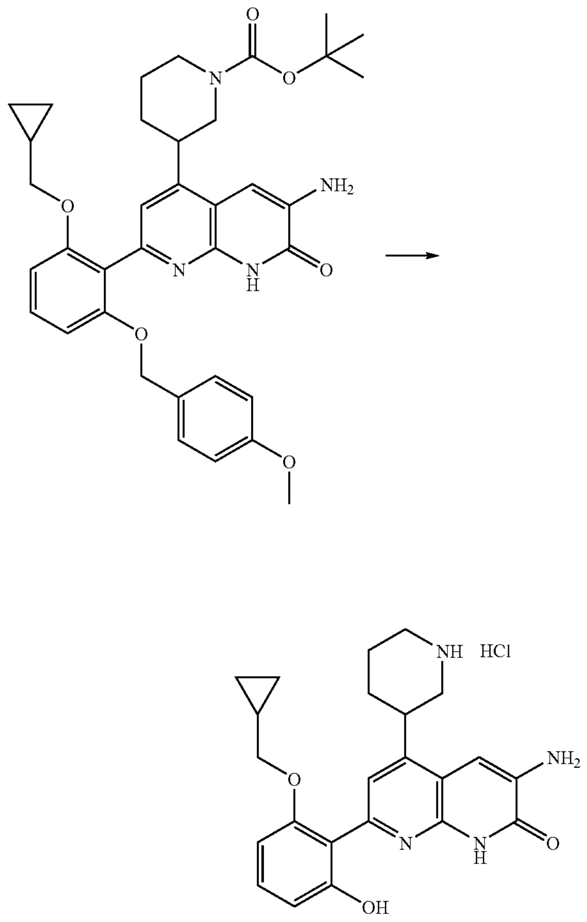

(3) Then benzyl moiety and tert-butyl carbamate were removed in a similar manner as described in the step (2) of Example 25-4, to give 3-amino-7-[2-(cyclo-propylmethoxy)-6-hydroxyphenyl]-5-(3-piperidinyl)-1,8-naphthyridin-2(1H)-one hydrochloride.

Molecular weight: 442.95

Mass spectrometry: 407 $(M+H)^+$

In vitro activity grade: A

Cellular activity grade: (A549)-A $^1$H-NMR (500 MHz, DMSO-d6): 0.35 (2H, m), 0.62 (2H, m), 1.32 (1H, m), 1.73 (1H, ddd, J=4.1, 8.2, 8.2 Hz), 1.93 (3H, m), 2.90 (1H, dd, J=11.7, 12.3 Hz), 3.11 (1H, dd, J=11.0, 11.7 Hz), 6.54 (2H, d, J=8.2 Hz), 6.93 (1H, s), 7.17 (1H, t, J=8.2 Hz), 7.99 (1H, s), 9.10 (1H, br), 9.28 (1H, br), 12.55 (1H, s).

Example 29-2

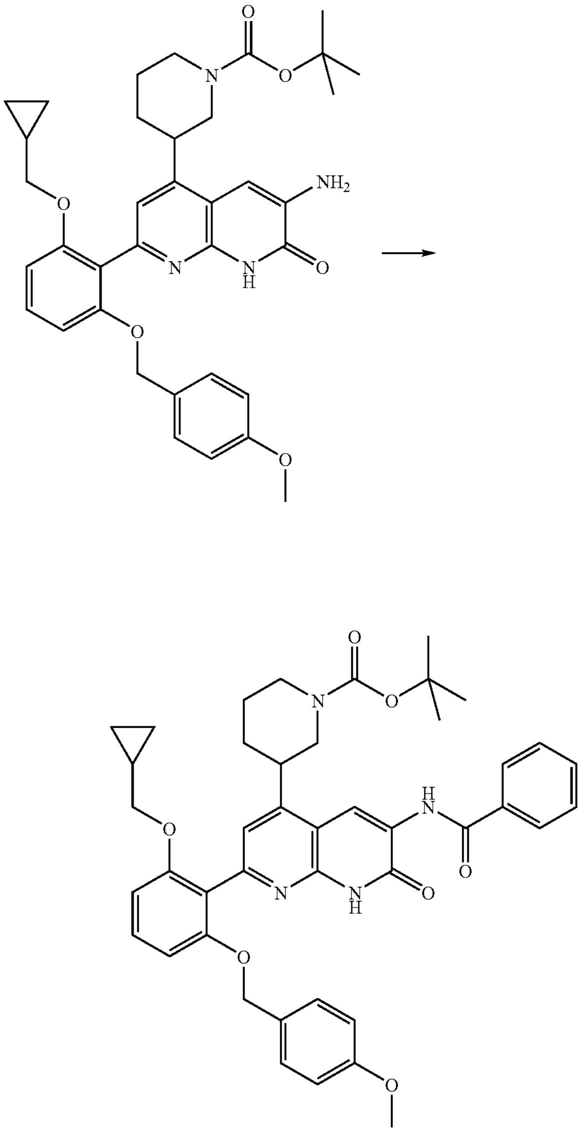

To a stirred solution of tert-butyl 3-(6-amino-2-{2-(cyclopropylmethoxy)-6-[(4-methoxybenzyl)oxy]phenyl}-7-oxo-7,8-dihydro-1,8-naphthyridin-4-yl)-1-piperidine-carboxylate (0.068 g, 0.109 mmol), which was obtained in the step (2) of Example 29-1, and triethyl amine (0.05 mL, 0.327 mmol) in methylene chloride (3 mL) were added benzoyl chloride (0.01 mL, 0.109 mmol) and 4-dimethylaminopyridine (0.001 g, 0.011 mmol). The mixture was stirred at room temperature for 19 hrs, and poured into water. The mixture was extracted with ethyl acetate. The separated organic phase was washed with brine, dried over $Na_2SO_4$, filtered, and concentrated under reduced. The resulting residue was purified by column chromatography on silica gel (hexane/ethyl acetate=5/1-3/2) to give tert-butyl 3-{2-{2-(cyclopropylmethoxy)-6-[(4-methoxy-benzyloxy]phenyl}-7-oxo-[(1-phenyl-methanoyl)-amino]-7,8-dihydro-1,8-naphthyridin-4-yl)-1-piperidinecarboxylate (0.022 g, yield; 28%).

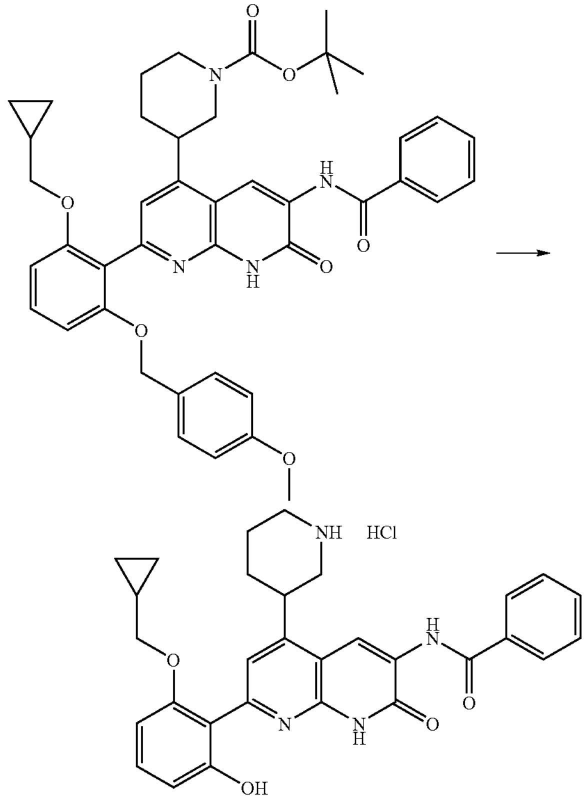

Then benzyl moiety and tert-butyl carbamate were removed in a similar manner as described in the step (2) of Example 25-4 to give N-[7-[2-(cyclopropylmethoxy)-6-hydroxyphenyl]-2-oxo-5-(3-piperidinyl)-1,2-dihydro-1,8-naphthyridin-3-yl]benzamide hydrochloride.

Molecular weight: 547.06

Mass spectrometry: 511 $(M+H)^+$

In vitro activity grade: A

Cellular activity grade: (A549)-B $^1$H-NMR (500 MHz, DMSO-d6): 0.34 (2H, m), 0.59 (2H, m), 1.29 (1H, m), 1.80–2.08 (4H, m), 2.96 (1H, br), 3.18 (1H, dd, J=11.4, 11.7 Hz), 6.59 (2H, d, J=8.2 Hz), 7.23 (1H, t, J=8.2 Hz), 7.61 (2H, t, J=7.9 Hz), 7.68 (1H, m), 8.01 (2H, m), 8.04 (1H, s), 8.80 (1H, br), 9.03 (2H, s), 9.61 (1H, s), 13.13 (1H, s).

Example 29-3

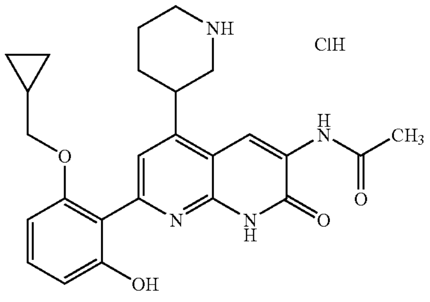

In a similar manner as that of Example 29-2, N-[7-[2-(cyclopropylmethoxy)-6-hydroxyphenyl]-2-oxo-5-(3-piperidinyl)-1,2-dihydro-1,8-naphthyridin-3-yl]acetamide hydrochloride was prepared.

Molecular weight: 484.99

Mass spectrometry: 449 $(M+H)^+$

In vitro activity grade: A

Cellular activity grade: (A549)-A (500 MHz, DMSO-d6): 0.33 (2H, m), 0.59 (2H, m), 1.28 (1H, m), 1.76 (1H, m), 1.89 (1H, m), 1.98 (1H, m), 2.92 (1H, dd, J=11.4, 12.0 Hz), 3.17 (1H, dd J=11.0, 12.0 Hz), 6.57 (2H, d, J=8.5 Hz), 7.21 (1H, t, J=8.5 Hz), 7.99 (1H, s), 8.78 (1H, br), 8.94 (1H, s), 9.02 (1H, br), 9.69 (1H, s), 11.92 (1H, br), 12.93 (1H, s).

Example 30-1

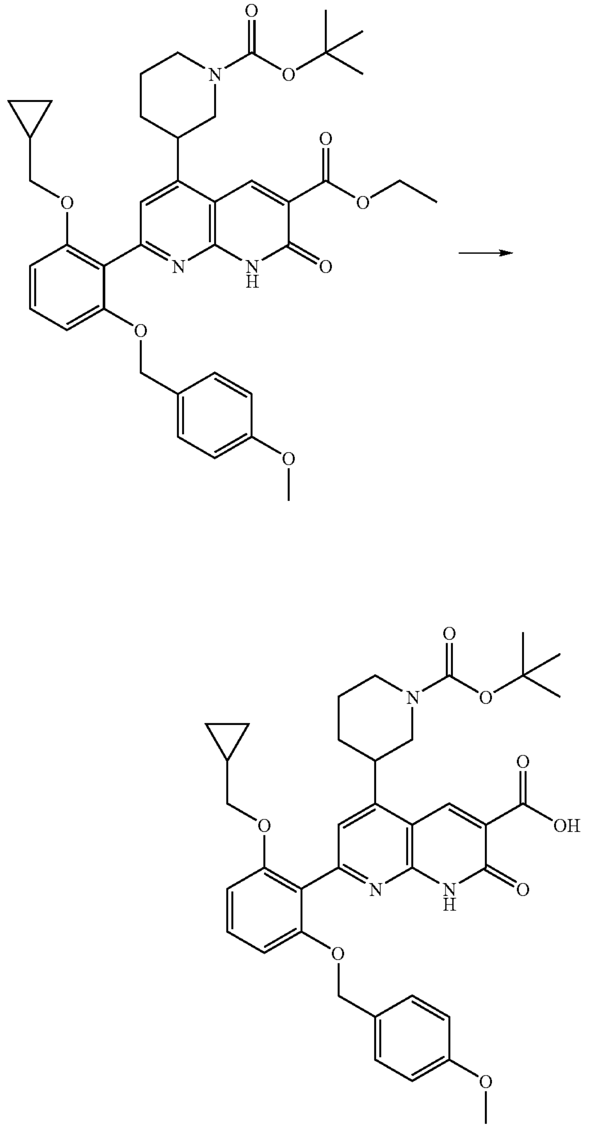

(1) To a stirred solution of ethyl 5-[1-(tert-butoxycarbonyl)-3-piperidinyl]-7-{2-(cyclopropylmethoxy)-6-[(4-methoxybenzyl)oxy]phenyl}-2-oxo-1,2-dihydro-1,8-naphthyridine-3-carboxylate (0.276 g, 0.403 mmol), which was obtained in a similar manner as that of the step (1) of Example 29-1 using diethyl malonate instead of ethyl nitroacetate, in tetrahydrofuran (4 mL) and water (1 mL) was added lithium hydroxide monohydrate (0.015 g, 0.605 mmol). The mixture was stirred at room temperature for 18 hrs and acidified (pH 3–4) with aqueous 1N hydrochloric acid solution. The mixture was extracted with ethyl acetate. The separated organic phase was washed with brine, dried over $Na_2SO_4$, filtered, and concentrated under reduced pressure to give 5-[1-(tert-butoxycarbonyl)-3-piperidinyl]-7-{2-(cyclopropyl-methoxy)-6-[(4-methoxybenzyl)oxy]phenyl}-2-oxo-1,2-dihydro-1,8-naphthyridine-3-carboxylic acid (0.259 g, yield; 98%).

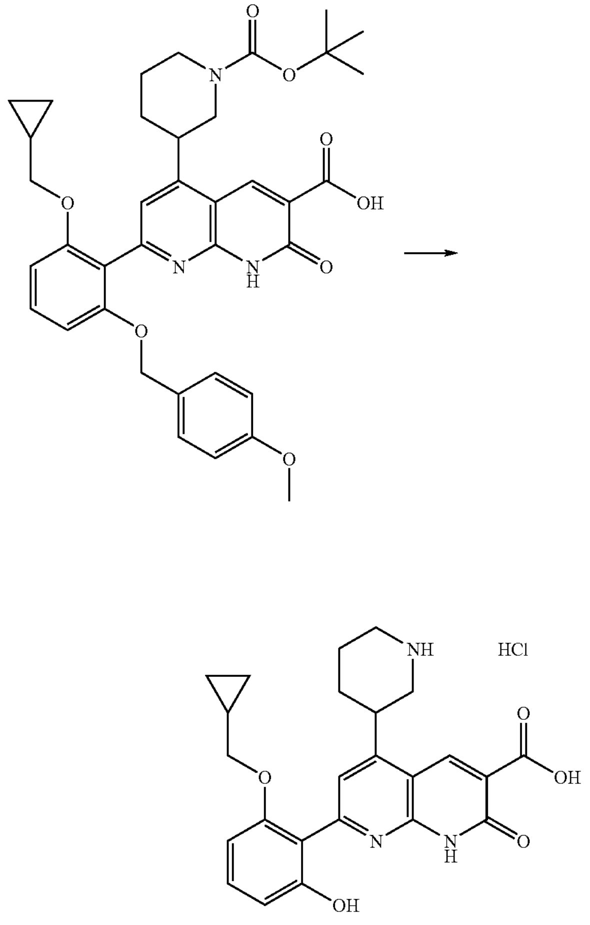

(2) Then benzyl moiety and tert-butyl carbamate were removed in a similar manner as described in the step (2) of Example 25-4 to give 7-(2-cyclopropylmethoxy-6-hydroxy-phenyl)-2-oxo-5-piperidin-3-yl-1,2-dihydro-[1,8]naphthyridine-3-carboxylic acid hydrochloride.

Molecular weight: 471.94

Mass spectrometry: 436 $(M+H)^+$

In vitro activity grade: A

Cellular activity grade: (A549)-B

'(500 MHz, DMSO-d6): 0.30–0.33 (2H, m), 0.54–0.55 (2H, m), 1.23 (1H, m), 1.92–1.98 (4H, m), 2.91 (1H, m), 3.04 (1H, m), 3.39–3.41 (3H, m), 3.86–3.89 (3H, m), 6.61 (2H, d, J=8.5 Hz), 7.27 (1H, t, J=8.2 Hz), 8.07 (1H, s), 8.72 (1H, s), 9.24 (1H, s), 13.74 (1H, s), 14.43 (1H, s).

Example 31 -1

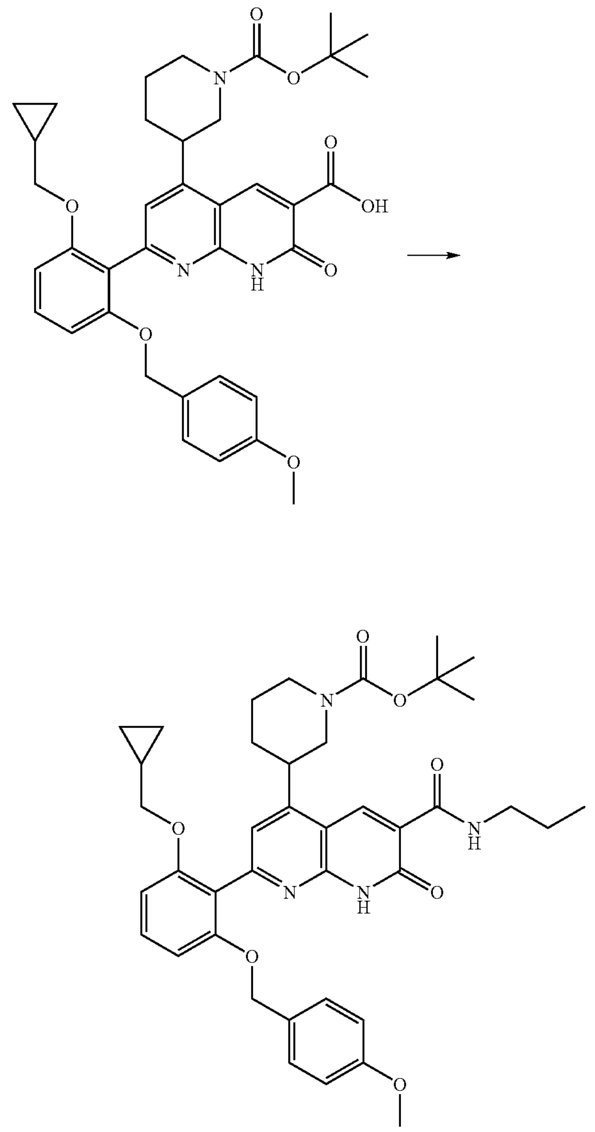

(1) To a stirred solution of 5-[1-(tert-butoxycarbonyl)-3-piperidinyl]-7-{2-(cyclo-propylmethoxy)-6-[(4-methoxy-benzyl)oxy]phenyl}-2-oxo-1,2-dihydro-1,8-naphthyridine-3-carboxylic acid (0.200 g, 0.305 mmol), which was obtained in the step (1) of Example 30-1, and 1-hydroxy-benzotriazole hydrate (0.062 g, 0.457 mmol) in dimethyl-formamide (4 mL) was added 1-(3-dimethylaminopropyl)-3-ethylcarbo-diimide hydrochloride (0.070 g, 0.366 mmol). The mixture was stirred at room temperature for 18 hrs, and then extracted with ethyl acetate and water. The separated organic phase was washed with brine, dried over $Na_2SO_4$, filtered, and concentrated under reduced pressure. The resulting residue was purified by column chromatography on silica gel (hexane/ethyl acetate=1/1) to give tert-butyl 3-{2-{2-(cyclopropylmethoxy)-6-[(4-methoxybenzyl)oxy]phenyl}-7-oxo-6-[(propylamino)-carbonyl]-7,8-dihydro-1,8-naphthyridin-4-yl}-1-piperidinecarboxylate (0.129 g, yield; 61%).

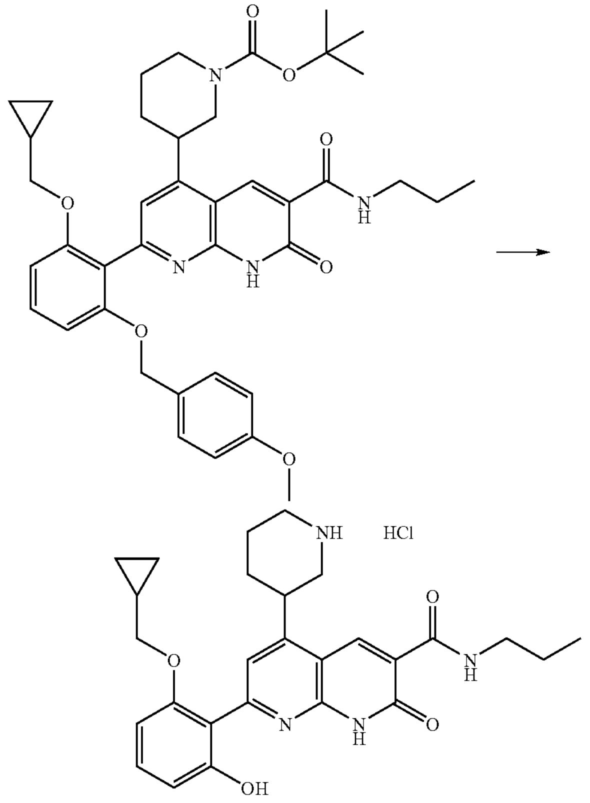

(2) Then benzyl moiety and tert-butyl carbamate were removed in a similar manner as described in the step (2) of Example 25-4 to give 7-[2-(cyclopropylmethoxy)-6-hydroxyphenyl]-2-oxo-5-(3-piperidinyl)-N-propyl-1,2-dihydro-1,8-naphthyridine-3-carboxamide.

Molecular weight: 513.04

Mass spectrometry: 477 $(M+H)^+$

In vitro activity grade: A

Cellular activity grade: (A549)-A $^1$H-NMR (500 MHz, DMSO-d6): 0.33 (2H, m), 0.57 (2H, m), 0.94 (3H, t, J=7.3 Hz), 1.27 (1H, m), 1.58 (2H, tq, J=7.3, 7.3 Hz), 1.92 (4H, m), 2.90 (1H, m), 3.06 (1H, t, J=12.3 Hz), 6.59 (2H, d, J=8.2 Hz), 7.26 (1H, t, J=8.2 Hz), 8.07 (1H, s), 9.01 (1H, s), 9.69 (1H, t, J=6.0 Hz), 11.80 (1H, s).

Reaction 31-2

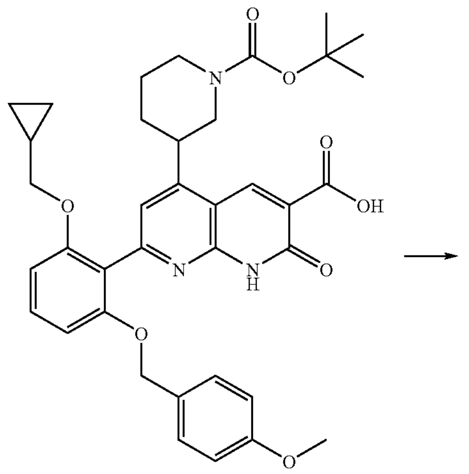

-continued

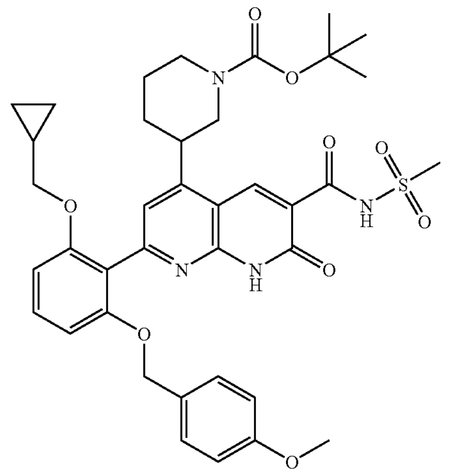

To a stirred solution of methanesulfonamide (0.026 g, 0.268 mmol) and triethylamine (0.030 mL, 0.229 mmol) in toluene (2 mL) was added trimethylsilyl chloride (0.020 mL, 0.152 mmol). The mixture was stirred at 90° C. for 1 hr, and then concentrated under reduced pressure. To the residue diluted with dichloromethane (2 mL) were added triethylamine (0.020 mL, 0.152 mmol), 4,4-dimethylaminopyridine (0.002 g, 0.015 mmol), benzotriazole-1-yloxy-tris(dimethylamino)phosphonium hexafluoro-phosphate (0.040 g, 0.091 mmol) and 5-[1-(tert-butoxycarbonyl)-3-piperidinyl]-7-{2-(cyclopropylmethoxy)-6-[(4-methoxybenzyl)oxy]phenyl}-2-oxo-1,2-dihydro-1,8-naphthyridine-3-carboxylic acid (0.050 g, 0.076 mmol) successively. The mixture was stirred at room temperature for 6 hrs. The mixture was extracted with ethyl acetate and water. The separated organic phase was washed with brine, dried over $Na_2SO_4$, filtered, and concentrated under reduced pressure. The resulting residue was purified by preparative TLC (hexane/ethyl acetate=1/1×2) to give tert-butyl 3-(2-{2-(cyclopropylmethoxy)-6-[(4-methoxybenzyl)oxy]phenyl}-6-{[(methylsulfonyl)-amino]carbonyl}-7-oxo-7,8-dihydro-1,8-naphthyridin-4-yl)-1-piperidinecarboxylate (0.024 g, yield; 43%).

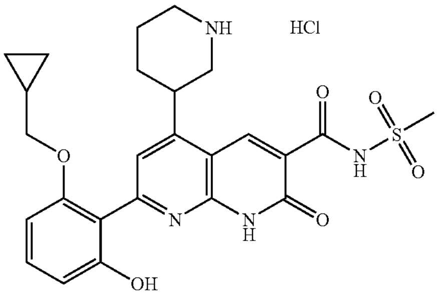

Then the benzyl moiety and tert-butyl carbamate were removed in a similar manner as described in the step (2) of Example 25-4 to give N-{[7-[2-(cyclopropylmethoxy)-6-hydroxyphenyl]-2-oxo-5-(3-piperidinyl)-1,2-dihydro-1,8-naphthyridin-3-yl]carbonyl}methanesulfonamide hydrochloride.

Molecular weight: 549.05
Mass spectrometry: 513 $(M+H)^+$
In vitro activity grade: A
Cellular activity grade: (A549)-B
$^1$H-NMR (500 MHz, DMSO-d6): 0.33 (2H, m), 0.55 (2H, m), 1.25 (1H, m), 1.95 (4H, m), 2.92 (1H, br), 3.06 (1H, t, J=12.0 Hz), 3.40 (2H, t, J=11.7 Hz), 3.45 (3H, s), 6.61 (2H, d, J=8.2 Hz), 7.28 (1H, t, J=8.2 Hz), 8.09 (1H, s), 8.74 (1H, br), 9.08 (1H, s), 11.62 (1H, br), 12.72 (1H, br), 13.56 (1H, br).

Example 31-3 to 31-27

According to the similar synthetic procedure of Example 31-1 to 31-2, compounds shown in Table 11 were prepared.

TABLE 11

| Ex. No | Structure | Mol weight | Mass | in vi-tro | A549 | NMR |
|---|---|---|---|---|---|---|
| 31-03 | 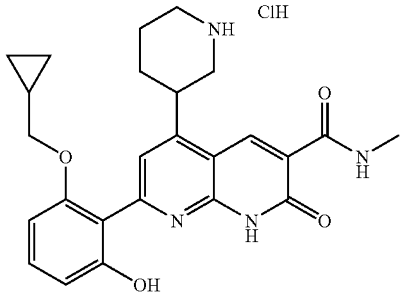 | 484.99 | 449 | A | A | (500MHz, DMSO-d6): 0.34(2H, m), 0.57 (2H, m), 1.27(1H, m), 1.92(4H, m), 2.91 (3H, d, J=4.7Hz), 3.05(1H, t, J=12.3 Hz), 6.59(2H, d, J=8.2Hz), 7.26(1H, t, J=8.2Hz), 8.06(1H, s), 9.00(1H, s), 9.53(1H, q, J=4.7Hz), 11.79(1H, s). |
| 31-04 | 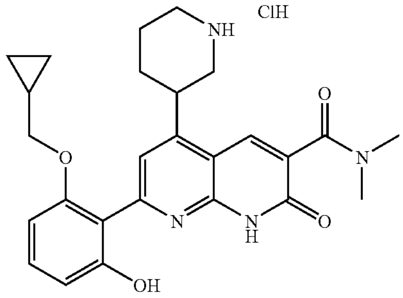 | 499.01 | 463 | A | B | (500MHz, DMSO-d6): 0.34(2H, m), 0.57 (2H, m), 1.27(1H, m), 1.94(4H, m), 2.92 (3H, s), 3.00(3H, s), 6.58(2H, d, J=8.2 Hz), 7.24(1H, t, J=8.2Hz), 8.00(1H, s), 8.19(1H, s), 8.58(1H, br), 9.10(1H, br), 11.84(1H, br), 12.72(1H, s). |
| 31-05 | 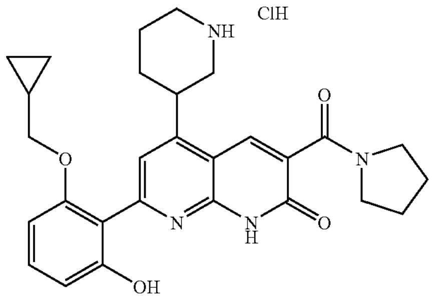 | 525.05 | 489 | A | B | (500MHz, DMSO-d6): 0.33(2H, m), 0.57 (2H, m), 1.25(1H, m), 1.89(9H, m), 2.90 (1H, m), 2.98(1H, dd, J=11.4, 12.6Hz), 6.58(2H, d, J=8.2Hz), 7.24(1H, t, J=8.2Hz), 8.00(1H, s), 8.22(1H, d, J=2.5 Hz), 8.46(1H, br), 9.05(1H, br), 11.82 (1H, br), 12.74(1H, s). |
| 31-06 | 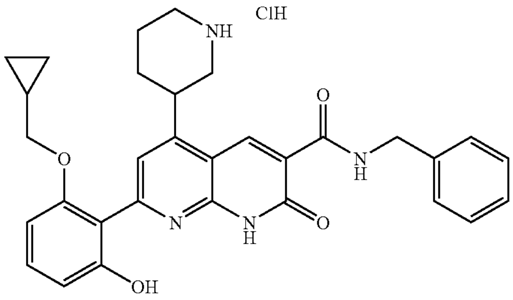 | 561.09 | 525 | A | A | (500MHz, DMSO-d6): 0.33(2H, m), 0.57 (2H, m), 1.27(1H, m), 1.92(4H, m), 2.91 (1H, m), 3.06(1H, t, J=12.3Hz), 4.61 (2H, d, J=6.0Hz), 6.59(2H, d, J=8.5 Hz), 7.28(2H, m), 7.37(4H, m), 8.08 (1H, s), 9.05(1H, s), 10.07(1H, t, J=6.0 Hz), 11.80(1H, s). |

TABLE 11-continued

| Ex. No | Structure | Mol weight | Mass | in vi- tro | A549 | NMR |
|---|---|---|---|---|---|---|
| 31-07 | 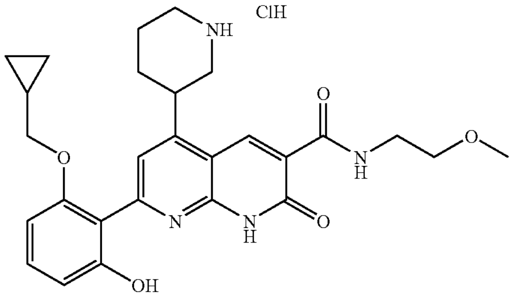 | 529.04 | 493 | A | A | (500MHz, DMSO-d6): 0.33(2H, m), 0.57 (2H, m), 1.27(1H, m), 1.92(4H, m), 2.91 (1H, m), 3.07(1H, t, J=12.3Hz), 3.50 (2H, m), 3.55(2H, m), 6.60(2H, d, J=8.2Hz), 7.26(1H, t, J=8.2Hz), 8.07 (1H, s), 9.02(1H, s), 9.78(1H, m), 11.80 (1H, s). |
| 31-08 | 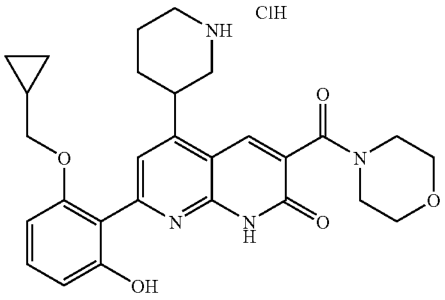 | 541.05 | 505 | A | B | (500MHz, DMSO-d6): 0.33(2H, m), 0.57 (2H, m), 1.26(1H, m), 1.93(4H, m), 2.90 (1H, m), 2.98(1H, dd, J=11.3, 12.0Hz), 3.73(1H, br), 3.88(2H, m), 6.58(2H, d, J=8.2Hz), 7.24(1H, t, J=8.2Hz), 8.00 (1H, s), 8.63(1H, br), 9.06(1H, br d, J=10.7Hz), 11.85(1H, br), 12.73(1H, s). |
| 31-09 | 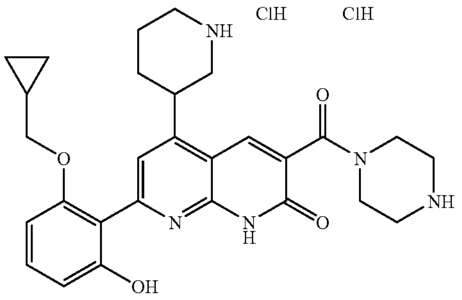 | 576.53 | 504 | A | C | (500MHz, DMSO-d6): 0.33(2H, m), 0.57 (2H, m), 1.26(1H, m), 1.94(4H, m), 2.90 (1H, m), 2.98(1H, dd, J=10.7, 11.4Hz), 3.18(4H, br s), 3.88(5H, m), 6.58(2H, d, J=8.2Hz), 7.24(1H, t, J=8.2Hz), 8.00 (1H, s), 8.38(1H, s), 9.03–9.21(4H, br), 11.81(1H, br), 12.78(1H, s). |
| 31-10 | 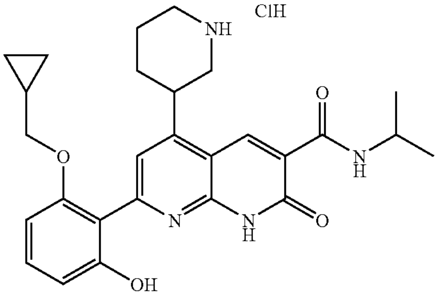 | 513.04 | 477 | A | A | (500MHz, DMSO-d6): 0.34(2H, m), 0.57 (2H, m), 1.23(6H, d, J=6.6Hz), 1.88–1.99(4H, m), 2.91(1H, m), 3.07(1H, dd, J=11.0, 12.0Hz), 4.11(1H, dq, J=6.6, 7.6Hz), 6.59(2H, d, J=8.2Hz), 7.26 (1H, t, J=8.2Hz), 8.07(1H, s), 8.72(1H, br), 9.01(1H, s), 9.59(1H, d, J=7.6Hz), 11.80(1H, br), 13.13(1H, s). |
| 31-11 | 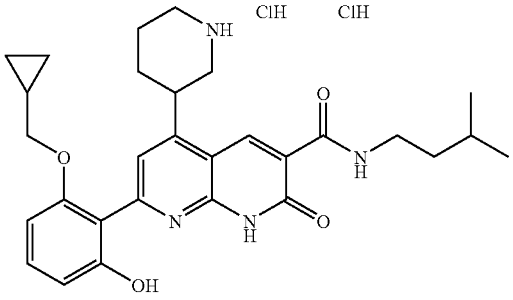 | 578.54 | 506 | A | A | (500MHz, DMSO-d6): 0.33(2H, m), 0.56 (2H, m), 1.26(1H, m), 1.88–1.99(4H, m), 2.85(6H, s), 3.11(1H, dd, J=11.0, 12.3Hz), 3.75(2H, t, J=5.7Hz), 6.59 (2H, d, J=8.2Hz), 7.27(1H, t, J=8.2 Hz), 8.07(1H, s), 8.83(1H, br), 9.01(1H, s), 9.14(1H, br), 9.66(1H, br), 9.83(1H, t, J=6.0Hz), 11.75(1H, s), 13.18(1H, s). |

TABLE 11-continued

| Ex. No | Structure | Mol weight | Mass | in vitro | A549 | NMR |
|---|---|---|---|---|---|---|
| 31-12 | 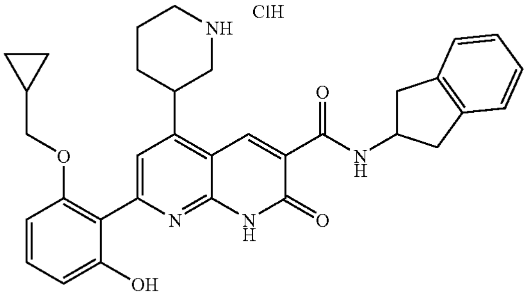 | 587.12 | 551 | A | A | (500MHz, DMSO-d6): 0.33(2H, m), 0.57 (2H, m), 1.26(1H, m), 1.88–1.99(4H, m), 2.92(3H, dd, J=5.4, 10.7Hz), 3.07 (1H, t, J=12.3Hz), 4.74(1H, ddd, J= 6.9, 6.9, 12.6Hz), 6.59(2H, d, J=8.2 Hz), 7.19(2H, m), 7.28(3H, m), 8.06 (1H, s), 9.03(1H, s), 9.91(1H, d, J=6.9 Hz), 11.76(1H, s), 13.09(1H, br). |
| 31-13 | 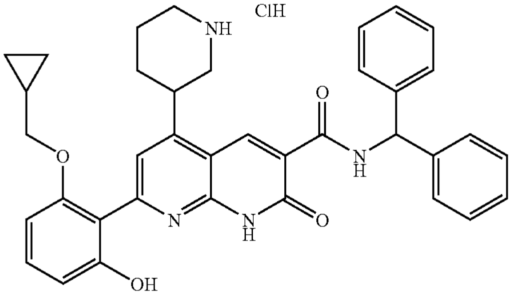 | 637.18 | 601 | A | A | (500MHz, DMSO-d6): 0.32(2H, m), 0.56 (2H, m), 1.25(1H, m), 1.88–1.97(4H, m), 2.90(1H, m), 3.05(1H, t, J=12.3 Hz), 6.33(1H, d, J=7.9Hz), 6.60(2H, d, J=8.2Hz), 7.28(3H, m), 7.38(8H, m), 8.04(1H, s), 9.03(1H, s), 10.07(1H, d, J= 7.9Hz), 11.69(1H, s), 13.20(1H, br). |
| 31-14 | 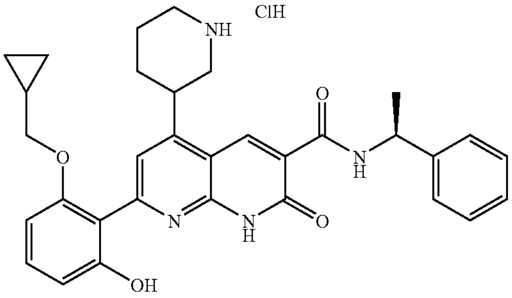 | 575.11 | 539 | A | A | (500MHz, DMSO-d6): 0.33(2H, m), 0.56 (2H, m), 1.26(1H, m), 1.53(3H, d, J= 6.9Hz), 1.86–1.98(4H, m), 2.91(1H, m), 3.06(1H, m), 5.19(1H, dq, J=6.9, 7.3Hz), 6.59(2H, d, J=8.2Hz), 7.28 (2H, m), 7.39(4H, m), 8.06(1H, d, J= 2.9Hz), 8.71(1H, br t, J=11.7Hz), 9.01 (1H, d, J=2.9Hz), 9.09(1H, br t, J= 11.7Hz), 10.11(1H, dd, J=5.7, 7.6Hz), 11.78(1H, br), 13.16(1H, s). |
| 31-15 | 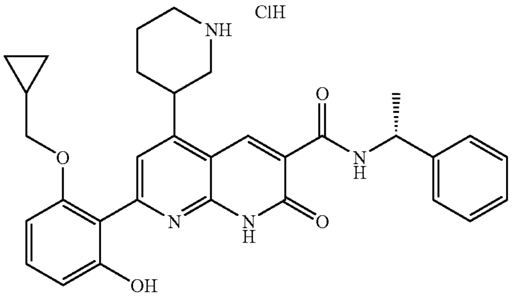 | 575.11 | 539 | A | A | (500MHz, DMSO-d6): 0.33(2H, m), 0.56 (2H, m), 1.26(1H, m), 1.53(3H, d, J= 6.9Hz), 1.86–1.98(4H, m), 2.91(1H, m), 3.06(1H, m), 5.19(1H, dq, J=6.9, Hz), 7.3Hz), 6.59(2H, d x 2, J=8.2 Hz), 7.28(2H, m), 7.39(4H, m), 8.06 (1H, d, J=2.9Hz), 8.73(1H, br t, J= 11.7Hz), 9.00(1H, d, J=2.9Hz), 9.16 (1H, br t, J=11.4Hz), 10.11(1H, dd, J= 5.7, 7.6Hz), 11.78(1H, br), 13.16(1H, s). |
| 31-16 | 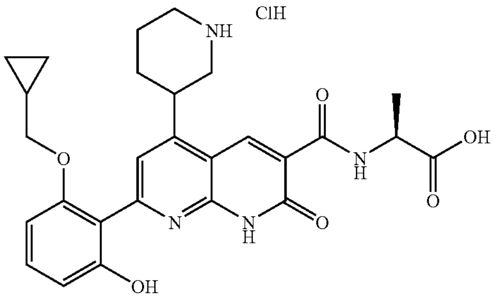 | 543.02 | 507 | A | B | (500MHz, DMSO-d6): 0.34(2H, m), 0.57 (2H, m), 1.28(1H, m), 1.44(3H, d, J= 7.3Hz), 1.88–1.99(4H, m), 2.92(1H, m), 3.07(1H, dd, J=11.4, 12.0Hz), 4.53 (1H, m), 6.59, 6.61(2H, d x 2, J=8.2 Hz), 7.27(1H, t, J=8.2Hz), 8.08(1H, s), 8.79(1H, br), 9.02(1H, s), 9.28(1H, br), 10.07, 10.08(1H, d x 2, J=6.9Hz), 13.17(1H, s). |

TABLE 11-continued

| Ex. No | Structure | Mol weight | Mass | in vi-tro | A549 | NMR |
|---|---|---|---|---|---|---|
| 31-17 | 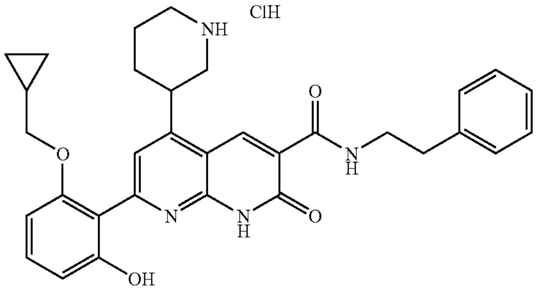 | 575.11 | 539 | A | B | (500MHz, DMSO-d6): 0.33(2H, m), 0.56 (2H, m), 1.26(1H, m), 1.88–1.99(4H, m), 2.88(2H, t, J=7.3Hz), 3.07(1H, dd, J=11.7, 12.0Hz), 3.63(2H, dt, J=6.3, 7.3Hz), 6.59(2H, d, J=8.2Hz), 7.21–7.33(6H, m), 8.05(1H, s), 8.69(1H, br), 8.99(1H, br d, J=5.1Hz), 9.01(1H, s), 9.73(1H, t, J=6.3Hz), 11.74(1H, br s), 13.11(1H, s). |
| 31-18 | 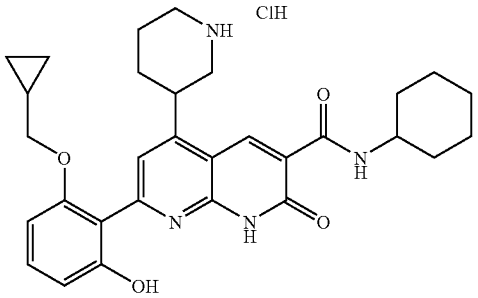 | 553.11 | 517 | A | A | (500MHz, CDCl3): 0.41–0.47(2H, m), 0.65–0.77(2H, m), 0.77–0.92(1H, m), 1.32–1.42(1H, m), 1.78–1.84(1H, m), 1.84–1.97(2H, m), 2.15–2.24(1H, m), 2.72(1H, dd, J=2.8, 12.0Hz), 2.80–2.88(m, 1H), 3.16–3.26(1H, m), 3.34–3.46(2H, m), 3.91(2H, d, J=6.9Hz), 5.95(2H, br s), 6.42(1H, dd, J=1.0, 8.2 Hz), 6.73(1H, dd, J=1.0, 8.2Hz), 7.23–7.26(1H, m), 8.63(1H, s), 8.69(1H, s), 15.00(1H, br). |
| 31-19 | 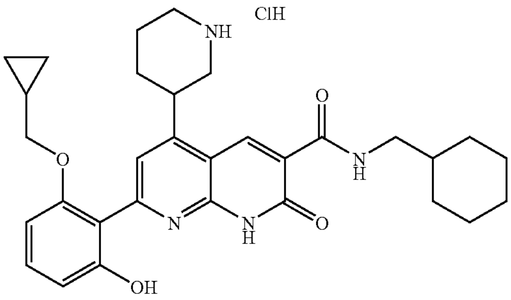 | 567.13 | 531 | A | C | (500MHz, DMSO-d6): 0.33(2H, m), 0.56 (2H, m), 1.02(2H, m), 1.14–1.26(4H, m), 1.53(1H, br), 1.64(1H, br d, J=11.4 Hz), 1.72(4H, m), 1.93(4H, m), 2.92 (1H, br), 3.07(1H, t, J=12.0Hz), 6.59 (2H, d, J=8.2Hz), 7.26(1H, t, J=8.2 Hz), 8.05(1H, s), 8.90(1H, br), 9.00(1H, br), 9.01(1H, s), 9.73(1H, d, J=11.7 Hz), 11.74(1H, s), 13.12(1H, br). |
| 31-20 | 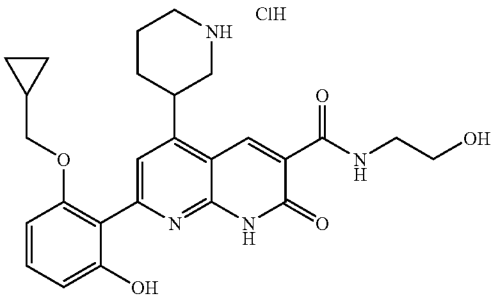 | 515.01 | 479 | A | B | (500MHz, DMSO-d6): 0.33(2H, m), 0.56 (2H, m), 1.27(1H, m), 1.93(4H, m), 2.91 (1H, m), 3.07(1H, t, J=12.0Hz), 3.39 (2H, br), 3.44(2H, dd, J=5.7, 6.0Hz), 3.56(2H, dd, J=5.4, 5.7Hz), 6.59(2H, d, J=8.2Hz), 7.26(1H, t, J=8.2Hz), 8.07(1H, s), 9.02(1H, s), 9.79(1H, d, J=5.4Hz), 11.82(1H, s), 13.13(1H, br). |
| 31-21 | 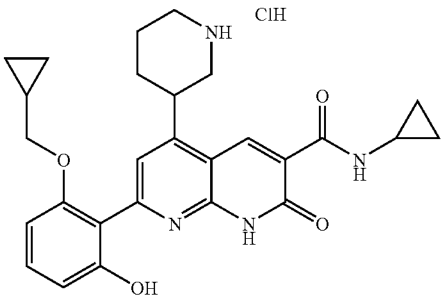 | 511.03 | 475 | A | A | (500MHz, DMSO-d6): 0.34(2H, m), 0.58 (2H, m), 0.79(2H, m), 1.26(1H, m), 1.91 (4H, m), 2.93(2H, m), 3.07(1H, t, J=12.0Hz), 6.60(2H, d, J=8.2Hz), 7.26 (1H, t, J=8.2Hz), 8.06(1H, s), 8.99(1H, s), 9.66(1H, d, J=4.4Hz), 11.76(1H, s), 13.13(1H, br). |

TABLE 11-continued

| Ex. No | Structure | Mol weight | Mass | in vi-tro | A549 | NMR |
|---|---|---|---|---|---|---|
| 31-22 | 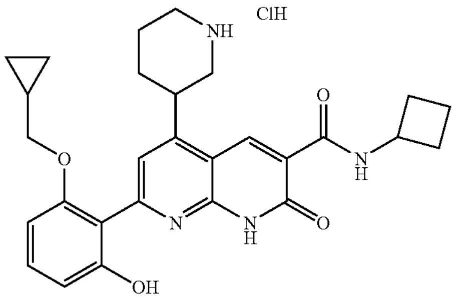 | 525.05 | 489 | A | A | (500MHz, DMSO-d6): 0.33(2H, m), 0.56 (2H, m), 1.26(1H, m), 1.74(2H, m), 1.87–2.05(6H, m), 2.91(1H, m), 3.05(1H, t, J=12.3Hz), 4.46(1H, m), 6.59(2H, d, J=8.2Hz), 7.26(1H, t, J=8.2Hz), 8.06 (1H, s), 8.99(1H, s), 9.84(1H, d, J=7.6 Hz), 11.79(1H, s), 13.13(1H, br). |
| 31-23 | 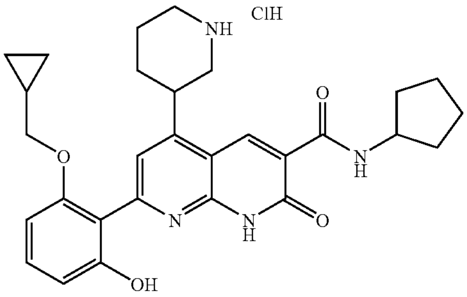 | 539.08 | 503 | A | A | (500MHz, DMSO-d6): 0.34(2H, m), 0.56 (2H, m), 1.26(1H, m), 1.50(2H, m), 1.62 (2H, m), 1.71(2H, m), 1.88–1.99(6H, m), 2.92(1H, m), 3.06(1H, t, J=12.0 Hz), 6.59(2H, d, J=8.2Hz), 7.26(1H, t, J=8.2Hz), 8.06(1H, s), 9.01(1H, s), 9.72(1H, d, J=6.9Hz), 11.77(1H, s), 13.12(1H, br). |
| 31-24 | 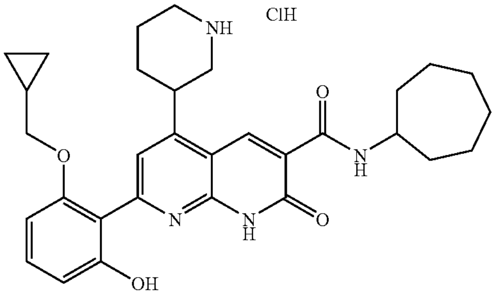 | 567.13 | 531 | A | A | (500MHz, DMSO-d6): 0.34(2H, m), 0.56 (2H, m), 1.26(1H, m), 1.59(10H, m), 1.87–1.99(6H, m), 2.90(1H, m), 3.06 (1H, t, J=11.7Hz), 4.07(1H, m), 6.59 (2H, d, J=8.5Hz), 7.26(1H, t, J=8.5 Hz), 8.06(1H, s), 9.01(1H, s), 9.78(1H, d, J=7.9Hz), 11.76(1H, s), 13.12(1H, br). |
| 31-25 | 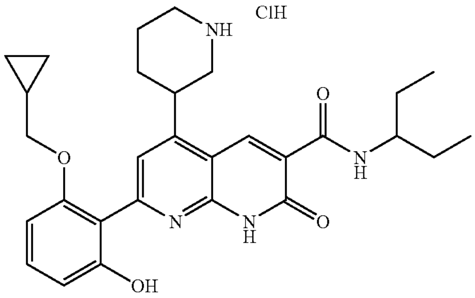 | 541.10 | 505 | A | A | (500MHz, DMSO-d6): 0.34(2H, m), 0.56 (2H, m), 0.90(6H, t, J=8.2Hz), 1.27 (1H, m), 1.51(2H, m), 1.61(2H, m), 1.88–1.99(4H, m), 2.92(1H, m), 3.07(1H, t, J=12.0Hz), 6.60(2H, d, J=8.2Hz), 7.26 (1H, t, J=8.2Hz), 8.07(1H, s), 8.67(1H, br), 8.98(1H, br), 9.03(1H, s), 9.54(1H, d, J=8.8Hz), 11.78(1H, s), 13.12(1H, br). |
| 31-26 | 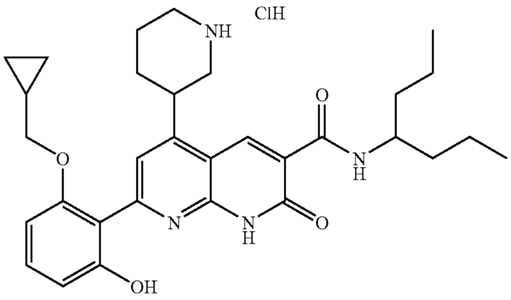 | 569.15 | 533 | A | A | (500MHz, DMSO-d6): 0.34(2H, m), 0.56 (2H, m), 0.90(6H, t, J=7.3Hz), 1.25–1.54(9H, m), 1.88–1.99(4H, m), 2.92 (1H, m), 3.06(1H, t, J=12.3Hz), 4.07 (1H, m), 6.59(2H, d, J=8.2Hz), 7.26 (1H, t, J=8.2Hz), 8.07(1H, s), 8.69(1H, br), 9.00(1H, br), 9.03(1H, s), 9.51(1H, d, J=9.1Hz), 11.78(1H, s), 13.11(1H, br). |

TABLE 11-continued

| Ex. No | Structure | Mol weight | Mass | in vitro | A549 | NMR |
|---|---|---|---|---|---|---|
| 31-27 | 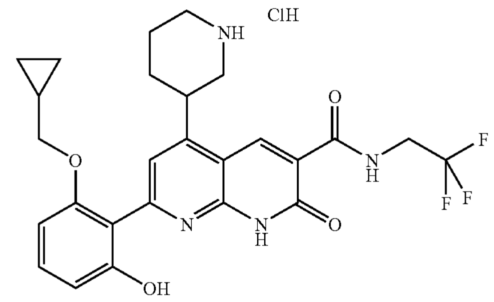 | 552.99 | 517 | A | A | (500MHz, DMSO-d6): 0.34(2H, m), 0.57 (2H, m), 1.27(1H, m), 1.88–1.99(4H, m), 2.92(1H, m), 3.06(1H, t, J=12.3 Hz), 4.28(2H, m), 6.60(2H, d, J=8.2 Hz), 7.27(1H, t, J=8.2Hz), 8.08(1H, s), 9.07(1H, s), 10.12(1H, d, J=6.6Hz), 11.76(1H, s), 13.26(1H, br). |

Example 32-1

With the use of the starting compound 1G, 2B, and other materials, tert-butyl 3-(2-amino-3-cyano-6-{2-(cyclopropylmethoxy)-6-[(4-methoxybenzyl)oxy]phenyl}-4-pyridinyl)-1-piperidinecarboxylate was prepared in a similar manner as that of the step (1) of Example 1-1.

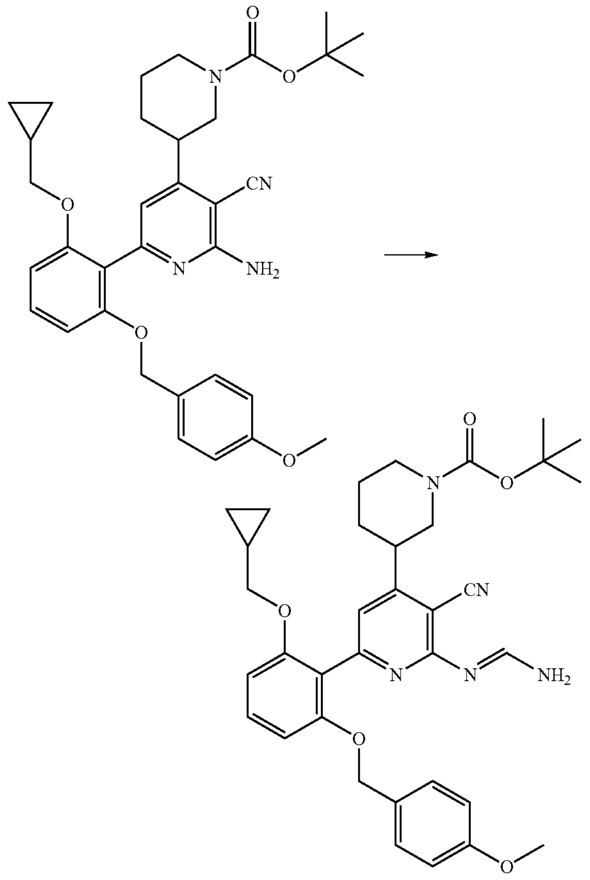

To a solution of tert-butyl 3-(2-amino-3-cyano-6-{2-(cyclopropylmethoxy)-6-[(4-methoxybenzyl)oxy]phenyl}-4-pyridinyl)-1-piperidinecarboxylate (0.580 g, 0.999 mmol) in triethyl orthoformate (1.2 mL) was added ammonium sulfate (0.004 g, 0.030 mmol), and the mixture was stirred at 150° C. for 2 hrs. After cooled to room temperature, EtOH (1.5 mL) and a solution of $NH_3$ in EtOH (8.6 N, 0.5 mL) were added successively. The mixture was stirred at room temperature overnight and concentrated under reduced pressure. The residue was triturated with hexane and isopropyl ether, and dried under reduced pressure to give tert-butyl 3-(2-{[(1E)-aminomethylidene]amino}-3-cyano-6-{2-(cyclopropyl-methoxy)-6-[(4-methoxy-benzyl)oxy]phenyl}-4-pyridinyl)-1-piperidinecarboxylate as a brown solid (0.543 g, yield; 89%).

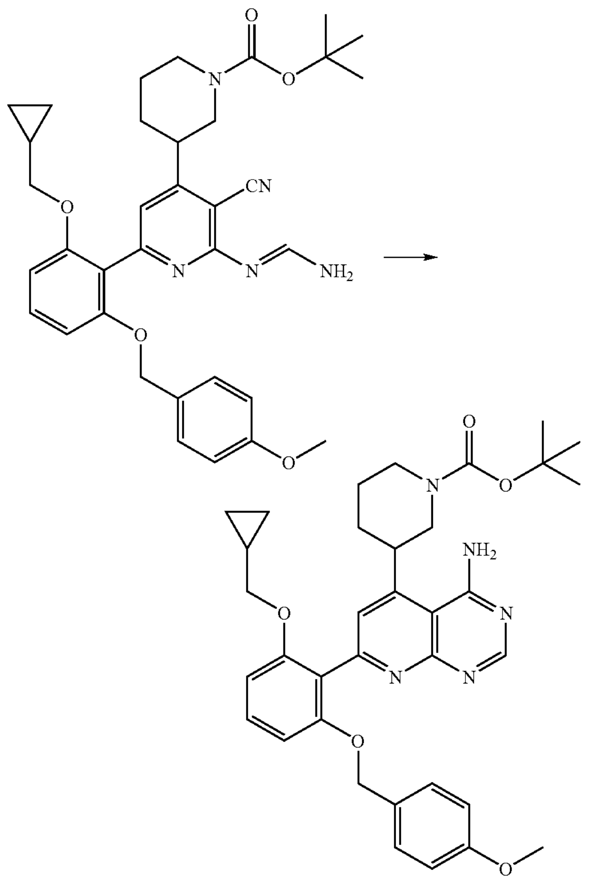

To a solution of tert-butyl 3-(2-{[(1E)-aminomethylidene] amino}-3-cyano-6-{2-(cyclopropylmethoxy)-6-[(4-methoxybenzyl)oxy]phenyl}-4-pyridinyl)-1-piperidine-carboxylate (0.180 g, 0.289 mmol) in MeOH (5 mL) and toluene (5 mL) was added trifluoroacetic acid (0.01 mL). The mixture was allowed to stand for 20 days and concentrated under reduced pressure. Purification by column chromatography on silica gel ($CH_2Cl_2$/MeOH 50:1 to 20:1) gave tert-butyl 3-(4-amino-7-{2-(cyclopropylmethoxy)-6-[(4-methoxybenzyl)oxy]-phenyl}pyrido[2,3-d]pyrimidin-5-yl)-1-piperidinecarboxylate as a colorless oil (0.026 g, yield; 15%).

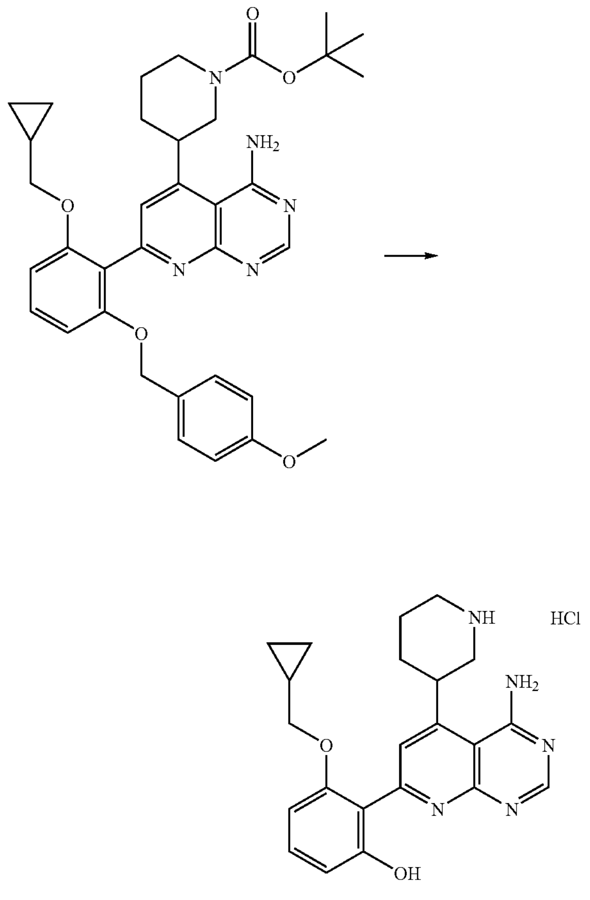

Then the benzyl moiety and tert-butyl carbamate were removed in a similar manner as described in the step (2) of Example 25-4 to give 2-[4-amino-5-(3-piperidinyl)pyrido[2,3-d]pyrimidin-7-yl]-3-(cyclopropylmethoxy)phenol hydrochloride as a yellow powder (0.004 g, 24%).

Molecular weight: 391.48

Mass spectrometry: 392 $(M+H)^+$

In vitro activity grade: C

Cellular activity grade: (A549)-B $^1$H-NMR (500 MHz, CDC13): 0.41–0.47 (2H, m), 0.65–0.77 (2H, m), 0.77–0.92 (1H, m), 1.32–1.42 (1H, m), 1.78–1.84 (1H, m), 1.84–1.97 (2H, m), 2.15–2.24 (1H, m), 2.72 (1H, dd, J=2.8, 12.0 Hz), 2.80–2.88 (m, 1H), 3.16–3.26 (1H, m), 3.34–3.46 (2H, m), 3.91 (2H, d, J=6.9 Hz), 5.95 (2H, br s), 6.42 (1H, dd, J=1.0, 8.2 Hz), 6.73 (1H, dd, J=1.0, 8.2 Hz), 7.23–7.26 (1H, m), 8.63 (1H, s), 8.69 (1H, s), 15.00 (1H, br).

Example 33-1

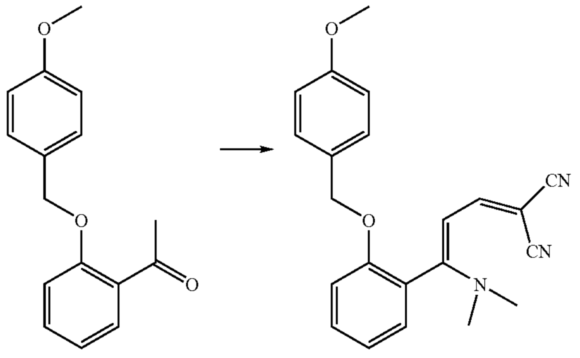

To a solution of oxalyl chloride (3.63 g, 28.6 mmol) in acetonitrile (5.00 mL) at room temperature was added DMF (5.00 mL). After 10 minutes, a solution of 2-(4-methoxyphenylmethoxy)acetophenone (3.33 g, 13.0 mmol)(starting compound 1D) in DMF (50 mL) was added, and the stirring was continued overnight. To the reaction mixture were adde malononitrile (1.03 g, 15.6 mmol) and $Et_3N$ (7.25 mL, 52.0 mmol) successively, and the stirring was continued overnight. The reaction mixture was poured into water, and then extracted with ether. The separated organic phase was washed with brine, and dried over $MgSO_4$, filtetred and concentrated under reduced pressure. The residue was purified by column chromatography on silica gel ($CHCl_3$) to give 2-((2Z)-3-(dimethylamino)-3-{2-[(4-methoxybenzyl)-oxy]phenyl}-2-propenylidene)malononitrile (1.27 g yield; 27%).

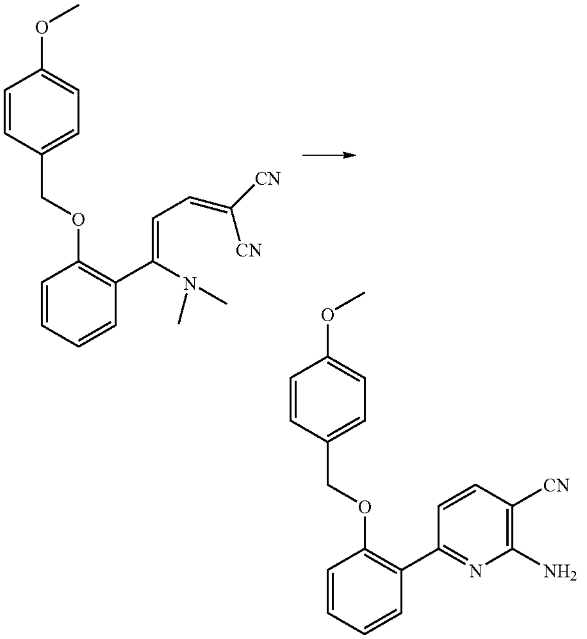

To a cold (−78° C.) solution of 2-((2Z)-3-(dimethylamino)-3-{2-[(4-methoxy-benzyl)oxy]phenyl}-2-propenylidene)malononitrile (1.26 g, 3.51 mmol) in MeOH was added liquid $NH_3$, and the mixture was heated at 120° C. in a sealed tube overnight. After cooled to room temperature, the reaction mixture was poured into water and the resulting mixture was extracted with ethyl acetate. The separated organic phase was washed with brine, and dried over $MgSO_4$, filtered, and concentrated under reduced pressure. The crude material was purified by column chromatography on silica gel (hexane:ethyl acetate, 70:30) to give 2-amino-6-({2-[(4-methoxybenzyl)oxy]phenyl}nicotinonitrile (0.050 g, yield; 4.3%).

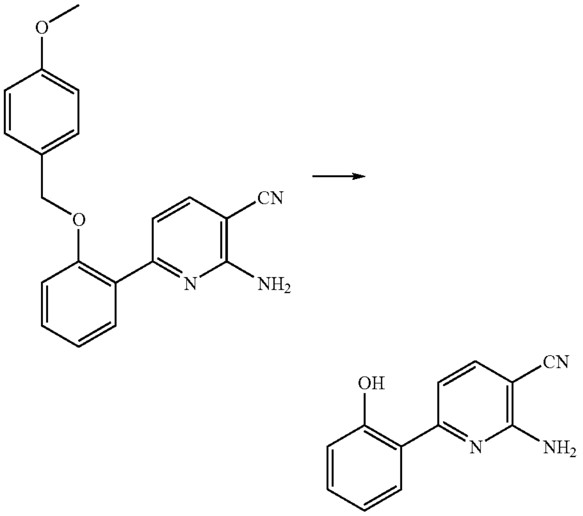

A mixture of 2-amino-6-({2-[(4-methoxybenzyl)oxy]phenyl}nicotinonitrile (0.050 g, 0.151 mmol), trifluoroacetic acid (3.00 mL), anisole (0.50 mL) and water (0.50 mL) was stirred at room temperature overnight. The reaction mixture was diluted with toluene, and concentrated under reduced pressure. The residue was dissolved in THF, and then hexane was added to give precipitates. The precipitates were collected by filtration and washed with hexane, and then dried under reduced pressure to give 2-amino-6-(2-hydroxyphenyl)nicotinonitrile. (0.026 g, yield; 82%)

Molecular weight: 211.23

Mass spectrometry: 212 $(M+H)^+$

In vitro activity grade: B

Cellular activity grade: (A549)-B $^1$H-NMR (500 MHz, DMSO-d6): 6.87–6.92 (2H, m), 7.31–7.39 (4H, m), 7.94 (1H, d, J=8.3 Hz), 8.01 (1H, d, J=8.3 Hz), 13.38 (1H, br s).

Example 34-1

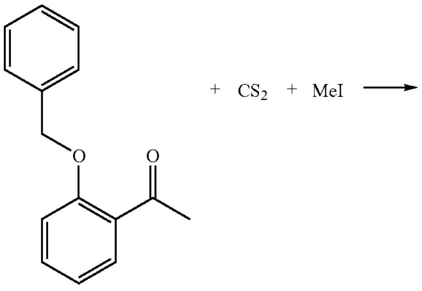

-continued

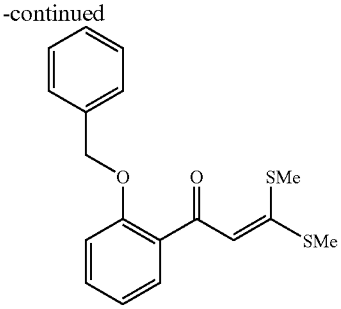

(1) To a solution of 2-(benzyloxy)acetophenone (5.66 g, 25 mmol) (starting compound 1A) in toluene (40 mL) were added carbon disulfide (6.0 mL, 99.8 mmol) and methyl iodide (10 mL, 245 mmol). To the mixture, sodium hydride (60% suspension, 2.00 g, 50 mmol) and N,N-dimethylacetamide (10 mL) were added. The resulting mixture was stirred at room temperature for 1 hr, and refluxed for 2 hrs. After cooled to room temperature, the reaction mixture was partitioned between $CH_2Cl_2$ and water. The organic phase was separated and washed with water, dried, and concentrated under reduced pressure. The residual solid was triturated with diisopropyl ether to give 1-[2-(benzyl)phenyl]-3,3-bis(methylthio)-2-propene-1-one as a light yellow solid (5.17 g, yield; 63%).

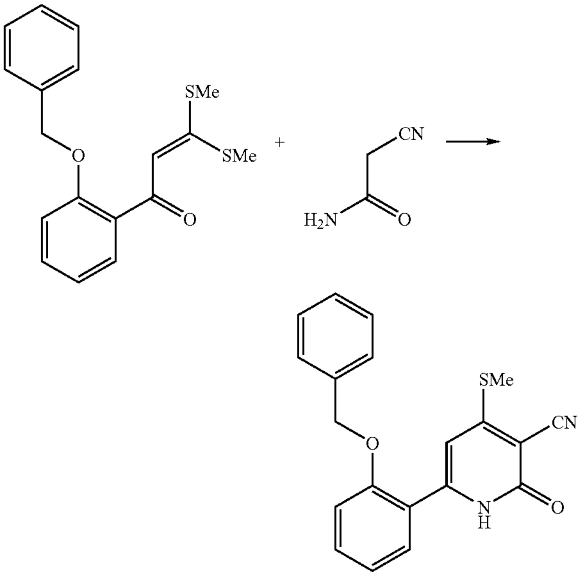

(2) To a suspension of cyanoacetamide (1.27 g, 15.1 mmol) in 2-propanol (50 mL) was added sodium hydride (60% suspension, 0.605 g, 15.1 mmol). The mixture was stirred at room temperature for 10 min. To this mixture, 1-[2-(benzyl)phenyl]-3,3-bis(methylthio)-2-propene-1-one (5.00 g, 15.1 mmol) was added in one portion. The resulting mixture was refluxed for 4 hrs. After being cooled to room temperature, the mixture was diluted with 1N HCl. The resulting precipitates were collected by filtration and washed with EtOH to give 6-[2-(benzyloxy)phenyl]-4-(methylthio)-2-oxo-1,2-dihydro-nicotinonitrile as a yellow crystalline solid (4.43 g, yield; 84%).

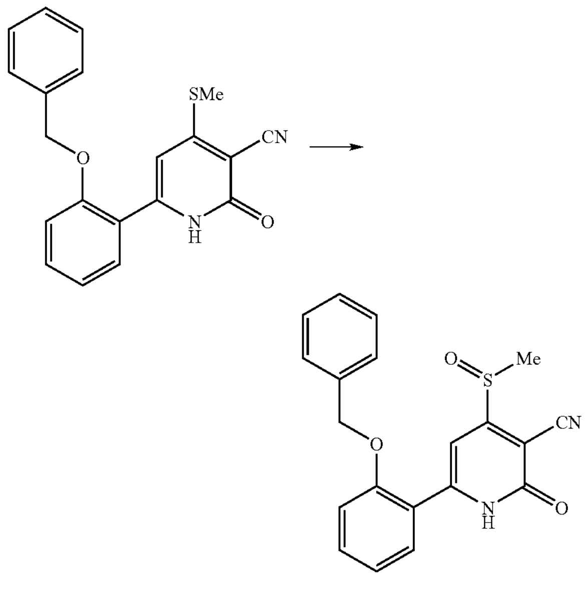

(3) To a cold (0° C.) solution of 6-[2-(benzyloxy)phenyl]-4-(methylthio)-2-oxo-1,2-dihydro-nicotinonitrile (4.00 g, 11.5 mmol) in $CH_2Cl_2$ was added m-chloroper-benzoic acid (mCPBA) (69%, 3.45 g, 13.8 mmol) in one portion. The reaction mixture was stirred at 0° C. to room temperature for 1 hr, quenched with saturated $NaHCO_3$ solution (80 mL) including $Na_2S_2O_3.5H_2O$ (5 g), and diluted with $CH_2Cl_2$. The separated organic phase was washed with saturated $NaHCO_3$ solution, dried over $Na_2SO_4$, filtered, and concentrated under reduced pressure. The residual solid was triturated with diisopropyl ether to give 6-[2-(benzyloxy)phenyl]-4-(methylsulfinyl)-2-oxo-1,2-dihydro-nicotinonitrile as a yellow solid (4.00 g, yield; 96%).

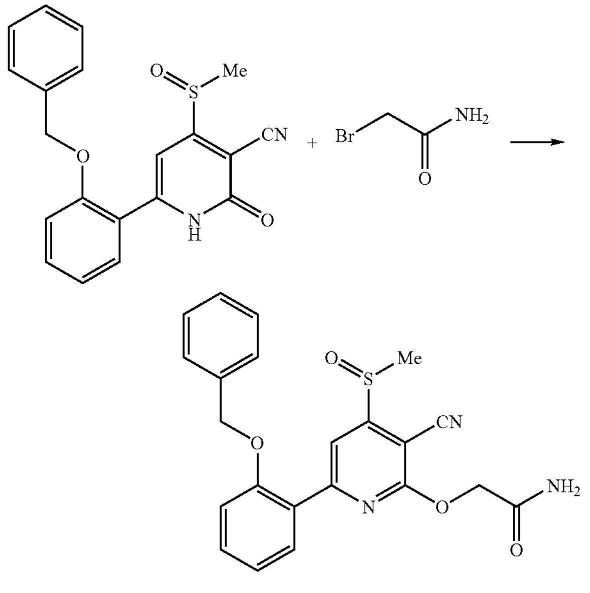

(4) A mixture of 6-[2-(benzyloxy)phenyl]-4-(methylsulfinyl)-2-oxo-1,2-dihydro-3-pyridinecarbonitrile (2.97 g, 8.16 mmol), bromoacetamide (1.27 g, 9.21 mmol), and $K_2CO_3$ (1.43 g, 10.4 mmol) in DMF (30 mL) was stirred at 60° C. for 1.5 hrs. The reaction mixture was poured into water, and the resulting precipitates were collected by filtration. The solid obtained was washed with acetone to give 2-{[6-[2-(benzyloxy)phenyl]-3-cyano-4-(methylsulfinyl)-2-pyridinyl]oxy}acetamide as a solid (2.09 g, yield; 61%).

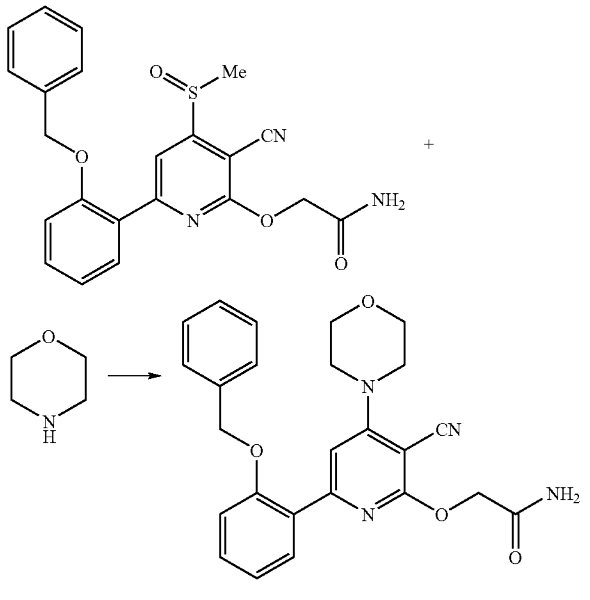

(5) A mixture of 2-{[6-[2-(benzyloxy)phenyl]-3-cyano-4-(methylsulfinyl)-2-pyridinyl]oxy}acetamide (300 mg, 0.71 mmol) and morpholine (1.0 mL) was stirred at 130° C. for 1 hr, and then water was added. The resulting precipitates were collected by filtration and dried under reduced pressure to give 2-{[6-[2-(benzyl-oxy)phenyl]-3-cyano-4-(4-morpholinyl)-2-pyridinyl]oxy}acetamide as a yellow solid (304 mg, yield; 96%).

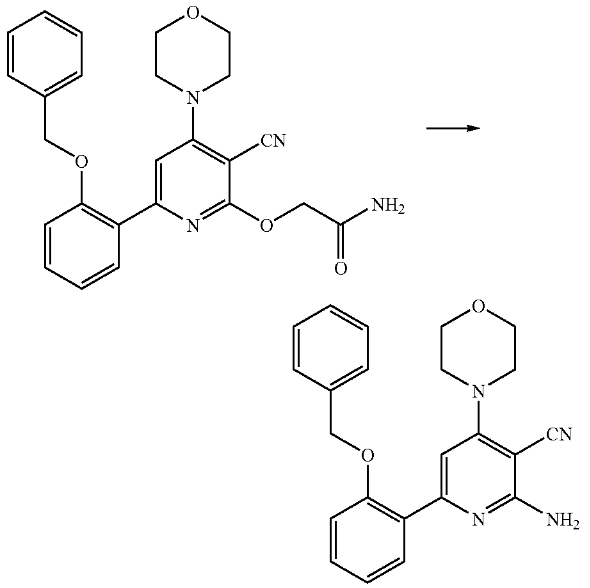

(6) To a solution of 2-{[6-[2-(benzyloxy)phenyl]-3-cyano-4-(4-morpholinyl)-2-pyridinyl]oxy}acetamide (318 mg, 0.72 mmol) in DMF (1 mL) was added $K_2CO_3$ (198 mg, 1.43 mmol), and the mixture was stirred at 130° C. for 24 hrs. The mixture was partitioned between ethyl acetate and water. The organic phase was washed with brine, dried over $Na_2SO_4$, and concentrated under reduced pressure. Purification by column chromatography on silica gel (hexane/ethyl acetate=3/1 to 2/1) followed by trituration with diisopropyl ether gave 2-amino-6-[2-(benzyloxy)phenyl]-4-(4-morpholinyl)nicotinonitrile as a white solid (141 mg, yield; 51%).

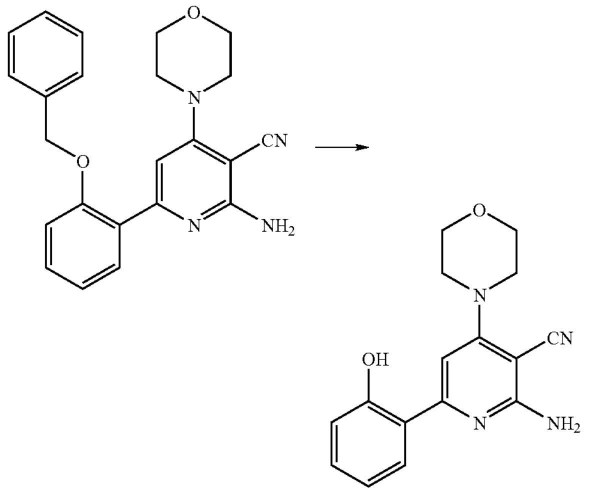

(7) Then the benzyl moiety was removed in a same manner as described in the step (2) of Example 1-1. The residue was triturated with $Et_2O$ and dried under reduced pressure to give 2-amino-6-(2-hydroxyphenyl)-4-(4-morpholinyl)nicotinonitrile as a solid (68 mg, yield; 76%).

Molecular weight: 296.33

Mass spectrometry: 297 $(M+H)^+$

In vitro activity grade: B

Cellular activity grade: (A549)-C $^1$H-NMR (300 MHz, DMSO-d6): 3.44–3.54 (4H, m), 3.68–3.78 (4H, m), 6.77–6.90 (3H, m), 7.08 (2H, br s), 7.25–7.35 (1H, m), 7.92–8.00 (1H, m), 13.77 (1H, s).

Example 34-2

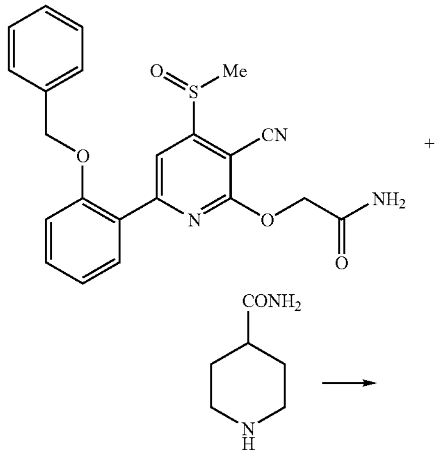

-continued

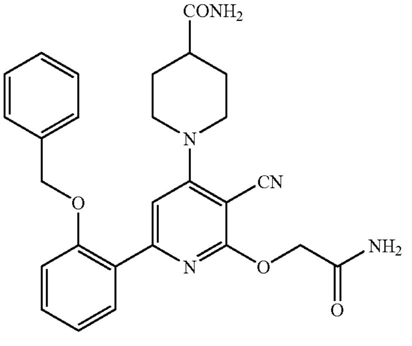

A mixture of 2-{[6-[2-(benzyloxy)phenyl]-3-cyano-4-(methylsulfinyl)-2-pyridinyl]-oxy}acetamide (500 mg, 1.19 mmol), which was obtained in the step (4) of Example 34-1, and isonipecotamide (228 mg, 1.78 mmol) in DMF (2 mL) was stirred at 130° C. for 5 hrs. After cooled to room temperature, the mixture was partitioned between ethyl acetate and water. The organic phase was washed with brine, dried over $Na_2SO_4$ and concentrated under reduced pressure to give 1-{2-(2-amino-2-oxoethoxy)-6-[2-(benzyloxy)phenyl]-3-cyano-4-pyridinyl}-4-piperidinecarboxamide as a solid (485 mg, yield; 84%).

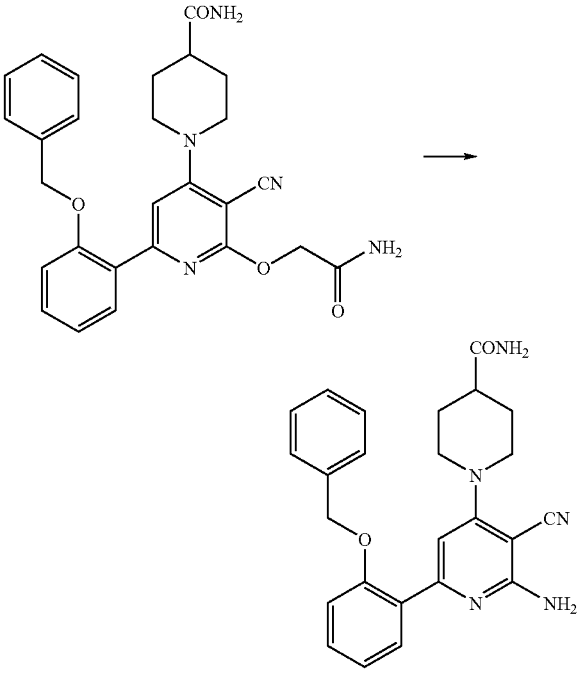

A mixture of 1-{2-(2-amino-2-oxoethoxy)-6-[2-(benzyloxy)phenyl]-3-cyano-4-pyridinyl}-4-piperidinecarboxamide (485 mg, 1.00 mmol) and $K_2CO_3$ (280 mg, 2.03 mmol) in DMF (2.5 mL) was stirred at 130° C. for 28 hrs. After cooled to room temperature, the mixture was diluted with water, and the resulting precipitates were collected by filtration. The precipitates were washed with EtOH and $CH_2Cl_2$ to give 1-{2-amino-6-[2-(benzyloxy)phenyl]-3-cyano-4-pyridinyl}-4-piperidinecarboxamide as a solid (119 mg, yield; 28%).

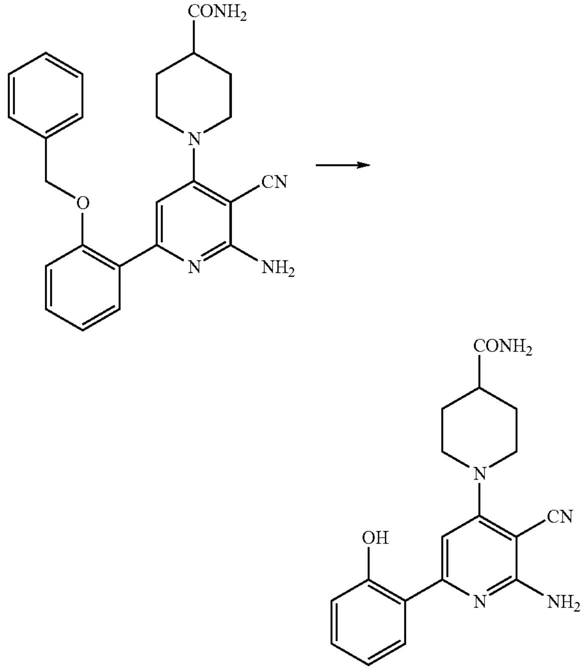

Then the benzyl moiety was removed in a similar manner as that of the step (2) of Example 1-1 to give 1-[2-amino-3-cyano-6-(2-hydroxyphenyl)-4-pyridinyl]-4-piperidinecarboxamide as a solid (19 mg, yield; 36%).

Molecular weight: 337.38

Mass spectrometry: 338 $(M+H)^+$

In vitro activity grade: B

Cellular activity grade: (A549)-C $^1$H-NMR (300 MHz, DMSO-d6): 1.58–1.77 (2H, m), 1.77–1.90 (2H, m), 2.30–2.46 (1H, m), 2.98–3.15 (2H, m), 3.97(2H, d, J=12.8 Hz), 6.73–6.90 (4H, m), 7.10 (2H, s), 7.22–7.36 (2H, m), 7.94 (1H, d, J=7.2 Hz), 13.85 (1H, s).

Example 34-3

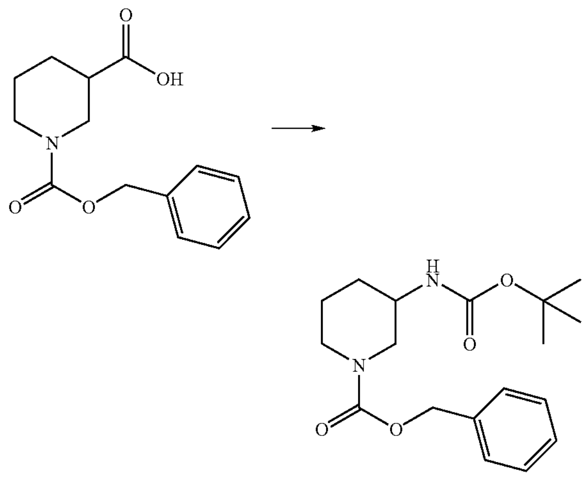

To a solution of 1-[(benzyloxy)carbonyl]-3-piperidinecarboxylic acid (3.00 g, 11.4 mmol) and $Et_3N$ (1.56 mL, 11.4 mmol) in t-BuOH (30 mL) was added diphenyl phosphoryl azide (DPPA) (2.46 mL, 11.4 mmol), and the mixture was refluxed for 21 hrs. After cooled to room temperature, the mixture was concentrated under reduced pressure, and the residue was partitioned between ethyl acetate and a saturated aqueous $NaHCO_3$ solution. The organic phase was washed with a saturated aqueous $NaHCO_3$ solution and brine, dried over $Na_2SO_4$, and concentrated under reduced pressure. Purification by column chromatography on silica gel (hexane/ethyl acetate=4/1 to 3/1) gave benzyl 3-[(tert-butoxycarbonyl)amino]-1-piperidinecarboxylate as a solid (2.22 g, yield; 58%).

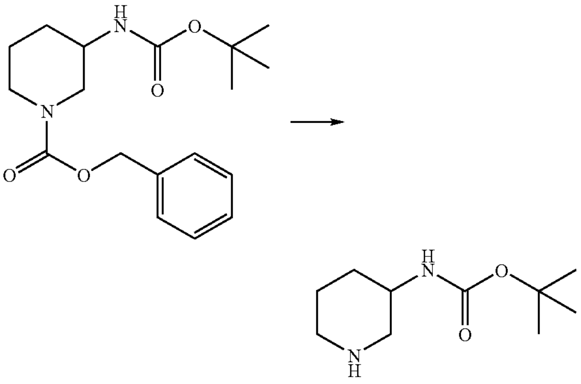

A mixture of benzyl 3-[(tert-butoxycarbonyl)amino]-1-piperidinecarboxylate (2.25 g, 6.73 mmol) and 10% Pd/C (0.229 g) in EtOH (20 mL) was stirred at room temperature under a hydrogen atmosphere (1 atm) for 14 hrs. The catalyst was removed by filtration through Celite®, and the filtrate was concentrated under reduced pressure to give tert-butyl 3-piperidinylcarbamate as a solid (1.22 g, yield; 91%).

The resulting tert-butyl 3-piperidinylcarbamate and 2-{[6-[2-(benzyloxy)phenyl]-3-cyano-4-(methylsulfinyl)-2-pyridinyl]oxy}acetamide were used as starting materials to prepare 2-amino-4-(3-amino-1-piperidinyl)-6-(2-hydroxyphenyl)nicotinonitrile hydrochloride in a similar manner as described in Example 34-1.

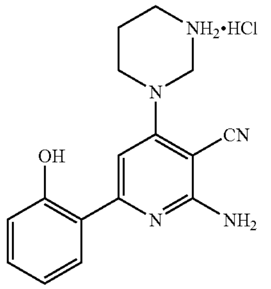

Molecular weight: 345.83

Mass spectrometry: 310 $(M+H)^+$

In vitro activity grade: B

Cellular activity grade: (A549)-B $^1$H-NMR (500 MHz, DMSO-d6): 1.59–1.76 (2H, m), 1.82–1.95 (1H, m), 2.02–2.14(1H, m), 3.27–3.50 (3H, m), 3.90–4.05 (1H, m), 4.08–4.22 (1H, m), 6.80 (1H, s), 6.92 (1H, t, J=7.6 Hz), 6.96–7.06 (1H, m), 7.37 (1H, t, J=6.9 Hz), 7.79 (3H, br s), 8.39 (3H, br s), 13.25 (1H, br s).

Example 34-4

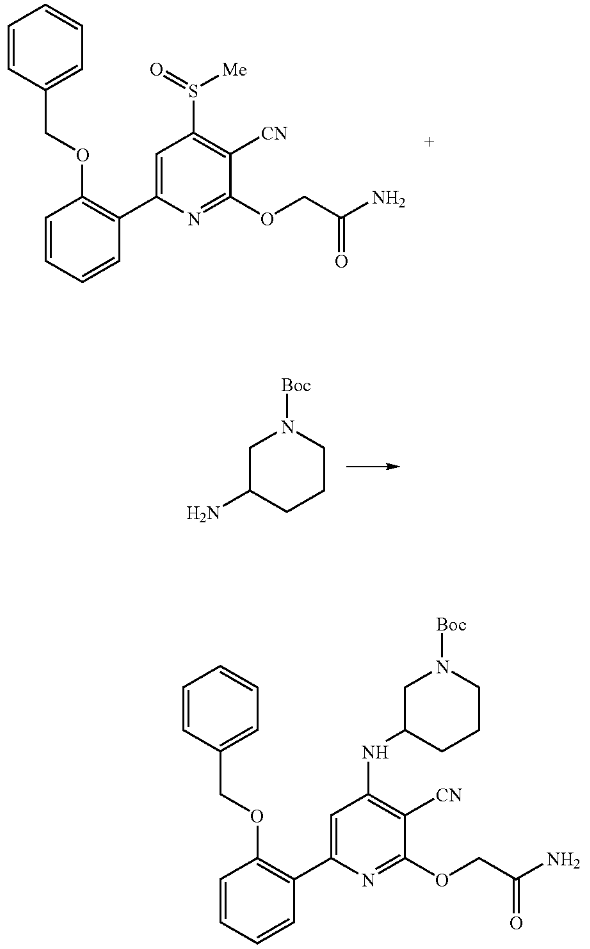

A mixture of 2-{[6-[2-(benzyloxy)phenyl]-3-cyano-4-(methylsulfinyl)-2-pyridinyl]-oxy}acetamide (500 mg, 1.19 mol), which was obtained in the step (4) of Example 34-1, and tert-butyl 3-amino-1-piperidinecarboxylate (555 mg, 2.77 mmol) in DMF (0.6 mL) was stirred at 130° C. for 24 hrs. After cooled to room temprature, the mixture was partitioned between ethyl acetate and water. The organic phase was washed with water and brine, dried over $Na_2SO_4$, filtered, and concentrated under reduced pressure. Purification by silica gel column chromatography (hexane/ethyl acetate=1/1) gave tert-butyl 3-({2-(carbamoylmethoxy)-6-[2-(benzyloxy)phenyl]-3-cyano-4-pyridinyl}amino)-1-piperidinecarboxylate as a foam (360 mg, yield; 64%).

With the use of the resulting compound, 2-amino-6-(2-hydroxyphenyl)-4-(3-piperidinylamino)nicotinonitrile hydrochloride was prepared in a similar manner as described in Example 34-2.

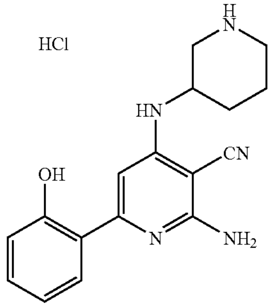

Molecular weight: 345.83
Mass spectrometry: 310 $(M+H)^+$
In vitro activity grade: A
Cellular activity grade: (A549)-A $^1$H-NMR (300 MHz, DMSO-d6): 1.68–2.06 (4H, m), 2.66–2.96 (2H, m), 3.17–3.38 (2H, m), 4.23 (1H, br s), 6.73 (1H, s), 6.92 (1H, t, J=7.5 Hz), 7.01 (1H, d, J=7.5 Hz), 7.37 (1H, t, J=7.5 Hz), 7.55 (3H, br), 7.78 (1H, d, J=7.5 Hz), 9.20 (2H, br s), 13.20 (1H, br).

Example 34-5 to 34-19

According to the similar synthetic procedure of Example 34-1 to 34-4, compounds shown in Table 12 were prepared.

TABLE 12

| Ex. No | Structure | Mol weight | Mass | in vitro | A549 | NMR |
|---|---|---|---|---|---|---|
| 34-05 | 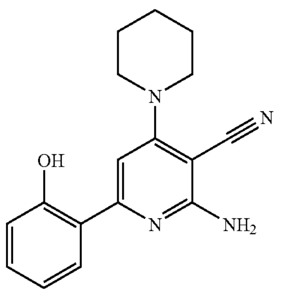 | 294.36 | 295 | D | | (300MHz, DMSO-d6): 1.64(6H, br s), 3.48(4H, br s), 6.76(1H, s), 6.78–6.89 (2H, m), 6.98(1H, br s), 7.28(1H, t, J=7.2Hz), 7.93(1H, d, J=7.2Hz), 13.86 (1H, br s). |

TABLE 12-continued
| Ex. No | Structure | Mol weight | Mass | in vitro | A549 | NMR |
|---|---|---|---|---|---|---|
| 34-06 | 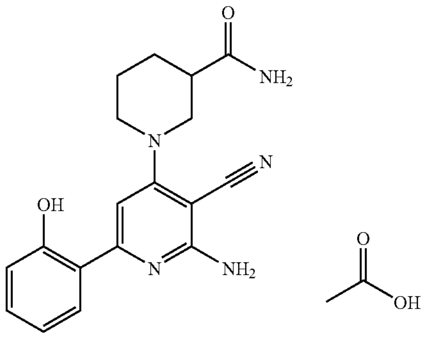 | 397.44 | 338 | C | C | (300MHz, DMSO-d6): 1.49–1.71(2H, m), 1.71–1.87(1H, m), 1.91(3H, s), 1.87–2.02(1H, m), 2.37–2.54(1H, m), 2.94–3.08(1H, m), 3.09(1H, dd, J=11.3, 12.8Hz), 3.88–4.04(2H, m), 6.76–6.92(4H, m), 7.01(2H, s), 7.24–7.33 (1H, m), 7.34(1H, br s), 7.95(1H, d, J=7.2Hz), 11.92(1H, br). |
| 34-07 | 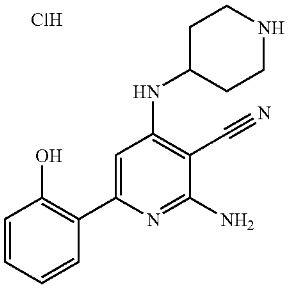 | 345.83 | 310 | A | B | (500MHz, DMSO-d6): 1.90(2H, br s), 1.96(2H, br s), 2.98(2H, br s), 3.31(2H, br s), 4.07(1H, br s), 6.67–6.75(1H, m), 6.90–6.99(1H, m), 7.04(1H, br s), 7.30–7.47(1H, m), 7.63(1H, br s), 7.81(3H, br), 8.84(1H, br s), 9.09(1H, br s), 12.94 (1H, br). |
| 34-08 | 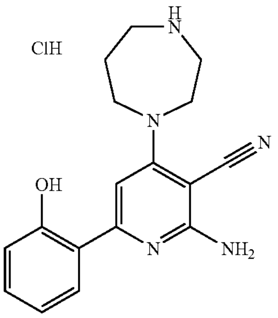 | 345.83 | 310 | B | B | (500MHz, DMSO-d6): 2.20(2H, br s), 3.24(2H, br s), 3.36(2H, br s), 3.91(2H, br s), 4.09(2H, br s), 6.69(1H, s), 6.94 (1H, t, J=7.6Hz), 7.03(1H, d, J=7.9 Hz), 7.37(1H, t, J=7.9Hz), 7.68(1H, d, J=7.3Hz), 7.84(2H, br), 9.36(2H, br s), 13.15(1H, br). |
| 34-09 | 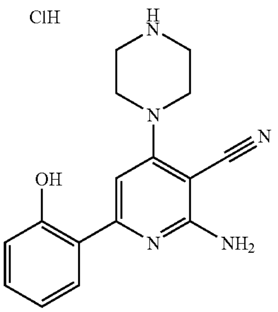 | 331.81 | 296 | A | B | (500MHz, DMSO-d6): 3.26(4H, br s), 3.86(4H, br s), 6.86(1H, s), 6.92(1H, t, J=7.5Hz), 6.93–7.03(1H, m), 7.36 (1H, t, J=7.5Hz), 7.70(1H, br), 7.82 (1H, d, J=7.5Hz), 9.57(2H, br). |

TABLE 12-continued
| Ex. No | Structure | Mol weight | Mass | in vitro | A549 | NMR |
|---|---|---|---|---|---|---|
| 34-10 | 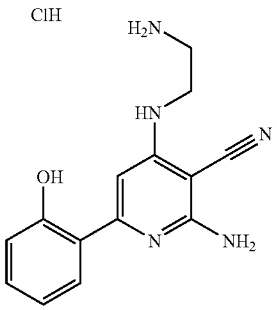 | 305.77 | 270 | A | A | (500MHz, DMSO-d6): 2.92–3.07(2H, m), 3.71(2H, br s), 6.71(1H, d, J=2.8 Hz), 6.94(1H, t, J=7.6Hz), 7.03–7.11 (1H, m), 7.38(1H, t, J=7.6Hz), 7.71 (1H, br s), 7.95(3H, br), 8.13(3H, br s), 12.98(1H, br). |
| 34-11 | 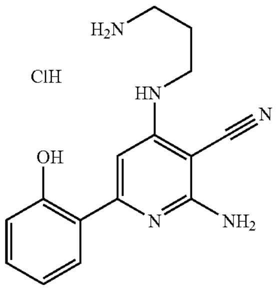 | 319.80 | 284 | A | B | (500MHz, DMSO-d6): 1.81–1.95(2H, m), 2.79–2.91(2H, m), 3.45–3.63(2H, m), 6.67(1H, s), 6.92–6.98(1H, m), 7.10(1H, d, J=8.2Hz), 7.35–7.43(1H, m), 7.63(1H, d, J=7.6Hz), 7.85–8.55 (6H, m), 12.80(1H, br). |
| 34-12 | 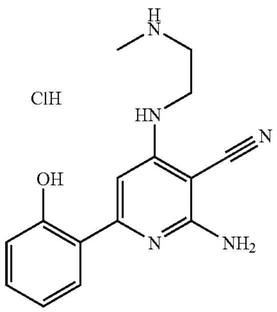 | 319.80 | 284 | A | A | (500MHz, DMSO-d6): 2.55–2.61(3H, m), 3.08(2H, br s), 3.77(2H, br s), 6.73 (1H, s), 6.94(1H, t, J=7.6Hz), 7.02–7.11(1H, m), 7.38(1H, t, J=7.6Hz), 7.74(1H, br), 7.96(2H, br), 9.06(2H, br), 12.99(1H, br). |
| 34-13 | 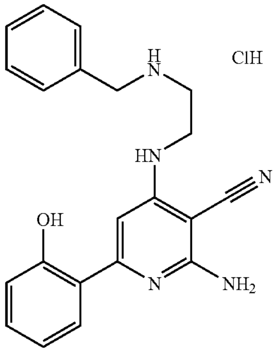 | 395.90 | 360 | A | A | (500MHz, DMSO-d6): 3.11(2H, br s), 3.77–3.93(2H, m), 4.15–4.23(2H, m), 6.76(1H, s), 6.90–6.98(1H, m), 7.07 (1H, d, J=8.2Hz), 7.33–7.48(4H, m), 7.55–7.64(2H, m), 7.66–7.79(1H, m), 7.98(3H, br), 9.57(2H, br s), 12.97(1H, br). |

TABLE 12-continued
| Ex. No | Structure | Mol weight | Mass | in vitro | A549 | NMR |
|---|---|---|---|---|---|---|
| 34-14 | 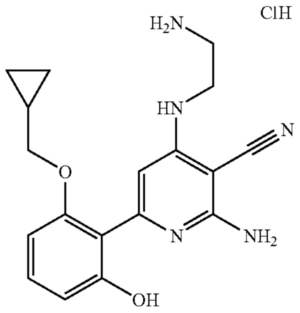 | 375.86 | 340 | A | | (500MHz, DMSO-d6): 0.26–0.37(2H, m), 0.44–0.55(2H, m), 1.11–1.20(1H, m), 2.95(2H, br s), 3.63(2H, br s), 3.84 (2H, d, J=6.9Hz), 6.51–6.72(3H, m), 7.26(1H, t, J=8.4Hz), 7.75–8.35(6H, m), 10.39(1H, br), 12.89(1H, br). |
| 34-15 | 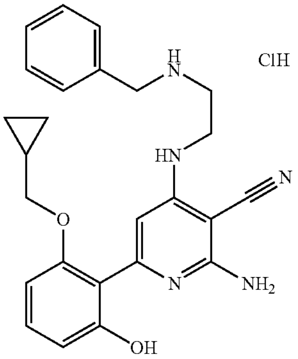 | 465.99 | 430 | A | A | (500MHz, DMSO-d6): 0.26–0.37(2H, m), 0.44–0.55(2H, m), 1.10–1.22(1H, m), 3.11(2H, br s), 3.74(2H, br s), 3.85 (2H, d, J=6.6Hz), 4.18(2H, br s), 6.50–6.74(3H, m), 7.22–7.32(1H, m), 7.39–7.48(3H, m), 7.52–7.58(2H, m), 7.86 and 8.21(2H, br), 9.21 and 10.35(2H, br), 12.81(1H, br). |
| 34-16 | 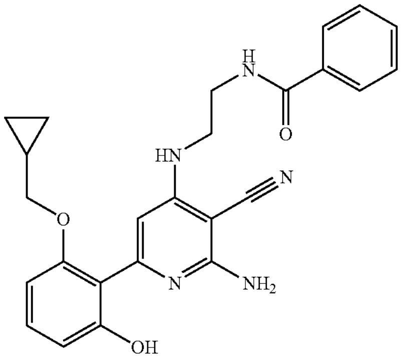 | 443.51 | 444 | A | A | (500MHz, DMSO-d6): 0.25–0.37(2H, m), 0.47–0.57(2H, m), 1.22–1.33(1H, m), 3.41–3.54(4H, m), 3.83(2H, d, J=6.9Hz), 6.39–6.49(2H, m), 6.60–7.00 (3H, m), 7.14(1H, t, J=8.2Hz), 7.23 (1H, br s), 7.43(2H, t, J=7.3Hz), 7.51 (1H, t, J=7.3Hz), 7.80(2H, d, J=7.3 Hz), 8.62(1H, br s), 14.39(1H, br). |
| 34-17 | 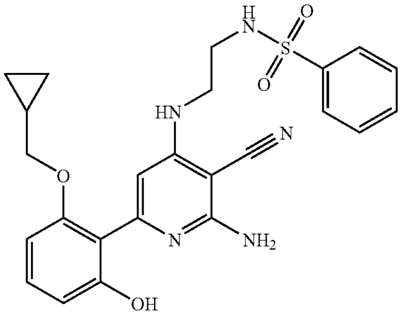 | 479.56 | 480 | A | C | (500MHz, DMSO-d6): 0.25–0.36(2H, m), 0.47–0.58(2H, m), 1.18–1.30(1H, m), 2.96(2H, q, J=6.0Hz), 3.33(2H, q, J=6.0Hz), 3.82(2H, d, J=6.9Hz), 6.40–6.48(2H, m), 6.60(1H, t, J=6.0Hz), 6.76(2H, s), 7.07(1H, s), 7.13(1H, t, J=8.2Hz), 7.52(2H, t, J=7.3Hz), 7.59 (1H, t, J=7.3Hz), 7.75(2H, d, J=7.3 Hz), 7.80(1H, t, J=6.0Hz), 14.28(1H, br s). |

TABLE 12-continued

| Ex. No | Structure | Mol weight | Mass | in vitro | A549 | NMR |
|---|---|---|---|---|---|---|
| 34-18 | 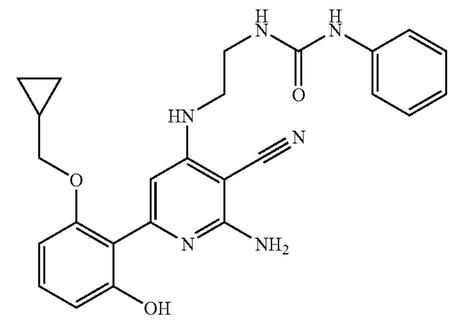 | 458.52 | 459 | A | A | (500MHz, DMSO-d6): 0.26–0.37(2H, m), 0.50–0.62(2H, m), 1.22–1.34(1H, m), 3.35(4H, br s), 3.83(2H, d, J=6.9 Hz), 6.33(1H, br s), 6.40–6.48(2H, m), 6.80(2H, br), 6.85–6.92(1H, m), 7.10–7.25(4H, m), 7.37(2H, d, J=7.6Hz), 8.57(1H, s), 14.44(1H, br). |
| 34-19 | 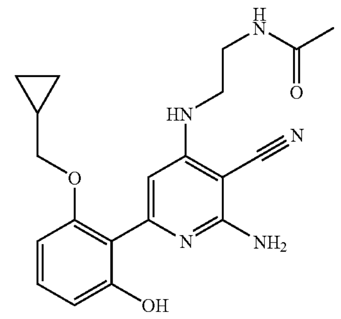 | 381.44 | 382 | A | A | (300MHz, CDC13): 0.31–0.41(2H, m), 0.60–0.70(2H, m), 1.21–1.38(1H, m), 1.96(3H, s), 3.40–3.50(4H, m), 3.84 (2H, d, J=7.2Hz), 5.60(2H, br s), 6.11 (1H, br s), 6.37(1H, d, J=8.3Hz), 6.53 (1H, d, J=8.3Hz), 7.13(1H, t, J=8.3 Hz), 7.35(1H, s), 7.48(1H, br s), 14.44 (1H, br s). |

Example 35-1

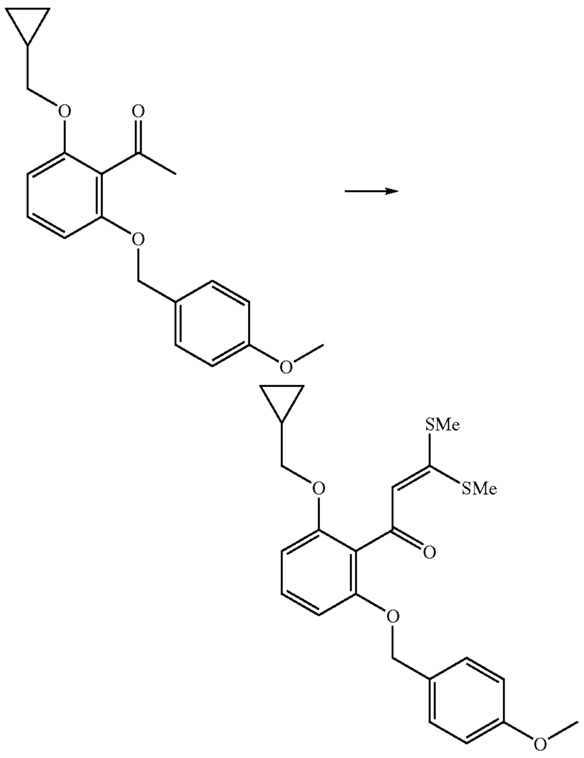

To a suspension of potassium tert-butoxide (0.809 g, 6.128 mmol) in THF (5 mL) was added a solution of 1-{2-(cyclopropylmethoxy)-6-[(4-methoxybenzyl)oxy]-phenyl}ethanone (1.00 g, 3.064 mmol) (starting compound 1G) in THF (5 mL) followed by carbon disulfide (0.23 mL, 3.83 mmol) and methyl iodide (0.57 mL, 9.19 mmol) successively. The resulting mixture was stirred at room temperature for 40 min, and then partitioned between ethyl acetate and water. The organic phase was washed with brine, dried over $Na_2SO_4$, filtered, and concentrated under reduced pressure. Purification by column chromatography on silica gel (hexane/ethyl acetate 4:1 to 3:1) gave 1-{2-(cyclopropylmethoxy)-6-[(4-methoxybenzyl)oxy]phenyl}-3,3-bis(methylsulfanyl)-2-propene-1-one as a pale yellow oil (0.825 g, yield; 63%).

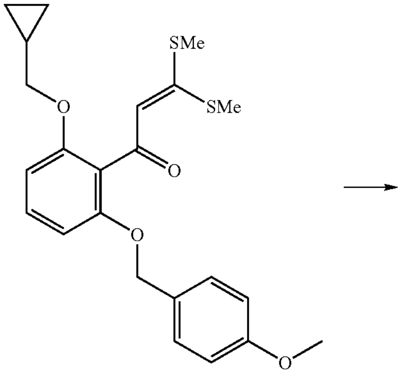

-continued

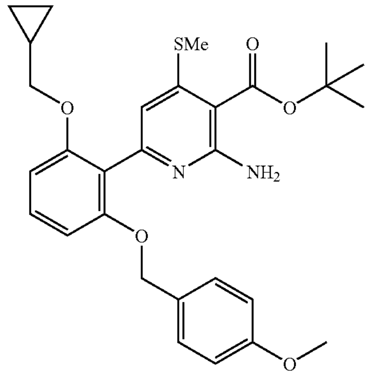

To a suspension of NaH (60%, 0.056 g, 1.39 mmol) in THF (3 mL) was added a solution of t-butyl cyanoacetate (0.197 g, 1.392 mmol) in THF (1 mL) in one portion. After 10 min, a solution of 1-{2-(cyclopropylmethoxy)-6-[(4-methoxybenzyl)-oxy]phenyl}-3,3-bis(methylsulfanyl)-2-propene-1-one (0.500 g, 1.16 mmol) in THF (3 mL) was added followed by dibenzo-18-crown-6 (0.013 g, 0.035 mmol). The resulting mixture was refluxed for 4 hrs. After cooled to room temperature, the mixture was partitioned between 0.1 N acetic acid solution and $CH_2Cl_2$. The organic phase was separated, dried over $Na_2SO_4$, filtered, and concentrated under reduced pressure. The residual oil was dissolved in 1,2-dichloroethane (1 mL) and acetic acid (1 mL), and ammonium acetate (1.20 g, 15.57 mmol) was added. The mixture was stirred at 120° C. for 0.5 hrs. After cooled to room temperature, the mixture was partitioned between ethyl acetate and saturated aqueous $NaHCO_3$ solution. The organic phase was washed with saturated aqueous $NaHCO_3$ solution and brine, dried over $Na_2SO_4$, filtered, and concentrated under reduced pressure. Purification by column chromatography on silica gel (hexane/ethyl acetate 4:1 to 3:1) gave tert-butyl 2-amino-6-{2-(cyclopropylmethoxy)-6-[(4-methoxybenzyl)oxy]phenyl-}-4-(methylsulfanyl)nicotinate as an pale yellow oil (0.177 g, yield; 29%).

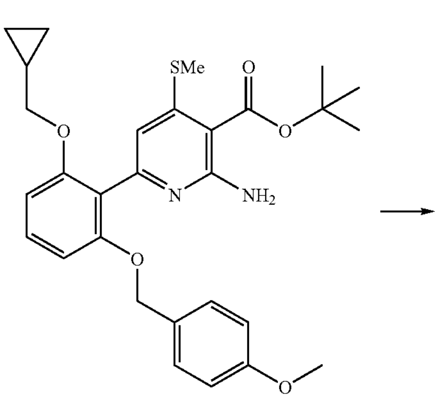

-continued

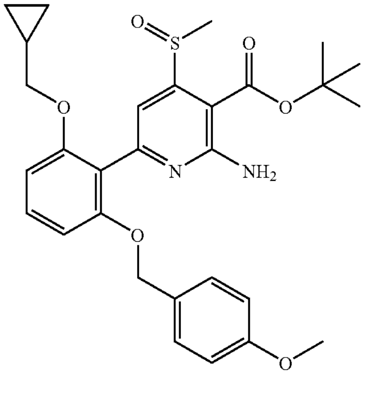

To a cold (0° C.) solution of tert-butyl 2-amino-6-{2-(cyclopropylmethoxy)-6-[(4-methoxybenzyl)oxy]phenyl}-4-(methylsulfanyl)nicotinate (1.72 g, 3.30 mmol) in $CH_2Cl_2$ (20 mL) was added m-CPBA (69%, 0.82 g, 3.30 mmol). The reaction mixture was stirred at 0° C. for 15 min, quenched with saturated aqueous $NaHCO_3$ solution (20 mL) containing $Na_2S_2O_3$ (1 g). The organic phase was separated, dried over $Na_2SO_4$, filtered, and concentrated under reduced pressure. Purification by column chromatography on silica gel (hexane/ethyl acetate=3:2 to 1:1) gave solid, which was triturated with ethyl acetate and diisoproyl ether to give tert-butyl 2-amino-6-{2-(cyclopropylmethoxy)-6-[(4-methoxybenzyl)oxy]phenyl}-4-(methylsulfinyl)nicotinate as a white powder (1.112 g, yield; 63%).

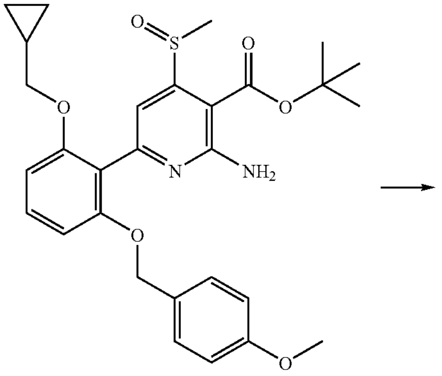

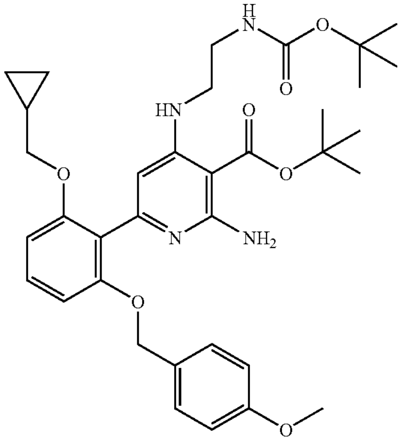

A mixture of tert-butyl 2-amino-6-{2-(cyclopropylmethoxy)-6-[(4-methoxy-benzyl)oxy]phenyl}-4-(methylsulfinyl)nicotinate (0.118 g, 0.219 mmol) and ethylenediarnine (0.29 mL) was stirred at 100° C. for 8 hrs. After cooled to room temperature, the mixture was partitioned between ethyl acetate and water. The separated organic phase was washed with brine, dried over $Na_2SO_4$, filtered, and concentrated under reduced pressure. The residue was dissolved in $CH_2Cl_2$ (2 mL), and di-tert-butyl dicarbonate (0.060 g, 0.275 mmol) was added. The mixture was stirred at room temperature for 2 hrs and concentrated under reduced pressure. The residue was purified by column chromatography to give tert-butyl 2-amino-4-({2-[(tert-butoxycarbonyl)amino]ethyl}amino)-6-{2-(cyclopropylmethoxy)-6-[(4-methoxybenzyl)oxy]phenyl}nicotinate as a foam (0.121 g, 92%).

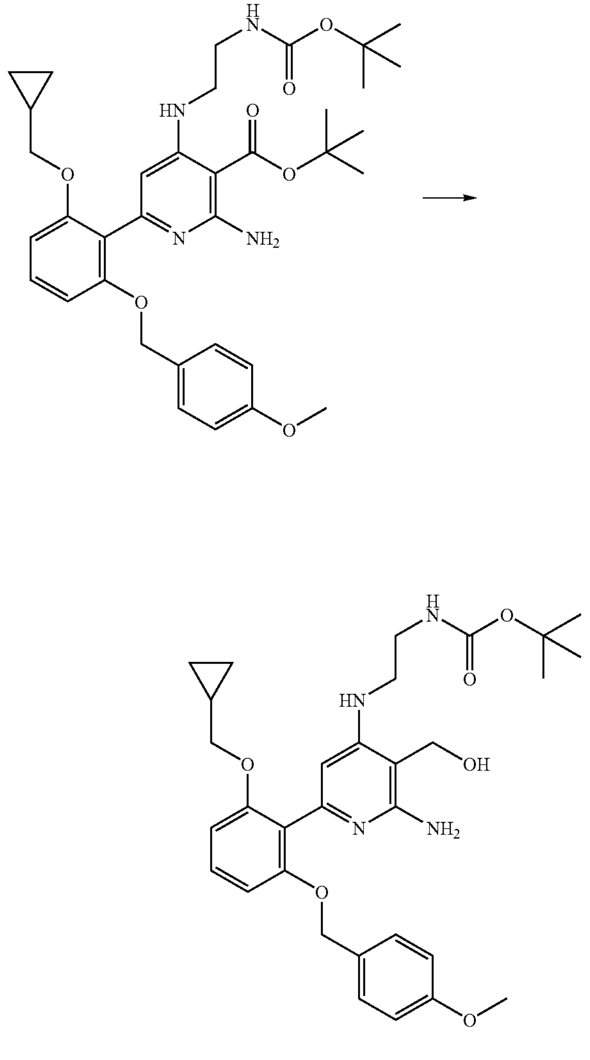

To a cold (0° C.) solution of tert-butyl 2-amino-4-({2-[(tert-butoxycarbonyl)-amino]ethyl}amino)-6-{2-(cyclopropylmethoxy)-6-[(4-methoxybenzyl)oxy]phenyl}-nicotinate (0.113 g, 0.178 mmol) in THF (5 mL) was added a solution of Vitride® (3.4 M, 1.0 mL, 3.4 mmol). The mixture was stirred at 0° C. for 0.5 hrs, quenched with saturated aqueous potassium sodium tartaric acid solution, and then partitioned between ethyl acetate and water. The organic phase was washed with brine, dried over $Na_2SO_4$, filtered, and concentrated under reduced pressure to give a solid, which was triturated with ethyl acetate and diisopropyl ether to give tert-butyl 2-{[2-amino-6-{2-(cyclopropylmethoxy)-6-[(4-methoxybenzyl)oxy]-phenyl}-3-(hydroxymethyl)-4-pyridinyl]amino}ethylcarbamate as a pink solid (0.078 g, yield; 78%).

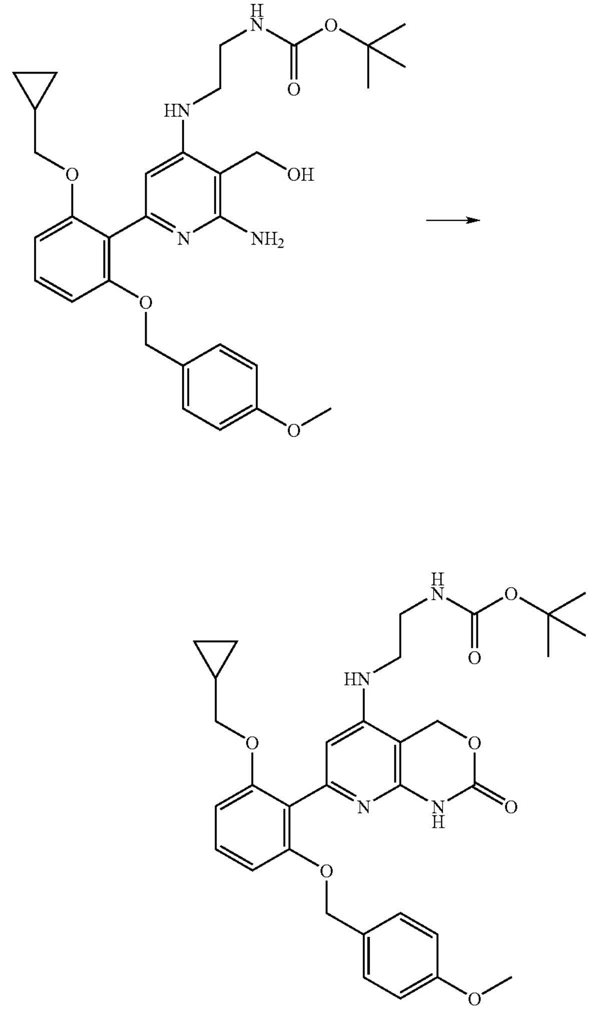

To a cold (0° C.) solution of tert-butyl 2-{[2-amino-6-{2-(cyclopropylmethoxy)-6-[(4-methoxybenzyl)oxy]phenyl}-3-(hydroxymethyl)-4-pyridinyl]amino}ethylcarbamate (0.050 g, 0.089 mmol) and $Et_3N$ (0.074 mL, 0.531 mmol) in THF (10 mL) was added triphosgene (0.013 g, 0.044 mmol) in one portion. The mixture was stirred at 0° C. for 1 hr, and then partitioned between ethyl acetate and water. The organic phase was washed with brine, dried over $Na_2SO_4$, filtered, and concentrated under reduced pressure. Purification by column chromatography on silica gel (ethyl acetate) gave tert-butyl 2-[(7-{2-(cyclopropylmethoxy)-6-[(4-methoxybenzyl)-oxy]phenyl}-2-oxo-1,4-dihydro-2H-pyrido[2,3-d][1,3]oxazin-5-yl)amino]ethylcarbamate as colorless oil (0.036 g, yield; 69%).

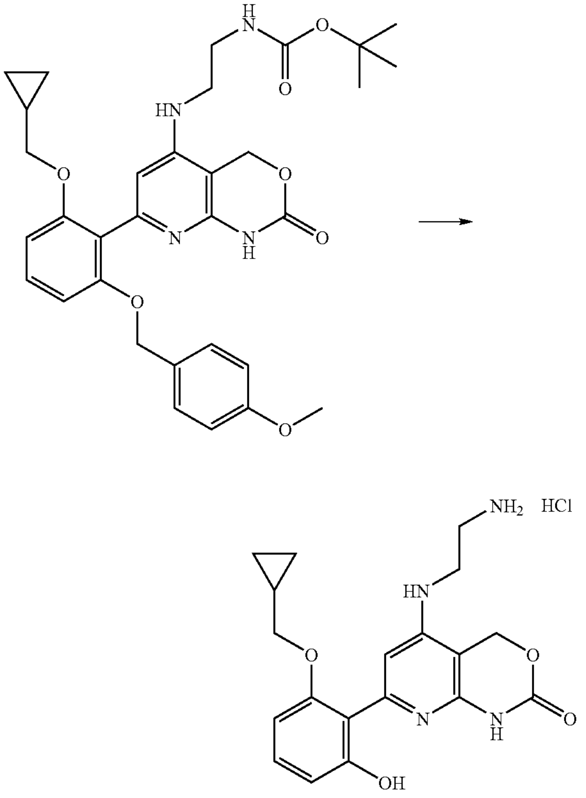

To a solution of tert-butyl 2-[(7-{2-(cyclopropylmethoxy)-6-[(4-methoxybenzyl)-oxy]phenyl}-2-oxo-1,4-dihydro-2H-pyrido[2,3-d][1,3]oxazin-5-yl)amino]ethyl-carbamate (0.032 g, 0.054 mmol) in 1,4-dioxane (1 mL) was added 4N HCl in 1,4-dioxane (1 mL). The mixture was stirred at room temperature overnight. The resulting precipitate was collected by filtration, washed with ethyl acetate to give 5-[(2-aminoethyl)amino]-7-[2-(cyclopropylmethoxy)-6-hydroxyphenyl]-1,4-dihydro-2H-pyrido[2,3-d][1,3]oxazin-2-one hydrochloride as a solid (0.013 g, yield; 59%).

Molecular weight: 406.87

Mass spectrometry: 370 $(M+H)^+$

In vitro activity grade: A

Cellular activity grade: (A549)-A $^1$H-NMR (500 MHz, DMSO-d6): 0.26–0.36 (2H, m), 0.47–0.57 (2H, m), 1.15–1.25 (1H, m), 2.96–3.07 (2H, m), 3.50–3.60 (2H, m), 3.85 (2H, d, J=6.9 Hz), 5.45 (2H, br s), 6.57 (1H, d, J=8.2 Hz), 6.56–6.68 (1H, m), 6.96 (1H, br s), 7.24 (1H, t, J=8.2 Hz), 7.75 (1H, br), 8.18 (3H, br s), 10.86 (1H, br).

Example 35-2

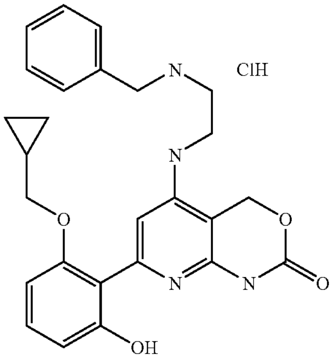

In a similar manner as that of Example 35-1, 5-(2-benzylamino-ethylamino)-6-(2-cyclopropylmethoxy-6-hydroxy-phenyl)-1,4-dihydro-pyrido[2,3-d][1,3]oxazin-2-one hydrochloride was prepared.

Molecular weight: 497.00

Mass spectrometry: 461 $(M+H)^+$

In vitro activity grade: A (500 MHz, DMSO-d6): 0.26–0.35 (2H, m), 0.45–0.58 (2H, m), 1.10–1.28 (1H, m), 3.16 (2H, br s), 3.67 (2H, br), 3.85 (2H, d, J=6.8 Hz), 4.13–4.25 (2H, m ), 5.43 (2H, br s), 6.50–6.65 (2H, m), 7.04 (1H, br s), 7.22 (1H, t, J=8.3 Hz), 7.35–7.50 (4H, m), 7.50–7.65 (3H, m), 9.44 (2H, br), 10.74 (1H, br).

The invention claimed is:

1. A process for producing 2-amino-4,6-disubstituted nicotinic acid ester analogs and salts thereof, comprising reacting the compounds of formulae (I), (II), (III), and an ammonium salt in accordance with the following scheme:

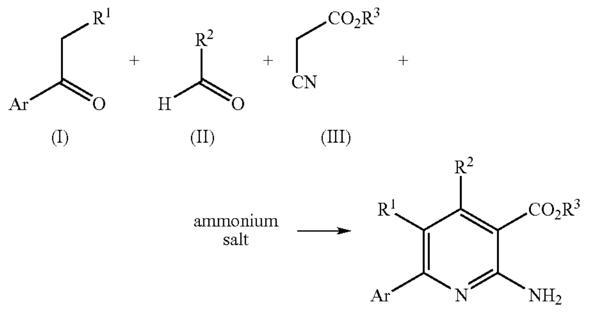

(I) (II) (III) (IV)

wherein

Ar is an aryl or heteroaryl group, and optionally substituted by one or more substituents;

$R^1$ is hydrogen, halogen, or $C_{1-6}$ alkyl;

$R_2$ is optionally substituted aryl, heteroaryl, alkyl or alkenyl; and $R^3$ is —$CR^{21}R^{22}R^{23}$, wherein $R^{21}$, $R^{22}$ and $R^{23}$ are each independently $C_{1-6}$ alkyl or aryl.

2. The process as claimed in claim 1, wherein:

Ar is phenyl, 2-pyridyl, 3-pyridyl, 4-pyridyl, 2-thienyl, 3-thienyl, 2-furyl, 3-furyl, 1-naphthyl, 2-naphthyl, 2-quinolyl, 3-quinolyl, 4-quinolyl, 5-quinolyl, 6-quinolyl, 7-quinolyl or 8-quinolyl and optionally substituted by one or more substituents, wherein the optional substituents are each independently hydrogen, $C_{1-6}$ alkyl, halogen, $C_{1-12}$ alkoxy, cyano, nitro, $C_{1-6}$ alkylsulfonylamino, $C_{1-6}$ alkoxycarbonyl, di $C_{1-6}$ alkylamino, $C_{1-6}$ alkylcarbonylamino, —S—$(CH_2)_n$—$R^{11}$ or —O—$(CH_2)_n$—$R^{11}$, wherein n represents an integer selected from 0 to 6, and $R^{11}$ is $C_{2-6}$ alkenyl, benzoyl, diphenylmethyl, di($C_{1-6}$ alkyl)amino, $C_{1-6}$ alkanoyl, $C_{1-6}$ alkoxycarbonyl, or an optionally substituted 3 to 10 membered saturated or unsaturated ring having 0 to 3 heteroatoms selected from the group consisting of S, O and N as heteroatoms;

$R^1$ is hydrogen, halogen, or $C_{1-6}$ alkyl;

$R^2$ is optionally substituted phenyl or styryl;

wherein the optional substituents are each independently hydrogen, halogen, $C_{1-6}$ alkoxy, di $C_{1-6}$ alkylamino, $C_{1-6}$ alkanoylamino, $C_{1-6}$ alkyl(hydroxy $C_{1-6}$ alkyl)amino, $C_{1-6}$ alkyl(benzyl)amino, morpholino, $C_{1-6}$ alkylsulfonylamino, optionally substituted piperidino, optionally substituted pyrrolidino, piperidino-$C_{1-6}$ alkylene-oxy, —CO—$NHR^{51}$, or NH—$COR^{51}$, wherein $R^{51}$ represents piperidino-$C_{1-6}$ alkylene, carboxy-$C_{1-6}$ alkylene, $C_{1-6}$ alkyl, $C_{1-6}$ alkoxy, $C_{1-6}$ alkoxy-$C_{1-6}$ alkylene, oxotetrahydrofuryl, oxopyrrolidinyl, —$CH(OH)R^{51a}$, or —$C_{1-6}$ alkylene-$R^{51b}$, wherein $R^{51}$ is carboxy-$C_{1-6}$ alkylene or $C_{1-6}$ alkoxycarbonyl-$C_{1-6}$ alkylene, $R^{51b}$ is optionally substituted piperidino, optionally substituted piperazino, optionally substituted amino, or —$CH(NH_2)$— carboxy, N-protected amino-$C_{1-6}$ alkylene, or 5 to 8 membered saturated ring having 0 to 3 N as heteroatoms and the N atom is protected;

—$CR^{31}R^{32}R^{33}$, wherein $R^{31}$ is hydrogen or $C_{1-6}$ alkyl, $R^{32}$ is hydrogen, a 5 to 8 membered saturated ring having 0 to 3 atoms selected from the group consisting of S, O and N as heteroatoms, or optionally substituted $C_{1-6}$ alkyl, and $R^{33}$ is hydrogen, amino, $C_{1-6}$ alkoxycarbonylamino, $C_{2-6}$ alkenyl-oxycarbonylamino, benzyloxycarbonylamino or $R^{32}$ and $R^{33}$ may form, together with the adjacent carbon atom, an optionally substituted or optionally benzene fused 5 to 8 membered saturated ring having 0 to 3 heteroatoms selected from the group consisting of N, O and S as heteroatoms; and $R^3$ is a —$CR^{21}R^{22}R^{23}$, wherein $R^{21}$, $R^{22}$ and $R^{23}$ are each independently $C_{1-6}$ alkyl or phenyl.

3. The process as claimed in claim 1, wherein:

Ar is phenyl, 2-pyridyl, 3-pyridyl, 4-pyridyl, 2-thienyl, 3-thienyl, 2-furyl, 3-furyl, 1-naphthyl, 2-naphthyl, 2-quinolyl, 3-quinolyl, 4-quinolyl, 5-quinolyl, 6-quinolyl, 7-quinolyl or 8-quinolyl and optionally substituted by one or more substituents, wherein the optional substituents are each independently hydrogen, $C_{1-6}$ alkyl, halogen, $C_{1-12}$ alkoxy, cyano, nitro, $C_{1-6}$ alkylsulfonylamino, $C_{1-6}$ alkoxycarbonyl, di $C_{1-6}$ alkylamino, $C_{1-6}$ alkylcarbonylamino, —S—$(CH_2)_n$—$R^{11}$, or —O—$(CH_2)_n$—$R^{11}$, wherein n represents an integer selected from 0 to 6, and $R^{11}$ is $C_{2-6}$ alkenyl, benzoyl, diphenylmethyl, di ($C_{1-6}$ alkyl)amino, $C_{1-6}$ alkanoyl, $C_{1-6}$ alkoxycarbonyl, optionally substituted 3 to 10 membered saturated or unsaturated ring having 0 to 3 heteroatoms selected from the group consisting of S, O and N as heteroatoms, which ring is optionally substituted by one or more substituents selected from the group consisting of $C_{1-6}$ alkyl, $C_{1-6}$ alkoxy, halogen, $C_{1-6}$ alkoxycarbonyl, $C_{1-6}$ alkylsulfonyl, halogen substituted alkyl, nitro, cyano, hydroxy, phenyl, amino, $C_{1-6}$ alkylamino, $C_{3-8}$ cycloalkylamino, benzylamino, carbamoyl, —O—$_{1-6}$ alkylene-phenyl, and —O-phenyl;

$R^1$ is hydrogen, halogen, or $C_{1-6}$ alkyl;

$R^2$ is optionally substituted phenyl or styryl;

wherein the optional substituents are each independently hydrogen, halogen, amino, $C_{1-6}$ alkoxy, di $C_{1-6}$ alkylamino, $C_{1-6}$ alkanoylamino, $C_{1-6}$ alkyl(hydroxy $C_{1-6}$ alkyl)amino, $C_{1-6}$ alkyl(benzyl)amino, morpholino, $C_{1-6}$ alkylsulfonylamino, optionally substituted piperidino, optionally substituted pyrrolidino, piperidino-$C_{1-6}$ alkylene-oxy, —CO—$NHR^{51}$, or —NH—$COR^{51}$, wherein $R^{51}$ represents piperidino-$C_{1-6}$ alkylene, carboxy-$C_{1-6}$ alkylene, $C_{1-6}$ alkyl, $C_{1-6}$ alkoxy, $C_{1-6}$ alkoxy-$C_{1-6}$ alkylene, oxotetrahydrofuryl, oxopyrrolidinyl, —CH(OH)$R^{51a}$, or —$C_{1-6}$ alkylene-$R^{51b}$, wherein $R^{51a}$ is carboxy-$C_{1-6}$ alkylene or $C_{1-6}$ alkoxycarbonyl-$C_{1-6}$ alkylene, $R^{51b}$ is —$NHR^{51b-1}$ (wherein $R^{51b-1}$ represents hydrogen, $C_{1-6}$ alkyl, —$C_{1-6}$ alkylene-O—$C_{1-6}$ alkyl, hydroxy-$C_{1-6}$ alkylene, or piperidino-$C_{1-6}$ alkylene), —$CH(NH_2)$—COOH, pyrroline, or —$N(C_{1-6}$ alkyl)$R^{51b-2}$ (wherein $R^{51b-2}$ represents $C_{1-6}$ alkyl or ethylpyrrolidine), piperidino optionally substituted by carboxy or $C_{1-6}$ alkoxycarbonyl, piperazino fused with cyclohexane, piperazino optionally substituted by $C_{1-6}$ alkyl, benzyl, hydroxy-$C_{1-6}$ alkylene, $C_{1-6}$ alklyl-carbonyl, cyclohexane, benzodioxane-$C_{1-6}$ alkylene, or furyl-carbonyl, N-protected amino-$C_{1-6}$ alkylene, N-protected 2-piperidyl, N-protected 3-piperidyl or N-protected 4-piperidyl;

—$CR^{31}R^{32}R^{33}$, wherein $R^{31}$ is hydrogen or $C_{1-6}$ alkyl, $R^{32}$ is hydrogen; $C_{1-6}$ alkyl optionally substituted by hydroxy, amino, phenyl, $C_{1-6}$ alkoxyphenyl, halophenyl or aminophenyl; or a 5 to 8 membered saturated ring having 0 to 3 atoms selected from the group consisting of S, O and N as heteroatoms, and $R^{33}$ is hydrogen, amino, $C_{1-6}$ alkoxycarbonylamino, $C_{2-6}$ alkenyloxy-carbonylamino, or benzyloxycarbonylamino or $R^{32}$ and $R^{33}$ may form, together with the adjacent carbon atom, an optionally substituted 5 to 8 membered saturated ring having 0 to 3 heteroatoms selected from the group consisting of N, O and S as heteroatoms, which ring is optionally be substituted by one or more substituents selected from the group consisting of $C_{1-6}$ alkyl, $C_{1-6}$ alkoxy, $C_{1-6}$ alkoxycarbonyl, $C_{1-6}$ alkylsulfonyl, halogen substituted alkyl, nitro, cyano, hydroxy, phenyl, amino, $C_{1-6}$ alkylamino, $C_{3-8}$ cycloalkylamino, benzylamino, carbamoyl, —O—$C_{1-6}$ alkylene-phenyl, —O-phenyl, phenyl-$C_{1-6}$ alkyl, di $C_{1-6}$ alkylamino, and piperidino-$C_{1-6}$ alkylcarbonyl, or said ring may be fused with a benzene ring; and $R^3$ is t-butyl, 1,1-dimetlylpropyl or trityl group.

4. The process as claimed in claim 1, wherein:

Ar is phenyl, and optionally substituted by one substituent, wherein the optional substituent is hydrogen, $C_{1-2}$ alkoxy, or —O—$C_{1-6}$ alkylene-$R^{11}$, wherein $R^{11}$ is vinyl, diphenylmethyl, $C_{1-6}$ alkanoyl, optionally substituted $C_{5-10}$ aryl, or optionally substituted 5 to 10 membered heteroaryl, optionally substituted 3 to 8 membered cycloalkyl optionally interrupted by O atom, or a 5 to 8 membered saturated heterocyclic ring interrupted by NH and/or O;

$R^1$ is hydrogen;

$R^2$ is optionally substituted phenyl or styryl;

wherein the optional substituents are each independently hydrogen, halogen, amino, $C_{1-6}$ alkoxy, di $C_{1-6}$ alkylamino, $C_{1-6}$ alkanoylamino, $C_{1-6}$ alkyl(hydroxy $C_{1-6}$ alkyl)amino, $C_{1-6}$ alkyl(benzyl)amino, morpholino, $C_{1-6}$ alkylsulfonylamino, optionally substituted piperidino, optionally substituted pyrrolidino, piperidino-$C_{1-6}$ alkylene-oxy, —CO—$NHR^{51}$, or —NH—$COR^{51}$, wherein $R^{51}$ represents piperidino-$C_{1-6}$ alkylene, carboxy-$C_{1-6}$ alkylene, $C_{1-6}$ alkyl, $C_{1-6}$ alkoxy, $C_{1-6}$ alkoxy-$C_{1-6}$ alkylene, oxotetrahydrofuryl, oxopyrrolidinyl, —CH(OH)$R^{51a}$, or —$C_{1-6}$ alkylene-$R^{51b}$, wherein $R^{51a}$ is carboxy-$C_{1-6}$ alkylene or $C_{1-6}$ alkoxycarbonyl-$C_{1-6}$ alkylene, $R^{51b}$ is —$NHR^{51b-1}$ (wherein $R^{51b-1}$ represents hydrogen, $C_{1-6}$ alkyl, —$C_{1-6}$ alkylene-O—$C_{1-6}$ alkyl, hydroxy-$C_{1-6}$ alkylene, piperidino-$C_{1-6}$ alkylene), —$CH(NH_2)$—COOH, pyrroline, —$N(C_{1-6}$ alkyl)$R^{51b-2}$ (wherein $R^{51b-2}$ represents $C_{1-6}$ alkyl or ethylpyrrolidine), piperidino optionally substituted by carboxy or $C_{1-6}$ alkoxycarbonyl, piperazino fused with cyclohexane, or piperazino optionally substituted by $C_{1-6}$ alkyl, benzyl, hydroxy-$C_{1-6}$ alkylene, $C_{1-6}$ alkyl-carbonyl, cyclohexane, benzodioxane-$C_{1-6}$ alkylene, or furyl-carbonyl, N-protected amino-$C_{1-6}$ alkylene, N-protected 2-piperidyl, N-protected 3-piperidyl or N-protected 4-piperidyl;

—$CR^{31}R^{32}R^{33}$, wherein $R^{31}$ is hydrogen or $C_{1-6}$ alkyl, $R^{32}$ is hydrogen, or $C_{1-6}$ alkyl optionally substituted by hydroxy, amino, phenyl, $C_{1-6}$ alkoxyphenyl, halophenyl, or aminophenyl, and $R^{33}$ is hydrogen, amino, or benzyloxycarbonylamino; or $R^{32}$ and $R^{33}$ may form optionally substituted $C_{5-8}$ cycloalkyl optionally interrupted by NH, wherein said substituent is $C_{1-6}$ alkyl, phenyl-$C_{1-6}$ alkyl, amino, $C_{1-6}$ alkylamino, benzylamino, di $C_{1-6}$ alkylamino, carbamoyl, $C_{1-6}$ alkoxy-carbonyl, piperidino-$C_{1-6}$ alkylcarbonyl, or $C_{1-6}$ alkylsulfonyl, and said ring may be fused with a benzene ring;

$R^3$ is t-butyl group.

5. The process as claimed in claim 1, wherein the ammonium salt is ammonium acetate.

* * * * *